United States Patent
Stamova-Kiossepacheva et al.

(10) Patent No.: US 11,525,161 B2
(45) Date of Patent: Dec. 13, 2022

(54) METHODS OF DISTINGUISHING ISCHEMIC STROKE FROM INTRACEREBRAL HEMORRHAGE

(71) Applicant: The Regents of the University of California, Oakland, CA (US)

(72) Inventors: Boryana Stamova-Kiossepacheva, Davis, CA (US); Glen C. Jickling, Davis, CA (US); Frank Sharp, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 49 days.

(21) Appl. No.: 15/572,965

(22) PCT Filed: May 5, 2016

(86) PCT No.: PCT/US2016/031028
§ 371 (c)(1),
(2) Date: Nov. 9, 2017

(87) PCT Pub. No.: WO2016/182855
PCT Pub. Date: Nov. 17, 2016

(65) Prior Publication Data
US 2018/0230538 A1    Aug. 16, 2018

Related U.S. Application Data

(60) Provisional application No. 62/159,502, filed on May 11, 2015.

(51) Int. Cl.
*C12Q 1/6883* (2018.01)
*G01N 33/68* (2006.01)

(52) U.S. Cl.
CPC ....... *C12Q 1/6883* (2013.01); *G01N 33/6896* (2013.01); *C12Q 2600/156* (2013.01); *G01N 2800/2871* (2013.01)

(58) Field of Classification Search
None
See application file for complete search history.

(56) References Cited

U.S. PATENT DOCUMENTS

| | | | |
|---|---|---|---|
| 6,399,364 B1 * | 6/2002 | Reeve | C12Q 1/6874 435/287.1 |
| 8,058,055 B2 * | 11/2011 | Barrett | C12Q 1/6841 435/6.12 |
| 2010/0086481 A1 | 4/2010 | Baird et al. | |
| 2010/0092985 A1 * | 4/2010 | Lee | G01N 33/54306 435/6.14 |
| 2012/0015904 A1 | 1/2012 | Sharp et al. | |
| 2012/0065087 A1 | 3/2012 | Sharp et al. | |
| 2014/0079836 A1 * | 3/2014 | McDaniel | A61K 36/13 424/777 |
| 2014/0220580 A1 | 8/2014 | Brown et al. | |
| 2014/0329704 A1 * | 11/2014 | Melton | C12Q 1/6881 506/9 |
| 2015/0018234 A1 | 1/2015 | Sharp et al. | |

FOREIGN PATENT DOCUMENTS

| WO | WO 2012/115885 | 8/2012 |
|---|---|---|
| WO | WO 2012/121978 | 9/2012 |

OTHER PUBLICATIONS

Boehringer Mannheim, 1997 Biochemical Catalog, pp. 1-2 (Year: 1997).*
Gao (Science of the Total Environment, 2014, vol. 472, pp. 872-879).*
PCT International Search Report and Written Opinion dated Aug. 26, 2016 issued in PCT/US16/31028.
Coelho, Tiago Krug, "Stroke Genetics and Genomics" Faculdade de Medicina da Universidade de Lisboa, PhD Thesis pp. 1-225, 2010.
Perisic, et al., "Profiling of Atherosclerotic Lesions by Gene and Tissue Microarrays Reveals PCSK6 as a Novel Protease in Unstable Carotid Atherosclerosis" Arterioscler Thromb Vasc Biol. 33:2432-2443, 2013.

* cited by examiner

*Primary Examiner* — Sarae L Bausch
(74) *Attorney, Agent, or Firm* — Kilpatrick Townsend & Stockton LLP

(57) ABSTRACT

Provided are compositions and methods for differentiating and diagnosing ischemic stroke and subgroups thereof (e.g., cardioembolic stroke, large vessel stroke, atherothrombotic stroke, lacunar stroke) from intracerebral hemorrhage.

13 Claims, 3 Drawing Sheets

Alternative splicing of primary mRNA results in multiple mRNA and protein isoforms

METHODS OF DISTINGUISHING ISCHEMIC STROKE FROM INTRACEREBRAL HEMORRHAGE

CROSS-REFERENCE TO RELATED APPLICATIONS

This application is the U.S. national phase under 35 U.S.C. § 371 of Intl. Appl. No. PCT/US2016/031028, which claims the benefit under 35 U.S.C. § 119(e) of U.S. Provisional Application No. 62/159,502, filed on May 11, 2015, which are hereby incorporated herein by reference in their entireties for all purposes.

STATEMENT OF GOVERNMENTAL SUPPORT

This invention was made with Government support under Grant Nos. NS075035, NS079153 and AG042292, all awarded by the National Institutes of Health. The government has certain rights in this invention.

FIELD

Provided are compositions and methods for differentiating and diagnosing ischemic stroke and subgroups thereof (e.g., cardioembolic stroke, large vessel stroke, atherothrombotic stroke, lacunar stroke) from intracerebral hemorrhage.

BACKGROUND

Clinicians diagnose stroke based on patient history, neurological exams and brain imaging. This can be difficult and distinguishing ischemic stroke (IS) from hemorrhage can be challenging when imaging is unavailable in the acute setting.

Blood transcriptomes have provided insights into the immune response following human stroke and show promise as diagnostic biomarkers [1-6]. However, these studies have investigated only a proportion of the protein coding transcriptome, since they have used 3'-biased microarrays to measure blood mRNA expression [1-6]. Though these studies provided proof-of-principle, the vast complexity of the stroke transcriptome which is comprised of alternatively spliced isoforms remains unstudied in stroke. The importance of alternative splicing (AS) in stroke is supported by increasing evidence implicating AS in the pathogenesis of many diseases [7, 8].

AS is the process whereby exons from a single gene are included or excluded in the final mRNA transcript (FIG. 1). A single gene produces several AS isoforms with specific functions in different cells, tissues, developmental stages and disease states. Thus, the ~20,000 known genes code for >250,000 different mRNAs and proteins. Differential alternative splicing (DAS) is AS that differs between groups. We investigated whether DAS would vary for different IS causes (cardioembolic, large vessel and lacunar) compared to intracerebral hemorrhage (ICH) and controls. Therefore, we used RNA sequencing (RNA-Seq) to measure DAS in whole blood samples of humans with ICH and with different causes of IS and compared these to controls. RNA-Seq is a new technology that allows for estimation of expression of each splice variant (FIG. 1), a significant advance over previously used technologies in stroke. To date, there have been no RNA-Seq studies for AS markers of stroke etiology, or for distinguishing between ischemic stroke and ICH either in humans or in animal models.

SUMMARY

In one aspect, provided are methods for diagnosing cardioembolic ischemic stroke (CE IS) or a predisposition for experiencing CE IS. In some embodiments, the methods comprise determining a level of exon or splice variant usage or expression of a plurality of biomarkers in a biological sample from a patient, wherein an increase of the level of exon usage or expression compared to a control indicates that the patient has suffered or is at risk of experiencing CE IS, wherein the plurality of exons or splice variants of the biomarkers is selected from the biomarkers set forth in Table 1A, thereby diagnosing CE IS or a predisposition for experiencing CE IS.

In a further aspect, provided are methods for diagnosing large vessel ischemic stroke (LV IS) or a predisposition for experiencing LV IS. In some embodiments, the methods comprise determining a level of exon or splice variant usage or expression of a plurality of biomarkers in a biological sample from a patient, wherein an increase of the level of exon usage or expression compared to a control indicates that the patient has suffered or is at risk of experiencing LV IS, wherein the plurality of exons or splice variants of the biomarkers is selected from the biomarkers set forth in Table 1B, thereby diagnosing LV IS or a predisposition for experiencing LV IS.

In a further aspect, provided are methods for diagnosing lacunar ischemic stroke (L IS) or a predisposition for experiencing L IS. In some embodiments, the methods comprise determining a level of exon or splice variant usage or expression of a plurality of biomarkers in a biological sample from a patient, wherein an increase of the level of exon usage or expression compared to a control indicates that the patient has suffered or is at risk of experiencing L IS, wherein the plurality of exons or splice variants of the biomarkers is selected from the biomarkers set forth in Table 1C, thereby diagnosing L IS or a predisposition for experiencing L IS.

In a further aspect, provided are methods for diagnosing intracerebral hemorrhage (ICH) or a predisposition for experiencing ICH. In some embodiments, the methods comprise determining a level of exon usage or expression of a plurality of biomarkers in a biological sample from a patient, wherein an increase of the level of exon or splice variant usage or expression compared to a control indicates that the patient has suffered or is at risk of experiencing ICH, wherein the plurality of exons or splice variants of the biomarkers is selected from the biomarkers set forth in Table 1D, thereby diagnosing ICH or a predisposition for experiencing ICH.

In a further aspect, provided are methods of differentiating between ischemic stroke (IS) from intracerebral hemorrhage (ICH). In some embodiments, the methods comprise determining a level of exon or splice variant usage or expression of a plurality of biomarkers set forth in Table 1A, a plurality of biomarkers set forth in Table 1B, a plurality of biomarkers set forth in Table 1C, and a plurality of biomarkers set forth in Table 1D, in a biological sample from a patient, wherein detecting:

a) an increase of the level of exon or splice variant usage or expression of a plurality of exons of the biomarkers set forth in Table 1A compared to a control indicates that the patient has suffered or is at risk of experiencing cardioembolic ischemic stroke (CE IS);

b) an increase of the level of exon or splice variant usage or expression of a plurality of exons of the biomarkers set forth in Table 1B compared to a control indicates that the patient has suffered or is at risk of experiencing large vessel ischemic stroke (LV IS);

c) an increase of the level of exon or splice variant usage or expression of a plurality of exons of the biomarkers set forth in Table 1C compared to a control indicates that the patient has suffered or is at risk of experiencing lacunar ischemic stroke (L IS); and d) an increase of the level of exon or splice variant usage or expression of a plurality of exons of the biomarkers set forth in Table 1D compared to a control indicates that the patient has suffered or is at risk of experiencing ICH; thereby differentiating between ischemic stroke (IS) from ICH.

With respect to embodiments of the methods, in some embodiments, the determining step is performed at 3 or more hours after a suspected ischemic stroke or ICH. In some embodiments, the determining step is performed at 3 or fewer hours after a suspected ischemic stroke or ICH. In some embodiments, the determining step is performed at 24 or fewer hours after a suspected ischemic stroke or ICH. In some embodiments, the determining step is performed at least 24 hours after a suspected ischemic stroke or ICH. In some embodiments, the level of expression of the biomarker is determined at the transcriptional level. In varying embodiments, the level of expression is determined by detecting hybridization of a nucleic acid probe to gene transcripts of the biomarkers in the biological sample. In varying embodiments, the hybridization step is performed on a nucleic acid microarray chip. In varying embodiments, the hybridization step is performed in a microfluidics assay plate. In varying embodiments, the level of expression is determined by direct RNA sequencing of gene transcripts of the biomarkers. In varying embodiments, the level of expression is determined by amplification of gene transcripts of the biomarkers. In varying embodiments, the amplification reaction is a polymerase chain reaction (PCR). In varying embodiments, the amplification reaction comprises quantitative reverse transcription polymerase chain reaction (qRT-PCR). In varying embodiments, the amplification reaction comprises reverse transcription (RT) followed by a ligase detection reaction (LDR) with single-pair fluorescence resonance energy transfer (spFRET) (RT-LDR/spFRET). In varying embodiments, the level of expression of the biomarker isoform is determined at the protein level. In varying embodiments, the level of expression of at least 15 biomarkers, e.g., at least 20, 25, 30, 35, 40, 45, 50, 55, 60, 65, 70, 75, 80, 85, 90, 95, 100 biomarkers, or all listed biomarkers in the identified Table (e.g., Table 1A, Table 1B, Table 1C, Table 1D and/or Table 1E), are determined. In varying embodiments, the methods further comprise the step of obtaining a biological sample. In varying embodiments, the biological sample is blood, serum or plasma. In varying embodiments, the increased level of exon usage of a biomarker is at least about 1.2-fold in comparison to a control. In varying embodiments, the control is the expression level of the same biomarker in an individual with no history of stroke, heart attack, or peripheral vascular disease. In varying embodiments, the control is a threshold level of expression representative of a population of individuals with no history of stroke, heart attack, peripheral vascular disease. In varying embodiments, the individual or the population of individuals has at least one vascular risk factor. In varying embodiments, the control is an individual or population of individuals who have increased expression of one or more biomarkers set forth in Table 1E. In varying embodiments, the methods further comprise the step of providing a diagnosis for ischemic stroke/ICH to the patient based on the determination and identification of the level of expression of the set of ischemic stroke/ICH biomarkers. In varying embodiments, the methods further comprise the step of providing an appropriate treatment or prevention regime for ischemic stroke/ICH to the patient. In varying embodiments, the subject has experienced or is suspected of having experienced ischemic stroke or ICH. In varying embodiments, if the patient has experienced or has a predisposition to experience ischemic stroke or ICH, further comprising the step of determining the cause or risk of the ischemic stroke or ICH In a further aspect, provided are solid supports. In varying embodiments, the solid supports comprise a plurality of oligonucleotide probes that hybridize to a plurality of the biomarkers set forth in Table 1A. In varying embodiments, the solid supports comprise a plurality of oligonucleotide probes that hybridize to a plurality of the biomarkers set forth in Table 1B. In varying embodiments, the solid supports comprise a plurality of oligonucleotide probes that hybridize to a plurality of the biomarkers set forth in Table 1C. In varying embodiments, the solid supports comprise a plurality of oligonucleotide probes that hybridize to a plurality of the biomarkers set forth in Table 1D. In varying embodiments, the solid supports comprise a plurality of oligonucleotide probes that hybridize to a plurality of the biomarkers set forth in Table 1A, Table 1B, Table 1C and/or Table 1D. In varying embodiments, the solid support is a microarray. In varying embodiments, the microarray is suitable or configured for use in a microfluidic device. In varying embodiments, the solid supports further comprise a plurality of oligonucleotide probes that hybridize to a plurality of the biomarkers set forth in Table 1E. In varying embodiments, the solid supports further comprise a plurality of oligonucleotide probes that hybridize to a plurality of the biomarkers for diagnosing one or more of cardioembolic stroke, atherothrombotic stroke, carotid stenosis, atrial fibrillation, lacunar stroke, transient ischemic attack, transient neurological events, and hemorrhagic transformation. In varying embodiments, plurality refers to at least 15 biomarkers, e.g., at least 20, 25, 30, 35, 40, 45, 50, 55, 60, 65, 70, 75, 80, 85, 90, 95, 100 biomarkers, or all listed biomarkers in the identified Table (e.g., Table 1A, Table 1B, Table 1C, Table 1D and/or Table 1E).

In another aspect, provided are reaction mixtures for amplifying one or more exons of a plurality (e.g., 2, 15, 20, 25, 30, 35, 40, 45, 50, 55, 60, 65, 70, 75, 80, 85, 90, 95, 100 biomarkers, or all listed biomarkers in the identified Table, e.g., Table 1A, Table 1B, Table 1C, Table 1D and/or Table 1E) of biomarkers listed in Tables 1A-E. In varying embodiments, the reaction mixture comprises one or more primer pairs or a set of primers for amplifying one or more exons of a plurality of the biomarkers set forth in Table 1A. In varying embodiments, the reaction mixture comprises one or more primer pairs or a set of primers for amplifying one or more exons of a plurality of the biomarkers set forth in Table 1B. In varying embodiments, the reaction mixture comprises one or more primer pairs or a set of primers for amplifying one or more exons of a plurality of the biomarkers set forth in Table 1C. In varying embodiments, the reaction mixture comprises one or more primer pairs or a set of primers for amplifying one or more exons of a plurality of the biomarkers set forth in Table 1D. In varying embodiments, the reaction mixture comprises one or more primer pairs or a set of primers for amplifying one or more exons of a plurality of the biomarkers set forth in Table 1A, Table 1B, Table 1C and Table 1D. In varying embodiments, the reaction mixture further comprises one or more primer pairs or a set of primers for amplifying one or more exons of a plurality of the biomarkers set forth in Table 1E. Further provided is a kit comprising the reaction mixtures, as described above and herein.

In a related aspect, provided are kits. In varying embodiments, the kits comprise one or more solid supports, as described herein. In varying embodiments, the kits comprise one or more primer pairs or a set of primers for amplifying one or more exons of a plurality of the biomarkers set forth in Table 1A. In varying embodiments, the kits comprise one or more primer pairs or a set of primers for amplifying one or more exons of a plurality of the biomarkers set forth in Table 1B. In varying embodiments, the kits comprise one or more primer pairs or a set of primers for amplifying one or more exons of a plurality of the biomarkers set forth in Table 1C. In varying embodiments, the kits comprise one or more primer pairs or a set of primers for amplifying one or more exons of a plurality of the biomarkers set forth in Table 1D. In varying embodiments, the kits comprise one or more primer pairs or a set of primers for amplifying one or more exons of a plurality of the biomarkers set forth in Table 1A, Table 1B, Table 1C and Table 1D. In varying embodiments, the kits further comprising a set of primers for amplifying one or more exons of a plurality of the biomarkers set forth in Table 1E.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Green and Sambrook, MOLECULAR CLONING: A LABORATORY MANUAL, 4th ed. (2012) Cold Spring Harbor Laboratory Press, Cold Spring Harbor, N.Y. and Ausubel, et al., CURRENT PROTOCOLS IN MOLECULAR BIOLOGY, 1987-2015, Wiley Interscience; Wiley Online Library at http://onlinelibrary.wiley.com/book/10.1002/0471142727/homepage/archive.htm), which are provided throughout this document. The nomenclature used herein and the laboratory procedures in analytical chemistry and organic synthesis described below are those well-known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy).

The term "transient ischemic attack," "TIA," or "mini-stroke" interchangeably refer to a change in the blood supply to a particular area of the brain, resulting in brief neurologic dysfunction that persists, by definition, for less than 24 hours. By definition, a TIA resolves within 24 hours, but most TIA symptoms resolve within a few minutes. If symptoms persist longer, then it is categorized as a stroke. Symptoms include temporary loss of vision (typically amaurosis fugax); difficulty speaking (aphasia); weakness on one side of the body (hemiparesis); numbness or tingling (paresthesia), usually on one side of the body, and dizziness, lack of coordination or poor balance. The symptoms of a TIA usually last a few seconds to a few minutes and most symptoms disappear within 60 minutes.

Transient neurological attacks (TNA) or transient neurological events (TNE) interchangeably refer to events involving neurological symptoms typically lasting only a few minutes or hours and no more than 24 hours. TIAs are considered focal TNAs; other events—including quickly resolving amnesia, confusion, or dizziness and fainting—are considered nonfocal TNAs.

The term "small deep infarct" or "small deep infarction" or "SDI" interchangeably refer to focal infarction of the brain due to an uncertain cause, including but not limited to, cardioembolic, atheroembolic, atherosclerotic disease of the parent artery or disease of the perforating artery.

The term "lacunar stroke" or "lacune" interchangeably refer to focal infarction of the brain due to perforating branch occlusion from microatheroma or lipohyalinosis. Implicit in this definition of lacunar stroke is that the: 1) infarction is not due to cardioembolic source; 2) infarction is not due to atherosclerotic disease of parent arteries; 3) infarction occurs in regions of the brain supplied by penetrating arteries, e.g., basal ganglia, thalamus, internal capsule, corona radiata or pons; 4) lacunar stroke is oftentimes associated with the presence of hypertension, diabetes or other vascular risk factors; and 5) infarcts tend to be smaller, generally less than 50 mm in diameter. When the cause of stroke is uncertain or likely other than perforating artery disease, then the more general term—small deep infarct—is appropriate. See, e.g., Caplan, Stroke (2003) 34(3):653-9; Norrving, Pract Neurol (2008) 8:222-228; Lastilla, Clin Exp Hypertens. (2006) 28(3-4):205-15; and Arboix and Marti-Vilalta, Expert Rev Neurother. (2009) 9(2): 179-96.

The term "intracerebral hemorrhage" and "ICH" interchangeably refer to a type of stroke caused by bleeding within the brain tissue itself. Intracerebral hemorrhage occurs when a diseased blood vessel within the brain bursts, allowing blood to leak inside the brain.

An "ischemic stroke/ICH reference expression profile" refers to the pattern of expression of a set of gene exons or splice variants or isoforms (e.g., a plurality of the exons/splice variants or isoforms of the biomarkers set forth in Tables 1A, 1B, 1C, 1D and/or 1E differentially expressed (i.e., overexpressed or underexpressed) in an individual who has suffered or is at risk of experiencing ischemia (e.g., transient cerebral ischemia, transient ischemic attacks (TIA), cerebral ischemia, cardioembolic stroke, large vessel stroke, atherothrombotic stroke, lacunar stroke), intracerebral hemorrhage (ICH) relative to the expression in a control (e.g., the expression level in an individual free of an ischemic stroke/ICH event or the expression level of a stably expressed endogenous reference biomarker). A gene exon/splice variant or isoform from Tables 1A, 1B, 1C, 1D and/or 1E that is expressed at a level that is at least about 1.2-fold, e.g., at least about 1.3-, 1.4-, 1.5-, 1.6-, 1.7-, 1.8-, 1.9-, 2.0-fold, higher than the level in a control is a gene exon/splice variant or isoform overexpressed in ischemic stroke/ICH and a gene exon/splice variant or isoform from Tables 1A, 1B, 1C, 1D and/or 1E that is expressed at a level that is at least about 1.2-fold, e.g., at least about 1.3-, 1.4-, 1.5-, 1.6-, 1.7-, 1.8-, 1.9-, 2.0-fold, lower than the level in a control is a gene isoform underexpressed in ischemic stroke/ICH. Alternately, gene exons/splice variants or isoforms that are expressed at a level that is at least about 10%, 20%, 30%, 40%, 50%, 60%, 70%, 80%, 90%, or 100% higher than the level in a control is a gene exon/splice variant or isoform overexpressed in ischemic stroke/ICH and a gene exon/splice variant or isoform that is expressed at a level that is at least about 10%, 20%, 30%, 40%, 50%, 60%, 70%, 80%, 90%, or 100% lower than the level in a control is a gene exon/splice variant or isoform underexpressed in ischemic stroke/ICH.

A "plurality" refers to two or more, for example, 2, 3, 4, 5, 6, 7, 8, 9, 10, 11, 12, 13, 14, 15, 16, 17, 18, 19, 20, 21, 22, 23, 25, 50, 55, 60, 65, 70, 75, 80, 85, 90, 95, 100, 150, 200, 250, 300, 500, 1000, 2000, 5000, or more (e.g., genes). In some embodiments, a plurality refers to concurrent determination of expression levels about 15-85, 20-60 or 40-50 genes, for example, about 15, 20, 25, 30, 35, 40, 45, 50, 55, 60, 65, 70, 75, 80, 85, 90, 95, 100, 150, 200, 250, 300, 500, 1000, 2000, 5000, or more, genes. In some embodiments, "plurality" refers to all genes listed in one or more or all tables, e.g., all genes listed in Tables 1A, 1B, 1C, 1D and/or 1E.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination of one or more markers that are characteristic of the pathology or disease.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., Science, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800,992. Arrays may be packaged in such a manner as to allow for diagnostics or other manipulation of an all-inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
 1) Alanine (A), Glycine (G);
 2) Aspartic acid (D), Glutamic acid (E);
 3) Asparagine (N), Glutamine (Q);

4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of a ischemic stroke/ICH-associated gene (e.g., a gene set forth in Tables 1A-E), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to TIA-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

DETAILED DESCRIPTION

1. Introduction

Figure 1:
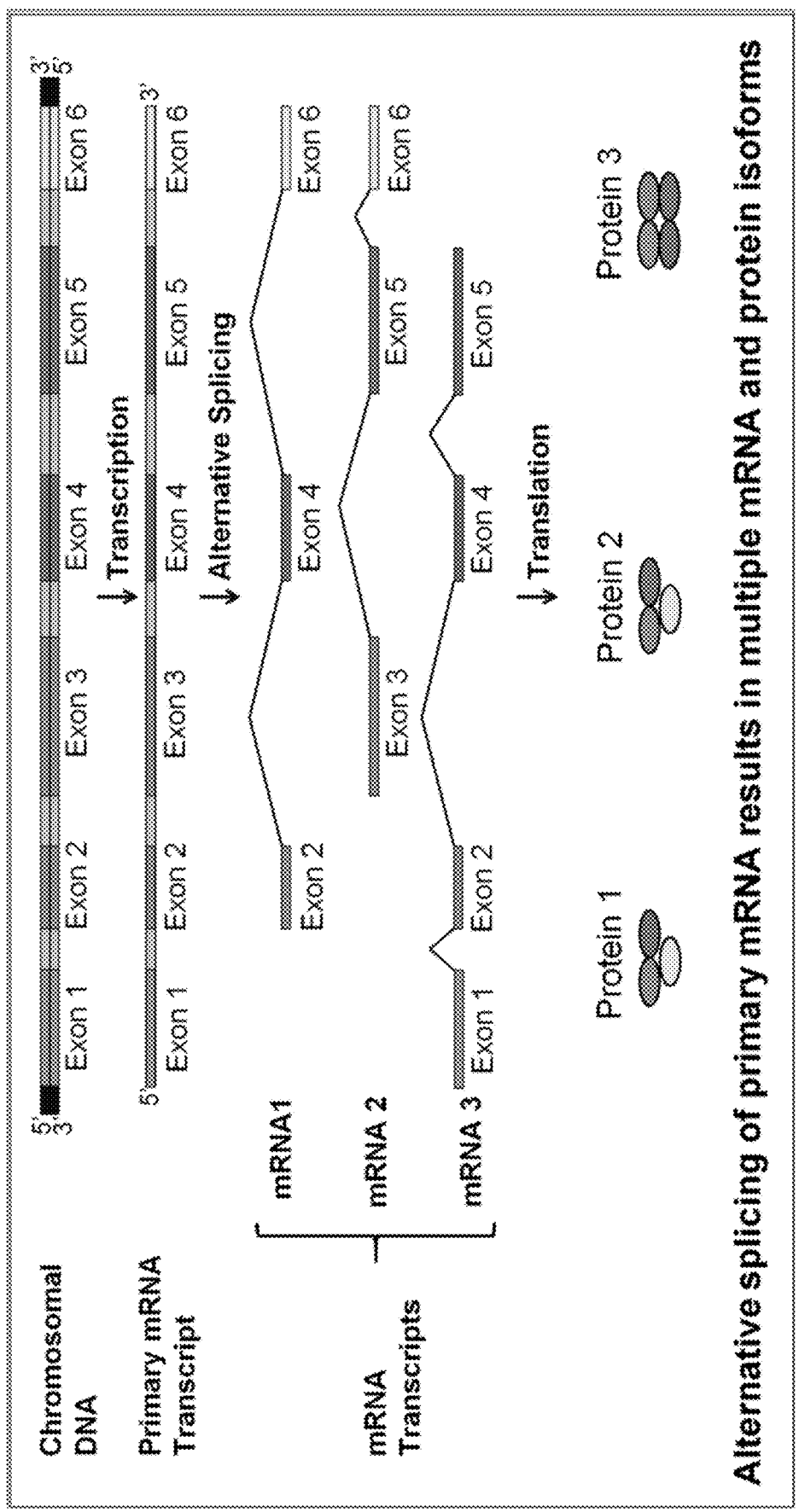
FIG. 1 illustrates a schematic of alternative splicing. The 3' and 5' untranslated regions in mRNA are not depicted.

Provided are exon or splice variant biomarkers, and methods and tools for using such biomarkers, that can distinguish in a subject suspected of having an ischemic event between no stroke, ischemic stroke (e.g., cardioembolic stroke, large vessel stroke and lacunar stroke) and intracerebral hemorrhage.

2. Subjects Who Can Benefit from the Present Methods

Individuals who will benefit from the present methods may be exhibiting symptoms of or suspected of having experienced a neurological event, ischemic or non-ischemic. In some embodiments, the subject has experienced or is suspected of having experienced an ischemic stroke or ICH. For example, the subject may have suffered, be currently experiencing or suspected of experiencing a small deep infarct (SDI), a transient ischemic attack (TIA), intracerebral hemorrhage (ICH), an ischemic stroke, a myocardial infarction, peripheral vascular disease, or venous thromboembolism. The subject may have or have been diagnosed with cerebral vascular disease or have one or more vascular risk factors (e.g., hypertension, diabetes mellitus, hyperlipidemia, or tobacco smoking).

In some embodiments, the subject has not experienced and/or is not at risk of having an intracerebral hemorrhage. In some embodiments, the subject has not experienced and/or is not at risk of having an intracerebral hemorrhage or hemorrhagic stroke. In some embodiments, the subject has been diagnosed as having not experienced and/or not at risk of having an intracerebral hemorrhage or hemorrhagic stroke.

In some embodiments, the levels of expression of the panel of biomarkers is determined within 3 hours of a suspected ischemic stroke or ICH. In some embodiments, the levels of expression of the panel of biomarkers are determined at 3 or more hours after a suspected ischemic stroke or ICH. In some embodiments, the levels of expression of the panel of biomarkers are determined within 6, 12, 18, 24, 36, 48 hours of a suspected ischemic stroke or ICH.

In some cases, the subject is asymptomatic, but may have a risk or predisposition to experiencing ischemic stroke/ICH, e.g., based on genetics, a related disease condition, environment or lifestyle. For example, in some embodiments, the patient suffers from a chronic inflammatory condition, e.g., has an autoimmune disease (e.g., rheumatoid arthritis, Crohn's disease inflammatory bowel disease), atherosclerosis, hypertension, or diabetes. In some embodiments, the patient has high LDL-cholesterol levels or suffers from a cardiovascular disease (e.g., atherosclerosis, coronary artery disease). In some embodiments, the patient has an endocrine system disorder, a neurodegenerative disorder, a connective tissue disorder, or a skeletal and muscular disorder. Exemplary disorders associated with, related to, or causative of TIA are discussed in co-pending application Ser. No. 13/182,630 and PCT/US2011/044023, which are hereby incorporated herein by reference in their entirety for all purposes. In some embodiments, the subject has an ABCD score that is 4 or greater (see, e.g., Josephson, et al., Stroke. (2008) 39(11):3096-8; Rothwell et al., Lancet (2005) 366(9479):29-36; and Johnston, et al., Lancet. (2007) 369 (9558):283-92).

In varying embodiments, the subject may be experiencing or suspected of experiencing a small deep infarct (SDI) or a lacunar stroke. Patients presenting with clinical symptoms of lacunar infarcts or diagnosed as having lacunar syndrome will also benefit from the present diagnostic gene expression profiling. Clinical symptoms of lacunar infarcts include

- pure motor hemiparesis
- pure sensory stroke
- sensorimotor stroke
- dysarthria-clumsy hand syndrome
- ataxic hemiparesis Face, arm and leg involvement are characteristic of the first three listed symptoms. A component of ataxia is also present in the last two. Patients with a lacunar syndrome typically have no aphasia, no visuospatial disturbance, no visual field defect, generally no clear disturbance of brainstem function such as pupil abnormalities and eye movement disturbances, and no decreased level of consciousness (as a direct effect rather than as a complication of the stroke) at any time after the stroke. See, Norrving, Pract Neurol (2008) 8:222-228.

3. Biomarkers Indicative of the Occurrence or Risk of Ischemic Stroke/ICH

Biomarkers useful for the prediction, diagnosis or confirmation of the occurrence of ischemic stroke (e.g., a cardioembolic stroke, a large vessel stroke, a lacunar stroke) from an intracerebral hemorrhage (ICH) are listed in Tables 1A-1E. Determination of the gene exon/splice variant or isoform expression levels of a plurality of the biomarkers of Tables 1A-1E can be performed for the prediction, diagnosis or confirmation of the occurrence of ischemic stroke (e.g., a cardioembolic stroke, a large vessel stroke, a lacunar stroke) versus an intracerebral hemorrhage in conjunction with other biomarkers known in the art for the prediction, diagnosis or confirmation of the occurrence of ischemic stroke, in conjunction with other methods known in the art for the diagnosis of ischemic stroke, in conjunction with biomarkers described herein and known in the art useful for determining the cause of ischemic stroke and/or in conjunction with methods known in the art for determining the cause of ischemic stroke. Such biomarkers are described in co-pending and co-owned U.S. Patent Publications Nos. 2015/0018234 ("BIOMARKERS FOR DIAGNOSING ISCHEMIA"); 2012/0316076 ("BIOMARKERS FOR THE DIAGNOSIS OF LACUNAR STROKE"); 2012/0065087 ("BIOMARKERS FOR DIAGNOSIS OF STROKE AND ITS CAUSES"); 2012/0015904 ("BIOMARKERS FOR DIAGNOSIS OF TRANSIENT ISCHEMIC ATTACKS"); and 2010/0197518 ("METHODS FOR DIAGNOSING ISCHEMIA"), each of which is hereby incorporated herein by reference in its entirety for all purposes.

Determination of the expression levels of a plurality of the biomarkers of Tables 1A, 1B, 1C, 1D and/or 1E can be performed for the prediction, diagnosis or confirmation of the occurrence of ischemic stroke/ICH can also be performed independently, e.g., to diagnose whether ischemic stroke and/or ICH has occurred, to distinguish between ischemic stroke and ICH, or to determine the risk that a patient may suffer an ischemic stroke and/or ICH.

As appropriate, the expression levels of at least about 3, 5, 10, 15, 20, 25, 30, 40, 50, 60, 70, 80, 90, 100 or more biomarkers (e.g., gene exons/splice variants or isoforms) from Tables 1A, 1B, 1C, 1D and/or 1E are determined. In some embodiments, the expression levels of a plurality of biomarkers in Tables 1A, 1B, 1C, 1D and/or 1E are determined. In some embodiments, the expression levels of all listed biomarkers in Tables 1A, 1B, 1C, 1D and/or 1E are determined.

In some embodiments, the level of expression of biomarkers indicative of the occurrence of ischemic stroke/ICH is determined within 72 hours, for example, within 60, 48, 36, 24, 12, 6 or 3 hours of a suspected ischemic stroke or ICH.

In various embodiments, an increased expression level of one or more (e.g., 1, 2, 3, 4, 5, 6, 7, 8, 9, 10, 11, 12, 13, 14, 15, 16, 17, 18, 19, 20, 21, 22, 23, or all, ischemic stroke-associated biomarkers of Table 1A indicates that the subject has or is likely to have experienced, is or is likely to be experiencing cardioembolic ischemic stroke:

TABLE 1A

Exon Usage Upregulated in Cardioembolic Ischemic Stroke (CE IS)

| Marker ID | Gene Symbol |
|---|---|
| chr17.73000302-73002235>CDR2L | CDR2L |
| chr8.104406853-104407321>shuskeebu | shuskeebu |
| chr3.48456585-48456758>PLXNB1 | PLXNB1 |
| chr1.86861716-86861980>ODF2L | ODF2L |
| chr19.58427747-58427961>ZNF417andZNF814 | ZNF417 and ZNF814 |
| chr19.58427747-58427962>ZNF417andZNF814 | ZNF417 and ZNF814 |
| chr22.19115606-19115964>skatee | Skate |
| chr10.49253461-49254185>BMS1P7 | BMS1P7 |
| chr14.70242552-70243107>SLC10A1 | SLC10A1 |
| chr7.142630429-142630907>TRPV5 | TRPV5 |
| chr10.38299602-38299713>ZNF33A | ZNF33A |
| chr10.38299604-38299713>ZNF33A | ZNF33A |
| chr2.119988299-119988612>STEAP3 | STEAP3 |
| chr2.179463448-179463833>CCDC141andTTN | CCDC141 and TTN |
| chr2.25258142-25260100>LOC729723 | LOC729723 |
| chr17.34856670-34856801>MYO19 | MYO19 |
| chr7.158334118-158334470>PTPRN2 | PTPRN2 |
| chr3.188326949-188327341>LPP | LPP |
| chr19.18959976-18960257>UPF1 | UPF1 |
| chr6.37225553-37225751>TBC1D22B | TBC1D22B |
| chr20.43995515-43996066>SYS1-DBNDD2 | SYS1-DBNDD2 |
| chr3.49448633-49449168>myforbo | myforbo |
| chr4.15570247-15570815>klawgu | klawgu |

In various embodiments, an increased expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or all, ischemic stroke-associated biomarkers of Table 1B indicates that the subject has or is likely to have experienced, is or is likely to be experiencing large vessel or atherothrombotic stroke:

TABLE 1B

Exon Usage Upregulated in Large Vessel Ischemic Stroke (LV IS)

| Marker ID | Gene Symbol |
|---|---|
| chr6.37225553-37225751>TBC1D22B | TBC1D22B |
| chr20.43995515-43996066>SYS1-DBNDD2 | SYS1-DBNDD2 |

TABLE 1B-continued

Exon Usage Upregulated in Large Vessel Ischemic Stroke (LV IS)

| Marker ID | Gene Symbol |
|---|---|
| chr3.49448633-49449168>myforbo | Myforbo |
| chr4.15570247-15570815>klawgu | Klawgu |
| chr14.53248502-53248631>GNPNAT1 | GNPNAT1 |
| chr22.29141852-29141991>HSCB | HSCB |
| chr16.72146312-72146551>DHX38 | DHX38 |
| chr5.176715528-176715928>NSD1 | NSD1 |
| chr6.100023529-100023949>RPS3P5 | RPS3P5 |
| chr13.103506107-103506224>BIVMandERCC5 | BIVM and ERCC5 |
| chr7.2282560-2282685>NUDT1 | NUDT1 |
| chr12.54645834-54646013>CBX5 | CBX5 |
| chr20.33056659-33057238>vytaw | Vytaw |
| chr5.162902464-162902680>HMMR | HMMR |
| chr11.62389338-62389650>B3GAT3 | B3GAT3 |
| chr15.101847418-101849510>PCSK6 | PCSK6 |
| chr5.61688639-61688819>DIMT1L | DIMT1L |
| chr12.56334947-56335111>DGKA | DGKA |
| chr10.46918169-46918364>FAM35BandRHEBP1 | FAM35B and RHEBP1 |
| chr2.20756227-20757430>dawgorbu | Dawgorbu |
| chrX.152226503-152227130>PNMA3 | PNMA3 |
| chr22.18613610-18614500>PEX26andTUBA8 | PEX26 and TUBA8 |
| chr6.111619174-111619775>slyjey | Slyjey |
| chr17.43002077-43003869>KIF186 | KIF186 |
| chr8.90798887-90799403>RIPK2 | RIPK2 |
| chr1.214836934-214837428>CENPF | CENPF |
| chr3.8606070-8609807>LMCD1 | LMCD1 |
| chr20.52560545-52561537>BCAS1 | BCAS1 |
| chr2.173420100-173420449>PDK1 | PDK1 |
| chr15.81584265-81585380>IL16 | IL16 |
| chr9.131486273-131486411>ZDHHC12 | ZDHHC12 |
| chr16.4475881-4476095>DNAJA3 | DNAJA3 |

In various embodiments, an increased expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or all, ischemic stroke-associated biomarkers of Table 1C indicates that the subject has or is likely to have experienced, is or is likely to be experiencing lacunar stroke:

TABLE 1C

Exon Usage Upregulated in Lacunar IS

| Marker ID | Gene Symbol |
|---|---|
| chr11.119039480-119040013>NLRX1 | NLRX1 |
| chr15.52970203-52970321>KIAA1370 | KIAA1370 |
| chr11.62475067-62475389>GNG3 | GNG3 |
| chr12.94914730-94915696>LOC400061 | LOC400061 |
| chr16.15013757-15013942>zoner | Zoner |
| chr2.29258330-29258512>FAM179A | FAM179A |
| chr18.33077683-33077897>IN080C | IN080C |
| chr2.160143094-160143419>WDSUB1 | WDSUB1 |
| chr22.44514918-44515022>PARVB | PARVB |
| chr5.156821041-156822689>ADAM19 | ADAM19 |
| chr6.146285293-146285561>SHPRH | SHPRH |
| chr6.146285293-146285527>SHPRH | SHPRH |
| chr22.24316496-24316681>GSTTP1andDDT | GSTTP1 and DDT |
| chr12.2966630-2968831>FOXM1 | FOXM1 |
| chr7.99674926-99675058>ZNF3 | ZNF3 |
| chr6.30610545-30612434>C6orf134 | C6orf134 |
| chr19.35173682-35173956>ZNF302 | ZNF302 |
| chr21.47706315-47706714>C21orf57 | C21orf57 |
| chr12.111065735-111066031>TCTN1 | TCTN1 |
| chrX.40495835-40495966>CXorf38 | CXorf38 |
| chr9.46687439-46688199>KGFLP1 | KGFLP1 |
| chr2.101627502-101628004>TBC1D8 | TBC1D8 |
| chr1.160580214-160580590>SLAMF1 | SLAMF1 |
| chr8.10340434-10340743>LOC346702 | LOC346702 |
| chr6.168370462-168372590>MLLT4 | MLLT4 |
| chr1.155691308-155691473>DAP3 | DAP3 |
| chr12.123262038-123262232>CCDC62 | CCDC62 |
| chr14.96795821-96795973>ATG2B | ATG2B |
| chr20.32079185-32079984>spawvor | spawvor |

TABLE 1C-continued

Exon Usage Upregulated in Lacunar IS

| Marker ID | Gene Symbol |
|---|---|
| chr6.163984476-163984753>QKI | QKI |
| chr1.246729640-246730093>CNST | CNST |

In various embodiments, an increased expression level of one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 50, 75, 100, 125, 150, 175, 200, or all, ICH-associated biomarkers of Table 1D indicates that the subject has or is likely to have experienced, is or is likely to be experiencing intracerebral hemorrhage:

TABLE 1D

Exon Usage Upregulated in Intracerebral Hemorrhage (ICH)

| Marker ID | Gene Symbol |
|---|---|
| chr19.44128266-44128396>CADM4 | CADM4 |
| chr5.139929370-139930498>APBB3andSRA1 | APBB3 and SRA1 |
| chr1.85127881-85128060>SSX21P | SSX21P |
| chr22.31733654-31734033>sneypoy | sneypoy |
| chr17.40280569-40280820>RAB5C | RAB5C |
| chr3.23929058-23929282>UBE2E1 | UBE2E1 |
| chr7.149598-152549>kehera | kehera |
| chr3.122283274-122283462>DTX3L | DTX3L |
| chr14.76107075-76107405>FLVCR2andTTLL5andC14orf179 | FLVCR2 and TTLL5 and C14orf179 |
| chr1.235956803-235956914>LYST | LYST |
| chr2.198175302-198175505>ANKRD44 | ANKRD44 |
| chr22.20093700-20093802>DGCR8 | DGCR8 |
| chr1.112991564-112991796>CTTNBP2NL | CTTNBP2NL |
| chr1.19470474-19470587>UBR4 | UBR4 |
| chr5.134343647-134343831>PCBD2andCATSPER3 | PCBD2 and CATSPER3 |
| chr19.49314066-49314180>BCAT2 | BCAT2 |
| chr2.118864235-118864481>INSIG2 | INSIG2 |
| chr18.48443613-48443880>ME2 | ME2 |
| chr22.45254869-45255778>PRR5-ARHGAP8 | PRR5-ARHGAP8 |
| chr1.27431807-27432580>SLC9A1 | SLC9A1 |
| chr8.133984843-133984988>TG | TG |
| chr6.41751200-41751978>PRICKLE4andTOMM6 | PRICKLE4 and TOMM6 |
| chr17.57728564-57728679>CLTC | CLTC |
| chr3.150280329-150280449>EIF2A | EIF2A |
| chr2.242282407-242282510>SEPT2 | SEPT2 |
| chr21.40619627-40619760>BRWD1 | BRWD1 |
| chr1.26799700-26800020>HMGN2 | HMGN2 |
| chr5.140895496-140896577>DIAPH1 | DIAPH1 |
| chr5.140895875-140896577>DIAPH1 | DIAPH1 |
| chr1.180049625-180049798>CEP350 | CEP350 |
| chr1.180049652-180049798>CEP350 | CEP350 |
| chr5.70531277-70532283>goychyby | goychyby |
| chr13.100543572-100543868>CLYBL | CLYBL |
| chr19.36515246-36515536>CLIP3 | CLIP3 |
| chr6.144289727-144290117>PLAGL1andHYMAI | PLAGL1 and HYMAI |
| chr21.47608408-47608857>klorley | klorley |
| chr9.17135038-17135425>CNTLN | CNTLN |
| chr1.114499947-114500542>wawleybo | wawleybo |
| chr17.18486655-18486839>CCDC1446 | CCDC1446 |
| chr4.40800804-40800923>NSUN7 | NSUN7 |
| chr3.39162488-39162682>TTC21A | TTC21A |
| chr1.161196029-161196396>TOMM40L | TOMM40L |
| chr7.45083306-45083699>CCM2 | CCM2 |
| chr19.13009896-13010201>SYCE2 | SYCE2 |
| chr3.20019802-20020398>RAB5A | RAB5A |
| chr6.122792844-122793052>SERINC1 | SERINC1 |
| chr2.231663444-231663881>CAB39 | CAB39 |
| chr1.145790974-145791172>GPR89A | GPR89A |
| chr4.175223190-175223339>KIAA1712 | KIAA1712 |
| chr2.182339687-182340017>ITGA4 | ITGA4 |
| chr16.18799866-18800442>ARL6IP1andRPS15A | ARL6IP1 and RPS15A |
| chr6.3021094-3022354>teyvybo | teyvybo |
| chr16.22277711-22277847>EEF2K | EEF2K |
| chr11.7479027-7479176>veemee | veemee |
| chrX.77303661-77305894>ATP7A | ATP7A |
| chr1.78207302-78207435>USP33 | USP33 |
| chrX.76776266-76776396>ATRX | ATRX |
| chr12.6761437-6761586>ING4 | ING4 |
| chr17.77079383-77079674>ENGASE | ENGASE |
| chr11.111889680-111893376>DIXDC1 | DIXDC1 |
| chr11.111889680-111893312>DIXDC1 | DIXDC1 |
| chr4.157731989-157732171>PDGFC | PDGFC |
| chr20.18449588-18449707>POLR3F | POLR3F |
| chr11.47738539-47739066>FNBP4 | FNBP4 |

TABLE 1D-continued

Exon Usage Upregulated in Intracerebral Hemorrhage (ICH)

| Marker ID | Gene Symbol |
| --- | --- |
| chr16.30593851-30595168>syrar | syrar |
| chr13.41593364-41593570>ELF1 | ELF1 |
| chr22.51221467-51221716>RABL2B | RABL2B |
| chr9.33264164-33264495>CHMP5 | CHMP5 |
| chr1.154928545-154928782>SHC1andPYGO2andPBXIP1 | SHC1 and PYGO2 and PBXIP1 |
| chr19.1953385-1953507>C19orf34 | C19orf34 |
| chr2.113175261-113175493>RGPD8 | RGPD8 |
| chr1.145509166-145509614>RBM8A.1 | RBM8A.1 |
| chr1.89271574-89271702>PKN2 | PKN2 |
| chr10.99433338-99433904>DHDPSLandPI4K2A | DHDPSL and PI4K2A |
| chr7.74166365-74166899>GTF2I | GTF2I |
| chr18.54318248-54318826>TXNL1 | TXNL1 |
| chr12.58345541-58345680>XRCC6BP1 | XRCC6BP1 |
| chr7.76870183-76870366>CCDC146 | CCDC146 |
| chr3.52385978-52386121>DNAH1 | DNAH1 |
| chr12.96258857-96259168>SNRPF | SNRPF |
| chr1.63269390-63269535>ATG4C | ATG4C |
| chr2.172848099-172848601>HAT1 | HAT1 |
| chr18.67508480-67516325>DOK6 | DOK6 |
| chr8.30948350-30948460>WRN | WRN |
| chr2.208446079-208446886>FAM119A | FAM119A |
| chr7.5938415-5938552>CCZ1 | CCZ1 |
| chr19.44619641-44619997>ZNF225 | ZNF225 |
| chr1.243652316-243652444>SDCCAG8 | SDCCAG8 |
| chr4.122723829-122723985>EXOSC9 | EXOSC9 |
| chr4.122723829-122723950>EXOSC9 | EXOSC9 |
| chr1.46805848-46806593>NSUN4andFAAH | NSUN4 and FAAH |
| chr10.51592090-51592621>LOC100287554 | LOC100287554 |
| chrX.138864706-138864889>ATP11C | ATP11C |
| chr14.50246313-50246526>KLHDC2 | KLHDC2 |
| chr7.22980878-22987336>FAM126A | FAM126A |
| chr1.150778337-150778494>CTSK | CTSK |
| chr12.48094974-48095389>RPAP3 | RPAP3 |
| chr15.38619054-38620018>koyzawbu | koyzawbu |
| chr11.836251-836527>CD151 | CD151 |
| chr17.27581220-27581515>CRYBA1 | CRYBA1 |
| chr14.105236090-105236709>AKT1 | AKT1 |
| chr10.69828759-69829526>HERC4 | HERC4 |
| chr22.50320903-50321183>CRELD2 | CRELD2 |
| chr12.10561988-10562185>KLRC4andKLRK1 | KLRC4 and KLRK1 |
| chr8.104455023-104455430>DCAF13 | DCAF13 |
| chr12.40441853-40442014>SLC2A13 | SLC2A13 |
| chrX.16870674-16871151>RBBP7 | RBBP7 |
| chr12.54789679-54790162>ITGA5 | ITGA5 |
| chr1.150939858-150940192>LASS2 | LASS2 |
| chr13.113864293-113864814>PCID2 | PCID2 |
| chr15.80191177-80191469>ST20andMTHFS | ST20 and MTHFS |
| chr5.145493406-145493876>LARS | LARS |
| chr16.3493611-3493839>ZNF174andNAT15andCLUAP1 | ZNF174 and NAT15 and CLUAP1 |
| chr6.79664949-79665571>PHIPandTRNAF13P | PHIP and TRNAF13P |
| chr17.62745780-62746128>LOC146880 | LOC146880 |
| chr17.61473104-61473291>TANC2 | TANC2 |
| chr15.59102429-59102589>FAM63B | FAM63B |
| chr10.11272033-11272458>CELF2 | CELF2 |
| chr20.34487292-34487563>PHF20 | PHF20 |
| chr8.74558684-74559057>TCEB1 | TCEB1 |
| chr2.17953901-17954053>GEN1 | GEN1 |
| chr14.88431849-88431975>GALC | GALC |
| chr19.1877203-1877426>FAM108A1 | FAM108A1 |
| chr17.18087711-18088069>jeeroy | jeeroy |
| chr1.168262382-168262518>SFT2D2andTBX19 | SFT2D2 and TBX19 |
| chr6.158088239-158089559>fyjaw | fyjaw |
| chr15.30711214-30711350>rukaru | rukaru |
| chr8.24256387-24256555>ADAMDEC1 | ADAMDEC1 |
| chr15.57545460-57545668>stoyguby | stoyguby |
| chr10.75230828-75230969>PPP3CB | PPP3CB |
| chr20.43808628-43808777>rotora | rotora |
| chr1.46467098-46468409>MAST2 | MAST2 |
| chr7.2635311-2636064>dochuby | dochuby |
| chr19.11411543-11411914>tojaw | tojaw |
| chrX.153744234-153744568>FAM3A | FAM3A |
| chr2.73957016-73957158>TPRKB | TPRKB |
| chr2.234112772-234113221>INPP5D | INPP5D |
| chr6.41036580-41036694>C6orf130andUNC5CL | C6orf130 and UNC5CL |
| chr15.75165540-75165690>SCAMP2 | SCAMP2 |
| chrX.74282163-74282419>ABCB7 | ABCB7 |

TABLE 1D-continued

Exon Usage Upregulated in Intracerebral Hemorrhage (ICH)

| Marker ID | Gene Symbol |
| --- | --- |
| chr2.88336462-88336572>KRCC1 | KRCC1 |
| chrX.2839944-2840067>ARSD | ARSD |
| chr11.89933252-89935721>CHORDC1 | CHORDC1 |
| chr8.62438536-62438673>ASPH | ASPH |
| chr3.69028819-69028940>C3orf64 | C3orf64 |
| chr5.35053745-35054336>fugey | Fugey |
| chr9.35737655-35737938>GBA2 | GBA2 |
| chr15.94774950-94775236>MCTP2 | MCTP2 |
| chr3.52561845-52561949>NT5DC2 | NT5DC2 |
| chr1.85039599-85040105>CTBSandGNG5 | CTBS and GNG5 |
| chr10.99195666-99196310>EXOSC1 | EXOSC1 |
| chr20.23401942-23402099>NAPB | NAPB |
| chr17.36351796-36351998>TBC1D3 | TBC1D3 |
| chrX.118985730-118985838>UPF3B | UPF3B |
| chr15.66811217-66811418>ZWILCH | ZWILCH |
| chr15.66811217-66811469>ZWILCH | ZWILCH |
| chr11.125490667-125490903>STT3AandCHEK1 | STT3A and CHEK1 |
| chr3.15778540-15778742>ANKRD28 | ANKRD28 |
| chr19.9720432-9722014>ZNF562andZNF561 | ZNF562 and ZNF561 |
| chr3.167452594-167452719>PDCD10 | PDCD10 |
| chr1.10509776-10510381>APITD1andCORT | APITD1 and CORT |
| chr6.34360041-34360262>RPS10andNUDT3 | RPS10 and NUDT3 |
| chr19.52207575-52207735>NCRNA00085 | NCRNA00085 |
| chr11.62105383-62105786>saroro | Saroro |
| chr1.17056-17744>WASH7P | WASH7P |
| chr1.45987501-45987611>PRDX1 | PRDX1 |
| chr1.243419358-243419544>SDCCAG8 | SDCCAG8 |
| chr2.111302237-111302385>RGPD6 | RGPD6 |
| chr2.110584278-110584426>RGPD5 | RGPD5 |
| chr6.109248281-109249438>ARMC2 | ARMC2 |
| chr14.96997812-96999042>PAPOLA | PAPOLA |
| chr19.58423428-58423556>ZNF417andZNF814 | ZNF417 and ZNF814 |
| chr19.58423428-58423559>ZNF417andZNF814 | ZNF417 and ZNF814 |
| chrX.149924161-149924398>MTMR1 | MTMR1 |
| chr19.5208248-5208404>PTPRS | PTPRS |
| chr14.20872770-20872933>TEP1 | TEP1 |
| chr20.416929-419487>TBC1D20 | TBC1D20 |
| chr15.59943710-59944527>GTF2A2 | GTF2A2 |
| chrX.15862547-15863641>AP1S2 | AP1S2 |
| chr15.64017491-64017714>HERC1 | HERC1 |
| chr5.77656415-77656554>SCAMP1 | SCAMP1 |
| chr19.47646729-47646864>SAE1 | SAE1 |
| chr19.47646751-47646864>SAE1 | SAE1 |
| chr3.81552424-81552867>chordybo | chordybo |
| chr1.201780731-201780887>NAV1 | NAV1 |
| chr11.61129205-61129722>CYBASC3 | CYBASC3 |
| chr11.6523983-6524158>FXC1andDNHD1 | FXC1 and DNHD1 |
| chr19.8441789-8441953>lyta | Lyta |
| chr6.153291674-153292551>FBXO5 | FBXO5 |
| chr6.153291660-153292551>FBXO5 | FBXO5 |
| chr6.153291654-153292551>FBXO5 | FBXO5 |
| chr7.29549802-29552167>klerky | Klerky |
| chr22.41175013-41175131>SLC25A17 | SLC25A17 |
| chr4.76874494-76874940>sporsmorby | sporsmorby |
| chr5.39274505-39274632>FYB | FYB |
| chr10.32324818-32324924>KIF5B | KIF5B |
| chr14.52957557-52957725>TXNDC16 | TXNDC16 |
| chr14.88452833-88452948>GALC | GALC |
| chr20.30720816-30720931>TM9SF4 | TM9SF4 |
| chr19.54610118-54610268>NDUFA3 | NDUFA3 |
| chr10.92500578-92502287>HTR7 | HTR7 |
| chr3.25637911-25639425>RARB | RARB |
| chr5.14381239-14381363>TRIO | TRIO |
| chr2.243168539-243168821>samemo | samemo |
| chr3.137963865-137964525>vusmyby | vusmyby |
| chr3.137963930-137964525>ARMC8 | ARMC8 |
| chr3.137963930-137964526>ARMC8 | ARMC8 |
| chr14.100743755-100744115>YY1 | YY1 |

In varying embodiments, the increased expression level of the gene exon or isoform is at least about 1.2-, e.g., at least about 1.3-, 1.4-, 1.5-, 1.6-, 1.7-, 1.8-, 1.9-, 2.0-fold higher than the expression level in a control.

The overexpression or the underexpression of the biomarkers are determined with reference to a control level of expression. The control level of expression can be determined using any method known in the art. For example, the control level of expression can be from a population of individuals known to not have or be at risk for ischemic stroke or ICH or can be determined with reference to a panel of stably expressed reference biomarkers. Also, threshold levels of expression can be determined based on levels of expression in predetermined populations (e.g., known to not have or be at risk for an ischemic stroke or ICH versus known to have or be at risk for ischemic stroke/ICH). Overexpression or underexpression of a plurality of biomarkers from Tables 1A, 1B, 1C and/or 1D that is at least about 1.2-fold, e.g., at least about 1.3-fold, 1.4-fold, 1.5-fold, 1.6-fold, 1.7-fold, 1.8-fold, 1.9-fold, 2.0-fold, or more, in comparison to the expression levels of a plurality of stably expressed endogenous reference biomarkers, e.g., as described herein or known in the art, is correlative with or indicates that the subject has experienced or is at risk of experiencing an ischemic stroke/ICH. Overexpression or underexpression of a plurality of biomarkers from Tables 1A, 1B, 1C and/or 1D that is at least about 1.2-fold, e.g., 1.3-fold, 1.4-fold, 1.5-fold, 1.6-fold, 1.7-fold, 1.8-fold, 1.9-fold, 2.0-fold, or more, in comparison to the expression level of the same biomarker in an individual or a population of individuals who have not experienced a vascular event is correlative with or indicates that the subject has experienced or is at risk of experiencing an ischemic stroke/ICH.

Biomarkers useful for the determination and diagnosis of the cause of stroke are described, e.g., in co-owned and co-pending U.S. Patent Publications Nos. 2015/0018234 ("BIOMARKERS FOR DIAGNOSING ISCHEMIA"); 2012/0316076 ("BIOMARKERS FOR THE DIAGNOSIS OF LACUNAR STROKE"); 2012/0065087 ("BIOMARKERS FOR DIAGNOSIS OF STROKE AND ITS CAUSES"); 2012/0015904 ("BIOMARKERS FOR DIAGNOSIS OF TRANSIENT ISCHEMIC ATTACKS"); and 2010/0197518 ("METHODS FOR DIAGNOSING ISCHEMIA"), each of which is hereby incorporated herein by reference in its entirety for all purposes. In addition to evaluating the expression levels of a plurality of ischemic stroke/ICH biomarkers of differential gene exon/splice variant/isoform usages, the expression levels of a plurality of biomarkers can be measured to determine whether a suspected or predicted ischemic stroke is cardioembolic, atherosclerotic or lacunar. Furthermore, the expression levels of a plurality of biomarkers can be measured to determine if the cause of stroke is due to carotid stenosis, atrial fibrillation, lacunar stroke or transient ischemic attacks. Classification of stroke subtypes is known in the art and reviewed in, e.g., in Amarenco, et al., *Cerebrovasc Dis* (2009) 27:493-501. Accordingly, in some embodiments, the expression levels of at least about 3, 5, 10, 15, 20, 25, 30, 40, 50, 60, 70, 80, 85, 100, 200, 500, 1000 or more, ischemic stroke-associated biomarkers are independently determined. In some embodiments, the expression levels of all ischemic stroke-associated biomarkers in a panel are determined.

In various embodiments, the expression levels of a plurality of ischemic stroke-associated exon/splice variant biomarkers are co-determined together with the expression levels of a plurality of genes useful in the determination of whether a patient has experienced or has a predisposition to experience cardioembolic stroke (a.k.a., cardiac embolism, cardioembolism emboligenic heart disease). A cardioembolic stroke occurs when a thrombus (clot) dislodges from the heart, travels through the cardiovascular system and lodges in the brain, first cutting off the blood supply and then often causing a hemorrhagic bleed. In some embodiments an increased expression level of one or more ischemic stroke-associated biomarkers selected from the group consisting of IRF6 (NM_006147), ZNF254 (NM_203282), GRM5 (NM_000842///NM_001143831), EXT2 (NM_000401///NM_207122), AP3S2 (NM_005829///NR_023361), PIK3C2B (NM_002646), ARHGEFS (NM_005435), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), PTPN20A///PTPN20B (NM_001042357///NM_001042358///NM_001042359///NM_001042360///NM_001042361///NM_001042362///NM_001042363///NM_001042364///NM_001042365///NM_001042387///NM_001042389///NM_001042390///NM_001042391///NM_001042392///NM_001042393///NM_001042394///NM_001042395///NM_001042396///NM_001042397///NM_015605), LHFP (NM_005780), BANK1 (NM_001083907///NM_001127507///NM_017935), HLA-DOA (NM_002119), EBF1 (NM_024007), TMEM19 (NM_018279), LHFP (NM_005780), FCRL1 (NM_001159397///NM_001159398///NM_052938), OOEP (NM_001080507) and LRRC37A3 (NM_199340) is correlative with or indicates that the patient has experienced or is at risk for cardioembolic stroke. In some embodiments, a decreased expression level of one or more ischemic stroke-associated biomarkers selected from the group consisting of LOC284751 (NM_001025463), CD46 (NM_002389///NM_153826///NM_172350///NM_172351///NM_172352///NM_172353///NM_172354///NM_172355///NM_172356///NM_172357///NM_172358///NM_172359///NM_172360///NM_172361), ENPP2 (NM_001040092///NM_001130863///NM_006209), C19orf28 (NM_001042680///NM_021731///NM_174983), TSKS (NM_021733), CHURC1 (NM_145165), ADAMTSL4 (NM_019032///NM_025008), FLJ40125 (NM_001080401), CLEC18A (NM_001136214///NM_182619), ARHGEF12 (NM_015313), C16orf68 (NM_024109), TFDP1 (NM_007111///NR_026580) and GSTK1 (NM_001143679///NM_001143680///NM_001143681///NM_015917) is correlative with or indicates that the patient has experienced or is at risk for cardioembolic stroke.

In various embodiments, the expression levels of a plurality of ischemic stroke-associated exon/splice variant biomarkers are co-determined together with the expression levels of a plurality of genes useful in the determination of whether a patient has experienced or has a predisposition to experience carotid stenosis. Carotid stenosis is a narrowing or constriction of the inner surface (lumen) of the carotid artery, usually caused by atherosclerosis. An inflammatory buildup of plaque can narrow the carotid artery and can be a source of embolization. Emboli break off from the plaque and travel through the circulation to blood vessels in the brain, causing ischemia that can either be temporary (e.g., a transient ischemic attack), or permanent resulting in a thromboembolic stroke (a.k.a., atherothrombosis, large-artery atherosclerosis, atherosclerosis with stenosis). In some embodiments, an increased expression level of one or more ischemic stroke-associated biomarkers selected from the group consisting of NT5E (NM_002526), CLASP2 (NM_015097), GRM5 (NM_000842///NM_001143831), PROCR (NM_006404), ARHGEF5 (NM_005435), AKR1C3 (NM_003739), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), LHFP (NM_005780), RNF7 (NM_014245///NM_183237), CYTH3 (NM_004227), EBF1 (NM_024007), RANBP10 (NM_020850), PRSS35 (NM_153362), C12orf42 (NM_001099336///NM_198521) and LOC100127980 (XM_001720119///XM_001722650) is correlative with or indicates that the patient has experienced or is at risk for carotid stenosis. In some embodiments, a decreased expression level of one or more ischemic stroke-associated biomarkers selected from the group consisting of FLJ31945 (XM_001714983///XM_001716811///XM_001718431), LOC284751 (NM_001025463), LOC100271832 (NR_027097), MTBP (NM_022045), ICAM4 (NM_001039132///NM_001544///NM_022377), SHOX2 (NM_001163678///NM_003030///NM_006884), DOPEY2 (NM_005128), CMBL (NM_138809), LOC146880 (NR_026899///NR_027487), SLC20A1 (NM_005415), SLC6A19 (NM_001003841), ARHGEF12 (NM_015313), C16orf68 (NM_024109), GIPC2 (NM_017655) and LOC100144603 (NR_021492) is correlative with or indicates that the patient has experienced or is at risk for carotid stenosis.

In various embodiments, the expression levels of a plurality of ischemic stroke-associated exon/splice variant biomarkers are co-determined together with the expression levels of a plurality of genes useful in the determination of whether a patient has experienced or has a predisposition to experience atrial fibrillation. Atrial fibrillation (AF or A-fib) is the most common cardiac arrhythmia and involves the two upper chambers (atria) of the heart fibrillating (i.e., quivering) instead of a coordinated contraction. In some instances, cardioembolic stroke can occur as a result of atrial fibrillation. Cardioembolic stroke can be a downstream result of atrial fibrillation in that stagnant blood in the fibrillating atrium can form a thrombus that then embolises to the cerebral circulation, blocking arterial blood flow and causing ischaemic injury. In some embodiments, an increased expression level of one or more ischemic stroke-associated biomarkers selected from the group consisting of SMC1A (NM_006306), SNORA68 (NR_000012), GRLF1 (NM_004491), SDC4 (NM_002999), HIPK2 (NM_001113239///NM_022740///XM_001716827///XM_925800), LOC100129034 (NR_027406///XR_079577), CMTM1 (NM_052999///NM_181268///NM_181269///NM_181270///NM_181271///NM_181272///NM_181283///NM_181296) and TTC7A (NM_020458) is correlative with or indicates that the patient has experienced or is at risk for atrial fibrillation. In some embodiments, a decreased expression level of one or more ischemic stroke-associated biomarkers selected from the group consisting of LRRC43 (NM_001098519///NM_152759), MIF///SLC2A11 (NM_001024938///NM_001024939///NM_002415///NM_030807), PER3 (NM_016831), PPIE (NM_006112///NM_203456///NM_203457), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), DUSP16 (NM_030640), BRUNOL6 (NM_052840), GPR176 (NM_007223), C6orf164 (NR_026784) and MAP3K7IP1 (NM_006116///NM_153497) is correlative with or indicates that the patient has experienced or is at risk for atrial fibrillation.

In various embodiments, the expression levels of a plurality of ischemic stroke-associated exon/splice variant biomarkers are co-determined together with the expression levels of a plurality of genes useful in the determination of whether a patient has experienced or has a predisposition to experience transient ischemic attacks (TIA). A transient ischemic attack is a change in the blood supply to a particular area of the brain, resulting in brief neurologic dysfunction that persists, by definition, for less than 24 hours. If symptoms persist longer, then it is categorized as a stroke. In some embodiments, an increased expression level of one or more TIA-associated biomarkers selected from the group consisting of GABRB2 (NM_000813///NM_021911), ELAVL3 (NM_001420///NM_032281), COL1A1 (NM_000088), SHOX2 (NM_003030///NM_006884), TWIST1 (NM_000474), DPPA4 (NM_018189), DKFZP434P211 (NR_003714), WIT1 (NM_015855///NR_023920), SOX9 (NM_000346), DLX6 (NM_005222), ANXA3 (NM_005139), EPHA3 (NM_005233///NM_182644), SOX11 (NM_003108), SLC26A8 (NM_052961///NM_138718), CCRL1 (NM_016557///NM_178445), FREM2 (NM_207361), STOX2 (NM_020225), ZNF479 (NM_033273///XM_001714591///XM_001719979), LOC338862 (NR_038878.1), ASTN2 (NM_014010///NM_198186///NM_198187///NM_198188), FOLH1 (NM_001014986///NM_004476), SNX31 (NM_152628), KREMEN1 (NM_001039570///NM_001039571), ALS2CR11 (NM_152525), FIGN (NM_018086), RORB (NM_006914), LOC732096 (XM_001720784///XM_001725388///XR_016064), GYPA (NM_002099), ALPL (NM_000478///NM_001127501), LHX2 (NM_004789), GALNT5 (NM_014568), SRD5A2L2 (NM_001010874), GALNT14 (NM_024572), OVOL2 (NM_021220), BMPR1B (NM_001203), UNC5B (NM_170744), ODZ2 (NM_001080428///NM_001122679), RASAL2 (NM_004841///NM_170692), SHOX (NM_000451///NM_006883), C19orf59 (NM_174918), ZNF114 (NM_153608), SRGAP1 (NM_020762), ELAVL2 (NM_004432), NCRNA00032 (XM_376821///XM_938938), LOC440345 (XR_015786), FLJ30375 (XM_001724993///XM_001725199///XM_001725628), TFPI (NM_001032281///NM_006287), PTGR1 (NM_012212), ROBO1 (NM_002941///NM_133631), NR2F2 (NM_021005), GRM5 (NM_000842///NM_001143831), LUM (NM_002345), FLJ39051 (NR_033839.1), COL1A2 (NM_000089), CASP5 (NM_001136109///NM_001136110///NM_001136111///NM_001136112///NM_004347//), OPCML (NM_001012393///NM_002545), TTC6 (NM_001007795), TFAP2B (NM_003221), CRISP2 (NM_001142407///NM_001142408///NM_001142417///NM_001142435///NM_003296), SOX11 (NM_003108), ANKRD30B (XM_001716904///XM_001717561///XM_001717810), SCN2A (NM_001040142///NM_001040143///NM_021007), MYNN (NM_018657), FOXA2 (NM_021784///NM_153675), DKFZP434B061 (XR_015528///XR_040812), LOC645323 (NR_015436///NR_024383///NR_024384///XR_041118///XR_041119///XR_041120), SNIP (NM_025248), LOC374491 (NR_002815), ADAM30 (NM_021794), SIX3 (NM_005413), FLJ36144 (XR_040632///XR_040633///XR_040634), CARD8 (NM_014959), RP1-127L4.6

(NM_001010859), FAM149A (NM_001006655///NM_015398), B3GAT2 (NM_080742), SPOCK3 (NM_001040159///NM_016950), ITGBL1 (NM_004791), IQGAP3 (NM_178229), C7orf45 (NM_145268), ZNF608 (NM_020747), LOC375010 (XR_041271), LRP2 (NM_004525), TGFB2 (NM_001135599///NM_003238), SHOX2 (NM_003030///NM_006884), HOXC4///HOXC6 (NM_004503///NM_014620///NM_153633///NM_153693), ELTD1 (NM_022159), FAM182B///RP13-401N8.2 (XM_001132551///XM_001133521///XM_001718365///XM_933752), LIFR (NM_001127671///NM_002310), FOLH1 (NM_001014986///NM_004476), EHF (NM_012153), NDST3 (NM_004784), BRUNOL5 (NM_021938), LOC728460 (XM_001128581///XM_001129498///XM_001723364), PDE1A (NM_001003683///NM_005019), POU2AF1 (NM_006235), FAT1 (NM_005245), PCDH11X///PCDH11Y (NM_014522///NM_032967///NM_032968///NM_032969///NM_032971///NM_032972), FLJ37786 (XR_041472///XR_041473), SLC22A4 (NM_003059), DHRS13 (NM_144683), MEG3 (NR_002766///NR_003530///NR_003531), PIWIL1 (NM_004764), LOC203274 (AL117607.1///BC080605.1), LOC100133920///LOC286297///(NR_024443///XM_001714612///XM_372109///XM_933054///XM_933058), DMRT1 (NM_021951), ADM (NM_001124), VWA3B (NM_144992), GAFA3 (XM_001715321///XM_001722922///XM_001723636), HESX1 (NM_003865), ADAMDEC1 (NM_014479), CAV1 (NM_001753), LAMB4 (NM_007356), TPTE (NM_199259///NM_199260///NM_199261), PPP1R1C (NM_001080545), HPSE (NM_001098540///NM_006665), AIM2 (NM_004833), RUNDC3B (NM_001134405///NM_001134406///NM_138290), CARD16 (NM_001017534///NM_052889), FAM124A (NM_145019), MGC39584 (XR_017735///XR_017787///XR_041937), OSM (NM_020530), RFX2 (NM_000635///NM_134433), MYBPC1 (NM_002465///NM_206819///NM_206820///NM_206821), LTBR (NM_002342), C18orf2 (NM_031416///NR_023925///NR_023926///NR_023927///NR_023928), SNRPN (NM_003097///NM_022805///NM_022806///NM_022807///NM_022808///NR_001289), FLJ36031 (NM_175884), IL1B (NM_000576), TRPM1 (NM_002420), OSTCL (NM_145303), MAPK14 (NM_001315///NM_139012///NM_139013///NM_139014), KCNJ15///LOC100131955 (NM_002243///NM_170736///NM_170737///XM_001713900///XM_001715532///XM_0), FIGN (NM_018086), HNT (NM_001048209///NM_016522), S100A12 (NM_005621), CHIT1 (NM_003465), C7orf53 (NM_001134468///NM_182597), FAM13A1 (NM_001015045///NM_014883), GNAO1 (NM_020988///NM_138736), MAPK14 (NM_001315///NM_139012///NM_139013///NM_139014), FAM55D (NM_001077639///NM_017678), PRKD2 (NM_001079880///NM_001079881///NM_001079882///NM_016457), LIMK2 (NM_001031801///NM_005569///NM_016733), C18orf54 (NM_173529), IGFBP5 (NM_000599), EVI1 (NM_001105077///NM_001105078///NM_005241), PLSCR1 (NM_021105), FOXC1 (NM_001453), LOC646627 (NM_001085474), ZNF462 (NM_021224), CNTLN (NM_001114395///NM_017738), ZNF438 (NM_001143766///NM_001143767///NM_001143768///NM_001143769///NM_001143770), DEFB105A///DEFB105B (NM_001040703///NM_152250), LOC340017 (NR_026992.1), C1orf67 (NM_144989), ACSL1 (NM_001995), ADH1B (NM_000668), SLC2A14///SLC2A3 (NM_006931///NM_153449), IL1B (NM_000576), ST3GAL4 (NM_006278///XM_001714343///XM_001726541///XM_001726562), UBE2J1 (NM_016021), PNPLA3 (NM_025225) and PAPPA (NM_002581) is correlative with or indicates that the patient has experienced or is at risk for TIA. In some embodiments, a decreased expression level of one or more TIA-associated biomarkers selected from the group consisting of NBPF10///RP11-9412.2 (NM_001039703///NM_183372///XM_001722184), SFXN1 (NM_022754), SPIN3 (NM_001010862), UNC84A (NM_001130965///NM_025154), OLFM2 (NM_058164), PPM1K (NM_152542), P2RY10 (NM_014499///NM_198333), ZNF512B (NM_020713), MORF4L2 (NM_001142418///NM_001142419///NM_001142420///NM_001142421///NM_001142422), GIGYF2 (NM_001103146///NM_001103147///NM_001103148///NM_015575), ERAP2 (NM_001130140///NM_022350), SLFN13 (NM_144682), LOC401431 (XR_040272///XR_040273///XR_040274///XR_040275), MED6 (NM_005466), BAIAP2L1///LOC100128461 (NM_018842///XM_001722656///XM_001724217///XM_001724858), LNPEP (NM_005575///NM_175920), MBNL1 (NM_021038///NM_207292///NM_207293///NM_207294///NM_207295///NM_207296), NOS3 (NM_000603), MCF2L (NM_001112732///NM_024979), KIAA1659 (XM_001723799///XM_001725435///XM_001726785), SCAMP5 (NM_138967), LOC648921 (XM_001715629///XM_001720571///XR_018520), ANAPC5 (NM_001137559///NM_016237), SPON1 (NM_006108), FUS (NM_004960), GPR22 (NM_005295), GAL3ST4 (NM_024637), METTL3 (NM_019852), LOC100131096 (XM_001720907///XM_001726205///XM_001726705), FAAH2 (NM_174912), SMURF2 (NM_022739), SNRPN (NM_003097///NM_022805///NM_022806///NM_022807///NM_022808///NR_001289), FBLN7 (NM_001128165///NM_153214), GLS (NM_014905), G3BP1 (NM_005754///NM_198395), RCAN3 (NM_013441), EPHX2 (NM_001979), DIP2C (NM_014974), CCDC141 (NM_173648), CLTC (NM_004859), FOSB (NM_001114171///NM_006732), CACNA1I (NM_001003406///NM_021096), UNQ6228 (XM_001725293///XM_001725359///XM_001726164), ATG9B (NM_173681), AK5 (NM_012093///NM_174858), RBM14 (NM_006328), MAN1C1 (NM_020379), HELLS (NM_018063), EDAR (NM_022336), SLC3A1 (NM_000341), ZNF519 (NM_145287), LOC100130070///LOC100130775///LOC100131787///LOC100131905///LOC100132291///LOC100132488///RPS27 (NM_001030///XM_001721002///XM_001722161///XM_001722965///XM_001723889//), ZC3H12B (NM_001010888), IQGAP2 (NM_006633), SOX8 (NM_014587), WHDC1L2 (XM_926785), TNPO1 (NM_002270///NM_153188), TNFRSF21 (NM_014452), TSHZ2 (NM_173485), DMRTC1///DMRTC1B (NM_001080851///NM_033053), GSTM1 (NM_000561///NM_146421), GSTM2 (NM_000848///NM_001142368), PNMA6A (NM_032882), CAND1 (NM_018448), CCND3 (NM_001136017///NM_001136125///NM_001136126///NM_001760), GSTM1 (NM_000561///NM_146421), and GUSBL2 (NR_003660///XR_042150///XR_042151) is correlative with or indicates that the patient has experienced or is at risk for TIA. Further biomarkers of interest are published in Zhan, et al., *Neurology*. (2011) 77(19):1718-24.

In various embodiments, the expression levels of a plurality of ischemic stroke-associated exon/splice variant biomarkers are co-determined together with the expression levels of a plurality of genes useful in the determination of whether a patient has experienced or has a predisposition to experience a transient neurological event (TNE). In some embodiments, an increased expression level of one or more (e.g., 2, 3, 4, 5, 6, 7, 8, 9, 10, 11, 12, 13, 14, 15 or all) ischemic stroke-associated biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105 indicates that the patient has suffered or is at risk of experiencing a transient neurological event (TNE). In some embodiments, an increased expression level of one or more (e.g., 2, 3, 4, 5, 6, 7, 8, 9, 10, 11, 12, 13, 14, 15, 20, 25, 30, 35, 40 or all) ischemic stroke-associated biomarkers selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16 III CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B indicates that the patient has suffered or is at risk of experiencing a transient neurological event (TNE). In some embodiments, an increased expression level of one or more (e.g., 2, 3, 4, 5, 6, 7, 8, 9, 10, 11, 12, 13, 14, 15, 20, 25, 30 or all) ischemic stroke-associated biomarkers selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1 indicates that the patient has suffered or is at risk of experiencing a transient neurological event (TNE). In some embodiments, an increased expression level of one or more (e.g., 2, 3, 4, 5, 6, 7, 8, 9, 10, 11, 12, 13, 14, 15, 20, 25, 30, 35, 40 or all) ischemic stroke-associated biomarkers selected from the group consisting of UBE2J1, CARD16, LOC203274, ZNF608, CARD16///CASP1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 indicates that the patient has suffered or is at risk of experiencing a transient neurological event (TNE). Conversely, in some embodiments, a decreased expression level of one or more (e.g., 2, 3, 4, 5, 6, 7, 8, 9, 10, 11, 12, 13, 14, 15 or all) ischemic stroke-associated biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105 indicates that the patient has not suffered or is not at risk of experiencing a transient neurological event (TNE). In some embodiments, a decreased expression level of one or more (e.g., 2, 3, 4, 5, 6, 7, 8, 9, 10, 11, 12, 13, 14, 15, 20, 25, 30, 35, 40 or all) ischemic stroke-associated biomarkers selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B indicates that the patient has not suffered or is not at risk of experiencing a transient neurological event (TNE). In some embodiments, a decreased expression level of one or more (e.g., 2, 3, 4, 5, 6, 7, 8, 9, 10, 11, 12, 13, 14, 15, 20, 25, 30 or all) ischemic stroke-associated biomarkers selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1 indicates that the patient has not suffered or is not at risk of experiencing a transient neurological event (TNE). In some embodiments, a decreased expression level of one or more (e.g., 2, 3, 4, 5, 6, 7, 8, 9, 10, 11, 12, 13, 14, 15, 20, 25, 30, 35, 40 or all) ischemic stroke-associated biomarkers selected from the group consisting of UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 indicates that the patient has not suffered or is not at risk of experiencing a transient neurological event (TNE).

In various embodiments, the expression levels of a plurality of ischemic stroke-associated exon/splice variant biomarkers are co-determined together with the expression levels of a plurality of genes useful in the determination of whether a patient has experienced or has a predisposition to experience lacunar stroke. In some embodiments, an increase of the expression level of one or more biomarkers selected from the group consisting of RASEF (NM_152573), CALM1 (NM_006888), TTC12 (NM_017868), CCL3///CCL3L1///CCL3L3 (NM_001001437///NM_002983///NM_021006), CCDC78 (NM_001031737), PRSS23 (NM_007173), LAIR2 (NM_002288///NM_021270), C18orf49 (AK000229.1///BC047606.1), UTS2 (NM_006786///NM_021995), LGR6 (NM_001017403///NM_001017404///NM_021636), PROCR (NM_006404), LAG3 (NM_002286), OASL (NM_003733///NM_198213), LOC100132181 (XM_001722051.1), HLA-DRB4 (NM_021983///XM_002346251), CCL2 (NM_002982), ALS2CR11 (NM_152525), SCAND2 (NR_003654///NR_004859), GBP4 (NM_052941), RUNX3 (NM_001031680///NM_004350), TSEN54 (NM_207346), UBA7 (NM_003335), FAM179A (NM_199280), TGFBR3 (NM_003243), CCDC114 (NM_144577), AKAP9 (NM_005751///NM_147185), BNC2 (NM_017637), BZRAP1 (NM_004758///NM_024418), CCL4 (NM_002984), CHST2 (NM_004267), CSF1 (NM_000757///NM_172210///NM_172211///NM_172212), ERBB2 (NM_001005862///NM_004448), GBR56 (NM_001145770///NM_001145771///NM_001145772///NM_001145773///NM_001145774), GRAMD3 (NM_001146319///NM_001146320///NM_001146321///NM_001146322///NM_023927), GRHL2 (NM_024915), GRK4 (NM_001004056///NM_001004057///NM_182982), ITIH4 (NM_002218), KIAA1618 (NM_020954), LOC147646 (XM_001134195///XM_001134326///XM_001726058), LOC150622 (NR_026832), LOC161527 (NM_002675///NM_033238///NM_033239///NM_033240///NM_033244///NM_033246), PLEKHF1 (NM_024310), PRKD2 (NM_001079880///

NM_001079881///NM_001079882///NM_016457), RGNEF (NM_001080479), SESN2 (NM_031459), SLAMF7 (NM_021181), SPON2 (NM_001128325///NM_012445), STAT1 (NM_007315///NM_139266), SYNGR1 (NM_004711///NM_145731///NM_145738), TRX21 (NM_013351), TMEM67 (NM_001142301///NM_153704///NR_024522), TUBE1 (NM_016262), and ZNF827 (NM_178835), and/or a decrease of the expression level of one or more biomarkers selected from the group consisting of HLA-DQA1 (NM_002122), FLJ13773 (AK023835.1), QKI (NM_006775///NM_206853///NM_206854///NM_206855), MPZL3 (NM_198275), FAM70B (NM_182614), LOC254128 (NR_037856.1///NR_037857.1///NR_037858.1), IL8 (NM_000584), CHML (NM_001821), STX7 (NM_003569), VAPA (NM_003574///NM_194434), UGCG (NM_003358), PDXDC1 (NM_015027), LRRC8B (NM_001134476///NM_015350), STK4 (NM_006282), GTF2H2 (NM_001515), AGFG1 (NM_001135187///NM_001135188///NM_001135189///NM_004504), BTG1 (NM_001731), CFDP1 (NM_006324), CNPY2 (NM_014255), FAM105A (NM_019018), GATM (NM_001482), GTF2H2B (NM_001042490///NM_001098728///NM 001098729///NM_001515), IGHG1 (NG 001019.5///NC 000014.8), IL18RAP (NM_003853), N4BP2 (NM_018177), PHACTR1 (NM_030948), RTKN2 (NM_145307), SLC16A1 (NM_003051), SOCS1 (NM_003745), SPAG17 (NM_206996), ST6GALNAC1 (NM_018414), STK17B (NM_004226), STT3B (NM_178862), STX16 (NM_001001433///NM_001134772///NM_001134773///NM_003763), TBC1D12 (NM_015188), TRIM4 (NM_033017///NM_033091), UACA (NM_001008224///NM_018003), and WHAMML2 (NR_026589) is correlative with or indicates that the patient has experienced or is at risk for experiencing lacunar stroke.

In various embodiments, the expression levels of a plurality of exon/splice variant biomarkers are co-determined together with the expression levels of a plurality of genes useful in the determination of whether a patient has experienced or has a predisposition to experience a hemorrhagic transformation. In varying embodiments, detecting an increase of the expression level of one or more biomarkers (e.g., 1, 2, 3, 4, 5 or 6 biomarkers) selected from the group consisting of MARCH7, SMAD4, AREG and INPP5D, and/or a decrease of the expression level of one or more biomarkers selected from the group consisting of TNFSF15 and MCFD22, compared to the control level of expression indicates that the patient suffers from or is at risk of experiencing hemorrhagic transformation of ischemic stroke. In some embodiments the methods further comprise determining a level of expression of a plurality of biomarkers (e.g., 1, 2, 3, 4, 5, 6, 7, 8, 9, 10, 11, 12, 13, 14, 15, 16, 17, 18, 19, 20, 21, 22, 23 or all biomarkers) selected from the group consisting of MARCH7, SMAD4, AREG, INPP5D, IRAK3, PELI1, CPD, PRKDC, GAFA3, AMACR, MKLN1, IQCK, TSC22D2, TAF8, POLH, SYTL3, EXOC6, RIF1, RNF144B, ATXN1L, TSPYL1, RAPGEF2, MTPAP, ABHD12B, LRRC18, LOC151438, NCRNA00081, TNFSF15 and MCFD22, wherein an increase of the expression level of one or more biomarkers selected from the group consisting of MARCH7, SMAD4, AREG, INPP5D, IRAK3, PELI1, CPD, PRKDC, GAFA3, AMACR, MKLN1, TSC22D2, TAF8, SYTL3, EXOC6, RIF1, RNF144B, RAPGEF2, ABHD12B, LRRC18, LOC151438 and NCRNA00081, and/or a decrease of the expression level of one or more biomarkers selected from the group consisting of TNFSF15 MCFD22, IQCK, POLH, ATXN1L, TSPYL1 and MTPAP compared to a control level of expression indicates that the patient suffers from or is at risk of experiencing hemorrhagic transformation of ischemic stroke, thereby diagnosing the occurrence of hemorrhagic transformation of ischemic stroke or the predisposition for experiencing hemorrhagic transformation of ischemic stroke.

4. Comparison to a Control Level of Expression

The expression of the ischemic stroke/ICH-associated biomarkers are compared to a control level of expression. As appropriate, the control level of expression can be the expression level of the same ischemic stroke/ICH-associated biomarker in an otherwise healthy individual (e.g., in an individual who has not experienced and/or is not at risk of experiencing ischemic stroke/ICH). In some embodiments, the control level of expression is the expression level of a plurality of stably expressed endogenous reference biomarkers, as described herein or known in the art. In some embodiments, the control level of expression is a predetermined threshold level of expression of the same ischemic stroke/ICH-associated biomarker, e.g., based on the expression level of the biomarker in a population of otherwise healthy individuals. In some embodiments, the expression level of the ischemic stroke/ICH-associated biomarker and the ischemic stroke/ICH-associated biomarker in an otherwise healthy individual are normalized to (i.e., divided by), e.g., the expression levels of a plurality of stably expressed endogenous reference biomarkers.

In varying embodiments, a subject may experience a vascular event that may be incorrectly diagnosed as ischemic stroke/ICH. In assessing a patient with a possible ischemic stroke or intracerebral hemorrhage, sometimes patients will have events that seem like ischemic stroke/ICH but are not—for example, a simple faint. Such patients will have a biomarker profile that is negative for stroke. To determine and distinguish subjects who have not experienced an ischemic stroke/ICH from subjects who have experienced an ischemic stroke or an intracerebral hemorrhage, provided herein are exon or splice variant biomarkers that identify subjects who have not experienced ischemic stroke or an intracerebral hemorrhage as distinguished from subjects who likely have experienced an ischemic stroke and intracerebral hemorrhage. These exon or splice variant biomarkers facilitate determining and distinguishing those patients who did not have an ischemic stroke or an intracerebral hemorrhage, even if presenting with one or more symptoms that might be diagnosed as ischemic stroke/ICH.

Accordingly, in varying embodiments, an increased expression level in comparison to a control of one or more (e.g., 1, 2, 3, 4, 5, 6, 7, 8, 9, 10, 11, 12, 13, 14, 15, 16, 17, 18, or all), ischemic stroke/ICH-associated biomarkers of Table 1E indicates that the subject has not or is unlikely to have experienced, ischemic stroke/ICH. High levels of expression of the exon or splice variant biomarkers, e.g., as compared to historical controls, indicate that the subject has not or is unlikely to have experienced, ischemic stroke/ICH. Low levels of expression of these control exon or splice variant biomarkers, e.g., as compared to historical controls, indicate that the subject has or is likely to have experienced ischemic stroke/ICH.

TABLE 1E

Exon Usage Upregulated in Subjects Who Have Not Experienced ischemic Stroke/ICH

| Marker ID | Gene Symbol |
|---|---|
| chr20.32880178-32880361>AHCY | AHCY |
| chr2.242611606-242612018>ATG4B | ATG4B |
| chr9.96866557-96866669>PTPDC1 | PTPDC1 |
| chr17.42982993-42984758>GFAP | GFAP |
| chr22.41252435-41253038>ST13 | ST13 |
| chr1.53416427-53416560>SCP2 | SCP2 |
| chr6.32806430-32806549>TAP2andHLA-DOB | TAP2 and HLA-DOB |
| chr14.19683027-19683436>DUXAP10 | DUXAP10 |
| chr9.95018962-95019084>IARS | IARS |
| chr19.39138368-39138549>ACTN4 | ACTN4 |
| chr9.140473077-140473342>WDR85 | WDR85 |
| chrX.48367956-48368346>PORCN | PORCN |
| chr2.101606718-101606910>NPAS2 | NPAS2 |
| chr7.101475858-101476867>snorkar | snorkar |
| chr19.45543176-45543571>SFRS16 | SFRS16 |
| chr18.28642978-28643441>DSC2 | DSC2 |
| chr22.36892014-36892257>FOXRED2andTXN2 | FOXRED2 and TXN2 |
| chr18.43417478-43417852>SIGLEC15 | SIGLEC15 |

In some embodiments, the overexpression or underexpression of a ischemic stroke/ICH-associated biomarker is determined with reference to the expression of the same ischemic stroke/ICH-associated biomarker in an otherwise healthy individual. For example, a healthy or normal control individual has not experienced and/or is not at risk of experiencing ischemic stroke/ICH. The healthy or normal control individual generally has not experienced a vascular event (e.g., cardioembolic stroke, large vessel stroke, lacunar stroke, TIA, ischemic stroke, myocardial infarction, peripheral vascular disease, venous thromboembolism or intracerebral hemorrhage). The healthy or normal control individual generally does not have one or more vascular risk factors (e.g., hypertension, diabetes mellitus, hyperlipidemia, or tobacco smoking). As appropriate, the expression levels of the target ischemic stroke/ICH-associated biomarker in the healthy or normal control individual can be normalized (i.e., divided by) the expression levels of a plurality of stably expressed endogenous reference biomarkers.

In some embodiments, the overexpression or underexpression of a ischemic stroke/ICH-associated biomarker is determined with reference to one or more stably expressed endogenous reference biomarkers. Internal control biomarkers or endogenous reference biomarkers are expressed at the same or nearly the same expression levels in the blood of patients who have experienced ischemic stroke/ICH as compared to control patients. Target biomarkers are expressed at higher or lower levels in the blood, serum and/or plasma of patients who have experienced or are at risk of experiencing ischemic stroke/ICH. The expression levels of the target biomarker to the reference biomarker are normalized by dividing the expression level of the target biomarker to the expression levels of a plurality of stably expressed endogenous reference biomarkers. The normalized expression level of a target biomarker can be used to predict the occurrence or lack thereof of ischemic stroke/ICH, and/or the cause of the ischemic stroke/ICH.

In some embodiments, the expression level of the ischemic stroke/ICH-associated biomarker (e.g., from Tables 1A-1D and biomarkers associated with cardioembolic stroke, atherothrombotic stroke, lacunar stroke, transient ischemic attack (TIA), hemorrhagic transformation described herein) from a patient suspected of having or experiencing an ischemic and from a control patient are normalized with respect to the expression levels of a plurality of stably expressed endogenous reference biomarkers. The expression levels of the normalized expression of the ischemic stroke/ICH-associated biomarkers are compared to the expression levels of the normalized expression of the same ischemic stroke/ICH-associated biomarker in a control patient. The determined fold change in expression=normalized expression of target biomarker in the ischemic stroke/ICH patient/normalized expression of target biomarker in control patient. In varying embodiments, ischemic stroke/ICH-associated biomarker of interest (e.g., whole gene or exon/slice variant/isoform) is divided by the geometric average of the stably expressed endogenous reference biomarkers. If the normalized values are similar to historical controls (e.g., within two standard deviations), then the samples from such patients are diagnosed as indicating that the individual has not experienced and/or is not at risk of experiencing an ischemic stroke or intracerebral hemorrhage. If the expression levels of these exons are higher or lower than expected from historical controls (e.g., greater than two standard deviations), then the samples from such patients are diagnosed as indicating that the individual has experienced and/or is at risk of experiencing an ischemic stroke or intracerebral hemorrhage. In varying embodiments, software may be employed involving Support Vector Machine (SVM) or PAM signature determination and determining which side of the hyperplane subjects falls into for classification as having an ischemic stroke or an ICH. Overexpression or underexpression of the normalized ischemic stroke/ICH-associated biomarker in the ischemic stroke/ICH patient by at least about 1.2-fold, e.g., at least about 1.3-fold, 1.4-fold, 1.5-fold, 1.6-fold, 1.7-fold, 1.8-fold, 1.9-fold, 2.0-fold, or more, in comparison to the expression levels of the normalized ischemic stroke/ICH-associated biomarker in a healthy control patient indicates that the patient has experienced or is at risk of experiencing an ischemic stroke/ICH.

The biomarkers of Table 1E can also be normalized in comparison to internal control biomarkers or stably expressed endogenous reference biomarkers, as described above. The control exon biomarkers in Table 1E (upregulated in subjects who have not experienced ischemic stroke/ICH) can be divided by the geometric average of the endogenous control exons. If the normalized expression levels of the biomarkers listed in Table 1E are similar to historical controls (e.g., within two standard deviations), then the samples from these patients are diagnosed as controls who have not experienced or are unlikely to experience ischemic stroke or intracerebral hemorrhage. That is, the biomarkers of Table 1E are expressed at higher levels in controls compared to patients with ischemic stroke or intracerebral hemorrhage. If the expression levels of these exons are lower than expected from historical controls (greater than two standard deviations), then the samples from these patients are diagnosed as controls who have experienced or are likely to experience ischemic stroke or intracerebral hemorrhage. Additional biomarkers (e.g., from Tables 1A-1D and biomarkers associated with cardioembolic stroke, atherothrombotic stroke, lacunar stroke, transient ischemic attack (TIA), hemorrhagic transformation described herein) can then be used to distinguish whether the patient had an ischemic stroke or an intracerebral hemorrhage. The biomarkers of Table 1E are expressed at higher levels in subjects who have not experienced ischemic stroke/ICH compared to ischemic stroke and hemorrhage patients. They are thus lower in ischemic stroke and hemorrhage patients compared to controls. The expression of the biomarkers of Table 1E can be normalized to or divided by the expression of stably expressed endogenous reference biomarkers, described herein. If low levels of expression of the biomarkers of Table 1E compared to a normalized control are detected, this indicates the subject has experienced or is at risk to experience ischemic stroke or intracerebral hemorrhage. If higher levels of expression of the biomarkers of Table 1E compared to a normalized control are detected this indicates the subject has not experienced or is not at risk to experience ischemic stroke or intracerebral hemorrhage.

In some embodiments, the control level of expression is a predetermined threshold level. The threshold level can correspond to the level of expression of the same ischemic stroke/ICH-associated biomarker in an otherwise healthy individual or a population of otherwise healthy individuals, optionally normalized to the expression levels of a plurality of stably expressed endogenous reference biomarkers. After expression levels and normalized expression levels of the ischemic stroke/ICH-associated biomarkers are determined in a representative number of otherwise healthy individuals and individuals predisposed to experiencing ischemic stroke/ICH, normal and ischemic stroke/ICH-predisposed expression levels of the ischemic stroke/ICH-associated biomarkers can be maintained in a database, allowing for determination of threshold expression levels indicative of the presence or absence of risk to experience ischemic stroke/ICH or the occurrence of ischemic stroke/ICH. If the predetermined threshold level of expression is with respect to a population of normal control patients, then overexpression or underexpression of the ischemic stroke/ICH-associated biomarker (usually normalized) in the patient by at least about 1.2-fold, e.g., at least about 1.3-fold, 1.4-fold, 1.5-fold, 1.6-fold, 1.7-fold, 1.8-fold, 1.9-fold, 2.0-fold, or more, in comparison to the threshold level indicates that the patient has experienced or is at risk of experiencing ischemic stroke/ICH. If the predetermined threshold level of expression is with respect to a population of patients known to have experienced an ischemic stroke/ICH or known to be at risk for experiencing ischemic stroke/ICH, then an expression level in the patient suspected of experiencing ischemic stroke/ICH that is approximately equal to the threshold level (or overexpressed or underexpressed greater than the threshold level of expression), indicates that the patient has experienced or is at risk of experiencing an ischemic stroke/ICH.

With respect to the stably expressed endogenous reference biomarkers used for comparison, preferably, the endogenous reference biomarkers are stably expressed in blood. Exemplary endogenous reference biomarkers that find use are published, e.g., in Stamova, et al., *BMC Medical Genomics* (2009) 2:49. Additional endogenous reference biomarkers include without limitation, e.g., GAPDH, ACTB, B2M, HMBS, PPIB, USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110, PEX16. In some embodiments, the expression levels of a plurality of stably expressed endogenous reference biomarkers are determined as a control. In some embodiments, the expression levels of at least about 2, 3, 4, 5, 6, 7, 8, 9, 10, 15, 20, 25, 30, 35, or more, stably expressed endogenous reference biomarkers described herein or known in the art, are determined as a control.

In some embodiments, the expression levels of the stably expressed endogenous reference biomarkers GAPDH, ACTB, B2M, HMBS and PPIB are determined as a control. In some embodiments, the expression levels of 2, 3, 4, 5, 6, 7, 8, 9, 10, 15, 20, 25, or more, endogenous reference biomarkers selected from the group consisting of USP7, MAPRE2, CSNK1G2, SAFB2, PRKAR2A, PI4KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHCS, C9orf23, LRRC45, NACC1, LOC100133445///LOC115110, PEX16 are determined as a control.

5. Methods of Detecting Biomarkers Associated with Ischemic stroke/ICH

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Green and Sambrook, supra and Ausubel, supra) and may be used to detect the expression of the biomarkers set forth in Tables 1A-1E. Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. All forms of RNA can be detected, including, e.g., message RNA (mRNA), microRNA (miRNA), ribosomal RNA (rRNA) and transfer RNA (tRNA).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins Nucleic Acid Hybridization, A Practical Approach, IRL Press (1985); Gall and Pardue, Proc. Natl. Acad. Sci. U.S.A., 63:378-383 (1969); and John et al. Nature, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tij ssen, "Practice and Theory of Enzyme Immunoassays," Laboratory Techniques in Biochemistry and Molecular Biology, Burdon and van Knippenberg Eds., Elsevier (1985), pp. 9-20).

The probes can be labeled either directly, e.g., with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, N.Y. (1997); and in Haugland Handbook of Fluorescent Probes and Research Chemicals, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array has a reproducible pattern of a plurality of nucleic acids (e.g., a plurality of oligonucleotide probes that hybridize to a plurality of the biomarkers set forth in Tables 1A-1E) attached to a solid support. In one embodiment, the array contains a plurality of oligonucleotide probes that hybridize to a plurality of the biomarkers listed in Table 1A. In one embodiment, the array contains a plurality of oligonucleotide probes that hybridize to a plurality of the biomarkers listed in Table 1B. In one embodiment, the array contains a plurality of oligonucleotide probes that hybridize to a plurality of the biomarkers listed in Table 1C. In one embodiment, the array contains a plurality of oligonucleotide probes that hybridize to a plurality of the biomarkers listed in Table 1D. In one embodiment, the array contains a plurality of oligonucleotide probes that hybridize to a plurality of the biomarkers listed in Table 1E. In one embodiment, the array further contains a plurality of oligonucleotide probes that hybridize to a plurality of genes useful for diagnosing ischemic stroke, cardioembolic stroke, carotid stenosis, atrial fibrillation, transient ischemic attacks, lacunar stroke, and/or hemorrhagic transformation, as described herein and/or known in the art. In various embodiments, the array further contains a plurality of stably expressed endogenous reference biomarkers. Labeled RNA or DNA is hybridized to complementary probes on the array and then detected by laser scanning. Hybridization intensities for each probe on the array are determined and converted to a quantitative read-out of relative gene expression levels in ischemic stroke/ICH (e.g., correlative with or associative of ischemic stroke/ICH, or allowing the differentiation of a transient neurological event as ischemic or non-ischemic).

In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, Nat. Biotechnol. 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) Science, 251: 767-777; Sheldon et al. (1993) Clinical Chemistry 39(4): 718-719, and Kozal et al. (1996) Nature Medicine 2(7): 753-759. Integrated microfluidic systems and other point-of-care diagnostic devices available in the art also find use. See, e.g., Liu and Mathies, Trends Biotechnol. (2009) 27(10):572-81 and Tothill, Semin Cell Dev Biol (2009) 20(1):55-62. Microfluidics systems for use in detecting levels of expression of a plurality of nucleic acids are commercially available, e.g., from NanoString Technologies (on the internet at nanostring.com), Applied Biosystems (Life Technologies) (appliedbiosystems.com) and Fluidigm (fluidigm.com).

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) Analytical Biochemistry 181: 153-162; Bogulayski (1986) et al. J. Immunol. Methods 89:123-130; Prooijen-Knegt (1982) Exp. Cell Res. 141:397-407; Rudkin (1976) Nature 265:472-473, Stollar (1970) Proc. Nat'l Acad. Sci. USA 65:993-1000; Ballard (1982) Mol. Immunol. 19:793-799; Pisetsky and Caster (1982) Mol. Immunol. 19:645-650; Viscidi et al. (1988) J. Clin. Microbial. 41:199-209; and Kiney et al. (1989) J. Clin. Microbiol. 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) Fundamental Immunology Raven Press, Ltd., N.Y. (1993); Coligan, et al., Current Protocols in Immunology, Wiley Interscience (1991-2008); Harlow and Lane, Antibodies: A Laboratory Manual Cold Spring Harbor Press, N.Y. (1988); Harlow and Lane, Using Antibodies, Cold Spring Harbor Press, N.Y. (1999); Stites et al. (eds.) Basic and Clinical Immunology (4th ed.) Lange Medical Publications, Los Altos, Calif., and references cited therein; Goding Monoclonal Antibodies: Principles and Practice (2d ed.) Academic Press, New York, N.Y., (1986); and Kohler and Milstein Nature 256: 495-497 (1975)). Other suitable techniques for antibody preparation include selection of libraries of recombinant antibodies in phage or similar vectors (see, Huse et al. Science 246:1275-1281 (1989); and Ward et al. Nature 341:544-546 (1989)). Specific monoclonal and polyclonal antibodies and antisera will usually bind with a dissociation constant ($K_D$) of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. High throughput multiplex nucleic acid sequencing or "deep sequencing" to detect captured expressed biomarker genes also finds use. High throughput sequencing techniques are known in the art (e.g., 454 Sequencing on the internet at 454.com). In varying embodiments, next generation sequencing, deep sequencing or ultra deep sequencing methodologies are applied. Deep sequencing data analysis is described, e.g., in "Deep Sequencing Data Analysis (Methods in Molecular Biology)," Noam Shomron (Editor), Humana Press; 2013 edition. Next generation sequencing is described, e.g., in "Next-Generation DNA Sequencing Informatics," Stuart M. Brown (Editor), Cold Spring Harbor Laboratory Press; 1st edition (2013); "Next-generation Sequencing: Current Technologies and Applications," Jianping Xu (Editor), Caister Academic Press (2014); Wilhelm, et al., *Nature*. (2008) 453:1239-1243; Nagalakshmi, et al., *Science*. (2008) 320:1344-1349; and Mortazavi, et al., *Nat. Methods*. (2008) 5:621-628.

In varying embodiments, the biomarkers (e.g., exons or splice variants or whole genes) are detected using RNA sequencing techniques. Methodologies for direct sequencing of RNA, e.g., without an intervening step of producing cDNA are known in the art, and described for example, in Nagalakshmi, et al., *Curr Protoc Mol Biol*. (January 2010) Chapter 4:Unit 4.11.1-13; Wang, et al., *Nat Rev Genet*. (2009) 10(1):57-63; Kwok, et al, *Trends Biochem Sci*. (2015) 40(4):221-232; Ramsköld, et al., *Methods Mol Biol*. (2012) 802:259-74; Krupp, et al., *Bioinformatics*. (2012) 28(8):1184-5; Oudej ans, *Clin Biochem*. (2015) Mar. 16. pii: S0009-9120(15)00081-8; Eij a Korpelainen and Jarno Tuimala, "RNA-seq Data Analysis: A Practical Approach (Chapman & Hall/CRC Mathematical and Computational Biology," Chapman and Hall/CRC (Sep. 19, 2014); Ernesto Picardi, "RNA Bioinformatics (Methods in Molecular Biology)," Humana Press; 2015 edition (Jan. 11, 2015); and Shashikant Kulkarni and John Pfeifer, "Clinical Genomics," Academic Press; 1 edition (Nov. 21, 2014).

An alternative means for determining the level of expression of the nucleic acids of the present invention is in situ hybridization. In situ hybridization assays are well known and are generally described in Angerer et al., Methods Enzymol. 152:649-660 (1987). In an in situ hybridization assay, cells, preferentially human cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In other embodiments, quantitative RT-PCR is used to detect the expression of a plurality of the biomarkers set forth in one or more of Tables 1A-1E. In one embodiment, quantitative RT-PCR is used to further detect a plurality of the biomarkers useful for the diagnosis of ischemic stroke, cardioembolic stroke, carotid stenosis, atrial fibrillation, transient ischemic attacks, intracerebral hemorrhage and/or hemorrhagic transformation, as described herein and known in the art. A general overview of the applicable technology can be found, for example, in A-Z of Quantitative PCR, Bustin, ed., 2004, International University Line; Quantitative PCR Protocols, Kochanowski and Reischl, eds., 1999, Humana Press; Clinical Applications of PCR, Lo, ed., 2006, Humana Press; PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202. Methods for multiplex PCR, known in the art, are applicable to the present invention.

In varying embodiments, detection is accomplished by performing reverse transcription (RT) followed by a ligase detection reaction (LDR) with single-pair fluorescence resonance energy transfer (spFRET) (RT-LDR/spFRET). Methods for performing RT-LDR/spFRET are known in the art and described, e.g., in Peng, et al., *Anal Chem*. 2013 Aug. 20; 85(16):7851-8.

Accordingly, in one embodiment, provided is a reaction mixture comprising a plurality of polynucleotides which specifically hybridize (e.g., primers) to a plurality of nucleic acid sequences of the genes set forth in one or more of Tables 1A-1E. In some embodiments, the invention provides a reaction mixture further comprising a plurality of polynucleotides which specifically hybridize (e.g., primers) to a plurality of nucleic acid sequences of the genes useful for the diagnosis of ischemic stroke, cardioembolic stroke, carotid stenosis, atrial fibrillation, transient ischemic attacks, intracerebral hemorrhage and/or hemorrhagic transformation, as described herein and known in the art. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Green and Sambrook et al., Molecular Cloning, A Laboratory Manual ($4^{th}$ ed. 2012); Kriegler, Gene Transfer and Expression: A Laboratory Manual (1990); and Current Protocols in Molecular Biology (Ausubel et al., eds., 1987-2015, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

In some embodiments, the expression level of the biomarkers described herein are detected at the translational or protein level. Detection of proteins is well known in the art, and methods for protein detection known in the art find use. Exemplary assays for determining the expression levels of a plurality of proteins include, e.g., ELISA, flow cytometry, mass spectrometry (e.g., MALDI or SELDI), surface plasmon resonance (e.g., BiaCore), microfluidics and other biosensor technologies. See, e.g., Tothill, Semin Cell Dev Biol (2009) 20(1):55-62.

6. Providing Appropriate Treatment and Prevention Regimes to the Patient

Upon a positive determination or confirmation that a patient has experienced ischemic stroke/ICH, and a determination of the cause of the ischemic stroke/ICH, e.g., using established clinical procedures and/or the biomarkers provided herein and known in the art (e.g., employing biomarkers described in co-pending and co-owned U.S. Patent Publications Nos. 2015/0018234 ("BIOMARKERS FOR DIAGNOSING ISCHEMIA"); 2012/0316076 ("BIOMARKERS FOR THE DIAGNOSIS OF LACUNAR STROKE"); 2012/0065087 ("BIOMARKERS FOR DIAGNOSIS OF STROKE AND ITS CAUSES"); 2012/0015904 ("BIOMARKERS FOR DIAGNOSIS OF TRANSIENT ISCHEMIC ATTACKS"); and 2010/0197518 ("METHODS FOR DIAGNOSING ISCHEMIA") for the diagnosis of ischemic stroke/ICH), the methods further provide for the step of prescribing, providing or administering a regime for the prophylaxis or treatment of ischemic stroke/ICH. By diagnosing the occurrence and/or the cause of ischemic stroke/ICH using the biomarkers described herein, a patient can rapidly receive treatment that is tailored to and appropriate for the type of ischemic stroke/ICH that has been experienced, or that the patient is at risk of experiencing.

For example, if the expression levels of the plurality of ischemic stroke/ICH-associated biomarkers indicate the occurrence or risk of ischemic stroke/ICH, a positive diagnosis of ischemic stroke/ICH can be supported or confirmed using methods known in the art. For example, the patient can be subject to MRI imaging of brain and vessels, additional blood tests, EKG, and/or echocardiogram. Patients who have experienced ischemic transient neurological events may undergo extensive evaluation of the heart, vasculature, blood and brain, and may receive stroke prevention therapy such as antiplatelet/anticoagulation, anti-hypertensive medication and lipid lowering therapy.

If the expression levels of the plurality of biomarkers indicate the occurrence or risk of an ischemic transient neurological event (e.g., transient ischemic attacks (TIA) or transient cerebral ischemia), the patient can be prescribed a regime of medications and/or life-style adjustments (e.g., diet, exercise, stress) to minimize risk factors can be recommended, including reducing blood pressure and cholesterol levels, and controlling diabetes. Several medications can be used to decrease the likelihood of a stroke after a transient ischemic attack. The medication selected will depend on the location, cause, severity and type of TIA, if TIA has occurred. For example, the patient may be prescribed a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use to prevent or reduce the risk of stroke in patients who have experienced TIA. In some embodiments, the patient may be prescribed a regime of an anticoagulant. Exemplary anticoagulants include aspirin, heparin, warfarin, and dabigatran. Patients having a moderately or severely narrowed neck (carotid) artery, may require or benefit from carotid endarterectomy to clear carotid arteries of fatty deposits (atherosclerotic plaques) before another TIA or stroke can occur. In some embodiments, the patient may require or benefit from carotid angioplasty, or stenting.

In cases where a non-ischemic transient neurological event (TNE) is indicated, further evaluation to the cause of the non-ischemic TNE can be performed. For example, the subject can be given tests to determine if a migraine or seizure was experienced, and receive proper treatment. Patients with non-ischemic transient neurological events undergo different diagnostic evaluation and therapy, such as EEG and anti-seizure medication for seizures, and anti-migraine medication for migraines.

If the expression levels of the plurality of biomarkers indicate the occurrence or risk of cardioembolic stroke, the patient can be prescribed or administered a regime of an anticoagulant. Exemplary anticoagulants include aspirin, heparin, warfarin, and dabigatran.

If the expression levels of the plurality of biomarkers indicate the occurrence or risk of carotid stenosis, the patient can be prescribed or administered a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

If the expression levels of the plurality of biomarkers indicate the occurrence or risk of atrial fibrillation, the patient can be prescribed a regime of an anti-coagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

If the expression levels of the plurality of ischemic stroke/ICH-associated biomarkers indicate the occurrence or risk of lacunar stroke, a positive diagnosis of lacunar stroke can be supported or confirmed using methods known in the art. For example, the patient can be subject to clinical evaluation (e.g., determination of one or more of the lacunar syndromes, including (1) Pure motor stroke/hemiparesis, (2) Ataxic hemiparesis, (3) Dysarthria/clumsy hand, (4) Pure sensory stroke, and (5) Mixed sensorimotor stroke), radiologic imaging, retinal imaging, evaluation of blood-brain barrier permeability, evidence of microhemorrhage and blood endothelial markers (e.g., (homocysteine, intercellular adhesion molecule 1 (ICAM1), thrombomodulin (TM), tissue factor (TF) and tissue factor pathway inhibitor (TFPI); Hassan, et al., *Brain* (2003) 126(Pt 2):424-32; and Hassan, et al., *Brain*. (2004) 127(Pt 1):212-9). Upon a positive diagnosis of lacunar stroke, the patient may be administered tissue plasminogen activator within three hours of experiencing ischemic stroke/ICH if the patient is without contraindications (i.e. a bleeding diathesis such as recent major surgery or cancer with brain metastases). High doses aspirin may be given within 48 hours of experiencing ischemic stroke/ICH. For long term prevention of recurrence, medical regimens may be aimed towards correcting the underlying risk factors for lacunar infarcts such as hypertension, diabetes mellitus and cigarette smoking.

If the expression levels of the plurality of ischemic stroke/ICH-associated biomarkers indicate the occurrence or risk of hemorrhagic transformation, a positive or negative diagnosis of hemorrhagic transformation of ischemic stroke can be supported or confirmed using methods known in the art. For example, the patient can be subject to MRI imaging of brain and vessels, additional blood tests, EKG, and/or echocardiogram. Patients who have experienced or who are at risk of hemorrhagic transformation of ischemic stroke may undergo extensive evaluation of the heart, vasculature, blood and brain, and may receive reduced dosages of tissue plasminogen activator (tPA), or administration of tPA may be withdrawn or discontinued. In some embodiments, patients who have experienced or who are at risk of hemorrhagic transformation of ischemic stroke may receive an interventional therapy instead of administration of tPA. In some embodiments, patients who have experienced or who are at risk of hemorrhagic transformation of ischemic stroke may receive may receive tPA co-administered with one or more pharmacological agents to prevent, inhibit, reduce and/or mitigate the symptoms of HT, e.g., minocycline, Edaravone, Fingolimide (see, Campos, et al., *Stroke*. (2013) 44(2):505-11), a matrix metalloproteinase (MMP) inhibitor (e.g., an inhibitor of MMP9), an anti-inflammatory agent and/or an antioxidant. Inhibitors of MMP9 that find use are known in the art and have been described, e.g., in Intl. Appl. Nos. PCT/US2010/023585, PCT/GB2003/002138, PCT/GB2003/000741, in U.S. Patent Publ. Nos. 2004/0147573, 2005/0113344, 2010/0098659, and in Tandon, et al, *Bioinformation*. (2011) 5(8):310-4, Tuccinardi, et al., *Bioorg Med Chem*. (2008) 16(16):7749-58. Patients who have not experienced or who are not at risk of hemorrhagic transformation of ischemic stroke may also undergo extensive evaluation of the heart, vasculature, blood and brain, and may receive tissue plasminogen activator (tPA).

7. Reaction Mixtures

Further provided are reaction mixtures for diagnosing ischemic stroke/ICH or a predisposition for developing ischemic stroke/ICH. In varying embodiments, the reaction mixtures comprise a plurality of nucleic acid probes or primer sets useful for the amplification of a plurality of biomarkers (e.g., 2, 15, 20, 25, 30, 35, 40, 45, 50, 55, 60, 65, 70, 75, 80, 85, 90, 95, 100 biomarkers, or all listed biomarkers in the identified Table, e.g., e.g., Table 1A, Table 1B, Table 1C, Table 1D and/or Table 1E) of the biomarkers set forth in Tables 1A-E. In one embodiment, the reaction mixtures comprise a plurality of nucleic acid probes or primer sets that hybridize to a plurality of the biomarkers set forth in Table 1A. In one embodiment, the reaction mixtures comprise a plurality of nucleic acid probes or primer sets that hybridize to a plurality of the biomarkers set forth in Table 1B. In one embodiment, the reaction mixtures comprise a plurality of nucleic acid probes or primer sets that hybridize to a plurality of the biomarkers set forth in Table 1C. In one embodiment, the reaction mixtures comprise a plurality of nucleic acid probes or primer sets that hybridize to a plurality of the biomarkers set forth in Table 1D. In one embodiment, the reaction mixtures further comprise a plurality of nucleic acid probes or primer sets that hybridize to a plurality of the biomarkers set useful for the diagnosis of ischemic stroke, cardioembolic stroke, atherothrombotic stroke, carotid stenosis, lacunar stroke, atrial fibrillation, transient ischemic attacks (TIA), transient neurological events (TNEs), intracerebral hemorrhage and/or hemorrhagic transformation, as described herein. The probes may be immobilized on an array as described herein.

In varying embodiments, the reaction mixtures further can comprise appropriate buffers, salts, polymerases, dNTPs and other reagents to facilitate amplification and/or detection reactions (e.g., primers, labels) for amplifying one or more exons of a plurality of the biomarkers set forth in Tables 1A-E.

In some embodiments, the reaction mixtures can be provided in one or more reaction vessels that have aliquots of some or all of the reaction components of the reaction mixtures in them. Aliquots can be in liquid or dried (e.g., freeze-dried) form. Reaction vessels can include sample processing cartridges or other vessels that allow for the containment, processing and/or amplification of samples in the same vessel.

Further contemplated are kits comprising the reaction mixtures described above and herein.

8. Solid Supports and Kits

The invention further provides, a solid support comprising a plurality of nucleic acid probes that hybridize to a plurality (e.g., two or more, or all) of the biomarkers set forth in Tables 1A-E, and optionally stably expressed endogenous reference biomarkers, as described herein. For example, the solid support can be a microarray attached to a plurality of nucleic acid probes that hybridize to a plurality (e.g., two or more, or all) of the biomarkers set forth in Tables 1A-E, and optionally stably expressed endogenous reference biomarkers.

In various embodiments, the solid supports are configured to exclude genes not associated with or useful to the diagnosis, prediction or confirmation of ischemic stroke or ICH. For example, oligonucleotide probes that hybridize to genes or gene exons/splice variants/isoforms that are overexpressed or underexpressed less than 1.2-fold in subjects with ischemic stroke/ICH in comparison to a control level of expression can be excluded from the present solid supports. In some embodiments, oligonucleotide probes that hybridize to genes or gene exons that are overexpressed or underexpressed less than 1.2-fold in subjects with ischemic stroke, including transient cerebral ischemia, lacunar stroke, cardioembolic stroke, atherothrombotic stroke, TIA, TNE, carotid stenosis, and stroke subsequent to atrial fibrillation, in comparison to a control level of expression can be excluded from the present solid supports.

In various embodiments, the solid supports are configured to include only oligonucleotide probes that hybridize to genes or gene exons associated with or useful to the diagnosis, prediction or confirmation of ischemic stroke and/or ICH. For example, in some embodiments, only oligonucleotide probes that hybridize to genes or gene exons that are overexpressed or underexpressed more than 1.2-fold in subjects with ischemic stroke/ICH in comparison to a control level of expression are included in the present solid supports. In some embodiments, only oligonucleotide probes that hybridize to genes or gene exons that are overexpressed or underexpressed more than 1.2-fold in subjects with ICH or ischemic stroke (e.g., including transient cerebral ischemia, lacunar stroke, cardioembolic stroke, atherothrombotic stroke, TIA, TNE, carotid stenosis and stroke subsequent to atrial fibrillation), in comparison to a control level of expression are included in the present solid supports.

The solid support may optionally further comprise a plurality of oligonucleotide probes that hybridize to a plurality (e.g., two or more, or all) of the biomarkers useful for the diagnosis of ICH/ischemic stroke (e.g., cardioembolic stroke, carotid stenosis, and/or atrial fibrillation), as described herein. In various embodiments, the solid support comprises 5000, 4000, 3000, 2000, 1000 or fewer (e.g., 900, 800, 700, 600, 500 or fewer) nucleic acid probes that hybridize to a plurality of ischemic stroke/ICH-associated genes, as described herein. The solid support may be a component in a kit.

The invention also provides kits for diagnosing ischemic stroke/ICH or a predisposition for developing ischemic stroke/ICH. For example, the invention provides kits that include one or more reaction vessels that have aliquots of some or all of the reaction components of the reaction mixtures in them. Aliquots can be in liquid or dried form. Reaction vessels can include sample processing cartridges or other vessels that allow for the containment, processing and/or amplification of samples in the same vessel. The kits may comprise a plurality of nucleic acid probes or primer sets that hybridize to a plurality (e.g., two or more, or all) of the biomarkers set forth in Tables 1A-E. In one embodiment, the kits comprise a plurality of nucleic acid probes or primer sets that hybridize to a plurality of the biomarkers set forth in Table 1A. In one embodiment, the kits comprise a plurality of nucleic acid probes or primer sets that hybridize to a plurality of the biomarkers set forth in Table 1B. In one embodiment, the kits comprise a plurality of nucleic acid probes or primer sets that hybridize to a plurality of the biomarkers set forth in Table 1C. In one embodiment, the kits comprise a plurality of nucleic acid probes or primer sets that hybridize to a plurality of the biomarkers set forth in Table 1D. In one embodiment, the kits further comprise a plurality of nucleic acid probes or primer sets that hybridize to a plurality of the biomarkers set useful for the diagnosis of ischemic stroke, cardioembolic stroke, atherothrombotic stroke, carotid stenosis, lacunar stroke, atrial fibrillation, transient ischemic attacks (TIA), transient neurological events (TNEs), intracerebral hemorrhage and/or hemorrhagic transformation, as described herein. The probes may be immobilized on an array as described herein.

In addition, the kit can comprise appropriate buffers, salts and other reagents to facilitate amplification and/or detection reactions (e.g., primers, labels) for determining the expression levels of a plurality of the biomarkers set forth in Tables 1A-E. In one embodiment, the kit comprises appropriate buffers, salts and other reagents to facilitate amplification and/or detection reactions (e.g., primers, labels) for determining the expression levels of a plurality of the biomarkers set forth in Table 1A. In one embodiment, the kit comprises appropriate buffers, salts and other reagents to facilitate amplification and/or detection reactions (e.g., primers) for determining the expression levels of a plurality of the biomarkers set forth in Table 1B. In one embodiment, the kit comprises appropriate buffers, salts and other reagents to facilitate amplification and/or detection reactions (e.g., primers, labels) for determining the expression levels of a plurality of the biomarkers set forth in Table 1C. In one embodiment, the kit comprises appropriate buffers, salts and other reagents to facilitate amplification and/or detection reactions (e.g., primers) for determining the expression levels of a plurality of the biomarkers set forth in Table 1D. In one embodiment, the kit further comprises appropriate buffers, salts and other reagents to facilitate amplification and/or detection reactions (e.g., primers) for determining the expression levels of a plurality of the biomarkers useful for the diagnosis of ischemic stroke, cardioembolic stroke, atherothrombotic stroke, lacunar stroke, carotid stenosis, atrial fibrillation, and/or transient ischemic attacks (TIA), transient neurological events (TNEs) as described herein. The kits can also include written instructions for the use of the kit.

In one embodiment, the kits comprise a plurality of antibodies that bind to a plurality of the biomarkers set forth in Tables 1A-E. The kits may further comprise a plurality of antibodies that bind to a plurality of the biomarkers useful for the diagnosis of ischemic stroke, cardioembolic stroke, carotid stenosis, atrial fibrillation, transient ischemic attacks (TIA), transient neurological events (TNEs), intracerebral hemorrhage and/or hemorrhagic transformation, as described herein. The antibodies may or may not be immobilized on a solid support, e.g., an ELISA plate.

EXAMPLES

The following examples are offered to illustrate, but not to limit the claimed invention.

Example 1

Intracerebral Hemorrhage and Ischemic Stroke of Different Etiologies Have Distinct Alternatively Spliced mRNA Profiles in Blood Abstract Background: Whole transcriptome studies have used 3'-biased expression microarrays to study genes regulated in blood of ischemic stroke patients. However, alternatively spliced messenger RNA isoforms have not been investigated for ischemic stroke or intracerebral hemorrhage (ICH) in animals or humans. Alternative splicing is the mechanism whereby a single gene's exons combine to produce distinct mRNA and protein isoforms. RNA-sequencing (RNA-Seq) was used to determine if alternative splicing varies for ICH and different ischemic stroke causes (cardioembolic, large vessel, lacunar) as compared to each other and controls.

Methods: Paired-end RNA-Seq was performed using Illumina Solexa technology to a depth of $200 \times 10^6$ reads for splicing analysis on twenty whole-blood samples. Differential alternative splicing was assessed using 1-way-ANOVA (FDR $p<0.05$). Differential exon-usage was calculated between each group ($p<0.0005$; |fold change|>1.2).

Results: 412 genes displayed differential alternative splicing among the groups. They were involved in cellular immune response, cell death and cell survival pathways implicated in stroke. Distinct expression signatures based on usage of 308 exons (292 genes) differentiated the groups.

Conclusions: This pilot study demonstrates alternatively spliced genes from whole blood differ in ICH compared to ischemic stroke, and differ between different ischemic stroke etiologies.

Methods

Stroke patients and control subjects were randomly selected from all those recruited at the UC Davis Medical Center between 2008 and 2012. Stroke patients were chosen to represent the major ischemic stroke etiologies (cardioembolic, large vessel, lacunar) or had intracerebral hemorrhages (ICH). Control subjects were selected to match the stroke subjects by age, race and sex, to have vascular risk factors and no cardiovascular events. All subjects provided Informed Consent. The UCD Institutional Review Board approved this study. IS diagnosis and causes were assessed as previously described [5, 9]. ICH patients had deep ICH confirmed by CT and/or MRI brain scans, and were associated with hypertension without evidence of vascular malformation, tumor or aneurysm. Controls had vascular risk factors without evidence of stroke. Blood was drawn into PAXgene tubes at 5.8 to 101.2 h following IS or ICH. RNA from whole blood was isolated as previously described [3].

Whole blood RNA was used to prepare mRNA libraries using the TruSeq RNA Sample Prep v2 kit and protocol (Illumina). Paired-end 100 bp RNA-Seq reads on whole blood RNA were obtained by Illumina Solexa sequencing by synthesis on Illumina HiSeq2000 to a depth of $200 \times 10^6$ reads. Bowtie 2 was used to map reads to a reference genome (Hg19) and generate bam files for analysis [10]. RNA transcript quantification was performed using Hg19 AceView transcripts in Partek Genomics Suite 6.6 RNA-Seq workflow. DAS was determined with ANOVA on Group (FDR $p<0.05$), and differential exon-usage was assessed between each two groups ($p<0.0005$, |fold change|>|1.2|).

Principal Component Analysis (PCA) and Hierarchical Clustering were performed in Partek. Ingenuity Pathway Analysis (IPA®) and DAVID identified regulated pathways and processes as described previously [6].

Results

Subject Demographics. Subject demographics and clinical characteristics are presented in Table 2. Only Caucasian males were studied because of the small group sizes. Demographics for age, time since event for IS or ICH, and vascular risk factors were not significantly different. Coverage of a wide range of post-stroke biology was obtained by selecting patients with early (5.8 hours) through late (101.2 hours) blood draw times after stroke event. Although this time range seems wide, means are similar between stroke groups. Cardioembolic post-event blood draw times were, on average, 33.7 hours; large vessel averaged 47.4 hours; lacunar averaged 34.6 hours; and ICH averaged 29.4 hours (Table 2).

TABLE 2

Subjects' Characteristics.

| | Ischemic Stroke | | | Intracerebral | |
| --- | --- | --- | --- | --- | --- |
| | Cardioembolic | Large Vessel | Lacunar | Hemorrhage | Controls |
| Subjects, no. (total n = 20) | 4 | 4 | 4 | 4 | 4 |
| Age, years (mean ± SD) | 62.3 ± 9.6 | 61.0 ± 8.2 | 58.9 ± 9.0 | 60.1 ± 2.3 | 60.8 ± 9.2 |
| Time since event, hours (mean ± SD) | 33.7 ± 18.9 | 47.4 ± 47.8 | 34.6 ± 23.7 | 29.4 ± 15.5 | N/A |
| Hypertension, no. | 4 | 3 | 2 | 3 | 3 |
| Diabetes, no. | 2 | 2 | 0 | 0 | 1 |
| Hyperlipidemia, no. | 3 | 2 | 2 | 0 | 2 |

RNA Sequencing Alignments. RNA sequencing alignments statistics for all samples among the five groups are presented in Table 3. Cardioembolic stroke samples had on average, 1.60E+08 alignments; large vessel had 1.65E+08 alignments; lacunar stroke had 1.64E+08 alignments; and ICH and control each averaged 1.59E+08 alignments.

TABLE 3

RNA-Seq Reads

All Samples

| | |
| --- | --- |
| Sequence Length | 100 |
| Average Quality per Read PH RED score | 37 |
| Total Sequence Reads Mean ± SD | 1.95E+08 ± 1.30E+07 |

TABLE 3-continued

| RNA-Seq Reads | |
|---|---|
| Total Alignments Mean ± SD | 1.61E+08 ± 1.01E+07 |
| % GC Alignments Mean ± SD | 54.20 ± 1.91 |
| Unmapped Sequences Mean ± SD | 3.33E+07 ± 4.44E+06 |
| % GC Unmapped Sequences Mean ± SD | 61.60 ± 3.45 |

| | Ischemic Stroke | | | Intracerebral Hemorrhage | Controls |
|---|---|---|---|---|---|
| | Cardioembolic | Large Vessel | Lacunar | | |
| Total Sequence Reads | | | | | |
| Mean ± SD Total Sequence Reads by Sample | 1.93E+08 ± 1.07E+07 | 1.99E+08 ± 1.14E+07 | 1.99E+08 ± 1.18E+07 | 1.91E+08 ± 1.53E+08 | 1.92E+08 ± 1.94E+09 |
| 1 | 177,117,828 | 203,837,628 | 203,564,103 | 191,131,791 | 185,714,780 |
| 2 | 195,150,937 | 182,750,587 | 213,336,146 | 199,832,252 | 218,687,770 |
| 3 | 198,658,650 | 209,078,152 | 188,188,692 | 169,147,880 | 172,555,000 |
| 4 | 200,504,201 | 198,375,293 | 190,420,476 | 202,961,105 | 192,521,761 |
| Number of Alignments | | | | | |
| Mean ± SD | 1.60E+08 ± 9.73E+06 | 1.65E+08 ± 1.25E+07 | 1.64E+08 ± 8.34E+06 | 1.59E+08 ± 1.18E+07 | 1.59E+08 ± 1.18E+07 |
| CV (%) | 6.073 | 7.61352 | 5.09486 | 7.42897 | 7.46071 |
| Mean % GC ± SD Alignments by Sample | 54.75 ± 2.36 | 55.75 ± 0.96 | 53.75 ± 1.89 | 52.00 ± 0.82 | 54.75 ± 1.26 |
| 1 | 164,675,690 | 171,375,517 | 166,034,796 | 160,755,434 | 157,275,379 |
| 2 | 164,012,069 | 146,190,367 | 174,444,217 | 168,409,440 | 174,121,248 |
| 3 | 145,627,854 | 172,988,643 | 157,269,390 | 142,396,412 | 145,330,668 |
| 4 | 166,272,000 | 168,785,456 | 156,892,385 | 166,405,048 | 157,539,078 |
| Number of Unmapped Sequences | | | | | |
| Mean ± SD | 3.27E+07 ± 3.14E+06 | 3.37E+07 ± 3.28E+06 | 3.52E+07 ± 3.66E+06 | 3.13E+07 ± 4.05E+06 | 3.38E+07 ± 7.94E+06 |
| Mean % GC ± SD Unmapped Sequences by Sample | 63.25 ± 2.63 | 62.25 ± 1.26 | 61.75 ± 1.89 | 57.25 ± 4.86 | 63.5 ± 2.38 |
| 1 | 35,828,511 | 32,462,111 | 37,529,307 | 30,376,357 | 28,439,401 |
| 2 | 34,646,581 | 36,560,220 | 38,891,929 | 31,422,812 | 44,566,522 |
| 3 | 31,489,974 | 36,089,509 | 30,919,302 | 26,751,468 | 27,224,332 |
| 4 | 28,878,937 | 29,589,837 | 33,528,091 | 36,556,057 | 34,982,683 |

Distinct Alternatively Spliced Transcriptomes from Whole Blood of Patients with ICH, Different IS Etiologies and Controls. 412 genes display DAS in the whole blood transcriptomes of patients with IS (cardioembolic, large vessel, and lacunar), ICH and controls (FDR p<0.05; Table 4). These genes are involved in cellular immunity, cytokine signaling and cell death and survival pathways (Table 5). Pathways with higher over-representation of DAS genes between groups include: CD28 signaling in T helper cells, CDC42 signaling, Nur77 signaling in T lymphocytes, fMLP signaling in neutrophils, and interferon signaling (Table 5). Molecular and cellular functions best representing the DAS genes are: cell death/survival of immune cells/leukocytes, cell-to-cell signaling and interaction, including activation, recruitment and adhesion of leukocytes, antigen presenting cells, activation of T lymphocytes, adhesion of vascular endothelial cells and immune response of neutrophils (Table 6).

Figure 2:
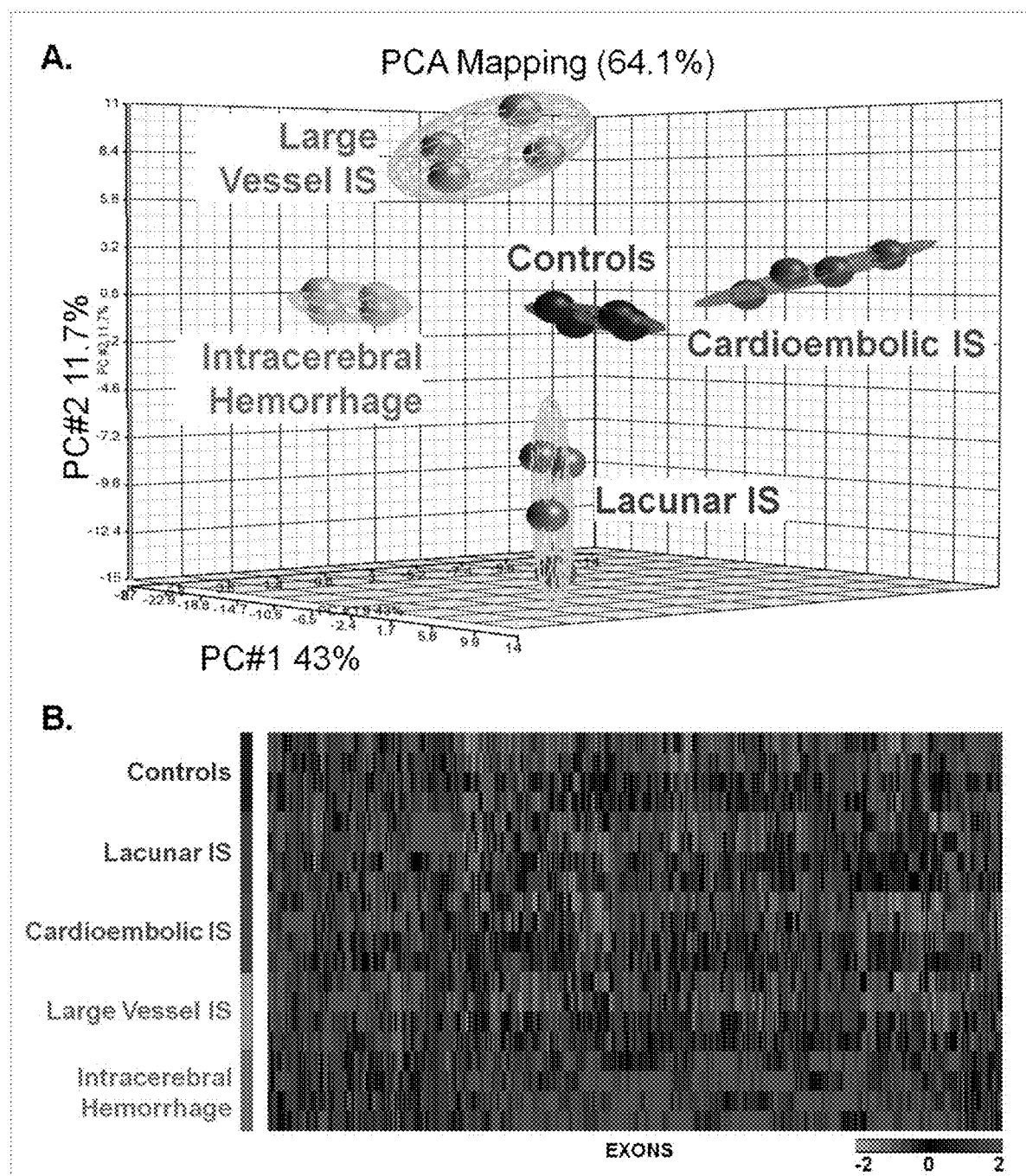
FIGS. 2A-B illustrates Principal Component Analysis (PCA) (FIG. 2A) and Unsupervised Hierarchical Clustering (FIG. 2B) of 308 exons (292 genes) with differential exon-usage among Intracerebral Hemorrhage, Ischemic Strokes (Cardioembolic, Large Vessel, and Lacunar) and Control. Dendrograms in FIG. 2B are not displayed.
Figure 3:
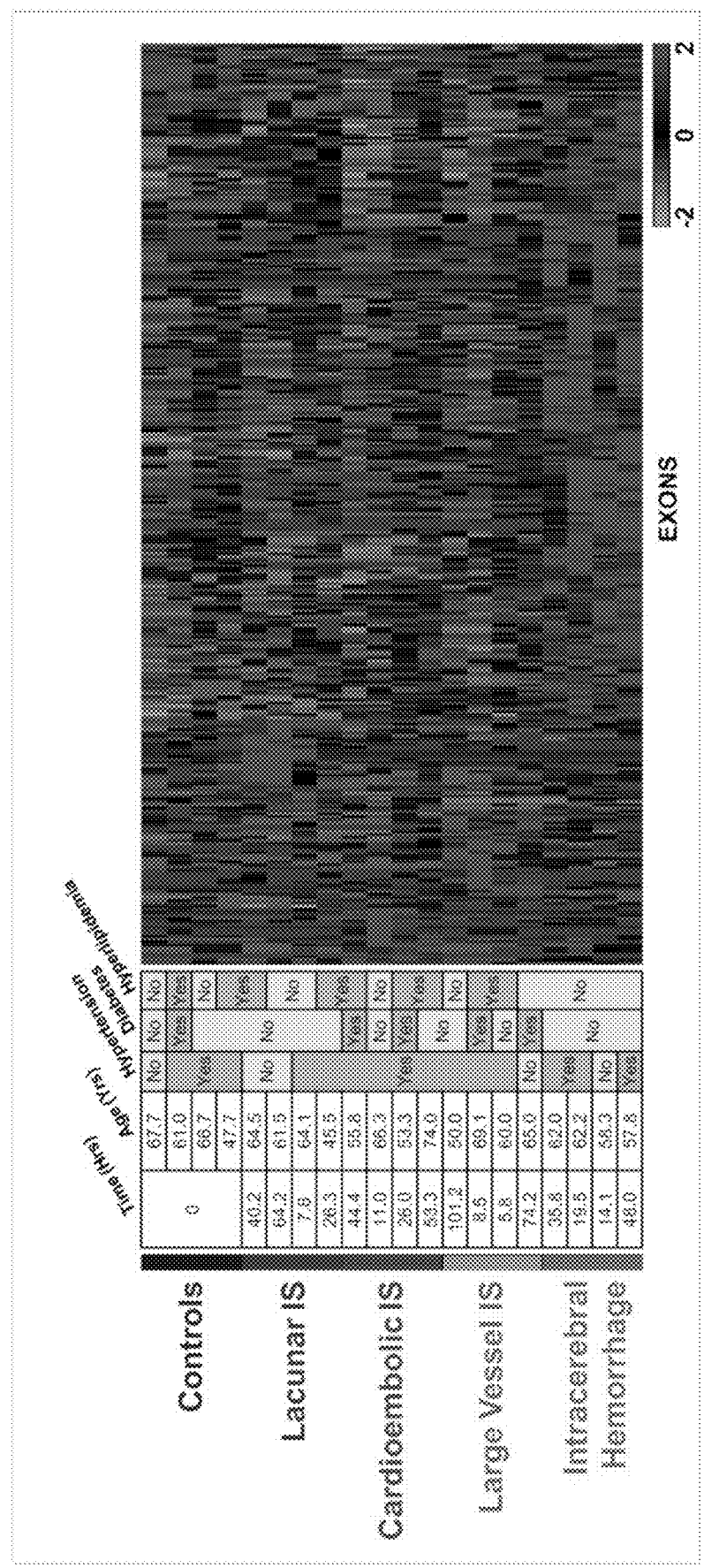
FIG. 3 illustrates Unsupervised Hierarchical Clustering of 308 exons (292 genes) with differential exon-usage among Intracerebral Hemorrhage, Ischemic Strokes (Cardioembolic, Large Vessel, and Lacunar) and Control. Dendrograms are not displayed. This is the same figure as FIG. 2B, with the addition of information on age, time since event, diabetes, hypertension and hyperlipidemia.

Specific Exon-Usage Profiles for IS and ICH. Distinct differential expression signatures based on 308 exons (292 genes) (p<0.0005, fold change>|1.2|; Table 1) separated the three causes of IS, as well as ICH and controls (PCA FIG. 2A; Unsupervised Hierarchical Clustering FIG. 2B). Biological functions and networks represented by genes with highly expressed exons in each group (in FIG. 2B) are displayed in Table 8. Cardioembolic stroke genes with differential exon usage are involved in ion binding and transport, cellular assembly and organization. Large vessel genes are associated with cell death, transcription and chromatin remodeling. Lacunar stroke genes are associated with cellular compromise, cell cycle, cell death and survival. ICH genes are involved with protein transport and localization (Table 8).

TABLE 4

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| MARCH7 | membrane-associated ring finger (C3HC4) 7 | 1.18E−05 | 9.07E−04 |
| SEPT15 | septin 5 | 3.38E−05 | 2.16E−03 |
| ABCA7 | ATP-binding cassette, sub-family A (ABC1), member 7 | 3.37E−08 | 7.73E−06 |

TABLE 4-continued

Genes (412) with Differential Alternative Splicing Among Large Vessel Ischemic Stroke
(IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| ACSL4/KCNE1L | acyl-CoA synthetase long-chain family member 4/KCNE1-like | 6.77E−05 | 3.66E−03 |
| ACTR2 | ARP2 actin-related protein 2 homolog (yeast) | 5.76E−20 | 2.57E−16 |
| ACTR3 | ARP3 actin-related protein 3 homolog (yeast) | 1.29E−03 | 3.34E−02 |
| ADCK2/NDUFB2 | aarF domain containing kinase 2/NADH dehydrogenase (ubiquinone) 1 beta subcomplex, 2, 8 kDa | 6.16E−05 | 3.42E−03 |
| ADCY7 | adenylate cyclase 7 | 6.29E−09 | 1.76E−06 |
| ADD3 | adducin 3 (gamma) | 1.14E−05 | 8.90E−04 |
| ADSS/TGIF2P1 | adenylosuccinate synthase/TGFB-induced factor homeobox 2 pseudogene 1 | 4.63E−05 | 2.67E−03 |
| AKAP8 | A kinase (PRKA) anchor protein 8 | 1.29E−03 | 3.34E−02 |
| ANAPC13 | anaphase promoting complex subunit 13 | 1.50E−03 | 3.70E−02 |
| ANKRD12 | ankyrin repeat domain 12 | 3.96E−06 | 3.97E−04 |
| ANKRD13A | ankyrin repeat domain 13A | 7.49E−05 | 3.95E−03 |
| ANXA1 | annexin A1 | 8.66E−08 | 1.65E−05 |
| ANXA7 | annexin A7 | 8.70E−06 | 7.20E−04 |
| AP1S2 | adaptor-related protein complex 1, sigma 2 subunit pseudogene; adaptor-related protein complex 1, sigma 2 subunit | 1.11E−03 | 2.93E−02 |
| APAF1 | apoptotic peptidase activating factor 1 | 1.80E−03 | 4.20E−02 |
| APH1A | anterior pharynx defective 1 homolog A (C. elegans) | 1.32E−03 | 3.40E−02 |
| APIP | APAF1 interacting protein; similar to APAF1 interacting protein | 1.35E−03 | 3.45E−02 |
| APOBEC3A/APOBEC3B | apolipoprotein B mRNA editing enzyme, catalytic polypeptide-like 3A/apolipoprotein B mRNA editing enzyme, catalytic polypeptide-like 3B | 5.87E−04 | 1.81E−02 |
| ARCN1 | archain 1 | 2.53E−04 | 9.85E−03 |
| ARFIP1/FHDC1 | ADP-ribosylation factor interacting protein 1/FH2 domain containing 1 | 1.69E−05 | 1.24E−03 |
| ARID4B/RBM34 | AT rich interactive domain 4B (RBP1-like)/RNA binding motif protein 34 | 4.36E−05 | 2.56E−03 |
| ARL6IP5 | ADP-ribosylation-like factor 6 interacting protein 5 | 2.89E−05 | 1.91E−03 |
| ARNTL | aryl hydrocarbon receptor nuclear translocator-like | 1.83E−05 | 1.32E−03 |
| ARPC3/ANAPC7 | actin related protein 2/3 complex, subunit 3, 21 kDa/anaphase promoting complex subunit 7 | 5.80E−11 | 3.45E−08 |
| ARPC4/TTLL3 | actin related protein 2/3 complex, subunit 4, 20 kDa/tubulin tyrosine ligase-like family member 3 | 3.14E−11 | 2.16E−08 |
| ARPC5L | actin related protein 2/3 complex, subunit 5-like | 2.44E−04 | 9.56E−03 |
| ATM | similar to Serine-protein kinase ATM (Ataxia telangiectasia mutated) (A-T, mutated); ataxia telangiectasia mutated | 6.24E−05 | 3.42E−03 |
| ATP2B4 | ATPase, Ca++ transporting, plasma membrane 4 | 2.42E−04 | 9.54E−03 |
| ATP5B/SNORD59A/SNORD59B | ATP synthase, H+ transporting, mitochondrial F1 complex, beta polypeptide/small nucleolar RNA, C/D box 59A/small nucleolar RNA, C/D box 59B | 3.76E−10 | 1.46E−07 |
| ATP6V1G2/BAT1(DDX39B)/SNORD84 | ATPase, H+ transporting, lysosomal 13 kDa, V1 subunit G2/DEAD (Asp-Glu-Ala-Asp) box polypeptide 39B/small nucleolar RNA, C/D box 84 | 2.39E−06 | 2.51E−04 |
| ATXN1L/KIAA0174(IST1) | ataxin 1-like/increased sodium tolerance 1 homolog (yeast) | 8.77E−05 | 4.38E−03 |
| AZIN1 | antizyme inhibitor 1 | 8.54E−04 | 2.38E−02 |
| baboy |  | 5.62E−04 | 1.76E−02 |
| BAZ1A | bromodomain adjacent to zinc finger domain, 1A | 7.63E−04 | 2.21E−02 |
| BAZ2B | bromodomain adjacent to zinc finger domain, 2B | 4.42E−04 | 1.49E−02 |
| BTN2A2/BTN3A1 | butyrophilin, subfamily 2, member A2/butyrophilin, subfamily 3, member A1 | 3.13E−06 | 3.21E−04 |
| C11orf73 | chromosome 11 open reading frame 73 | 1.71E−03 | 4.08E−02 |
| C15orf29 | chromosome 15 open reading frame 29 | 5.37E−08 | 1.17E−05 |
| C1orf59 | chromosome 1 open reading frame 59 | 5.42E−05 | 3.03E−03 |
| C1orf63 | chromosome 1 open reading frame 63 | 1.10E−12 | 1.40E−09 |
| C5orf15 | chromosome 5 open reading frame 15 | 5.26E−04 | 1.67E−02 |
| C6orf62 | chromosome 6 open reading frame 62 | 1.51E−04 | 6.62E−03 |
| C7orf27 | chromosome 7 open reading frame 27 | 7.25E−04 | 2.11E−02 |
| C9orf114 | chromosome 9 open reading frame 114 | 2.31E−04 | 9.15E−03 |
| C9orf72 | chromosome 9 open reading frame 72 | 5.43E−04 | 1.71E−02 |
| CAB39 | calcium binding protein 39 | 9.34E−05 | 4.56E−03 |
| CALM1 | calmodulin 3 (phosphorylase kinase, delta); calmodulin 2 (phosphorylase kinase, delta); calmodulin 1 (phosphorylase kinase, delta) | 2.24E−07 | 3.77E−05 |
| CALM2/C2orf61 | calmodulin 2 (phosphorylase kinase, delta)/chromosome 2 open reading frame 61 | 3.70E−12 | 3.00E−09 |
| CAPZA2 | capping protein (actin filament) muscle Z-line, alpha 2 | 6.35E−04 | 1.91E−02 |
| CARD8 | caspase recruitment domain family, member 8 | 5.51E−08 | 1.17E−05 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| CBARA1 | calcium binding atopy-related autoantigen 1 | 2.87E−04 | 1.08E−02 |
| CCAR1 | cell division cycle and apoptosis regulator 1 | 1.61E−05 | 1.19E−03 |
| CCNDBP1 | cyclin D-type binding-protein 1 | 3.17E−10 | 1.29E−07 |
| CCNY | cyclin Y | 1.68E−04 | 7.13E−03 |
| CCT8 | similar to chaperonin containing TCP1, subunit 8 (theta); chaperonin containing TCP1, subunit 8 (theta) | 2.19E−03 | 4.80E−02 |
| CD164 | CD164 molecule, sialomucin | 1.82E−05 | 1.32E−03 |
| CD244 | CD244 molecule, natural killer cell receptor 2B4 | 6.82E−04 | 2.03E−02 |
| CD300E | CD300e molecule | 1.05E−04 | 4.97E−03 |
| CD36 | CD36 molecule (thrombospondin receptor) | 2.83E−07 | 4.60E−05 |
| CD46 | CD46 molecule, complement regulatory protein | 4.46E−06 | 4.29E−04 |
| CD47 | CD47 molecule | 4.97E−15 | 9.66E−12 |
| CD53 | CD53 molecule | 1.52E−04 | 6.62E−03 |
| CD58 | CD58 molecule | 2.07E−04 | 8.41E−03 |
| CD74 | CD74 molecule, major histocompatibility complex, class II invariant chain | 6.89E−04 | 2.03E−02 |
| CD86 | CD86 molecule | 1.60E−03 | 3.88E−02 |
| CDC42SE1 | CDC42 small effector 1 | 1.70E−06 | 1.97E−04 |
| CDC42SE2 | CDC42 small effector 2 | 3.58E−04 | 1.26E−02 |
| CDKL3/PPP2CA | cyclin-dependent kinase-like 3/protein phosphatase 2, catalytic subunit, alpha isozyme | 3.66E−05 | 2.26E−03 |
| CDKN1C | cyclin-dependent kinase inhibitor 1C (p57, Kip2) | 2.33E−05 | 1.59E−03 |
| CECR1 | cat eye syndrome chromosome region, candidate 1 | 6.88E−06 | 5.97E−04 |
| CELF2 | CUG triplet repeat, RNA binding protein 2 | 3.17E−04 | 1.14E−02 |
| CFLAR/RNU7-45P | CASP8 and FADD-like apoptosis regulator/RNA, U7 small nuclear 45 pseudogene | 1.42E−08 | 3.64E−06 |
| CGGBP1 | CGG triplet repeat binding protein 1 | 7.87E−05 | 4.06E−03 |
| CHMP2B | chromatin modifying protein 2B | 1.42E−03 | 3.57E−02 |
| CLDND1 | claudin domain containing 1 | 2.13E−06 | 2.32E−04 |
| CLEC7A | C-type lectin domain family 7, member A | 8.25E−10 | 3.02E−07 |
| CLTC | clathrin, heavy chain (Hc) | 2.74E−04 | 1.04E−02 |
| CNIH | cornichon homolog (*Drosophila*) | 1.84E−04 | 7.55E−03 |
| CNOT6L | CCR4-NOT transcription complex, subunit 6-like | 6.04E−04 | 1.85E−02 |
| CNOT7 | CCR4-NOT transcription complex, subunit 7 | 2.15E−03 | 4.75E−02 |
| CNOT8 | CCR4-NOT transcription complex, subunit 8 | 3.00E−04 | 1.10E−02 |
| COMMD2 | canopy 2 homolog (zebrafish) | 1.41E−03 | 3.55E−02 |
| CRKL | COMM domain containing 2 | 1.14E−03 | 3.00E−02 |
| CSGALNACT2 | chondroitin sulfate N-acetylgalactosaminyltransferase 2; novel protein similar to chondroitin sulfate GalNAcT-2 (GALNACT-2) | 3.60E−05 | 2.26E−03 |
| CTDSP2 | similar to hCG2013701; CTD (carboxy-terminal domain, RNA polymerase II, polypeptide A) small phosphatase 2 | 5.61E−04 | 1.76E−02 |
| CTSS | cathepsin S | 1.46E−06 | 1.76E−04 |
| CYBB | cytochrome b-245, beta polypeptide | 7.15E−09 | 1.94E−06 |
| CYBRD1 | cytochrome b reductase 1 | 2.31E−05 | 1.59E−03 |
| CYLD | cylindromatosis (turban tumor syndrome) | 1.37E−03 | 3.47E−02 |
| DAP3 | death associated protein 3 | 2.13E−03 | 4.74E−02 |
| DCP2 | DCP2 decapping enzyme homolog (*S. cerevisiae*) | 3.88E−07 | 5.69E−05 |
| DDX19B/DDX19A | DEAD (Asp-Glu-Ala-Asp) box polypeptide 19B/DEAD (Asp-Glu-Ala-Asp) box polypeptide 19A | 3.10E−04 | 1.13E−02 |
| DDX3X | DEAD (Asp-Glu-Ala-Asp) box polypeptide 3, X-linked | 1.37E−12 | 1.53E−09 |
| DDX60L | DEAD (Asp-Glu-Ala-Asp) box polypeptide 60-like | 4.35E−06 | 4.27E−04 |
| DEGS1 | degenerative spermatocyte homolog 1, lipid desaturase (*Drosophila*) | 1.25E−04 | 5.67E−03 |
| DENND5A | DENN/MADD domain containing 5A | 3.64E−07 | 5.45E−05 |
| DHX40 | similar to DEAH (Asp-Glu-Ala-His) box polypeptide 40; DEAH (Asp-Glu-Ala-His) box polypeptide 40 | 7.11E−04 | 2.08E−02 |
| DMXL2 | Dmx-like 2 | 7.29E−12 | 5.43E−09 |
| DNAJB6 | DnaJ (Hsp40) homolog, subfamily B, member 6 | 1.20E−04 | 5.52E−03 |
| DNTTIP1 | deoxynucleotidyltransferase, terminal, interacting protein 1 | 1.88E−03 | 4.29E−02 |
| DPEP2/DPEP3 | dipeptidase 2/dipeptidase 3 | 5.43E−05 | 3.03E−03 |
| DPY30/MEM01 | dpy-30 homolog (*C. elegans*)/mediator of cell motility 1 | 2.26E−03 | 4.91E−02 |
| DPYD | dihydropyrimidine dehydrogenase | 8.13E−08 | 1.61E−05 |
| DTX3L | deltex 3-like (*Drosophila*) | 3.95E−04 | 1.37E−02 |
| DUSP22 | similar to mitogen-activated protein kinase phosphatase x; dual specificity phosphatase 22 | 7.74E−04 | 2.21E−02 |
| DYNC1LI1 | dynein, cytoplasmic 1, light intermediate chain 1 | 7.00E−04 | 2.06E−02 |
| DYNC1LI2 | dynein, cytoplasmic 1, light intermediate chain 2 | 3.68E−05 | 2.26E−03 |
| DYX1C1/CCPG1 | dyslexia susceptibility 1 candidate 1/cell cycle progression 1 | 7.61E−05 | 3.95E−03 |
| EAPP | E2F-associated phosphoprotein | 5.17E−04 | 1.67E−02 |
| ECHDC1 | enoyl Coenzyme A hydratase domain containing 1 | 7.45E−06 | 6.34E−04 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| ECHDC2 | enoyl Coenzyme A hydratase domain containing 2 | 9.29E−04 | 2.55E−02 |
| EGLN1 | egl nine homolog 1 (*C. elegans*) | 2.12E−04 | 8.51E−03 |
| EIF2AK2 | eukaryotic translation initiation factor 2-alpha kinase 2 | 1.63E−03 | 3.91E−02 |
| EIF2S1 | eukaryotic translation initiation factor 2, subunit 1 alpha, 35 kDa | 4.13E−04 | 1.42E−02 |
| ELP2 | elongation protein 2 homolog (*S. cerevisiae*) | 1.01E−05 | 8.06E−04 |
| EMB | embigin homolog (mouse) | 1.03E−10 | 5.41E−08 |
| EPHB4 | EPH receptor B4 | 1.48E−03 | 3.67E−02 |
| ERAP1 | endoplasmic reticulum aminopeptidase 1 | 8.18E−05 | 4.13E−03 |
| ERBB2IP | erbb2 interacting protein | 6.97E−05 | 3.73E−03 |
| ERN1 | endoplasmic reticulum to nucleus signaling 1 | 1.70E−03 | 4.07E−02 |
| ETNK1 | ethanolamine kinase 1 | 1.83E−03 | 4.23E−02 |
| FAM111B/FAM111A | family with sequence similarity 111, member B/family with sequence similarity 111, member A | 1.78E−03 | 4.16E−02 |
| FAM118A | family with sequence similarity 118, member A | 9.23E−10 | 3.13E−07 |
| FAM198B | chromosome 4 open reading frame 18 | 2.90E−04 | 1.08E−02 |
| FAM45A | family with sequence similarity 45, member A | 2.11E−04 | 8.51E−03 |
| FBXL3 | F-box and leucine-rich repeat protein 3 | 2.01E−04 | 8.22E−03 |
| FBXL5 | F-box and leucine-rich repeat protein 5 | 1.40E−06 | 1.71E−04 |
| FCER1A | Fc fragment of IgE, high affinity I, receptor for; alpha polypeptide | 6.21E−07 | 8.53E−05 |
| FKBP1A/SDCBP2 | FK506 binding protein 1A, 12 kDa/syndecan binding protein (syntenin) 2 | 1.09E−03 | 2.89E−02 |
| FNTA | farnesyltransferase, CAAX box, alpha | 2.84E−08 | 6.86E−06 |
| GALNT1 | UDP-N-acetyl-alpha-D-galactosamine:polypeptideN-acetylgalactosaminyltransferase 13 (GalNAc-T13); UDP-N-acetyl-alpha-D-galactosamine:polypeptide N-acetylgalactosaminyltransferase 1 (GalNAc-T1) | 3.80E−09 | 1.13E−06 |
| GBP4/GBP7/GBP2 | guanylate binding protein 4/guanylate binding protein 7/guanylate binding protein 2, interferon-inducible | 3.67E−05 | 2.26E−03 |
| GCA | grancalcin, EF-hand calcium binding protein | 2.92E−07 | 4.66E−05 |
| GGNBP2 | gametogenetin binding protein 2 | 1.12E−04 | 5.26E−03 |
| GHITM | growth hormone inducible transmembrane protein | 9.44E−07 | 1.22E−04 |
| GIT2 | G protein-coupled receptor kinase interacting ArfGAP 2 | 5.73E−04 | 1.78E−02 |
| GLRX | glutaredoxin (thioltransferase) | 5.22E−04 | 1.67E−02 |
| GLUD1 | glutamate dehydrogenase 1 | 4.22E−05 | 2.52E−03 |
| GMCL1 | germ cell-less homolog 1 (*Drosophila*)-like; germ cell-less homolog 1 (*Drosophila*) | 4.91E−04 | 1.62E−02 |
| GPX1 | glutathione peroxidase 1 | 1.77E−03 | 4.15E−02 |
| GSTK1 | glutathione S-transferase kappa 1 | 1.77E−04 | 7.34E−03 |
| GSTO1 | glutathione S-transferase omega 1 | 4.25E−04 | 1.44E−02 |
| GTF2I | general transcription factor II, i; general transcription factor II, i, pseudogene | 1.39E−05 | 1.04E−03 |
| GZMA | granzyme A (granzyme 1, cytotoxic T-lymphocyte-associated serine esterase 3) | 1.27E−03 | 3.31E−02 |
| H2AFZ | H2A histone family, member Z | 8.03E−04 | 2.26E−02 |
| H3F3B | H3 histone, family 3B (H3.3B); H3 histone, family 3A pseudogene; H3 histone, family 3A; similar to H3 histone, family 3B; similar to histone H3.3B | 1.90E−03 | 4.32E−02 |
| HBP1 | HMG-box transcription factor 1 | 7.69E−04 | 2.21E−02 |
| HDC | histidine decarboxylase | 1.26E−03 | 3.28E−02 |
| HERC3 | hect domain and RLD 3 | 4.70E−07 | 6.67E−05 |
| HERC5 | hect domain and RLD 5 | 1.03E−05 | 8.14E−04 |
| hetira | | 7.84E−04 | 2.22E−02 |
| HEXB | hexosaminidase B (beta polypeptide) | 3.00E−04 | 1.10E−02 |
| HIPK3 | homeodomain interacting protein kinase 3 | 2.01E−10 | 9.45E−08 |
| HLA-DMA/HLA-DMB | major histocompatibility complex, class II, DM alpha/major histocompatibility complex, class II, DM beta | 5.32E−05 | 3.01E−03 |
| HLA-DQA1 | similar to hCG2042724; similar to HLA class II histocompatibility antigen, DQ(1) alpha chain precursor (DC-4 alpha chain); major histocompatibility complex, II, DQ alpha 1 | 1.89E−03 | 4.31E−02 |
| HLA-DRB1 | major histocompatibility complex, class II, DR beta 4; major histocompatibility complex, class II, DR beta 1 | 2.35E−06 | 2.49E−04 |
| HMGB1 | high-mobility group box 1; high-mobility group box 1-like 10 | 1.45E−03 | 3.64E−02 |
| HMGCL/GALE | 3-hydroxymethyl-3-methylglutaryl-CoA lyase/UDP-galactose-4-epimerase | 1.02E−03 | 2.73E−02 |
| HMGN4 | high mobility group nucleosomal binding domain 4 | 7.64E−06 | 6.44E−04 |
| HNRNPA2B1 | heterogeneous nuclear ribonucleoprotein A2/B1 | 5.52E−06 | 4.93E−04 |
| HNRNPAB | heterogeneous nuclear ribonucleoprotein A/B | 3.04E−04 | 1.11E−02 |
| HNRNPH3 | heterogeneous nuclear ribonucleoprotein H3 (2H9) | 2.16E−06 | 2.32E−04 |
| HP1BP3 | heterochromatin protein 1, binding protein 3 | 1.62E−03 | 3.90E−02 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| HSD17B11/HSD17B13 | hydroxysteroid (17-beta) dehydrogenase 11/hydroxysteroid (17-beta) dehydrogenase 13 | 6.11E−04 | 1.86E−02 |
| HSD17B4/FAM170A | hydroxysteroid (17-beta) dehydrogenase 4/family with sequence similarity 170, member A | 2.19E−05 | 1.52E−03 |
| HSPC157 (LINC00339)/CDC42 | long intergenic non-protein coding RNA 339/cell division cycle 42 | 1.01E−03 | 2.72E−02 |
| IDH1 | isocitrate dehydrogenase 1 (NADP+), soluble | 7.39E−06 | 6.34E−04 |
| IFIH1 | interferon induced with helicase C domain 1 | 5.00E−04 | 1.65E−02 |
| IFNAR1 | interferon (alpha, beta and omega) receptor 1 | 3.13E−04 | 1.13E−02 |
| IFNGR1 | interferon gamma receptor 1 | 3.75E−11 | 2.39E−08 |
| IFRD1/C7orf53 (LSMEM1) | interferon-related developmental regulator 1/leucine-rich single-pass membrane protein 1 | 8.87E−04 | 2.44E−02 |
| IGFBP7 | insulin-like growth factor binding protein 7 | 3.17E−04 | 1.14E−02 |
| IKZF1 | IKAROS family zinc finger 1 (Ikaros) | 1.72E−03 | 4.10E−02 |
| ING4 | inhibitor of growth family, member 4 | 1.09E−06 | 1.39E−04 |
| IPMK | inositol polyphosphate multikinase | 5.25E−04 | 1.67E−02 |
| IQGAP2 | IQ motif containing GTPase activating protein 2 | 8.51E−04 | 2.38E−02 |
| ITGA4 | integrin, alpha 4 (antigen CD49D, alpha 4 subunit of VLA-4 receptor) | 5.23E−06 | 4.77E−04 |
| JAK2 | Janus kinase 2 | 5.67E−07 | 7.92E−05 |
| JMJD1C | jumonji domain containing 1C | 1.42E−05 | 1.05E−03 |
| KIAA1033 | KIAA1033 | 7.58E−05 | 3.95E−03 |
| kihire | | 2.02E−03 | 4.56E−02 |
| KLF13 | Kruppel-like factor 13 | 1.75E−03 | 4.14E−02 |
| LACTB | lactamase, beta | 2.22E−07 | 3.77E−05 |
| LAPTM4A | lysosomal protein transmembrane 4 alpha | 1.81E−03 | 4.20E−02 |
| LEMD3 | LEM domain containing 3 | 4.59E−04 | 1.54E−02 |
| LILRA3 | leukocyte immunoglobulin-like receptor, subfamily A (without TM domain), member 3 | 6.01E−04 | 1.84E−02 |
| LMBRD1 | LMBR1 domain containing 1 | 1.82E−03 | 4.21E−02 |
| LMO4 | LIM domain only 4 | 1.07E−04 | 5.08E−03 |
| LOC100093631 | general transcription factor II, i; general transcription factor II, i, pseudogene | 1.74E−04 | 7.26E−03 |
| LOC100132062 | hypothetical LOC100132062 | 2.07E−03 | 4.63E−02 |
| LOC100288778 | similar to WAS protein family homolog 1 | 1.53E−04 | 6.62E−03 |
| LOC146880 | hypothetical LOC146880 | 5.27E−04 | 1.67E−02 |
| LOC728054 | hypothetical LOC728054 | 1.76E−06 | 2.01E−04 |
| LPCAT2/CAPNS2 | lysophosphatidylcholine acyltransferase 2/calpain, small subunit 2 | 1.01E−04 | 4.87E−03 |
| LRMP | lymphoid-restricted membrane protein | 8.68E−04 | 2.42E−02 |
| LRRFIP2 | leucine rich repeat (in FLII) interacting protein 2 | 6.70E−07 | 9.07E−05 |
| LRRK2 | leucine-rich repeat kinase 2 | 2.43E−05 | 1.64E−03 |
| LTA4H | leukotriene A4 hydrolase | 8.88E−05 | 4.41E−03 |
| LY75/CD302 | lymphocyte antigen 75/CD302 molecule | 6.74E−18 | 2.01E−14 |
| MALAT1 | metastasis associated lung adenocarcinoma transcript 1 (non-protein coding) | 1.73E−04 | 7.26E−03 |
| MAN1A1 | mannosidase, alpha, class 1A, member 1 | 6.62E−05 | 3.61E−03 |
| MAT2B | methionine adenosyltransferase II, beta | 1.16E−04 | 5.41E−03 |
| MCL1 | myeloid cell leukemia sequence 1 (BCL2-related) | 2.05E−03 | 4.60E−02 |
| MED4 | mediator complex subunit 4 | 6.30E−06 | 5.52E−04 |
| MEGF9 | multiple EGF-like-domains 9 | 1.54E−03 | 3.77E−02 |
| METTL9 | methyltransferase like 9 | 7.05E−08 | 1.46E−05 |
| MFSD1 | major facilitator superfamily domain containing 1 | 2.99E−05 | 1.95E−03 |
| MGST1 | microsomal glutathione S-transferase 1 | 3.86E−05 | 2.33E−03 |
| MIAT | myocardial infarction associated transcript (non-protein coding) | 9.16E−08 | 1.70E−05 |
| MICA/HCP5 | MHC class I polypeptide-related sequence A/HLA complex P5 (non-protein coding) | 2.15E−05 | 1.50E−03 |
| MLX | MAX-like protein X | 2.24E−03 | 4.89E−02 |
| MMADHC | methylmalonic aciduria (cobalamin deficiency) cbID type, with homocystinuria | 1.65E−04 | 7.08E−03 |
| MOBKL1B | MOB1, Mps One Binder kinase activator-like 1B (yeast) | 7.62E−11 | 4.25E−08 |
| MPPE1 | metallophoesterase 1 | 4.29E−13 | 6.39E−10 |
| MRPL15 | mitochondrial ribosomal protein L15 | 6.55E−04 | 1.96E−02 |
| MS4A6E/MS4A7/MS4A14 | membrane-spanning 4-domains, subfamily A, member 6E/membrane-spanning 4-domains, subfamily A, member 7/membrane-spanning 4-domains, subfamily A, member 14 | 1.84E−04 | 7.55E−03 |
| MSMB/NCOA4 | microseminoprotein, beta-/nuclear receptor coactivator 4 | 9.13E−06 | 7.48E−04 |
| MTCH1 | mitochondrial carrier homolog 1 (C. elegans) | 1.04E−03 | 2.76E−02 |
| MTMR1 | myotubularin related protein 1 | 7.73E−04 | 2.21E−02 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| MTMR6 | myotubularin related protein 6 | 5.13E−04 | 1.67E−02 |
| MTO1 | mitochondrial translation optimization 1 homolog (S. cerevisiae) | 3.83E−05 | 2.33E−03 |
| MTPN/LUZP6 | myotrophin/leucine zipper protein 6 | 5.15E−04 | 1.67E−02 |
| MX1 | myxovirus (influenza virus) resistance 1, interferon-inducible protein p78 (mouse) | 3.36E−12 | 3.00E−09 |
| MYL12A | myosin, light chain 12A, regulatory, non-sarcomeric | 1.66E−06 | 1.95E−04 |
| MYLIP | myosin regulatory light chain interacting protein | 1.61E−03 | 3.88E−02 |
| NAB1 | NGFI-A binding protein 1 (EGR1 binding protein 1) | 7.51E−05 | 3.95E−03 |
| NAP1L1 | nucleosome assembly protein 1-like 1 | 1.58E−03 | 3.84E−02 |
| NAPSB | napsin B aspartic peptidase pseudogene | 5.81E−06 | 5.14E−04 |
| NARS | asparaginyl-tRNA synthetase | 1.26E−04 | 5.70E−03 |
| NBPF9/NOTCH2NL/NBPF10 | neuroblastoma breakpoint family, member 9/notch 2 N-terminal like/neuroblastoma breakpoint family, member 10 | 7.79E−04 | 2.21E−02 |
| NBR2/NBR1 | neighbor of BRCA1 gene 2 (non-protein coding)/neighbor of BRCA1 gene 1 | 1.77E−03 | 4.15E−02 |
| NCRNA00189 (LINC00189)/GAPDHP14/BACH1 | long intergenic non-protein coding RNA 189/glyceraldehyde-3-phosphate dehydrogenase pseudogene 14/BTB and CMC homology 1, basic leucine zipper transcription factor 1 | 4.89E−06 | 4.50E−04 |
| NDFIP1 | Nedd4 family interacting protein 1 | 2.26E−03 | 4.91E−02 |
| NEK9 | NIMA (never in mitosis gene a)- related kinase 9 | 2.94E−04 | 1.09E−02 |
| NFE2L2 | nuclear factor (erythroid-derived 2)-like 2 | 3.18E−04 | 1.14E−02 |
| NR3C1 | nuclear receptor subfamily 3, group C, member 1 (glucocorticoid receptor) | 3.02E−06 | 3.14E−04 |
| NSUN2 | NOL1/NOP2/Sun domain family, member 2 | 8.40E−06 | 7.02E−04 |
| OAS2 | 2′-5′-oligoadenylate synthetase 2, 69/71 kDa | 2.12E−04 | 8.51E−03 |
| OAS3 | 2′-5′-oligoadenylate synthetase 3, 100 kDa | 1.07E−03 | 2.84E−02 |
| OAZ2 | ornithine decarboxylase antizyme 2 | 7.72E−04 | 2.21E−02 |
| OGFRL1 | opioid growth factor receptor-like 1 | 4.09E−04 | 1.42E−02 |
| PAFAH1B1 | platelet-activating factor acetylhydrolase, isoform Ib, subunit 1 (45 kDa) | 4.60E−05 | 2.67E−03 |
| PAN2/CNPY2/CS | PAN2 poly(A) specific ribonuclease subunit/canopy FGF signaling regulator 2/citrate synthase | 2.94E−05 | 1.93E−03 |
| PAPOLA | poly(A) polymerase alpha | 1.41E−03 | 3.55E−02 |
| PARP14 | poly (ADP-ribose) polymerase family, member 14 | 3.54E−08 | 7.91E−06 |
| PARP9 | poly (ADP-ribose) polymerase family, member 9 | 1.25E−04 | 5.67E−03 |
| PCMTD2 | protein-L-isoaspartate (D-aspartate) O-methyltransferase domain containing 2 | 9.19E−05 | 4.51E−03 |
| PDPR | pyruvate dehydrogenase phosphatase regulatory subunit | 3.87E−04 | 1.35E−02 |
| PELI1 | pellino homolog 1 (Drosophila) | 2.46E−07 | 4.07E−05 |
| PGK1 | phosphoglycerate kinase 1 | 2.08E−05 | 1.48E−03 |
| PHB2/SCARNA12 | prohibitin 2/SCARNA12 | 6.25E−04 | 1.89E−02 |
| PHIP/TRNAF13P (TRF-GAA8-1) | pleckstrin homology domain interacting protein/transfer RNA-Phe (GAA) 8-1 | 2.70E−04 | 1.04E−02 |
| PJA2 | praja ring finger 2 | 4.33E−06 | 4.27E−04 |
| PLCL2 | phospholipase C-like 2 | 1.94E−03 | 4.40E−02 |
| PLDN (BLOC1S6)/SQRDL | biogenesis of lysosomal organelles complex-1, subunit 6, pallidin/sulfide quinone reductase-like (yeast) | 2.21E−03 | 4.84E−02 |
| PLEK | pleckstrin | 1.86E−09 | 5.93E−07 |
| PLEKHB2 | pleckstrin homology domain containing, family B (evectins) member 2 | 3.65E−07 | 5.45E−05 |
| PLEKHM1P | pleckstrin homology domain containing, family M (with RUN domain) member 1 pseudogene | 4.23E−04 | 1.44E−02 |
| PNRC1 | proline-rich nuclear receptor coactivator 1 | 1.57E−03 | 3.82E−02 |
| PPIL3/CLK1 | peptidylprolyl isomerase (cyclophilin)-like 3/CDC-like kinase 1 | 5.88E−04 | 1.81E−02 |
| PPP1CB/SPDYA | protein phosphatase 1, catalytic subunit, beta isozyme/speedy/RINGO cell cycle regulator family member A | 4.45E−06 | 4.29E−04 |
| PPP1CC | protein phosphatase 1, catalytic subunit, gamma isoform | 8.17E−05 | 4.13E−03 |
| PPP1R15B | protein phosphatase 1, regulatory (inhibitor) subunit 15B | 1.38E−03 | 3.50E−02 |
| PPP2R5A | protein phosphatase 2, regulatory subunit B′, alpha isoform | 1.25E−07 | 2.24E−05 |
| PPP3CB | protein phosphatase 3 (formerly 2B), catalytic subunit, beta isoform | 2.19E−04 | 8.68E−03 |
| PPP3R1/WDR92 | protein phosphatase 3, regulatory subunit B, alpha/WD repeat domain 92 | 1.50E−06 | 1.79E−04 |
| PPP4R1 | protein phosphatase 4, regulatory subunit 1 | 5.17E−04 | 1.67E−02 |
| PPP6C | protein phosphatase 6, catalytic subunit | 1.84E−04 | 7.55E−03 |
| PPTC7 | PTC7 protein phosphatase homolog (S. cerevisiae) | 4.64E−05 | 2.67E−03 |
| PRCP | prolylcarboxypeptidase (angiotensinase C) | 1.01E−03 | 2.72E−02 |
| PRMT2 | protein arginine methyltransferase 2 | 1.75E−03 | 4.14E−02 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| PRNP | prion protein | 5.70E−04 | 1.77E−02 |
| PRPF38B | PRP38 pre-mRNA processing factor 38 (yeast) domain containing B | 7.61 E−04 | 2.21E−02 |
| PSMA1/COPB1 | proteasome (prosome, macropain) subunit, alpha type, 1/coatomer protein complex, subunit beta 1 | 2.16E−03 | 4.76E−02 |
| PSMB3 | proteasome (prosome, macropain) subunit, beta type, 3 | 2.03E−03 | 4.56E−02 |
| PSMB8 | proteasome (prosome, macropain) subunit, beta type, 8 (large multifunctional peptidase 7) | 6.21E−05 | 3.42E−03 |
| PSMD13 | proteasome (prosome, macropain) 26S subunit, non-ATPase, 13 | 8.66E−07 | 1.14E−04 |
| PSMD6 | proteasome (prosome, macropain) 26S subunit, non-ATPase, 6 | 3.66E−07 | 5.45E−05 |
| PTGER4 | prostaglandin E receptor 4 (subtype EP4) | 6.30E−04 | 1.90E−02 |
| PTPRC | protein tyrosine phosphatase, receptor type, C | 1.77E−23 | 1.59E−19 |
| PXK | PX domain containing serine/threonine kinase | 2.74E−04 | 1.04E−02 |
| RAB10 | RAB10, member RAS oncogene family | 8.67E−07 | 1.14E−04 |
| RAB1A | RAB1A, member RAS oncogene family | 1.18E−04 | 5.47E−03 |
| RAB32 | RAB32, member RAS oncogene family | 1.48E−03 | 3.67E−02 |
| RAB6A | RAB6C, member RAS oncogene family; RAB6A, member RAS oncogene family; hypothetical LOC100130819; RAB6C-like | 1.20E−04 | 5.51E−03 |
| RAB8B | RAB8B, member RAS oncogene family | 2.86E−04 | 1.08E−02 |
| RAD21 | RAD21 homolog (S. pombe) | 2.14E−03 | 4.74E−02 |
| RAF1 | v-raf-1 murine leukemia viral oncogene homolog 1 | 4.83E−04 | 1.61E−02 |
| RAP1A | RAP1A, member of RAS oncogene family | 4.21E−09 | 1.21E−06 |
| RAP1B | RAP1B, member of RAS oncogene family | 3.01E−12 | 2.99E−09 |
| RASSF3 | Ras association (RalGDS/AF-6) domain family member 3 | 1.51E−03 | 3.70E−02 |
| RBBP4 | hypothetical LOC642954; retinoblastoma binding protein 4 | 9.69E−04 | 2.64E−02 |
| RBL2 | retinoblastoma-like 2 (p130) | 4.62E−06 | 4.30E−04 |
| RECQL | RecQ protein-like (DMA helicase Q1-like) | 4.93E−05 | 2.82E−03 |
| RFWD2 | ring finger and WD repeat domain 2 | 9.23E−06 | 7.50E−04 |
| RGS18 | regulator of G-protein signaling 18 | 8.81E−04 | 2.43E−02 |
| RICTOR | RPTOR independent companion of MTOR, complex 2 | 3.07E−08 | 7.22E−06 |
| RILPL2 | Rab interacting lysosomal protein-like 2 | 4.59E−06 | 4.30E−04 |
| RIT1 | Ras-like without CAAX 1 | 1.18E−04 | 5.47E−03 |
| RNF103/VPS24 (CHMP3) | ring finger protein 103/charged multivesicular body protein 3 | 5.29E−04 | 1.67E−02 |
| RNF13 | ring finger protein 13 | 1.73E−08 | 4.30E−06 |
| RNF141 | ring finger protein 141 | 1.20E−05 | 9.15E−04 |
| RNF145 | ring finger protein 145 | 7.82E−09 | 2.06E−06 |
| RNF213 | ring finger protein 213 | 1.13E−10 | 5.60E−08 |
| RNF31/IRF9 | ring finger protein 31/interferon regulatory factor 9 | 2.70E−04 | 1.04E−02 |
| RNF5 | ring finger protein 5; ring finger protein 5 pseudogene 1 | 1.97E−03 | 4.45E−02 |
| RNF6 | ring finger protein (C3H2C3 type) 6 | 4.21E−04 | 1.44E−02 |
| ROCK1 | similar to Rho-associated, coiled-coil containing protein kinase 1; Rho-associated, coiled-coil containing protein kinase 1 | 1.46E−03 | 3.65E−02 |
| RPL14.1 | ribosomal protein L14 | 1.80E−03 | 4.19E−02 |
| S100A6 | S100 calcium binding protein A6 | 1.51E−03 | 3.70E−02 |
| SACM1L | SAC1 suppressor of actin mutations 1-like (yeast) | 5.04E−04 | 1.66E−02 |
| SAR1A/TYSND1/AIFM2 | secretion associated, Ras related GTPase 1A/trypsin domain containing 1/apoptosis-inducing factor, mitochondrion-associated, 2 | 3.26E−07 | 5.12E−05 |
| SCP2 | sterol carrier protein 2 | 4.97E−05 | 2.83E−03 |
| SCPEP1 | serine carboxypeptidase 1 | 8.05E−05 | 4.11E−03 |
| SDHD | succinate dehydrogenase complex, subunit D, integral membrane protein | 2.18E−03 | 4.80E−02 |
| SEC22B | SEC22 vesicle trafficking protein homolog B (S. cerevisiae) | 4.13E−04 | 1.42E−02 |
| SEC61B | Sec61 beta subunit | 8.05E−05 | 4.11E−03 |
| SELE/SELL | selectin E/selectin L | 2.96E−04 | 1.10E−02 |
| SENP6 | SUMO1/sentrin specific peptidase 6 | 1.73E−03 | 4.10E−02 |
| SEPT5/GP1BB | septin 5/glycoprotein Ib (platelet), beta polypeptide | 1.31E−03 | 3.38E−02 |
| SERINC1 | serine incorporator 1 | 1.36E−07 | 2.39E−05 |
| SERINC3 | serine incorporator 3 | 1.02E−04 | 4.88E−03 |
| SKAP2 | src kinase associated phosphoprotein 2 | 1.03E−03 | 2.76E−02 |
| SKIV2L2 | superkiller viralicidic activity 2-like 2 (S. cerevisiae) | 1.61E−04 | 6.94E−03 |
| SLA | Src-like-adaptor | 3.32E−04 | 1.18E−02 |
| SLBP | stem-loop binding protein | 1.87E−03 | 4.29E−02 |
| SLC12A7 | solute carrier family 12 (potassium/chloride transporters), member 7 | 2.26E−03 | 4.91E−02 |
| SLC25A37 | solute carrier family 25, member 37 | 9.13E−05 | 4.51E−03 |
| SLK | STE20-like kinase (yeast) | 1.49E−04 | 6.55E−03 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| SLU7 | SLU7 splicing factor homolog (S. cerevisiae) | 8.40E−04 | 2.36E−02 |
| SMAP2 | small ArfGAP2 | 1.92E−03 | 4.35E−02 |
| SMARCA5 | SWI/SNF related, matrix associated, actin dependent regulator of chromatin, subfamily a, member 5 | 9.51E−04 | 2.60E−02 |
| SMCHD1 | structural maintenance of chromosomes flexible hinge domain containing 1 | 2.21E−10 | 9.86E−08 |
| SNX10 | sorting nexin 10 | 1.40E−06 | 1.71E−04 |
| SNX14 | sorting nexin 14 | 2.09E−06 | 2.30E−04 |
| SNX2 | sorting nexin 2 | 1.60E−03 | 3.88E−02 |
| SNX6 | sorting nexin 6 | 3.38E−05 | 2.16E−03 |
| SP140L/SP100/HMGB1L3 | SP140 nuclear body protein-like/SP100 nuclear antigen/high mobility group box 1 pseudogene 3 | 1.69E−04 | 7.17E−03 |
| SPATA13/C1QTNF9 | spermatogenesis associated 13/C1q and tumor necrosis factor related protein 9 | 1.80E−06 | 2.01E−04 |
| SPCS3 | signal peptidase complex subunit 3 homolog (S. cerevisiae) | 4.54E−06 | 4.30E−04 |
| SPOPL | speckle-type POZ protein-like | 8.45E−10 | 3.02E−07 |
| SPPL2A | signal peptide peptidase-like 2A | 3.22E−05 | 2.08E−03 |
| SRI | sorcin | 3.49E−06 | 3.54E−04 |
| SRP9/EPHX1 | signal recognition particle 9 kDa/epoxide hydrolase 1, microsomal (xenobiotic) | 7.37E−08 | 1.50E−05 |
| SSFA2 | sperm specific antigen 2 | 9.73E−04 | 2.64E−02 |
| ST8SIA4 | ST8 alpha-N-acetyl-neuraminide alpha-2,8-sialyltransferase 4 | 1.14E−03 | 3.00E−02 |
| STAT1 | signal transducer and activator of transcription 1, 91 kDa | 8.77E−04 | 2.43E−02 |
| STOM | stomatin | 4.35E−05 | 2.56E−03 |
| STXBP3 | syntaxin binding protein 3 | 1.24E−06 | 1.56E−04 |
| SURF4 | surfeit 4 | 1.20E−03 | 3.15E−02 |
| SYTL2 | synaptotagmin-like 2 | 9.74E−04 | 2.64E−02 |
| TAF1 | TAF1 RNA polymerase II, TATA box binding protein (TBP)-associated factor, 250 kDa | 4.42E−04 | 1.49E−02 |
| TAGAP | T-cell activation RhoGTPase activating protein | 1.01E−04 | 4.87E−03 |
| TAX1BP1 | Tax1 (human T-cell leukemia virus type I) binding protein 1 | 1.91E−05 | 1.36E−03 |
| TBC1D2B | TBC1 domain family, member 2B | 6.79E−05 | 3.66E−03 |
| TCF25/MC1R/TUBB3 | transcription factor 25 (basic helix-loop-helix)/melanocortin 1 receptor (alpha melanocyte stimulating hormone receptor)/tubulin, beta 3 class III | 2.12E−09 | 6.52E−07 |
| TCP11L2 | t-complex 11 (mouse)-like 2 | 3.73E−04 | 1.31E−02 |
| TDG | similar to G/T mismatch-specific thymine DMA glycosylase; thymine-DNA glycosylase | 1.87E−03 | 4.29E−02 |
| TDP2 | tyrosyl-DNA phosphodiesterase 2 | 1.70E−03 | 4.07E−02 |
| TES | testis derived transcript (3 LIM domains) | 2.74E−04 | 1.04E−02 |
| TGFBR2 | transforming growth factor, beta receptor II (70/80 kDa) | 1.05E−04 | 4.97E−03 |
| TM9SF2 | transmembrane 9 superfamily member 2 | 2.95E−10 | 1.25E−07 |
| TM9SF3 | transmembrane 9 superfamily member 3 | 1.74E−04 | 7.26E−03 |
| TMCC1 | transmembrane and coiled-coil domain family 1 | 2.13E−04 | 8.52E−03 |
| TMCO3 | transmembrane and coiled-coil domains 3 | 7.11E−05 | 3.78E−03 |
| TMEM167B | transmembrane protein 167B | 2.78E−05 | 1.85E−03 |
| TMEM222 | transmembrane protein 222 | 1.41E−04 | 6.27E−03 |
| TMEM49 | transmembrane protein 49 | 5.38E−06 | 4.86E−04 |
| TMEM59 | transmembrane protein 59 | 8.49E−05 | 4.26E−03 |
| TMSB4X | thymosin-like 2 (pseudogene); thymosin-like 1 (pseudogene); thymosin beta 4, X-linked | 6.06E−04 | 1.85E−02 |
| TNFSF13B | tumor necrosis factor (ligand) superfamily, member 13b | 3.47E−04 | 1.23E−02 |
| TNKS2 | tankyrase, TRF1-interacting ankyrin-related ADP-ribose polymerase 2 | 8.73E−04 | 2.42E−02 |
| TNPO3 | transportin 3 | 4.02E−05 | 2.41E−03 |
| TOPORS/DDX58 | topoisomerase I binding, arginine/serine-rich, E3 ubiquitin protein ligase/DEAD (Asp-Glu-Ala-Asp) box polypeptide 58 | 6.89E−04 | 2.03E−02 |
| TOR1A | torsin family 1, member A (torsin A) | 1.11E−07 | 2.02E−05 |
| TOR1AIP1 | torsin A interacting protein 1 | 5.49E−04 | 1.73E−02 |
| TPM3 | tropomyosin 3 | 4.32E−07 | 6.23E−05 |
| TRAM1 | translocation associated membrane protein 1 | 1.79E−06 | 2.01E−04 |
| TRPC4AP | transient receptor potential cation channel, subfamily C, member 4 associated protein | 1.30E−05 | 9.81E−04 |
| TSNAX/DISC1 | translin-associated factor X/disrupted in schizophrenia 1 | 4.89E−04 | 1.62E−02 |
| TSPAN14 | tetraspanin 14 | 1.16E−05 | 8.98E−04 |
| TXNRD1 | thioredoxin reductase 1; hypothetical LOC100130902 | 8.52E−08 | 1.65E−05 |
| U2AF1 | U2 small nuclear RNA auxiliary factor 1 | 3.82E−05 | 2.33E−03 |
| UBE2B | ubiquitin-conjugating enzyme E2B (RAD6 homolog) | 2.65E−04 | 1.02E−02 |
| UBE2E3 | ubiquitin-conjugating enzyme E2E 3 (UBC4/5 homolog, yeast) | 6.50E−04 | 1.95E−02 |

TABLE 4-continued

Genes (412) with Differential Alternative Splicing Among Large Vessel Ischemic Stroke (IS), Cardioembolic IS, Lacunar IS, Intracerebral Hemorrhage and Controls

| Gene Symbol | Gene Name | alt-splicing (Dx) | stepup (alt-splicing (Dx)) |
|---|---|---|---|
| UBL7 | ubiquitin-like 7 (bone marrow stromal cell-derived) | 2.09E−03 | 4.66E−02 |
| UBR2 | ubiquitin protein ligase E3 component n-recognin 2 | 7.78E−04 | 2.21E−02 |
| UHMK1 | U2AF homology motif (UHM) kinase 1 | 1.28E−03 | 3.32E−02 |
| USP1 | ubiquitin specific peptidase 1 | 1.36E−03 | 3.47E−02 |
| USP15 | ubiquitin specific peptidase 15 | 2.60E−05 | 1.75E−03 |
| USP33 | ubiquitin specific peptidase 33 | 7.17E−04 | 2.09E−02 |
| UTRN | utrophin | 5.40E−15 | 9.66E−12 |
| VAMP3 | vesicle-associated membrane protein 3 (cellubrevin) | 1.62E−04 | 6.94E−03 |
| VCP | valosin-containing protein | 6.72E−04 | 2.00E−02 |
| VNN2 | vanin 2 | 1.49E−03 | 3.69E−02 |
| VPS13C | vacuolar protein sorting 13 homolog C (*S. cerevisiae*) | 3.31E−04 | 1.18E−02 |
| WARS | tryptophanyl-tRNA synthetase | 1.44E−04 | 6.37E−03 |
| WDFY2 | WD repeat and FYVE domain containing 2 | 1.87E−03 | 4.29E−02 |
| WSB1 | WD repeat and SOCS box-containing 1 | 1.39E−04 | 6.20E−03 |
| yakeme | | 5.07E−04 | 1.66E−02 |
| YIPF4 | Yip1 domain family, member 4 | 2.65E−04 | 1.02E−02 |
| YWHAE | similar to 14-3-3 protein epsilon (14-3-3E) (Mitochondrial import stimulation factor L subunit) (MSF L); tyrosine 3-monooxygenase/tryptophan 5-monooxygenase activation protein, epsilon polypeptide | 9.45E−10 | 3.13E−07 |
| ZBED5/EIF4G2/SNORD97 | zinc finger, BED-type containing 5/eukaryotic translation initiation factor 4 gamma, 2/small nucleolar RNA, C/D box 97 | 4.27E−04 | 1.45E−02 |
| ZCCHC6 | zinc finger, CCHC domain containing 6 | 3.66E−05 | 2.26E−03 |
| ZEB2/GTDC1 | zinc finger E-box binding homeobox 2/glycosyltransferase-like domain containing 1 | 1.36E−04 | 6.12E−03 |
| ZFAND5 | zinc finger, AN1-type domain 5 | 2.10E−05 | 1.48E−03 |
| ZFP91-CNTF | zinc finger protein 91 homolog (mouse); ZFP91-CNTF readthrough transcript; ciliary neurotrophic factor | 9.98E−06 | 8.03E−04 |
| ZNF516 | zinc finger protein 516 | 2.98E−04 | 1.10E−02 |
| ZNF592 | zinc finger protein 592 | 1.35E−03 | 3.45E−02 |

TABLE 5

Canonical Pathways of the 412 Genes with Differential Alternative Splicing Among Large Vessel Ischemic Stroke (IS), Cardioembolic IS, Lacunar IS, Intracerebral Hemorrhage and Controls. B-H-Benjamini-Hochberg corrected p-value

| Ingenuity Canonical Pathways | -log(p-value) | -log(B-H p-value) | Ratio | Molecules |
|---|---|---|---|---|
| CD28 Signaling in T Helper Cells | 8.11E00 | 5.54E00 | 1.36E−01 | CDC42, ACTR2, CALM1 (includes others), ARPC3, HLA-DQA1, ATM, PPP3CB, ARPC5L, ACTR3, HLA-DRB1, PPP3R1, HLA-DMA, ARPC4, HLA-DMB, PTPRC, CD86 |
| Cdc42 Signaling | 5.99E00 | 3.72E00 | 9.58E−02 | CDC42, ACTR2, ARPC3, HLA-DQA1, RAF1, CDC42SE1, MYL12A, ARPC5L, ACTR3, HLA-DRB1, HLA-DMA, ARPC4, HLA-DMB, PPP1CB, ITGA4, IQGAP2 |
| Nur77 Signaling in T Lymphocytes | 5.38E00 | 3.33E00 | 1.58E−01 | HLA-DRB1, CALM1 (includes others), PPP3R1, APAF1, HLA-DMA, HLA-DQA1, HLA-DMB, PPP3CB, CD86 |
| fMLP Signaling in Neutrophils | 5.3E00 | 3.33E00 | 1.11E−01 | CDC42, ACTR2, CALM1 (includes others), PPP3R1, ARPC3, RAF1, ARPC4, ATM, PPP3CB, ARPC5L, CYBB, ACTR3 |
| Interferon Signaling | 4.92E00 | 3.04E00 | 1.94E−01 | IFNGR1, IRF9, JAK2, STAT1, MX1, IFNAR1, PSMB8 |
| Rac Signaling | 4.7E00 | 2.91E00 | 1.06E−01 | CDC42, ACTR2, ARPC3, RAF1, ARPC4, ATM, ITGA4, IQGAP2, ARPC5L, CYBB, ACTR3 |
| Actin Nucleation by ARP-WASP Complex | 4.51E00 | 2.83E00 | 1.43E−01 | CDC42, ACTR2, ARPC3, ARPC4, ROCK1, ITGA4, ARPC5L, ACTR3 |
| Regulation of Actin-based Motility by Rho | 4.47E00 | 2.83E00 | 1.1E−01 | CDC42, ACTR2, ARPC3, ARPC4, MYL12A, PPP1CB, ROCK1, ITGA4, ARPC5L, ACTR3 |
| Ephrin Receptor Signaling | 4.45E00 | 2.83E00 | 8.05E−02 | CDC42, ACTR2, JAK2, ARPC3, EPHB4, CRKL, RAF1, ARPC5L, RAP1A, ACTR3, ARPC4, RAP1B, ROCK1, ITGA4 |
| Integrin Signaling | 4.32E00 | 2.75E00 | 7.43E−02 | CDC42, ACTR2, ARPC3, CRKL, RAF1, ATM, MYL12A, ARPC5L, RAP1A, ACTR3, ARPC4, RAP1B, PPP1CB, ROCK1, ITGA4 |
| Protein Kinase A Signaling | 4.28E00 | 2.75E00 | 5.73E−02 | ANAPC13, PPP1CC, TDP2, CALM1 (includes others), MPPE1, ADCY7, RAF1, AKAP8, MYL12A, H3F3A/H3F3B, PPP3CB, YWHAE, RAP1A, ADD3, TGFBR2, PPP3R1, RAP1B, PPP1CB, ROCK1, PLCL2, PTPRC, ANAPC7 |
| B Cell Development | 4.04E00 | 2.54E00 | 1.76E−01 | HLA-DRB1, HLA-DMA, HLA-DQA1, HLA-DMB, PTPRC, CD86 |
| Actin Cytoskeleton Signaling | 3.97E00 | 2.51E00 | 6.91E−02 | CDC42, ACTR2, ARPC3, CRKL, RAF1, ATM, MYL12A, ARPC5L, ACTR3, ARPC4, PPP1CB, ROCK1, ITGA4, IQGAP2, TMSB10/TMSB4X |

TABLE 5-continued

Canonical Pathways of the 412 Genes with Differential Alternative Splicing Among Large Vessel Ischemic Stroke (IS), Cardioembolic IS, Lacunar IS, Intracerebral Hemorrhage and Controls. B-H=Benjamini-Hochberg corrected p-value

| Ingenuity Canonical Pathways | -log(p-value) | -log(B-H p-value) | Ratio | Molecules |
|---|---|---|---|---|
| Antigen Presentation Pathway | 3.83E00 | 2.4E00 | 1.62E-01 | HLA-DRB1, CD74, HLA-DMA, HLA-DQA1, HLA-DMB, PSMB8 |
| Role of JAK1, JAK2 and TYK2 in Interferon Signaling | 3.8E00 | 2.4E00 | 2.08E-01 | IFNGR1, JAK2, STAT1, RAF1, IFNAR1 |
| T Helper Cell Differentiation | 3.76E00 | 2.39E00 | 1.13E-01 | IFNGR1, TGFBR2, HLA-DRB1, HLA-DMA, HLA-DQA1, STAT1, HLA-DMB, CD86 |
| Calcium-induced T Lymphocyte Apoptosis | 3.28E00 | 1.96E00 | 1.09E-01 | HLA-DRB1, CALM1 (includes others), PPP3R1, HLA-DMA, HLA-DQA1, HLA-DMB, PPP3CB |
| Retinoic acid Mediated Apoptosis Signaling | 3.28E00 | 1.96E00 | 1.09E-01 | CFLAR, APAF1, TNKS2, PARP9, PARP14, DAP3, IFNAR1 |
| iCOS-iCOSL Signaling in T Helper Cells | 3.17E00 | 1.9E00 | 8.33E-02 | HLA-DRB1, CALM1 (includes others), PPP3R1, HLA-DMA, HLA-DQA1, ATM, HLA-DMB, PPP3CB, PTPRC |
| Dendritic Cell Maturation | 3.17E00 | 1.9E00 | 6.7E-02 | HLA-DRB1, JAK2, HLA-DMA, HLA-DQA1, CD58, STAT1, ATM, HLA-DMB, PLCL2, LY75, CD86, IFNAR1 |
| NRF2-mediated Oxidative Stress Response | 3.15E00 | 1.9E00 | 6.67E-02 | GSTO1, BACH1, RAF1, ATM, UBE2E3, TXNRD1, EPHX1, DNAJB6, VCP, GSTK1, MGST1, NFE2L2 |
| Type I Diabetes Mellitus Signaling | 3.11E00 | 1.88E00 | 8.18E-02 | IFNGR1, HLA-DRB1, APAF1, JAK2, HLA-DMA, HLA-DQA1, STAT1, HLA-DMB, CD86 |
| IL-3 Signaling | 3.01E00 | 1.81E00 | 9.86E-02 | PPP3R1, JAK2, CRKL, STAT1, RAF1, ATM, PPP3CB |
| ERK/MAPK Signaling | 3E00 | 1.81E00 | 6.42E-02 | PPP1CC, PPP2R5A, CRKL, STAT1, RAF1, ATM, RAP1B, H3F3A/H3F3B, PPP1CB, ITGA4, RAP1A, PPP2CA |
| Breast Cancer Regulation by Stathmin1 | 2.92E00 | 1.75E00 | 6.28E-02 | PPP1CC, CDC42, CALM1 (includes others), UHMK1, PPP2R5A, TUBB3, ADCY7, RAF1, ATM, PPP1CB, ROCK1, PPP2CA |
| Synaptic Long Term Potentiation | 2.87E00 | 1.71E00 | 7.56E-02 | PPP1CC, CALM1 (includes others), PPP3R1, RAF1, RAP1B, PPP3CB, PPP1CB, PLCL2, RAP1A |
| Ascorbate Recycling (Cytosolic) | 2.84E00 | 1.71E00 | 6.67E-01 | GSTO1, GLRX |
| IL-4 Signaling | 2.83E00 | 1.71E00 | 9.21E-02 | HLA-DRB1, JAK2, HLA-DMA, HLA-DQA1, NR3C1, ATM, HLA-DMB |
| Role of NFAT in Regulation of the Immune Response | 2.81E00 | 1.71E00 | 6.43E-02 | HLA-DRB1, CALM1 (includes others), PPP3R1, HLA-DMA, HLA-DQA1, RAF1, ATM, HLA-DMB, PPP3CB, FCER1A, CD86 |
| Epithelial Adherens Junction Signaling | 2.8E00 | 1.71E00 | 6.85E-02 | TGFBR2, CDC42, ACTR2, ARPC3, TUBB3, ARPC4, RAP1B, ARPC5L, RAP1A, ACTR3 |
| RhoA Signaling | 2.79E00 | 1.71E00 | 7.38E-02 | ACTR2, ARPC3, ARPC4, MYL12A, PPP1CB, ROCK1, ARPC5L, ACTR3, SEPT5 |
| Signaling by Rho Family GTPases | 2.64E00 | 1.57E00 | 5.56E-02 | CDC42, ACTR2, ARPC3, RAF1, ATM, MYL12A, ARPC5L, ACTR3, SEPT5, ARPC4, ROCK1, ITGA4, CYBB |
| Production of Nitric Oxide and Reactive Oxygen Species in Macrophages | 2.63E00 | 1.57E00 | 6.11E-02 | PPP1CC, IFNGR1, JAK2, PPP2R5A, STAT1, ATM, RAP1B, PPP1CB, CYBB, RAP1A, PPP2CA |
| GM-CSF Signaling | 2.61E00 | 1.56E00 | 9.68E-02 | PPP3R1, JAK2, STAT1, RAF1, ATM, PPP3CB |
| Leukotriene Biosynthesis | 2.48E00 | 1.47E00 | 2.14E-01 | DPEP3, DPEP2, LTA4H |
| Vitamin-C Transport | 2.48E00 | 1.47E00 | 2.14E-01 | GSTO1, GLRX, TXNRD1 |
| Mitotic Roles of Polo-Like Kinase | 2.47E00 | 1.47E00 | 9.09E-02 | SLK, ANAPC13, RAD21, PPP2R5A, ANAPC7, PPP2CA |
| CTLA4 Signaling in Cytotoxic T Lymphocytes | 2.47E00 | 1.47E00 | 7.95E-02 | JAK2, PPP2R5A, CLTC, ATM, AP1S2, CD86, PPP2CA |
| cAMP-mediated signaling | 2.43E00 | 1.45E00 | 5.48E-02 | RGS18, TDP2, CALM1 (includes others), PPP3R1, ADCY7, MPPE1, RAF1, AKAP8, PPP3CB, PTGER4, RAP1A, MC1R |
| Axonal Guidance Signaling | 2.41E00 | 1.44E00 | 4.39E-02 | CDC42, ACTR2, ARPC3, EPHB4, TUBB3, CRKL, RAF1, ATM, MYL12A, PPP3CB, ARPC5L, RAP1A, ACTR3, PPP3R1, ARPC4, RAP1B, ROCK1, ITGA4, PLCL2 |
| Remodeling of Epithelial Adherens Junctions | 2.4E00 | 1.44E00 | 8.82E-02 | ACTR2, ARPC3, TUBB3, ARPC4, ARPC5L, ACTR3 |
| Graft-versus-Host Disease Signaling | 2.39E00 | 1.43E00 | 1.04E-01 | HLA-DRB1, HLA-DMA, HLA-DQA1, HLA-DMB, CD86 |
| Autoimmune Thyroid Disease Signaling | 2.35E00 | 1.41E00 | 1.02E-01 | HLA-DRB1, HLA-DMA, HLA-DQA1, HLA-DMB, CD86 |
| Fcγ Receptor-mediated Phagocytosis in Macrophages and Monocytes | 2.33E00 | 1.4E00 | 7.53E-02 | CDC42, ACTR2, VAMP3, ARPC3, ARPC4, ARPC5L, ACTR3 |

TABLE 5-continued

Canonical Pathways of the 412 Genes with Differential Alternative Splicing Among Large Vessel Ischemic Stroke (IS),
Cardioembolic IS, Lacunar IS, Intracerebral Hemorrhage and Controls. B-H-Benjamini-Hochberg corrected p-value

| Ingenuity Canonical Pathways | -log(p-value) | -log(B-H p-value) | Ratio | Molecules |
|---|---|---|---|---|
| Protein Ubiquitination Pathway | 2.32E00 | 1.4E00 | 5.1E-02 | UBR2, UBE2E3, PSMD6, USP1, USP15, UBE2B, PSMD13, DNAJB6, PSMB3, PAN2, PSMA1, USP33, PSMB8 |
| PKCθ Signaling in T Lymphocytes | 2.32E00 | 1.4E00 | 6.78E-02 | HLA-DRB1, PPP3R1, HLA-DMA, HLA-DQA1, ATM, HLA-DMB, PPP3CB, CD86 |
| Glucocorticoid Receptor Signaling | 2.24E00 | 1.34E00 | 4.98E-02 | JAK2, RAF1, ATM, PPP3CB, SELE, ANXA1, TGFBR2, HMGB1, PPP3R1, NR3C1, STAT1, CDKN1C, TAF1 |
| Glutathione Redox Reactions I | 2.16E00 | 1.27E00 | 1.67E-01 | GPX1, GSTK1, MGST1 |
| PDGF Signaling | 2.14E00 | 1.27E00 | 7.79E-02 | EIF2AK2, JAK2, CRKL, STAT1, RAF1, ATM |
| Role of Pattern Recognition Receptors in Recognition of Bacteria and Viruses | 2.13E00 | 1.27E00 | 6.3E-02 | EIF2AK2, EIF2S1, IFIH1, OAS3, ATM, OAS2, DDX58, CLEC7A |
| D-myo-inositol (1,4,5,6)-Tetrakisphosphate Biosynthesis | 2.13E00 | 1.27E00 | 6.3E-02 | PPP1CC, PPTC7, PPP2R5A, PPP4R1, SACM1L, IPMK, PTPRC, MTMR6 |
| D-myo-inositol (3,4,5,6)-tetrakisphosphate Biosynthesis | 2.13E00 | 1.27E00 | 6.3E-02 | PPP1CC, PPTC7, PPP2R5A, PPP4R1, SACM1L, IPMK, PTPRC, MTMR6 |
| Clathrin-mediated Endocytosis Signaling | 2.07E00 | 1.22E00 | 5.41E-02 | CDC42, ACTR2, PPP3R1, ARPC3, CLTC, ARPC4, ATM, PPP3CB, ARPC5L, ACTR3 |
| HGF Signaling | 2.05E00 | 1.21E00 | 6.67E-02 | CDC42, CRKL, RAF1, ATM, RAP1B, ITGA4, RAP1A |
| Cardiac β-adrenergic Signaling | 2.01E00 | 1.18E00 | 6.02E-02 | PPP1CC, TDP2, PPP2R5A, ADCY7, MPPE1, AKAP8, PPP1CB, PPP2CA |
| Dopamine-DARPP32 Feedback in cAMP Signaling | 2E00 | 1.18E00 | 5.59E-02 | PPP1CC, CALM1 (includes others), PPP3R1, PPP2R5A, ADCY7, PPP3CB, PPP1CB, PLCL2, PPP2CA |
| Cardiac Hypertrophy Signaling | 1.95E00 | 1.13E00 | 4.93E-02 | TGFBR2, CALM1 (includes others), PPP3R1, ADCY7, RAF1, ATM, MYL12A, PPP3CB, ROCK1, PLCL2, ADSS |
| Role of PKR in Interferon Induction and Antiviral Response | 1.93E00 | 1.12E00 | 1E-01 | EIF2AK2, EIF2S1, APAF1, STAT1 |
| HIPPO signaling | 1.91E00 | 1.11E00 | 6.98E-02 | PPP1CC, PPP2R5A, MOB1A, PPP1CB, YWHAE, PPP2CA |
| Salvage Pathways of Pyrimidine Deoxyribonucleotides | 1.9E00 | 1.1E00 | 2.5E-01 | APOBEC3B, APOBEC3A |
| Altered T Cell and B Cell Signaling in Rheumatoid Arthritis | 1.87E00 | 1.09E00 | 6.82E-02 | TNFSF13B, HLA-DRB1, HLA-DMA, HLA-DQA1, HLA-DMB, CD86 |
| UVA-Induced MAPK Signaling | 1.87E00 | 1.09E00 | 6.82E-02 | STAT1, ATM, TNKS2, PARP9, PLCL2, PARP14 |
| Activation of IRF by Cytosolic Pattern Recognition Receptors | 1.86E00 | 1.09E00 | 7.81E-02 | IRF9, STAT1, IFIH1, DDX58, IFNAR1 |
| 3-phosphoinositide Degradation | 1.82E00 | 1.05E00 | 5.56E-02 | PPP1CC, MTMR1, PPTC7, PPP2R5A, PPP4R1, SACM1L, PTPRC, MTMR6 |
| RhoGDI Signaling | 1.81E00 | 1.05E00 | 5.2E-02 | CDC42, ACTR2, ARPC3, ARPC4, MYL12A, ROCK1, ITGA4, ARPC5L, ACTR3 |
| iNOS Signaling | 1.79E00 | 1.04E00 | 9.09E-02 | IFNGR1, CALM1 (includes others), JAK2, STAT1 |
| Death Receptor Signaling | 1.78E00 | 1.03E00 | 6.52E-02 | CFLAR, APAF1, TNKS2, ROCK1, PARP9, PARP14 |
| B Cell Receptor Signaling | 1.77E00 | 1.03E00 | 5.11E-02 | CDC42, CALM1 (includes others), PPP3R1, RAF1, ATM, RAP1B, PPP3CB, PTPRC, RAP1A |
| PI3K/AKT Signaling | 1.7E00 | 9.65E-01 | 5.69E-02 | JAK2, PPP2R5A, MCL1, RAF1, ITGA4, YWHAE, PPP2CA |
| T Cell Receptor Signaling | 1.68E00 | 9.48E-01 | 6.19E-02 | CALM1 (includes others), PPP3R1, RAF1, ATM, PPP3CB, PTPRC |
| Histamine Biosynthesis | 1.65E00 | 9.38E-01 | 1E00 | HDC |
| UDP-N-acetyl-D-galactosamine Biosynthesis I | 1.65E00 | 9.38E-01 | 1E00 | GALE |
| 3-phosphoinositide Biosynthesis | 1.65E00 | 9.38E-01 | 5.16E-02 | PPP1CC, PPTC7, PPP2R5A, PPP4R1, ATM, SACM1L, PTPRC, MTMR6 |
| CDK5 Signaling | 1.64E00 | 9.38E-01 | 6.06E-02 | PPP1CC, PPP2R5A, ADCY7, RAF1, PPP1CB, PPP2CA |
| Prolactin Signaling | 1.64E00 | 9.38E-01 | 6.85E-02 | JAK2, STAT1, NR3C1, RAF1, ATM |
| Glutathione-mediated Detoxification | 1.63E00 | 9.34E-01 | 1.07E-01 | GSTO1, GSTK1, MGST1 |
| Superpathway of Inositol Phosphate Compounds | 1.55E00 | 8.69E-01 | 4.69E-02 | PPP1CC, PPTC7, PPP2R5A, PPP4R1, ATM, SACM1L, IPMK, PTPRC, MTMR6 |
| CNTF Signaling | 1.55E00 | 8.69E-01 | 7.69E-02 | JAK2, STAT1, RAF1, ATM |

TABLE 5-continued

Canonical Pathways of the 412 Genes with Differential Alternative Splicing Among Large Vessel Ischemic Stroke (IS), Cardioembolic IS, Lacunar IS, Intracerebral Hemorrhage and Controls. B-H-Benjamini-Hochberg corrected p-value

| Ingenuity Canonical Pathways | -log(p-value) | -log(B-H p-value) | Ratio | Molecules |
|---|---|---|---|---|
| Dopamine Receptor Signaling | 1.53E00 | 8.51E−01 | 6.41E−02 | PPP1CC, PPP2R5A, ADCY7, PPP1CB, PPP2CA |
| Pancreatic Adenocarcinoma Signaling | 1.51E00 | 8.41E−01 | 5.66E−02 | TGFBR2, CDC42, JAK2, STAT1, RAF1, ATM |
| Regulation of IL-2 Expression in Activated and Anergic T Lymphocytes | 1.51E00 | 8.41E−01 | 6.33E−02 | TGFBR2, CALM1 (includes others), PPP3R1, RAF1, PPP3CB |
| NGF Signaling | 1.49E00 | 8.34E−01 | 5.61E−02 | CDC42, RAF1, ATM, RAP1B, ROCK1, RAP1A |
| Thrombopoietin Signaling | 1.47E00 | 8.18E−01 | 7.27E−02 | JAK2, STAT1, RAF1, ATM |
| Aryl Hydrocarbon Receptor Signaling | 1.43E00 | 7.84E−01 | 5E−02 | GSTO1, APAF1, RBL2, ATM, GSTK1, MGST1, NFE2L2 |
| Oncostatin M Signaling | 1.41E00 | 7.68E−01 | 8.82E−02 | JAK2, STAT1, RAF1 |
| Inhibition of Angiogenesis by TSP1 | 1.41E00 | 7.68E−01 | 8.82E−02 | CD47, TGFBR2, CD36 |
| D-myo-inositol-5-phosphate Metabolism | 1.39E00 | 7.6E−01 | 4.9E−02 | PPP1CC, PPTC7, PPP2R5A, PPP4R1, SACM1L, PTPRC, MTMR6 |
| Phospholipase C Signaling | 1.38E00 | 7.6E−01 | 4.18E−02 | CALM1 (includes others), PPP3R1, ADCY7, RAF1, MYL12A, RAP1B, PPP3CB, PPP1CB, ITGA4, RAP1A |
| Cell Cycle Regulation by BTG Family Proteins | 1.38E00 | 7.6E−01 | 8.57E−02 | PPP2R5A, CNOT7, PPP2CA |
| Allograft Rejection Signaling | 1.37E00 | 7.6E−01 | 5.81E−02 | HLA-DRB1, HLA-DMA, HLA-DQA1, HLA-DMB, CD86 |
| Telomere Extension by Telomerase | 1.37E00 | 7.6E−01 | 1.33E−01 | TNKS2, HNRNPA2B1 |
| Spliceosomal Cycle | 1.36E00 | 7.6E−01 | 5E−01 | LOC102724594/U2AF1 |
| S-methyl-5-thio-α-D-ribose 1-phosphate Degradation | 1.36E00 | 7.6E−01 | 5E−01 | APIP |
| Glutamate Biosynthesis II | 1.36E00 | 7.6E−01 | 5E−01 | GLUD1 |
| Glutamate Degradation X | 1.36E00 | 7.6E−01 | 5E−01 | GLUD1 |
| Regulation of eIF4 and p70S6K Signaling | 1.35E00 | 7.59E−01 | 4.79E−02 | EIF2S1, PPP2R5A, RAF1, ATM, ITGA4, EIF4G2, PPP2CA |
| Calcium Signaling | 1.34E00 | 7.57E−01 | 4.49E−02 | TPM3, ATP2B4, CALM1 (includes others), PPP3R1, RAP1B, PPP3CB, MICU1, RAP1A |
| Gαq Signaling | 1.34E00 | 7.57E−01 | 4.76E−02 | RGS18, CALM1 (includes others), PPP3R1, RAF1, ATM, PPP3CB, ROCK1 |
| RANK Signaling in Osteoclasts | 1.34E00 | 7.57E−01 | 5.68E−02 | CALM1 (includes others), PPP3R1, RAF1, ATM, PPP3CB |
| Role of NFAT in Cardiac Hypertrophy | 1.33E00 | 7.56E−01 | 4.47E−02 | TGFBR2, CALM1 (includes others), PPP3R1, ADCY7, RAF1, ATM, PPP3CB, PLCL2 |
| PAK Signaling | 1.32E00 | 7.48E−01 | 5.62E−02 | CDC42, RAF1, ATM, MYL12A, ITGA4 |
| p70S6K Signaling | 1.31E00 | 7.39E−01 | 5.04E−02 | PPP2R5A, RAF1, ATM, PLCL2, YWHAE, PPP2CA |

TABLE 6

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell Death and Survival | cell death | 1.32E-09 | ACSL4, AIFM2, AKAP8, ANXA1, ANXA7, APAF1, APH1A, APIP, APOBEC3B, ARL6IP5, ARNTL, ATM, ATP2B4, ATP6V1G2, BAZ1A, BRAT1, C1QTNF9, CALM1 (includes others), CARD8, CCAR1, CCT8, CD164, CD244, CD36, CD46, CD47, CD53, CD74, CD86, CDC42, CDKN1C, CFLAR, CHMP3, CNPY2, CTSS, CYBB, CYLD, DAP3, DDX19A, DDX3X, DDX58, DNAJB6, DPYD, DUSP22, EGLN1, EIF2AK2, EIF2S1, EIF4G2, EPHB4, EPHX1, ERN1, FCER1A, FKBP1A, FNTA, GLRX, GLUD1, GMCL1, GPX1, GZMA, HEXB, HIPK3, HLA-DMA, HLA-DRB1, HMGB1, IFIH1, IFNAR1, IFNGR1, IFRD1, IGFBP7, ING4, IPMK, IQGAP2, ITGA4, JAK2, KLF13, LMO4, LRRK2, MC1R, MCL1, MICA, MOB1A, MTCH1, MTMR6, MTPN, MX1, NCOA4, NFE2L2, NR3C1, OAS3, PAFAH1B1, PARP14, PHB2, PHIP, PPP1CC, PPP1R15B, PPP2CA, PPP2R5A, PPP3CB, PPP3R1, PRMT2, PRNP, PSMB8, PSMD6, PTGER4, PTPRC, RAB1A, RAB32, RAD21, RAF1, RAP1A, RAP1B, RASSF3, RBBP4, RBL2, RECQL, RFWD2, RICTOR, RIT1, RNF13, RNF31, RNF5, ROCK1, S100A6, SCP2, SELL, SERINC3, SLC12A7, SLK, SMARCA5, SRI, ST8SIA4, STAT1, TAX1BP1, TDP2, TGFBR2, TMSB10/TMSB4X, TNFSF13B, TNKS2, TOPORS, TPM3, TUBB3, TXNRD1, UBE2B, VAMP3, VCP, YWHAE, ZEB2, ZFAND5 | 148 |
| Cell Death and Survival | apoptosis | 4.11E-09 | ACSL4, AIFM2, AKAP8, ANXA1, ANXA7, APAF1, APH1A, APIP, APOBEC3B, ARL6IP5, ATM, ATP2B4, ATP6V1G2, BAZ1A, BRAT1, C1QTNF9, CARD8, CCAR1, CCT8, CD164, CD36, CD47, CD53, CD74, CDC42, CDKN1C, CFLAR, CTSS, CYBB, CYLD, DAP3, DDX19A, DDX3X, DDX58, DUSP22, EIF2AK2, EIF2S1, EIF4G2, EPHB4, EPHX1, ERN1, FCER1A, FKBP1A, FNTA, GLRX, GLUD1, GMCL1, GPX1, GZMA, HEXB, HIPK3, HLA-DMA, HMGB1, IFIH1, IFNAR1, IFNGR1, IGFBP7, ING4, IQGAP2, ITGA4, JAK2, KLF13, LMO4, LRRK2, MC1R, MCL1, MOB1A, MTCH1, MTMR6, MTPN, MX1, NCOA4, NFE2L2, NR3C1, OAS3, PAFAH1B1, PARP14, PHB2, PHIP, PPP1CC, PPP2CA, PPP3CB, PPP3R1, PRMT2, PRNP, PSMB8, PSMD6, PTGER4, PTPRC, RAB32, RAD21, RAF1, RAP1A, RAP1B, RASSF3, RBBP4, RBL2, RFWD2, RICTOR, RIT1, RNF5, ROCK1, S100A6, SELL, SERINC3, SLK, SRI, ST8SIA4, STAT1, TAX1BP1, TDP2, TGFBR2, TMSB10/TMSB4X, TNFSF13B, TOPORS, TXNRD1, UBE2B, VCP, YWHAE, ZEB2, ZFAND5 | 122 |
| Cell Death and Survival | necrosis | 6.80E-05 | ANXA1, APAF1, APIP, APOBEC3B, ATM, ATP2B4, ATP6V1G2, BAZIA, BRAT1, C1QTNF9, CARD8, CCAR1, CCT8, CD36, CD47, CD74, CD86, CDC42, CDKN1C, CFLAR, CNPY2, CTSS, CYBB, CYLD, DAP3, DDX3X, DDX58, DPYD, EGLN1, EIF2AK2, EIF2S1, EIF4G2, EPHX1, ERN1, FCER1A, FKBP1A, FNTA, GLRX, GLUD1, GPX1, GZMA, HLA-DMA, HMGB1, IFIH1, IFNAR1, IFRD1, IGFBP7, IPMK, IQGAP2, ITGA4, JAK2, KLF13, LMO4, LRRK2, MC1R, MCL1, MTMR6, MTPN, MX1, NFE2L2, NR3C1, OAS3, PAFAH1B1, PARP14, PHIP, PPP1CC, PPP2CA, PPP3CB, PPP3R1, PRMT2, PRNP, PSMB8, PSMD6, PTGER4, PTPRC, RAB32, RAD21, RAF1, RASSF3, RBBP4, RBL2, RECQL, RFWD2, RICTOR, RIT1, RNF13, RNF31, RNF5, ROCK1, S100A6, SCP2, SELL, SLK, SRI, STAT1, TAX1BP1, TDP2, TGFBR2, TMSB10/TMSB4X, TNFSF13B, TUBB3, TXNRD1, VCP, YWHAE | 106 |
| Cell Death and Survival | cell viability | 2.26E-04 | APAF1, APOBEC3A, ATM, C1QTNF9, CD47, CD74, CD86, CDC42, CDKL3, CDKN1C, CFLAR, CYBB, CYLD, DPYD, DUSP22, EPHB4, ERN1, FCER1A, GLUD1, GPX1, HMGB1, IFIH1, IGFBP7, IRF9, JAK2, LRRK2, MCL1, MGST1, MTMR1, MTMR6, MX1, NFE2L2, NR3C1, PARP14, PPP1CB, PPP1CC, PPP2CA, PPP2R5A, PPP4R1, PP6C, PRNP, PSMA1, PTPRC, RAD21, RAF1, RBBP4, RICTOR, RIT1, RNF31, S100A6, SELE, SELL, SPDYA, STAT1, TDP2, TGFBR2, TNFSF13B, TUBB3, VCP | 59 |
| Cell Death and Survival, DNA Replication, Recombination, and Repair | fragmentation of DNA | 3.36E-04 | APAF1, APOBEC3B, CD53, EIF2AK2, GPX1, GZMA, MCL1, MTCH1, NR3C1, PPP1CC, PRNP, SERINC3, STAT1 | 13 |
| Cell Death and Survival | cell death of tumor cell lines | 3.43E-04 | APAF1, ATM, BAZ1A, BRAT1, CARD8, CCAR1, CCT8, CD47, CDKN1C, CFLAR, CNPY2, CYLD, DAP3, DDX3X, DDX58, DPYD, EGLN1, EIF2AK2, EIF2S1, EIF4G2, EPHB4, ERN1, FCER1A, FKBP1A, GLRX, GPX1, IFNAR1, IFRD1, IGFBP7, IPMK, IQGAP2, ITGA4, JAK2, LMO4, MCL1, MTMR6, NFE2L2, NR3C1, OAS3, PARP14, PHIP, PPP2CA, PRNP, PTPRC, RAB32, RAD21, RAF1, RASSF3, RBL2, RFWD2, RICTOR, RIT1, RNF13, RNF5, S100A6, SRI, STAT1, TDP2, TGFBR2, TMSB10/TMSB4X, TNFSF13B, TUBB3, TXNRD1, VCP, YWHAE | 67 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell Death and Survival | cell survival | 3.95E-04 | APAF1, APOBEC3A, ATM, C1QTNF9, CD47, CD74, CD86, CDC42, CDKL3, CDKN1C, CFLAR, CYBB, CYLD, DDX3X, DPYD, DUSP22, EIF2S1, EPHB4, ERN1, FCER1A, GLRX, GLUD1, GPX1, HMGB1, IFIH1, IGFBP7, IRF9, JAK2, LRRK2, MCL1, MGST1, MTMR1, MTMR6, MX1, NFE2L2, NR3C1, PARP14, PPP1CB, PPP1CC, PPP2CA, PPP2R5A, PPP4R1, PPP6C, PRNP, PSMA1, PTPRC, RAD21, RAF1, RBBP4, RICTOR, RIT1, RNF31, S100A6, SELE, SELL, SPDYA, STAT1, TDP2, TGFBR2, TNFSF13B, TUBB3, VCP | 62 |
| Cell Death and Survival | cytolysis | 4.21E-04 | ANXA1, CD244, CD46, CD47, FCER1A, GZMA, IFNAR1, MICA, NFE2L2, NR3C1, PPP3CB, PPP3R1, PTPRC, TGFBR2 | 14 |
| Cardiovascular System Development and Function, Cell Death and Survival, Cellular Development, Organ Morphology, Tissue Development, Tissue Morphology | regeneration of cardiomyocytes | 4.91E-04 | HMGB1, MTPN | 2 |
| Cell Death and Survival, Connective Tissue Disorders, Hematological Disease | hemolysis | 5.26E-04 | ANXA1, CD47, IFNAR1, NFE2L2, NR3C1, PPP3CB, PPP3R1 | 7 |
| Cell Death and Survival | cell death of immune cells | 5.41E-04 | ANXA1, APAF1, ATM, CD47, CD74, CD86, CDC42, CFLAR, CYBB, CYLD, EIF2AK2, ERN1, FCER1A, GZMA, HMGB1, IFIH1, IFNAR1, IFNGR1, ITGA4, JAK2, KLF13, MCL1, MX1, NFE2L2, NR3C1, PARP14, PPP3CB, PTGER4, PTPRC, RAF1, STAT1, TGFBR2, TNFSF13B | 33 |
| Cancer, Cell Death and Survival, Tumor Morphology | cell death of cancer cells | 8.29E-04 | ANXA1, APAF1, ATM, CD47, CD74, CFLAR, EIF2AK2, HMGB1, JAK2, LRRK2, MCL1, NFE2L2, NR3C1, PARP14, PRNP, RAF1, SELL, TNFSF13B | 18 |
| Cell Death and Survival | cell death of kidney cell lines | 8.85E-04 | APOBEC3B, CDC42, CFLAR, DAP3, EIF2AK2, ERN1, JAK2, MCL1, NFE2L2, PPP3R1, PRMT2, PRNP, RAD21, RAF1, RNF31, S100A6, SLK, VCP | 18 |
| Cell Death and Survival | cell viability of tumor cell lines | 9.22E-04 | ATM, CDKL3, CDKN1C, CFLAR, CYBB, DUSP22, EPHB4, GLUD1, GPX1, HMGB1, IGFBP7, MCL1, MTMR1, MTMR6, NFE2L2, NR3C1, PARP14, PPP1CC, PPP2CA, PPP2R5A, PPP4R1, PPP6C, PRNP, PSMA1, RAD21, RAF1, RBBP4, RICTOR, RIT1, RNF31, S100A6, TDP2, TGFBR2, TNFSF13B, TUBB3, VCP | 36 |
| Cell Death and Survival | apoptosis of fibroblast cell lines | 9.87E-04 | APAF1, ATM, ATP6V1G2, CFLAR, CYLD, DDX3X, EIF2AK2, EIF2S1, EPHX1, IFNAR1, MCL1, NFE2L2, NR3C1, PRNP, PSMD6, RBL2, RNF13, STAT1, TAX1BP1 | 19 |
| Cell Death and Survival, Connective Tissue Disorders, Hematological Disease | hemolytic anemia | 9.89E-04 | ANXA1, CD47, IFNAR1, NR3C1, PPP3CB, PPP3R1 | 6 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cancer, Cell Death and Survival, Tumor Morphology | cell death of tumor cells | 1.00E-03 | ANXA1, APAF1, ATM, CARD8, CD47, CD74, CFLAR, EIF2AK2, HMGB1, JAK2, LRRK2, MCL1, NFE2L2, NR3C1, PARP14, PPP2CA, PRNP, RAF1, SELL, TGFBR2, TNFSF13B | 21 |
| Cell Death and Survival | cell death of connective tissue cells | 1.27E-03 | APAF1, ATM, ATP6V1G2, CDC42, CFLAR, CYLD, DDX3X, DDX58, EIF2AK2, EIF2S1, EPHX1, FNTA, GPX1, GZMA, IFNAR1, MCL1, NFE2L2, NR3C1, PRMT2, PRNP, PSMD6, RAF1, RBL2, RECQL, RNF13, SCP2, SLK, STAT1, TAX1BP1, VCP | 30 |
| Cell Death and Survival, Cellular Compromise, Neurological Disease, Tissue Morphology | degeneration of nerve ending | 1.45E-03 | ARNTL, ATM | 2 |
| Cell Death and Survival, Respiratory Disease | quantity of apoptotic pneumocytes | 1.45E-03 | CD36, NFE2L2 | 2 |
| Cell Death and Survival | cell death of fibroblast cell lines | 1.50E-03 | APAF1, ATM, ATP6V1G2, CFLAR, CYLD, DDX3X, EIF2AK2, EIF2S1, EPHX1, FNTA, IFNAR1, MCL1, NFE2L2, NR3C1, PRNP, PSMD6, RBL2, RECQL, RNF13, SCP2, STAT1, TAX1BP1, VCP | 23 |
| Cell Death and Survival | cell death of thymocytes | 1.50E-03 | APAF1, ATM, CFLAR, CYLD, GZMA, KLF13, MCL1, NFE2L2, NR3C1, PTPRC | 10 |
| Cell Death and Survival | cell death of epithelial cells | 1.52E-03 | APAF1, APOBEC3B, ATM, CDC42, CFLAR, CTSS, CYLD, DAP3, EIF2AK2, ERN1, HMGB1, IFNGR1, JAK2, MC1R, MCL1, NFE2L2, NR3C1, PPP3R1, PRMT2, PRNP, RAD21, RAF1, RBL2, RNF31, TGFBR2 | 25 |
| Cell Death and Survival | mitochondrial cell death of tumor cell lines | 1.57E-03 | DDX58, MCL1, SRI | 3 |
| Cell Death and Survival | apoptosis of leukocytes | 1.61E-03 | ANXA1, ATM, CD47, CDC42, CFLAR, CYBB, CYLD, EIF2AK2, FCER1A, GZMA, HMGB1, IFNGR1, JAK2, KLF13, MCL1, NFE2L2, NR3C1, PPP3CB, PTGFR4, PTPRC, RAF1, STAT1, TNFSF13B | 23 |
| Cell Death and Survival | apoptosis of tumor cell lines | 1.73E-03 | APAF1, ATM, BAZ1A, BRAT1, CARD8, CCAR1, CD47, CDC42, CDKN1C, CFLAR, CYLD, DDX58, EIF2AK2, EIF4G2, EPHB4, ERN1, FCER1A, GLRX, GPX1, IGFBP7, JAK2, LMO4, MCL1, MTMR6, NFE2L2, NR3C1, OAS3, PARP14, PHIP, PPP2CA, PRNP, PTPRC, RAB32, RAD21, RAF1, RASSF3, RBL2, RICTOR, RIT1, RNF13, RNF31, RNF5, S100A6, SRI, STAT1, TDP2, TGFBR2, TMSB10/TMSB4X, TNFSF13B, TXNRD1, VCP, YWHAE | 52 |
| Cell Death and Survival, Connective Tissue Disorders, Hematological Disease, Immunological Disease | autoimmune hemolytic anemia | 1.78E-03 | CD47, NR3C1, PPP3CB, PPP3R1 | 4 |
| Cell Death and Survival | cell viability of cervical cancer cell lines | 1.89E-03 | ATM, CDKL3, DUSP22, MCL1, MTMR1, MTMR6, PPP1CC, PPP2CA, PPP2R5A, PPP4R1, PPP6C, RAD21, TGFBR2 | 13 |
| Cell Death and Survival | cell death of colon cancer cell lines | 1.97E-03 | APAF1, CCAR1, CDC42, CDKN1C, CFLAR, EPHB4, MCL1, RAF1, RASSF3, SRI, STAT1, TGFBR2, TMSB10/TMSB4X, TXNRD1, VCP, YWHAE | 16 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell Death and Survival | cell viability of leukocytes | 2.26E-03 | CD47, CD74, CD86, CYLD, ERN1, FCER1A, HMGB1, JAK2, MCL1, MX1, PARP14, PTPRC, RAF1, STAT1, TNFSF13B | 15 |
| Cell Death and Survival | killing of natural killer cells | 2.42E-03 | CD244, IFNAR1, IFNGR1, STAT1 | 4 |
| Cell Death and Survival | cell death of myeloid cells | 2.46E-03 | ANXA1, CFLAR, CYBB, EIF2AK2, FCER1A, HMGB1, IFNAR1, JAK2, MCL1, NFE2L2, NR3C1, RAF1, STAT1 | 13 |
| Cell Death and Survival | cell death of epithelial cell lines | 2.68E-03 | APOBEC3B, CDC42, CFLAR, DAP3, EIF2AK2, ERN1, JAK2, MCL1, NFE2L2, PPP3R1, PRMT2, PRNP, RAD21, RAF1, RNF31, TGFBR2 | 16 |
| Cell Death and Survival | necrosis of epithelial tissue | 2.81E-03 | APAF1, APOBEC3B, ATM, CD36, CDC42, CFLAR, CTSS, CYLD, DAP3, EIF2AK2, ERN1, GPX1, HMGB1, IFNGR1, JAK2, MC1R, MCL1, NFE2L2, NR3C1, PPP3R1, PRMT2, PRNP, PSMB8, RAD21, RAF1, RBL2, RNF31, TGFBR2 | 28 |
| Cell Death and Survival | cell viability of blood cells | 2.85E-03 | CD47, CD74, CD86, CYLD, ERN1, FCER1A, HMGB1, JAK2, MCL1, MX1, PARP14, PTPRC, RAF1, SELE, STAT1, TNFSF13B | 16 |
| Cell Death and Survival | cytotoxicity | 2.87E-03 | CALM1 (includes others), CD244, CD46, CD74, CFLAR, CYBB, FKBP1A, GZMA, HLA-DRB1, IFNAR1, MICA, PTPRC, STAT1, TGFBR2 | 14 |
| Cell Death and Survival, Embryonic Development | cell death of embryonic cell lines | 2.97E-03 | APOBEC3B, CDC42, CFLAR, DAP3, EIF2AK2, ERN1, IFNAR1, MCL1, NFE2L2, PPP3R1, PRMT2, PRNP, RAD21, RNF31 | 14 |
| Cancer, Cell Death and Survival, Tumor Morphology | cell death of leukemia cells | 3.42E-03 | ATM, CD47, JAK2, MCL1, RAF1, SELL, TNFSF13B | 7 |
| Cell Death and Survival, Cellular Compromise | cytotoxicity of cells | 3.51E-03 | CALM1 (includes others), CD244, CD46, CD74, CFLAR, CYBB, GZMA, HLA-DRB1, IFNAR1, MICA, PTPRC, STAT1, TGFBR2 | 13 |
| Cell Death and Survival | killing of lymphocytes | 3.74E-03 | CD244, CD47, IFNAR1, IFNGR1, STAT1 | 5 |
| Cell Death and Survival | apoptosis of fibroblasts | 3.99E-03 | APAF1, ATM, CDC42, CFLAR, DDX58, EIF2AK2, EIF2S1, GZMA, MCL1, PRMT2, RAF1, SLK | 12 |
| Cell Death and Survival | cell death of fibroblasts | 4.36E-03 | APAF1, ATM, CDC42, CFLAR, DDX58, EIF2AK2, EIF2S1, EPHX1, GPX1, GZMA, MCL1, PRMT2, RAF1, SLK | 14 |
| Cell Death and Survival, Cell Signaling | activation of caspase | 4.56E-03 | APAF1, CARD8, JAK2, MTCH1, STAT1, VCP | 6 |
| Cancer, Cell Death and Survival, Tumor Morphology | cell viability of cancer cells | 4.64E-03 | CD74, HMGB1, MCL1, NFE2L2, PARP14, SELL, TNFSF13B | 7 |
| Cancer, Cell Death and Survival, Tumor Morphology | cell death of chronic lymphocytic leukemia cells | 4.68E-03 | ATM, CD47, SELL, TNFSF13B | 4 |
| Cell Death and Survival | cytolysis of lymphoblastoid cell lines | 4.70E-03 | CD244, MICA | 2 |
| Cell Death and Survival | loss of B lymphocytes | 4.70E-03 | CD74, SPPL2A | 2 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell Death and Survival | cell death of T lymphocytes | 5.03E-03 | APAF1, ATM, CD47, CDC42, CFLAR, CYLD, GZMA, IFNGR1, KLF13, MCL1, NFE2L2, NR3C1, PPP3CB, PTPRC, STAT1, TGFBR2 | 16 |
| Cancer, Cell Death and Survival, Tumor Morphology | cell viability of tumor cells | 5.07E-03 | CD74, HMGB1, LRRK2, MCL1, NFE2L2, PARP14, SELL, TNFSF13B | 8 |
| Cell Death and Survival | cell death of mononuclear leukocytes | 5.35E-03 | APAF1, ATM, CD47, CDC42, CFLAR, CYLD, EIF2AK2, FCER1A, GZMA, IFNGR1, KLF13, MCL1, NFE2L2, NR3C1, PPP3CB, PTPRC, STAT1, TGFBR2, TNFSF13B | 19 |
| Cell Death and Survival | apoptosis of colon cancer cell lines | 5.39E-03 | APAF1, CCAR1, CDC42, CDKN1C, CFLAR, EPHB4, MCL1, RASSF3, SRI, STAT1, TMSB10/TMSB4X, VCP, YWHAE | 13 |
| Cell Death and Survival | cell death of phagocytes | 5.46E-03 | ANXA1, CFLAR, CYBB, EIF2AK2, FCER1A, HMGB1, IFNAR1, MCL1, NFE2L2, NR3C1, PTGER4, STAT1 | 12 |
| Cell Death and Survival | apoptosis of myeloid cells | 5.60E-03 | ANXA1, CFLAR, CYBB, EIF2AK2, FCER1A, HMGB1, JAK2, MCL1, NFE2L2, RAF1, STAT1 | 11 |
| Cell Death and Survival | apoptosis of thymocytes | 6.47E-03 | ATM, CFLAR, CYLD, GZMA, KLF13, NFE2L2, NR3C1, PTPRC | 8 |
| Cell Death and Survival | apoptosis of kidney cell lines | 6.50E-03 | CFLAR, DAP3, EIF2AK2, JAK2, MCL1, NFE2L2, PPP3R1, PRMT2, RAD21, RAF1, RNF13, RNF31, SLK | 13 |
| Cell Death and Survival | necroptosis of tumor cell lines | 6.94E-03 | CYLD, STAT1 | 2 |
| Cell Death and Survival, DNA Replication, Recombination, and Repair | fragmentation of DNA fragment | 7.93E-03 | APOBEC3B, EIF2AK2, GZMA, MTCH1, PPP1CC | 5 |
| Cell Death and Survival | apoptosis of peritoneal macrophages | 8.07E-03 | CFLAR, MCL1, NFE2L2 | 3 |
| Cancer, Cell Death and Survival, Tumor Morphology | apoptosis of leukemia cells | 8.20E-03 | ATM, JAK2, MCL1, RAF1, SELL, TNFSF13B | 6 |
| Cell Death and Survival | cell death of lymphocytes | 8.22E-03 | APAF1, ATM, CD47, CDC42, CFLAR, CYLD, EIF2AK2, GZMA, IFNGR1, KLF13, MCL1, NFE2L2, NR3C1, PPP3CB, PTPRC, STAT1, TGFBR2, TNFSF13B | 18 |
| Cancer, Cell Death and Survival, Tumor Morphology | cell viability of chronic lymphocytic leukemia cells | 9.34E-03 | CD74, SELL, TNFSF13B | 3 |
| Cell Death and Survival | cell death of hematopoietic cells | 9.40E-03 | APAF1, ATM, CFLAR, CYLD, EIF2AK2, GZMA, KLF13, MCL1, NFE2L2, NR3C1, PTPRC, RAF1 | 12 |
| Cell Death and Survival, Cellular Compromise, Neurological Disease, | neurodegeneration of granule cells | 9.58E-03 | ATM, PRNP | 2 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Organismal Injury and Abnormalities, Tissue Morphology Cell Death and Survival | apoptosis of epithelial cell lines | 9.98E-03 | CFLAR, DAP3, EIF2AK2, JAK2, MCL1, NFE2L2, PPP3R1, PRMT2, RAD21, RAF1, RNF31, TGFBR2 | 12 |
| Cell Death and Survival | apoptosis of lymphoma cell lines | 1.05E-02 | CARD8, CFLAR, EIF2AK2, ERN1, FCER1A, IGFBP7, JAK2, MCL1, PTPRC, TNFSF13B | 10 |
| Cell-To-Cell Signaling and Interaction, Hematological System Development and Function, Immune Cell Trafficking, Inflammatory Response | activation of leukocytes | 6.10E-08 | ANXA1, ATM, BLOC1S6, CD244, CD36, CD46, CD47, CD58, CD74, CD86, CLEC7A, CTSS, CYBB, DDX58, ERAP1, FKBP1A, GZMA, HBP1, HLA-DMA, HLA-DMB, HLA-DQA1, HLA-DRB1, HMGB1, IFNAR1, JAK2, MGST1, MICA, NBR1, NDFIP1, NFE2L2, PELI1, PPP3CB, PRNP, PSMB8, PTGER4, PTPRC, RAB10, RAB32, RAB6A, RAB8B, SELE, SELL, STAT1, TGFBR2, TNFSF13B | 45 |
| Cell-To-Cell Signaling and Interaction, Hematological System Development and Function | activation of blood cells | 1.61E-07 | ANXA1, ATM, BLOC1S6, CD244, CD36, CD46, CD47, CD58, CD74, CD86, CLEC7A, CTSS, CYBB, DDX58, ERAP1, FKBP1A, GZMA, HBP1, HLA-DMA, HLA-DMB, HLA-DQA1, HLA-DRB1, HMGB1, IFNAR1, JAK2, MGST1, MICA, NBR1, NDFIP1, NFE2L2, PELI1, PLEK, PPP3CB, PRNP, PSMB8, PTGER4, PTPRC, RAB10, RAB32, RAB6A, RAB8B, SELE, SELL, STAT1, TGFBR2, TNFSF13B | 46 |
| Cell-To-Cell Signaling and Interaction | activation of cells | 4.70E-07 | ANXA1, ATM, BLOC1S6, CD244, CD36, CD46, CD47, CD58, CD74, CD86, CLEC7A, CTSS, CYBB, CYLD, DDX58, EIF2AK2, ERAP1, ERN1, FCER1A, FKBP1A, FNTA, GPX1, GZMA, HBP1, HLA-DMA, HLA-DMB, HLA-DQA1, HLA-DRB1, HMGB1, IFNAR1, JAK2, MGST1, MICA, MTCH1, NBR1, NDFIP1, NFE2L2, PELI1, PLEK, PPP2CA, PPP3CB, PRNP, PSMB8, PTGER4, PTPRC, RAB10, RAB32, RAB6A, RAB8B, RICTOR, SELE, SELL, STAT1, TGFBR2, TNFSF13B | 55 |
| Cell-To-Cell Signaling and Interaction, Hematological System Development and Function, Immune Cell Trafficking, Inflammatory Response | activation of antigen presenting cells | 5.45E-07 | ATM, CD36, CD47, CD74, CD86, CLEC7A, CTSS, CYBB, ERAP1, HBP1, HLA-DMA, HLA-DMB, HLA-DQA1, HMGB1, IFNAR1, JAK2, PELI1, PRNP, PSMB8, PTGER4, RAB32, RAB6A, RAB8B, STAT1 | 25 |
| Antimicrobial Response, Cell-To-Cell Signaling and Interaction, | antiviral response of fibroblasts | 1.08E-05 | DDX58, IFNAR1, STAT1 | 3 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Connective Tissue Development and Function, Inflammatory Response | | | | |
| Cell-To-Cell Signaling and Interaction, Cellular Movement, Hematological System Development and Function, Immune Cell Trafficking | recruitment of leukocytes | 2.61E-05 | ANXA1, CD36, CD47, CD74, CLEC7A, DDX58, FCER1A, GLRX, HDC, HMGB1, IFNAR1, ITGA4, LRRK2, NFE2L2, PELI1, PRMT2, RAP1A, ROCK1, SELE, SELL, TGFBR2 | 21 |
| Cell-To-Cell Signaling and Interaction, Tissue Development | adhesion of blood cells | 6.76E-05 | ANXA1, ANXA7, CD36, CD46, CD47, CD58, CD74, CDC42, CYBB, GALNT1, GLRX, HMGB1, IFNGR1, ITGA4, JAK2, PAFAH1B1, PTGER4, PTPRC, RICTOR, ROCK1, SELE, SELL, STAT1, TGFBR2 | 24 |
| Cell-To-Cell Signaling and Interaction, Hematological System Development and Function, Immune Cell Trafficking, Tissue Development | adhesion of immune cells | 1.31E-04 | ANXA1, CD36, CD46, CD47, CD58, CD74, CDC42, GALNT1, GLRX, HMGB1, IFNGR1, ITGA4, JAK2, PAFAH1B1, PTGER4, PTPRC, RICTOR, ROCK1, SELE, SELL, STAT1, TGFBR2 | 22 |
| Cell-To-Cell Signaling and Interaction, Hematological System Development and Function, Immune Cell Trafficking, Inflammatory Response | activation of lymphocytes | 1.39E-04 | ANXA1, BLOC1S6, CD244, CD46, CD47, CD58, CD74, CD86, CLEC7A, DDX58, GZMA, HLA-DRB1, HMGB1, IFNAR1, MGST1, MICA, NBR1, NDFIP1, NFE2L2, PELI1, PPP3CB, PRNP, PTPRC, STAT1, TGFBR2, TNFSF13B | 26 |
| Cell-To-Cell Signaling and Interaction, Hematological System | adhesion of mononuclear leukocytes | 2.18E-04 | ANXA1, CD47, CD58, HMGB1, IFNGR1, ITGA4, JAK2, RICTOR, ROCK1, SELE, SELL, TGFBR2 | 12 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Development and Function, Immune Cell Trafficking, Tissue Development | | | | |
| Cell-To-Cell Signaling and Interaction, Hematological System Development and Function, Immune Cell Trafficking, Inflammatory Response | activation of T lymphocytes | 2.25E-04 | ANXA1, CD244, CD46, CD47, CD58, CD74, CD86, CLEC7A, DDX58, GZMA, HLA-DRB1, IFNAR1, MGST1, NBR1, NDFIP1, NFE2L2, PPP3CB, PRNP, PTPRC, STAT1, TGFBR2 | 21 |
| Cell-To-Cell Signaling and Interaction, Cell-mediated Immune Response, Cellular Movement, Hematological System Development and Function, Immune Cell Trafficking, Tissue Development | adhesion of T lymphocytes | 3.06E-04 | ANXA1, CD47, CD58, IFNGR1, ITGA4, JAK2, RICTOR, SELE, SELL | 9 |
| Cell-To-Cell Signaling and Interaction, Inflammatory Response | response of phagocytes | 3.84E-04 | ABCA7, ANXA1, CD36, CD47, CLEC7A, DDX58, ERN1, FCER1A, GLRX, HMGB1, IFNAR1, ITGA4, NR3C1, ZEB2 | 14 |
| Cell-To-Cell Signaling and Interaction, Hematological System Development and Function, Immune Cell Trafficking, Tissue Development | adhesion of lymphocytes | 4.20E-04 | ANXA1, CD47, CD58, IFNGR1, ITGA4, JAK2, RICTOR, ROCK1, SELE, SELL | 10 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell-To-Cell Signaling and Interaction, Cellular Function and Maintenance, Hematological System Development and Function, Inflammatory Response | phagocytosis of granulocytes | 4.51E-04 | ANXA1, CD36, CD47, GLRX, HMGB1, IFNAR1 | 6 |
| Cell-To-Cell Signaling and Interaction, Connective Tissue Development and Function | response of fibroblasts | 4.52E-04 | CD36, DDX58, IFNAR1, STAT1 | 4 |
| Cell-To-Cell Signaling and Interaction, Cellular Function and Maintenance, Hematological System Development and Function, Inflammatory Response | phagocytosis of bone marrow-derived neutrophils | 4.91E-04 | CD47, HMGB1 | 2 |
| Cardiovascular System Development and Function, Cell-To-Cell Signaling and Interaction, Tissue Development | adhesion of endothelial cells | 5.03E-04 | ANXA7, CD36, CDC42, HMGB1, IGFBP7, ITGA4, RICTOR, SELE, SELL, TGFBR2, TMSB10/TMSB4X | 11 |
| Cell-To-Cell Signaling and Interaction | response of myeloid cells | 5.49E-04 | ABCA7, ANXA1, CD36, CD47, DDX58, ERN1, FCER1A, GLRX, HMGB1, IFNAR1, ITGA4, NR3C1, PTPRC | 13 |
| Cell-To-Cell Signaling and Interaction, Hematological System Development and | detachment of leukocytes | 8.24E-04 | ANXA1, PTPRC, SELL | 3 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell-To-Cell Signaling and Interaction, Inflammatory Response, Cellular Function, Immune Cell Trafficking, Tissue Development | immune response of leukocytes | 8.55E-04 | ABCA7, ANXA1, CD36, CD47, CD86, CTSS, DDX58, ERN1, FCER1A, GLRX, HMGB1, IFNAR1, IFNGR1, ITGA4, NR3C1, PTPRC, TGFBR2 | 17 |
| Cardiovascular System Development and Function, Cell-To-Cell Signaling and Interaction, Tissue Development | adhesion of vascular endothelial cells | 9.38E-04 | ANXA7, CD36, HMGB1, IGFBP7, ITGA4, RICTOR, SELE, TMSB10/TMSB4X | 8 |
| Cell-To-Cell Signaling and Interaction, Inflammatory Response | immune response of phagocytes | 1.30E-03 | ABCA7, ANXA1, CD36, CD47, DDX58, ERN1, FCER1A, GLRX, HMGB1, IFNAR1, ITGA4, NR3C1 | 12 |
| Cell-To-Cell Signaling and Interaction | response of granulocytes | 1.33E-03 | ANXA1, CD36, CD47, FCER1A, GLRX, HMGB1, IFNAR1, ITGA4 | 8 |
| Cell-To-Cell Signaling and Interaction, Hematological System Development and Function, Inflammatory Response | immune response of neutrophils | 1.37E-03 | CD36, CD47, FCER1A, GLRX, HMGB1, IFNAR1, ITGA4 | 7 |
| Cell-To-Cell Signaling and Interaction | response of antigen presenting cells | 1.42E-03 | ABCA7, ANXA1, CD36, CD47, CLEC7A, CTSS, DDX58, ERN1, HMGB1, IFNAR1, NR3C1 | 11 |
| Cell-To-Cell Signaling and Interaction, Cellular Movement, Hematological System Development and Function, Immune Cell Trafficking | recruitment of mononuclear leukocytes | 1.80E-03 | CD47, DDX58, FCER1A, HDC, HMGB1, ITGA4, PELI1, SELE, SELL | 9 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell-To-Cell Signaling and Interaction, Inflammatory Response | immune response of antigen presenting cells | 2.03E-03 | ABCA7, ANXA1, CD36, CD47, CTSS, DDX58, ERN1, HMGB1, IFNAR1, NR3C1 | 10 |
| Cell-To-Cell Signaling and Interaction, Hematological System Development and Function | binding of B-lymphocyte derived cell lines | 2.05E-03 | CD47, CRKL, ITGA4 | 3 |
| Cell Cycle, Cell-To-Cell Signaling and Interaction, Cellular Growth and Proliferation | contact growth inhibition of leukocytes | 2.05E-03 | HMGB1, IKZF1, PTPRC | 3 |
| Cell-To-Cell Signaling and Interaction, Cellular Function and Maintenance, Hematological System Development and Function, Immune Cell Trafficking, Inflammatory Response | phagocytosis of neutrophils | 2.53E-03 | CD36, CD47, GLRX, HMGB1, IFNAR1 | 5 |
| Cell-To-Cell Signaling and Interaction, Hematological System Development and Function, Immune Cell Trafficking, Tissue Development | cell-cell adhesion of leukocytes | 2.80E-03 | ITGA4, PTPRC, ROCK1, SELE | 4 |
| Cardiovascular System Development and Function, Cell-To-Cell Signaling and Interaction, Tissue Development | adhesion of HCAEC cells | 2.86E-03 | SELE, SELL | 2 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell-To-Cell Signaling and Interaction, Cellular Compromise, Tissue Development, Tumor Morphology | adhesion of acute myeloid leukemia blast cells | 2.86E-03 | SELE, SELL | 2 |
| Cell-To-Cell Signaling and Interaction, Nervous System Development and Function | afterhyperpolarization of central nervous system cells | 2.86E-03 | ATP2B4, LMO4 | 2 |
| Cell-To-Cell Signaling and Interaction, Cellular Movement, Hematological System Development and Function, Immune Cell Trafficking, Tissue Development | detachment of phagocytes | 2.86E-03 | ANXA1, PTPRC | 2 |
| Cell-To-Cell Signaling and Interaction, Cell-mediated Immune Response, Cellular Movement, Hematological System Development and Function, Immune Cell Trafficking | recruitment of CD8+ T lymphocyte | 2.86E-03 | DDX58, PELI1 | 2 |
| Cell Cycle, Cell-To-Cell Signaling and Interaction, Cellular Growth and Proliferation | contact growth inhibition | 3.09E-03 | CDC42, GBP2, HMGB1, IKZF1, ING4, JAK2, PTPRC, RAF1, RBL2, STAT1 | 10 |
| Cell-To-Cell Signaling and | fusion of leukocytes | 3.21E-03 | CD36, CD46, CD47, STAT1 | 4 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Interaction, Hematological System Development and Function, Immune Cell Trafficking, Infectious Disease, Tissue Development | | | | |
| Cell-To-Cell Signaling and Interaction, Inflammatory Response | response of macrophages | 3.89E-03 | ABCA7, ANXA1, CD36, CD47, CLEC7A, DDX58, ERN1, HMGB1, NR3C1 | 9 |
| Cell-To-Cell Signaling and Interaction, Cellular Function and Maintenance, Inflammatory Response | phagocytosis of cells | 4.10E-03 | ABCA7, ANXA1, CD302, CD36, CD47, CDC42, CLEC7A, CLTC, DNTTIP1, GLRX, HMGB1, IFNAR1, LY75, NR3C1 | 14 |
| Cell-To-Cell Signaling and Interaction | binding of blood cells | 4.16E-03 | CD47, CD58, CD86, HLA-DMA, HMGB1, IFNGR1, ITGA4, JAK2, NFE2L2, PTPRC, RAP1B, SELE, SELL | 13 |
| Cell-To-Cell Signaling and Interaction, Hematological System Development and Function, Tissue Development | binding of T lymphocytes | 4.25E-03 | CD47, CD58, CD86, HLA-DMA, IFNGR1, ITGA4 | 6 |
| Cell-To-Cell Signaling and Interaction, Hematological System Development and Function, Immune Cell Trafficking, Inflammatory Response, Tissue Development | adhesion of monocytes | 4.49E-03 | HMGB1, ROCK1, SELE, SELL, TGFBR2 | 5 |
| Cell-To-Cell Signaling and | recruitment of T lymphocytes | 4.56E-03 | CD47, DDX58, FCER1A, HDC, PELI1, SELE | 6 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Interaction, Cell-mediated Immune Response, Cellular Movement, Hematological System Development and Function, Immune Cell Trafficking | | | | |
| Cell-To-Cell Signaling and Interaction, Nervous System Development and Function | afterhyperpolarization of neurons | 4.70E-03 | ATP2B4, LMO4 | 2 |
| Cell Cycle, Cell-To-Cell Signaling and Interaction, Cellular Growth and Proliferation | contact growth inhibition of melanoma cell lines | 4.70E-03 | RAF1, STAT1 | 2 |
| Cell-To-Cell Signaling and Interaction, Cellular Growth and Proliferation, Hematological System Development and Function | suppression of effector T lymphocytes | 4.70E-03 | CD46, CD86 | 2 |
| Cell-To-Cell Signaling and Interaction, Hematological System Development and Function | binding of mononuclear leukocytes | 5.07E-03 | CD47, CD58, CD86, HLA-DMA, IFNGR1, ITGA4, SELE, SELL | 8 |
| Cell-To-Cell Signaling and Interaction, Hematological System Development and Function | binding of lymphocytes | 5.22E-03 | CD47, CD58, CD86, HLA-DMA, IFNGR1, ITGA4, SELL | 7 |
| Cell-To-Cell Signaling and | recruitment of lymphocytes | 5.52E-03 | CD47, DDX58, FCER1A, HDC, PELI1, SELE, SELL | 7 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Cell-To-Cell Signaling and Interaction, Cellular Movement, Hematological System Development and Function, Immune Cell Trafficking | adhesion of phagocytes | 5.85E−03 | ANXA1, GLRX, HMGB1, ITGA4, PAFAH1B1, ROCK1, SELE, SELL, TGFBR2 | 9 |
| Cell-To-Cell Signaling and Interaction, Hematological System Development and Function, Immune Cell Trafficking, Inflammatory Response, Tissue Development | binding of hematopoietic progenitor cells | 5.85E−03 | CD47, ITGA4, RAP1B | 3 |
| Cell-To-Cell Signaling and Interaction, Hematopoiesis | binding of leukemia cell lines | 6.81E−03 | CD36, CD47, ITGA4, JAK2, SELL | 5 |
| Cell-To-Cell Signaling and Interaction | binding of bone marrow cell lines | 6.90E−03 | CRKL, ITGA4, RAF1 | 3 |
| Cell-To-Cell Signaling and Interaction, Cell-mediated Immune Response, Cellular Movement, Hematological System Development and Function, Immune Cell | adhesion of Th1 cells | 6.94E−03 | ITGA4, SELE | 2 |

TABLE 6-continued

Functions, Associated with the Top 2 Molecular and Cellular Functions Over-Represented in the 412 Differentially Alternatively Spliced Genes - Cell Death and Survival, and Cell-to-Cell Signaling

| Categories | Diseases or Functions Annotation | p-Value | Molecules | # Molecules |
|---|---|---|---|---|
| Trafficking, Tissue Development Antigen Presentation, Cell-To-Cell Signaling and Interaction, Inflammatory Response | antigen presentation of antigen presenting cells | 6.94E-03 | CTSS, IFNAR1 | 2 |
| Cell-To-Cell Signaling and Interaction, Hematological System Development and Function, Immune Cell Trafficking, Tissue Development | detachment of myeloid cells | 6.94E-03 | ANXA1, PTPRC | 2 |
| Cell-To-Cell Signaling and Interaction, Inflammatory Response | response of mast cells | 6.94E-03 | FCER1A, ZEB2 | 2 |
| Cell-To-Cell Signaling and Interaction, Inflammatory Response | immune response of macrophages | 7.11E-03 | ABCA7, ANXA1, ATM, CD36, CD47, DDX58, ERN1, HMGB1, NR3C1 | 8 |
| Cell-To-Cell Signaling and Interaction | recognition of cells | 7.26E-03 | CD36, CD47, CLEC7A, MICA | 4 |
| Cell-To-Cell Signaling and Interaction, Hematological System Development and Function, Immune Cell Trafficking, Inflammatory Response | activation of phagocytes | 7.34E-03 | ANXA1, ATM, CD36, CD47, CD86, CLEC7A, CYBB, FKBP1A, GZMA, HMGB1, IFNAR1, JAK2, PELI1, PRNP, PTGER4, SELE, SELL, STAT1 | 18 |
| Cell-To-Cell Signaling and Interaction, Hematological System | binding of B lymphocytes | 8.07E-03 | CD47, CD86, ITGA4 | 3 |

TABLE 6-continued

Functions, Associated with the Top 2 Molecular and Cellular Functions Over-Represented in the 412 Differentially Aternatively Spliced Genes - Cell Death and Survival, and Cell-to-Cell Signaling

| Categories | Diseases or Functions Annotation | p-Value | Molecules | # Molecules |
|---|---|---|---|---|
| Development and Function, Humoral Immune Response Cardiovascular System | adhesion of postcapillary venule | 9.58E-03 | CD74, SELL | 2 |
| Development and Function, Cell-To-Cell Signaling and Interaction, Tissue Development | contact growth inhibition of lymphocytes | 9.58E-03 | IKZF1, PTPRC | 2 |
| Cell Cycle, Cell-To-Cell Signaling and Interaction, Cellular Growth and Proliferation | phagocytosis of blood cells | 1.06E-02 | ABCA7, ANXA1, CD36, CD47, CDC42, GLRX, HMGB1, IFNAR1 | 8 |
| Cell-To-Cell Signaling and Interaction, Cellular Function and Maintenance, Inflammatory Response | phagocytosis of phagocytes | 1.14E-02 | ABCA7, ANXA1, CD36, CD47, GLRX, HMGB1, IFNAR1 | 7 |
| Cell-To-Cell Signaling and Interaction, Cellular Function and Maintenance, Inflammatory Response | fusion of cells | 1.15E-02 | ANXA1, CD36, CD46, CD47, IFRD1, ROCK1, STAT1, UBE2B | 8 |
| Cell-To-Cell Signaling and Interaction | | | | |

TABLE 1

Differentiated Exon Usage in the 5 Groups (p < 0.005, |FC| > 1.2)

| Marker ID | Gene Symbol | Entrez GeneID | Ensembl | UniProtKB |
|---|---|---|---|---|
| Table 1A: Exon Usage Upregulated in Cardioembolic Ischemic Stroke (CE IS) | | | | |
| chr17.73000302-73002233>CDR2L | CDR2L | 30850 | ENSG00000109089 | Q86X02 |
| chr8.104406853-104407319>shuskeebu | shuskeebu | "NoInfo" | "NoInfo" | "NoInfo" |
| chr3.48456585-48456756>PLXNB1 | PLXNB1 | 5364 | ENSG00000164050 | O43157 |
| chr1.86861716-86861978>ODF2L | ODF2L | 57489 | ENSG00000122417 | Q9ULJ1 |
| chr19.58427747-58427959>ZNF417andZNF814 | ZNF417 and ZNF814 | 147687 and 730051 | ENSG00000173480 and ENSG00000204514 | Q8TAU3 and B7Z6K7 |
| chr19.58427747-58427960>ZNF417andZNF814 | ZNF417 and ZNF814 | 147687 and 730051 | ENSG00000173480 and ENSG00000204514 | Q8TAU3 and B7Z6K7 |
| chr22.19115606-19115962>skatee | skatee | "NoInfo" | "NoInfo" | "NoInfo" |
| chr10.49253461-49254183>BMS1P7 | BMS1P7 | 100133265 | ENSG00000243899 | |
| chr14.70242552-70243105>SLC10A1 | SLC10A1 | 6554 | ENSG00000100652 | Q14973 |
| chr7.142630429-142630905>TRPV5 | TRPV5 | 56302 | ENSG00000127412 | Q9NQA5 |
| chr10.38299602-38299711>ZNF33A | ZNF33A | 7581 | ENSG00000189180 | Q06730 |
| chr10.38299604-38299711>ZNF33A | ZNF33A | 7581 | ENSG00000189180 | Q06730 |
| chr2.119988299-119988610>STEAP3 | STEAP3 | 55240 | ENSG00000115107 | Q658P3 |
| chr2.179463448-179463831>CCDC141andTTN | CCDC141 and TTN | 285025 and 7273 | ENSG00000163492 and ENSG00000155657 | Q6ZP82 and Q8WZ42 |
| chr2.25258142-25260098>LOC729723 | LOC729723 | "NoInfo" | "NoInfo" | "NoInfo" |
| chr17.34856670-34856799>MYO19 | MYO19 | 80179 | ENSG00000141140 | Q96H55 |
| chr7.158334118-158334468>PTPRN2 | PTPRN2 | 5799 | ENSG00000155093 | Q92932 |
| chr3.188326949-188327339>LPP | LPP | 4026 | ENSG00000145012 | Q93052 |
| chr19.18959976-18960255>UPF1 | UPF1 | 5976 | ENSG00000005007 | Q92900 |
| chr6.37225553-37225749>TBC1D2213 | TBC1D226 | 55633 | ENSG00000065491 | Q9NU19 |
| chr20.43995515-43996064>SYS1-DBNDD2 | SYS1-DBNDD2 | 767557 | ENSG00000254806 | H3BUS1 |
| chr3.49448633-49449166>myforbo | myforbo | "NoInfo" | "NoInfo" | "NoInfo" |
| chr4.15570247-15570813>klawgu | klawgu | "NoInfo" | "NoInfo" | "NoInfo" |
| Table 1B: Exon Usage Upregulated in Large Vessel Ischemic Stroke (LV IS) | | | | |
| chr6.37225553-37225749>TBC1D22B | TBC1D22B | 55633 | ENSG00000065491 | Q9NU19 |
| chr20.43995515-43996064>SYS1-DBNDD2 | SYS1-DBNDD2 | 767557 | ENSG00000254806 | H3BUS1 |
| chr3.49448633-49449166>myforbo | myforbo | "NoInfo" | "NoInfo" | "NoInfo" |
| chr4.15570247-15570813>klawgu | klawgu | "NoInfo" | "NoInfo" | "NoInfo" |
| chr14.53248502-53248629>GNPNAT1 | GNPNAT1 | 64841 | ENSG00000100522 | Q96EK6 |
| chr22.29141852-29141989>HSCB | HSCB | 150274 | ENSG00000100209 | Q8IWL3 |
| chr16.72146312-72146549>DHX38 | DHX38 | 9785 | ENSG00000140829 | Q92620 |
| chr5.176715528-176715926>NSD1 | NSD1 | 64324 | ENSG00000165671 | Q96L73 |
| chr6.100023529-100023947>RPS3P5 | RPS3P5 | 100131956 | ENSG00000219755 | "NoInfo" |
| chr13.103506107-103506222>BIVMandERCC5 | BIVM and ERCC5 | 54841 and 2073 | ENSG00000134897 and ENSG00000134899 | Q86UB2 and P28715 |
| chr7.2282560-2282683>NUDT1 | NUDT1 | 4521 | ENSG00000106268 | P36639 |
| chr12.54645834-54646011>CBX5 | CBX5 | 23468 | ENSG00000094916 | P45973 |
| chr20.33056659-33057236>vytaw | vytaw | "NoInfo" | "NoInfo" | "NoInfo" |
| chr5.162902464-162902678>HMMR | HMMR | 3161 | ENSG00000072571 | O75330 |
| chr11.62389338-62389648>B3GAT3 | B3GAT3 | 26229 | ENSG00000149541 | O94766 |
| chr15.101847418-101849508>PCSK6 | PCSK6 | 5046 | ENSG00000140479 | P29122 |
| chr5.61688639-61688817>DIMT1L | DIMT1L (DIMT1) | 27292 | ENSG00000086189 | Q9UNQ2 |
| chr12.56334947-56335109>DGKA | DGKA | 1606 | ENSG00000065357 | P23743 |
| chr10.46918169-46918362>FAM35BandRHEBP1 | FAM35B(FAM35BP) and RHEBP1 | 414241 and 6008 | ENSG00000165874 and ENSG00000229927 | |
| chr2.20756227-20757428>dawgorbu | dawgorbu | "NoInfo" | "NoInfo" | "NoInfo" |
| chrX.152226503-152227128>PNMA3 | PNMA3 | 29944 | ENSG00000183837 | Q9UL41 |
| chr22.18613610-18614498>PEX26andTUBA8 | PEX26 and TUBA8 | 55670 and 51807 | ENSG00000183785 | ENSG00000215193 and Q7Z412 and Q9NY65 |
| chr6.111619174-111619773>slyjey | slyjey | "NoInfo" | "NoInfo" | "NoInfo" |
| chr17.43002077-43003867>KIF18B | KIF18B | 146909 | ENSG00000186185 | Q86Y91 |
| chr8.90798887-90799401>RIPK2 | RIPK2 | 8767 | ENSG00000104312 | O43353 |
| chr1.214836934-214837426>CENPF | CENPF | 1063 | ENSG00000117724 | P49454 |
| chr3.8606070-8609805>LMCD1 | LMCD1 | 29995 | ENSG00000071282 | Q9NZU5 |
| chr20.52560545-52561535>BCAS1 | BCAS1 | 8537 | ENSG00000064787 | O75363 |
| chr2.173420100-173420447>PDK1 | PDK1 | 5163 | ENSG00000152256 | Q15118 |
| chr15.81584265-81585378>IL16 | IL16 | 3603 | ENSG00000172349 | Q14005 |
| chr9.131486273-131486409>ZDHHC12 | ZDHHC12 | 84885 | ENSG00000160446 | Q96GR4 |
| chr16.4475881-4476093>DNAJA3 | DNAJA3 | 9093 | ENSG00000103423 | Q96EY1 |
| Table 1C: Exon Usage Upregulated in Lacunar Ischemic Stroke (L IS) | | | | |
| chr11.119039480-119040011>NLRX1 | NLRX1 | 79671 | ENSG00000160703 | Q86UT6 |
| chr15.52970203-52970319>KIAA1370 | KIAA1370 (FAM214A) | 56204 | ENSG00000047346 | Q32MH5 |
| chr11.62475067-62475387>GNG3 | GNG3 | 2785 | ENSG00000162188 | P63215 |
| chr2.94914730-94915694>LOC400061 | LOC400061 | 400061 | ENSG00000258357 | "NoInfo" |
| chr16.15013757-15013940>zoner | zoner | "NoInfo" | "NoInfo" | "NoInfo" |
| chr2.29258330-29258510>FAM179A | FAM179A | 165186 | ENSG00000189350 | Q6ZUX3 |
| chr18.33077683-33077895>INO80C | INO80C | 125476 | ENSG00000153391 | Q6P198 |

TABLE 1-continued

Differentiated Exon Usage in the 5 Groups (p < 0.005, |FC| > 1.2)

| Marker ID | Gene Symbol | Entrez GeneID | Ensembl | UniProtKB |
|---|---|---|---|---|
| chr2.160143094-160143317>WDSUB1 | WDSUB1 | 151525 | ENSG00000196151 | Q8N9V3 |
| chr22.44514918-44515020>PARVB | PARVB | 29780 | ENSG00000188677 | Q9H611 |
| chr5.156821041-156822687>ADAM19 | ADAM19 | 8728 | ENSG00000135074 | Q9H013 |
| chr6.146285293-146285559>SHPRH | SHPRH | 257218 | ENSG00000146414 | Q149N8 |
| chr6.146285293-146285525>SHPRH | SHPRH | 257218 | ENSG00000146414 | Q149N8 |
| chr22.24316496-24316679>GSTTP1andDDT | GSTTP1 and DDT | 25774 and 1652 | ENSG00000241850 and ENSG00000099977 | "NoInfo" and P30046 |
| chr12.2966630-2968829>FOXM1 | FOXM1 | 2305 | ENSG00000111206 | Q08050 |
| chr7.99674926-99675056>ZNF3 | ZNF3 | 7551 | ENSG00000166526 | P17036 |
| chr6.30610545-30612432>C6orf134 | C6orf134 (ATAT1) | 79969 | ENSG00000137343 | Q5SQ10 |
| chr19.35173682-35173954>ZNF302 | ZNF302 | 55900 | ENSG00000089335 | Q9NR11 |
| chr21.47706315-47706712>C21orf57 | C21orf57 (YBEY) | 54059 | ENSG00000182362 | P58557 |
| chr12.111065735-111066029>TCTN1 | TCTN1 | 79600 | ENSG00000204852 | Q2MV58 |
| chrX.40495835-40495964>CXorf38 | CXorf38 | 159013 | ENSG00000185753 | Q8TB03 |
| chr9.46687439-46688197>KGFLP1 | KGFLP1 | 387628 | ENSG00000227449 | Q2TVT4 |
| chr2.101627502-101628002>TBC1D8 | TBC1D8 | 11138 | ENSG00000204634 | O95759 |
| chr1.160580214-160580588>SLAMF1 | SLAMF1 | 6504 | ENSG00000117090 | Q13291 |
| chr8.10340434-10340741>LOC346702 | LOC346702 | "NoInfo" | "NoInfo" | "NoInfo" |
| chr6.168370462-168372588>MLLT4 | MLLT4 | 4301 | ENSG00000130396 | P55196 |
| chr1.155691308-155691471>DAP3 | DAP3 | 7818 | ENSG00000132676 | P5139 |
| chr12.123262038-123262230>CCDC62 | CCDC62 | 84660 | ENSG00000130783 | Q6P9F0 |
| chr14.96795821-96795971>ATG2B | ATG2B | 55102 | ENSG00000066739 | Q96BY7 |
| chr20.32079185-32079982>spawvor | spawvor | "NoInfo" | "NoInfo" | "NoInfo" |
| chr6.163984476-163984751>QKI | QKI | 9444 | ENSG00000112531 | Q96PU8 |
| chr1.246729640-246730091>CNST | CNST | 163882 | ENSG00000162852 | Q6PJW8 |

Table 1D: Exon Usage Upregulated in Intracerebral Hemorrhage (ICH)

| Marker ID | Gene Symbol | Entrez GeneID | Ensembl | UniProtKB |
|---|---|---|---|---|
| chr19.44128266-44128394>CADM4 | CADM4 | 199731 | ENSG00000105767 | Q8NFZ8 |
| chr5.139929370-139930496>APBB3andSRA1 | APBB3 and SRA1 | 10307 and 10011 | ENSG00000213523 | ENSG00000113108 and O95704 and Q9HD15 |
| chr1.85127881-85128058>SSX2IP | SSX2IP | 117178 | ENSG00000117155 | Q9Y2D8 |
| chr22.31733654-31734031>sneypoy | sneypoy | "NoInfo" | "NoInfo" | "NoInfo" |
| chr17.40280569-40280818>RAB5C | RAB5C | 5878 | ENSG00000108774 | P51148 |
| chr3.23929058-23929280>UBE2E1 | UBE2E1 | 7324 | ENSG00000170142 | P51965 |
| chr7.149598-152547>kehera | kehera | "NoInfo" | "NoInfo" | "NoInfo" |
| chr3.122283274-122283460>DTX3L | DTX3L | 151636 | ENSG00000163840 | Q8TDB6 |
| chr14.76107075-76107403>FLVCR2andTTLL5andC14orf179 | FLVCR2 and TILL5 and C14orf179 (IFT43) | 55640 and 23093 and 112752 | ENSG00000119685 and ENSG00000119650 | ENSG00000119686 and Q9UPI3 and Q6EMB2 and Q96FT9 |
| chr1.235956803-235956912>LYST | LYST | 1130 | ENSG00000143669 | Q99698 |
| chr2.198175302-198175503>ANKRD44 | ANKRD44 | 91526 | ENSG00000065413 | Q8N8A2 |
| chr22.20093700-20093800>DGCR8 | DGCR8 | 54487 | ENSG00000128191 | Q8WYQ5 |
| chr1.112991564-112991794>CTTNBP2NL | CTTNBP2NL | 55917 | ENSG00000143079 | Q9P2B4 |
| chr1.19470474-19470585>UBR4 | UBR4 | 23352 | ENSG00000127481 | Q5T4S7 |
| chr5.134343647-134343829>PCBD2andCATSPER3 | PCBD2 and CATSPER3 | 84105 and 347732 | ENSG00000132570 and ENSG00000152705 | Q9H0N5 and Q86XQ3 |
| chr19.49314066-49314178>BCAT2 | BCAT2 | 587 | ENSG00000105552 | O15382 |
| chr2.118864235-118864479>INSIG2 | INSIG2 | 51141 | ENSG00000125629 | Q9Y5U4 |
| chr18.48443613-48443878>ME2 | ME2 | 4200 | ENSG00000082212 | P23368 |
| chr22.45254869-45255776>PRR5-ARHGAP8 | PRR5-ARHGAP8 | 553158 | ENSG00000248405 | B1AHC4 |
| chr1.27431807-27432578>SLC9A1 | SLC9A1 | 6548 | ENSG00000090020 | P19634 |
| chr8.133984843-133984986>TG | TG | 7038 | ENSG00000042832 | P01266 |
| 41751976>PRICKLE4andTOMM6 | PRICKLE4 and TOMM6 | 29964 and 100188893 | ENSG00000124593 and ENSG00000214736 | Q2TBC4 and Q96649 |
| chr17.57728564-57728677>CLTC | CLTC | 1213 | ENSG00000141367 | Q00610 |
| chr3.150280329-150280447>EIF2A | EIF2A | 83939 | ENSG00000144895 | Q9BY44 |
| chr2.242282407-242282508>SEPT2 | SEPT2 | 4735 | ENSG00000168385 | Q15019 |
| chr21.40619627-40619758>BRWD1 | BRWD1 | 54014 | ENSG00000185658 | Q9NSI6 |
| chr1.26799700-26800018>HMGN2 | HMGN2 | 3151 | ENSG00000198830 | P05204 |
| chr5.140895496-140896575>DIAPH1 | DIAPH1 | 1729 | ENSG00000131504 | O60610 |
| chr5.140895875-140896575>DIAPH1 | DIAPH1 | 1729 | ENSG00000131504 | O60610 |
| chr1.180049625-180049796>CEP350 | CEP350 | 9857 | ENSG00000135837 | Q5VT06 |
| chr1.180049652-180049796>CEP350 | CEP350 | 9857 | ENSG00000135837 | Q5VT06 |
| chr5.70531277-70532281>goychyby | goychyby | "NoInfo" | "NoInfo" | "NoInfo" |
| chr13.100543572-100543866>CLYBL | CLYBL | 171425 | ENSG00000125246 | Q8NOX4 |
| chr19.36515246-36515534>CLIP3 | CLIP3 | 25999 | ENSG00000105270 | Q96DZ5 |
| chr6.144289727-144290115>PLAGL1andHYMAI | PLAGL1 and HYMAI | 5325 and 57061 | ENSG00000118495 and "NoInfo" | Q9UM63 and "NoInfo" |
| chr21.47608408-47608855>klorley | klorley | "NoInfo" | "NoInfo" | "NoInfo" |
| chr9.17135038-17135423>CNTLN | CNTLN | 54875 | ENSG00000044459 | Q9NXG0 |
| chr1.114499947-114500540>wawleybo | wawleybo | "NoInfo" | "NoInfo" | "NoInfo" |
| chr17.18486655-18486837>CCDC1446 | CCDC1446 | 284047 | ENSG00000154874 | Q3MJ40 |
| chr4.40800804-40800921>NSUN7 | NSUN7 | 79730 | ENSG00000179299 | Q8NE18 |
| chr3.39162488-39162680>TTC21A | TTC21A | 199223 | ENSG00000168026 | Q8NDW8 |
| chr1.161196029-161196394>TOMM40L | TOMM40L | 84134 | ENSG00000158882 | Q969M1 |
| chr7.45083306-45083697>CCM2 | CCM2 | 83605 | ENSG00000136280 | Q9 BSQ5 |

TABLE 1-continued

Differentiated Exon Usage in the 5 Groups (p < 0.005, |FC| > 1.2)

| Marker ID | Gene Symbol | Entrez GeneID | Ensembl | UniProtKB |
|---|---|---|---|---|
| chr19.13009896-13010199>SYCE2 | SYCE2 | 256126 | ENSG00000161860 | Q6PIF2 |
| chr3.20019802-20020396>RAB5A | RAB5A | 5868 | ENSG00000144566 | P20339 |
| chr6.122792844-122793050>SERINC1 | SERINC1 | 57515 | ENSG00000111897 | Q9NRX5 |
| chr2.231663444-231663853>CAB39 | CAB39 | 51719 | ENSG00000135932 | Q9Y376 |
| chr1.145790974-145791170>GPR89A | GPR89A | 653519 | ENSG00000117262 | B7ZAQ6 |
| chr4.175223190-175223337>KIAA1712 | KIAA1712 (CEP44) | 80817 | ENSG00000164118 | Q9C0F1 |
| chr2.182339687-182340015>ITGA4 | ITGA4 | 3676 | ENSG00000115232 | P13612 |
| chr6.18799866-18800440>ARL6IP1andRPS15A | ARL6IP1 and RPS15A | 23204 and 6210 | ENSG00000170540 and ENSG00000134419 | Q15041 and P62244 |
| chr6.3021094-3022352>teyvybo | teyvybo | "NoInfo" | "NoInfo" | "NoInfo" |
| chr16.22277711-22277845>EEF2K | EEF2K | 29904 | ENSG00000103319 | O00418 |
| chr11.7479027-7479174>veemee | veemee | "NoInfo" | "NoInfo" | "NoInfo" |
| chrX.77303661-77305892>ATP7A | ATP7A | 538 | ENSG00000165240 | Q04656 |
| chr1.78207302-78207433>USP33 | USP33 | 23032 | ENSG00000077254 | Q8TEY7 |
| chrX.76776266-76776394>ATRX | ATRX | 546 | ENSG00000085224 | P46100 |
| chr12.6761437-6761584>ING4 | ING4 | 51147 | ENSG00000111653 | Q9UNL4 |
| chr17.77079383-77079672>ENGASE | ENGASE | 64772 | ENSG00000167280 | Q8NFI3 |
| chr11.111889680-111893374>DIXDC1 | DIXDC1 | 85458 | ENSG00000150764 | Q155Q3 |
| chr11.111889680-111893310>DIXDC1 | DIXDC1 | 85458 | ENSG00000150764 | Q155Q3 |
| chr4.157731989-157732169>PDGFC | PDGFC | 56034 | ENSG00000145431 | Q9NRA1 |
| chr20.18449588-18449705>POLR3F | POLR3F | 10621 | ENSG00000132664 | Q9H1D9 |
| chr11.47738539-47739064>FNBP4 | FNBP4 | 23360 | ENSG00000109920 | Q8N3X1 |
| chr16.30593851-30595166>syrar | syrar | "NoInfo" | "NoInfo" | "NoInfo" |
| chr13.41593364-41593568>ELF1 | ELF1 | 1997 | ENSG00000120690 | P32519 |
| chr22.51221467-51221714>RABL2B | RABL2B | 11158 | ENSG00000079974 | Q9UNT1 |
| chr9.33264164-33264493>CHMP5 | CHMP5 | 51510 | ENSG00000086065 | Q9NZZ3 |
| chr1.154928545-154928780>SHC1andPYGO2andPBXIP1 | SHC1 and PYGO2 and PBXIP1 | 6464 and 90780 and 57326 | ENSG00000163348 and ENSG00000160691 and ENSG00000163346 | Q96AQ6 and P29353 and Q9BRQO |
| chr19.1953385-1953505>C19orf34 | C19orf34 (CSNK1G2-AS1) | 255193 | ENSG00000180846 | Q8NCQ2 |
| chr2.113175261-113175491>RGPD8 | RGPD8 | 727851 | ENSG00000169629 | O14715 |
| chr1.145509166-145509612>RBM8A.1 | RBM8A.1 | "NoInfo" | "NoInfo" | "NoInfo" |
| chr1.89271574-89271700>PKN2 | PKN2 | 5586 | ENSG00000065243 | Q16513 |
| chr10.99433338-99433902>DHOPSLandPI4K2A | DHDPSL (HOGA1) and PI4K2A | 112817 and 55361 | ENSG00000241935 and ENSG00000155252 | Q86XE5 and Q9BTU6 |
| chr7.74166365-74166897>GTF2I | GTF2I | 2969 | ENSG00000077809 | P78347 |
| chr18.54318248-54318824>TXNL1 | TXNL1 | 9352 | ENSG00000091164 | O43396 |
| chr12.58345541-58345678>XRCC6BP1 | XRCC6BP1 | 91419 | ENSG00000166896 | Q9Y6H3 |
| chr7.76870183-76870364>CCDC146 | CCDC146 | 57639 | ENSG00000135205 | Q8IYE0 |
| chr3.52385978-52386119>DNAH1 | DNAH1 | 25981 | ENSG00000114841 | Q9P2D7 |
| chr12.96258857-96259166>SNRPF | SNRPF | 6636 | ENSG00000139343 | P62306 |
| chr1.63269390-63269533>ATG4C | ATG4C | 84938 | ENSG00000125703 | Q96DT6 |
| chr2.172848099-172848599>HAT1 | HAT1 | 8520 | ENSG00000128708 | O14929 |
| chr18.67508480-67516323>DOK6 | DOK6 | 220164 | ENSG00000206052 | Q6PKX4 |
| chr8.30948350-30948458>WRN | WRN | 7486 | ENSG00000165392 | Q14191 |
| chr2.208446079-208446884>FAM119A | FAM119A (METTL21A) | 151194 | ENSG00000144401 | Q8WX61 |
| chr7.5938415-5938550>CCZ1 | CCZ1 | 51622 | ENSG00000122674 | P86791 |
| chr19.44619641-44619995>ZNF225 | ZNF225 | 7768 | ENSG00000256294 | Q9UK10 |
| chr1.243652316-243652442>SDCCAG8 | SDCCAG8 | 10806 | ENSG00000054282 | Q86SQ7 |
| chr4.122723829-122723983>EXOSC9 | EXOSC9 | 5393 | ENSG00000123737 | Q06265 |
| chr4.122723829-122723937>EXOSC9 | EXOSC9 | 5393 | ENSG00000123737 | Q06265 |
| chr1.46805848-46806591>NSUN4andFAAH | NSUN4 and FAAH | 387338 and 2166 | ENSG00000117481 and ENSG00000117480 | Q96C69 and O00519 |
| chr10.51592090-51592619>LOC100287554 | LOC100287554 | "NoInfo" | "NoInfo" | "NoInfo" |
| chrX.138864706-138864887>ATP11C | ATP11C | 286410 | ENSG00000101974 | Q8NB49 |
| chr14.50246313-50246524>KLHDC2 | KLHDC2 | 23588 | ENSG00000165516 | Q9Y2U9 |
| chr7.22980878-22987334>FAM126A | FAM126A | 84668 | ENSG00000122591 | Q9BYI3 |
| chr1.150778337-150778492>CTSK | CTSK | 1513 | ENSG00000143387 | P43235 |
| chr12.48094974-48095387>RPAP3 | RPAP3 | 79657 | ENSG00000005175 | Q9H6T3 |
| chr15.38619054-38620016>koyzawbu | koyzawbu | "NoInfo" | "NoInfo" | "NoInfo" |
| chr11.836251-836525>CD151 | CD151 | 977 | ENSG00000177697 | P48509 |
| chr17.27581220-27581513>CRYBA1 | CRYBA1 | 1411 | ENSG00000108255 | P05813 |
| chr14.105236090-105236707>AKT1 | AKT1 | 207 | ENSG00000142208 | P31749 |
| chr10.69828759-69829524>HERC4 | HERC4 | 26091 | ENSG00000148634 | Q5GLZ8 |
| chr22.50320903-50321181>CRELD2 | CRELD2 | 79174 | ENSG00000184164 | Q6UXH1 |
| chr12.10561988-10562183>KLRC4andKLRK1 | KLRC4 and KLRK1 | 8302 and 22914 | ENSG00000183542 and ENSG00000213809 | O43908 and P26718 |
| chr8.104455023-104455428>DCAF13 | DCAF13 | 25879 | ENSG00000164934 | Q9NVO6 |
| chr12.40441853-40442012>SLC2A13 | SLC2A13 | 114134 | ENSG00000151229 | Q96QE2 |
| chrX.16870674-16871149>RBBP7 | RBBP7 | 5931 | ENSG00000102054 | Q16576 |
| chr12.54789679-54790160>ITGA5 | ITGA5 | 3678 | ENSG00000161638 | P08648 |
| chr1.150939858-150940190>LASS2 | LASS2 (CERS2) | 29956 | ENSG00000143418 | Q96G23 |

TABLE 1-continued

Differentiated Exon Usage in the 5 Groups (p < 0.005, |FC| > 1.2)

| Marker ID | Gene Symbol | Entrez GeneID | Ensembl | UniProtKB |
|---|---|---|---|---|
| chr13.113864293-113864812>PCID2 | PCID2 | 55795 | ENSG00000126226 | Q5JVF3 |
| chr15.80191177-80191467>ST20andMTHFS | ST20 and MTHFS | 400410 and 10588 | ENSG00000180953 and ENSG00000136371 | Q9HBF5 and P49914 |
| chr5.145493406-145493874>LARS | LARS | 51520 | ENSG00000133706 | Q9P2J5 |
| chr16.3493611-3493837>ZNF174andNAT15andCLUAP1 | ZNF174 and NAT15 (NAA60) and CLUAP1 | 7727 and 79903 and 23059 | ENSG00000103343 and ENSG00000122390 and ENSG00000103351 | Q15697 and Q9H7X0 and Q96AJ1 |
| chr6.79664949-79665569>PHIPandTRNAF13P | PHIP and TRNAF13P | 55023 and 100189446 | ENSG00000146247 and "NoInfo" | Q8WWQ0 and "NoInfo" |
| chr17.62745780-62746126>LOC146880 | LOC146880 | 146880 | ENSG00000215769 | "NoInfo" |
| chr17.61473104-61473289>TANC2 | TANC2 | 26115 | ENSG00000170921 | Q9HCD6 |
| chr15.59102429-59102587>FAM636 | FAM636 | 54629 | ENSG00000128923 | Q8NBR6 |
| chr10.11272033-11272456>CELF2 | CELF2 | 10659 | ENSG00000048740 | O95319 |
| chr20.34487292-34487561>PHF20 | PHF20 | 51230 | ENSG00000025293 | Q9BVI0 |
| chr8.74858684-74859055>TCEB1 | TCEB1 | 6921 | ENSG00000154582 | Q15369 |
| chr2.17953901-17954051>GEN1 | GEN1 | 348654 | ENSG00000178295 | Q17RS7 |
| chr14.88431849-88431973>GALC | GALC | 2581 | ENSG00000054983 | P54803 |
| chr19.1877203-1877424>FAM108A1 | FAM108A1 (ABHD17A) | 81926 | ENSG00000129968 | Q96GS6 |
| chr17.18087711-18088067>jeeroy | jeeroy | "NoInfo" | "NoInfo" | "NoInfo" |
| chr1.168262382-168262516>SFT2D2andTBX19 | SFT2D2 and TBX19 | 375035 and 9095 | ENSG00000213064 and ENSG00000143178 | O95562 and O60806 |
| chr6.158088239-158089557>fyjaw | fyjaw | "NoInfo" | "NoInfo" | "NoInfo" |
| chr15.30711214-30711348>rukaru | rukaru | "NoInfo" | "NoInfo" | "NoInfo" |
| chr2.24256387-24256553>ADAMDEC1 | ADAMDEC1 | 27299 | ENSG00000134028 | O15204 |
| chr15.57545460-57545666>stoyguby | stoyguby | "NoInfo" | "NoInfo" | "NoInfo" |
| chr10.75230828-75230967>PPP3CB | PPP3CB | 5532 | ENSG00000107758 | P16298 |
| chr20.43808628-43808775>rotora | rotora | "NoInfo" | "NoInfo" | "NoInfo" |
| chr1.46467098-46468407>MAST2 | MAST2 | 23139 | ENSG00000086015 | Q6P0Q8 |
| chr7.2635311-2636062>dochuby | dochuby | "NoInfo" | "NoInfo" | "NoInfo" |
| chr19.11411543-11411912>tojaw | tojaw | "NoInfo" | "NoInfo" | "NoInfo" |
| chrX.153744234-153744566>FAM3A | FAM 3A | 60343 | ENSG00000071889 | P98173 |
| chr2.73957016-73957156>TPRKB | TPRKB | 51002 | ENSG00000144034 | Q9Y3C4 |
| chr2.234112772-234113219>INPP5D | INPP5D | 3635 | ENSG00000168918 | Q92835 |
| chr6.41036580-41036692>C6orf130andUNC5CL | C6orf130 (OARD1) and UNC5CL | 221443 and 222643 | ENSG00000124596 and ENSG00000124602 | Q9Y530 and Q8IV45 |
| chr15.75165540-75165688>SCAMP2 | SCAMP2 | 10066 | ENSG00000140497 | O15127 |
| chrX.74282163-74282417>ABCB7 | ABCB7 | 22 | ENSG00000131269 | O75027 |
| chr2.88336462-88336570>KRCC1 | KRCC1 | 51315 | ENSG00000172086 | Q9NPI7 |
| chrX.2839944-2840065>ARSD | ARSD | 414 | ENSG00000006756 | P51689 |
| chr11.89933252-89935719>CHORDC1 | CHORDC1 | 26973 | ENSG00000110172 | Q9UHD1 |
| chr8.62438536-62438671>ASPH | ASPH | 444 | ENSG00000198363 | Q12797 |
| chr3.69028819-69028938>C3orf64 | C3orf64 (EOGT) | 285203 | ENSG00000163378 | Q5NDL2 |
| chr5.35053745-35054334>fugey | fugey | "NoInfo" | "NoInfo" | "NoInfo" |
| chr9.35737655-35737936>GBA2 | GBA2 | 57704 | ENSG00000070610 | Q9HCG7 |
| chr15.94774950-94775234>MCTP2 | MCTP2 | 55784 | ENSG00000144563 | Q6DN12 |
| chr3.52561845-52561947>NT5DC2 | NT5DC2 | 64943 | ENSG00000168268 | Q9H857 |
| chr1.85039599-85040103>CTBSandGNG5 | CTBS and GNG5 | 1486 and 2787 | ENSG00000117151 and ENSG00000174021 | Q01459 and P63218 |
| chr10.99195666-99196308>EXOSC1 | EXOSC1 | 51013 | ENSG00000171311 | Q9Y3B2 |
| chr20.23401942-23402097>NAPB | NAPB | 63908 | ENSG00000125814 | Q9H115 |
| chr17.36351796-36351996>TBC1D3 | TBC1D3 | 729873 | ENSG00000197681 | Q8IZP1 |
| chrX.118985730-118985836>UPF3B | UPF3B | 65109 | ENSG00000125351 | Q9BZI7 |
| chr15.66811217-66811416>ZWILCH | ZWILCH | 55055 | ENSG00000174442 | Q9H900 |
| chr15.66811217-66811467>ZWILCH | ZWILCH | 55055 | ENSG00000174442 | Q9H900 |
| chr11.125490667-125490901>STT3AandCHEK1 | STT3A and CHEK1 | 3703 and 1111 | ENSG00000134910 and ENSG00000149554 | P46977 and O14757 |
| chr3.15778540-15778740>ANKRD28 | ANKRD28 | 23243 | ENSG00000206560 | O15084 |
| chr19.9720432-9722012>ZNF562andZNF561 | ZNF562 and ZNF561 | 54811 and 93134 | ENSG00000171466 and ENSG00000171469 | Q6V9R5 and Q8N587 |
| chr3.167452594-167452717>PDCD10 | PDCD10 | 11235 | ENSG00000114209 | Q9BUL8 |
| chr1.10509776-10510379>APITD1andCORT | APITD1 and CORT | 378708 and 1325 | ENSG00000175279 and ENSG00000241563 | Q8N2Z9 and O00230 |
| chr6.34360041-34360260>RPS10andNUDT3 | RPS10 and NUDT3 | 6204 and 11165 | ENSG00000124614 and ENSG00000272325 | P46783 and O95989 |
| chr19.52207575-52207733>NCRNA00085 | NCRNA00085 (SPACA6P) | 147650 | ENSG00000182310 | No Data |
| chr11.62105383-62105784>saroro | saroro | "NoInfo" | "NoInfo" | "NoInfo" |
| chr1.17056-17742>WASH7P | WASH7P | 653635 | ENSG00000227232 | NoData |
| chr1.45987501-45987609>PRDX1 | PRDX1 | 5052 | ENSG00000117450 | Q06830 |
| chr1.243419358-243419542>SDCCAG8 | SDCCAG8 | 10806 | ENSG00000054282 | Q86SQ7 |
| chr2.111302237-111302383>RGPD6 | RGPD6 | 729540 | ENSG00000183054 | Q99666 |
| chr2.110584278-110584424>RGPD5 | RG PDS | 84220 | ENSG00000015568 | Q99666 |
| chr6.109248281-109249436>ARMC2 | ARMC2 | 84071 | ENSG00000118690 | Q8NENO |
| chr14.96997812-96999040>PAPOLA | PAPOLA | 10914 | ENSG00000090060 | P51003 |
| chr19.58423428- | ZNF417 and ZNF814 | 147687 and 730051 | ENSG00000173480 and | Q8TAU3 and B7Z6K7 |

TABLE 1-continued

Differentiated Exon Usage in the 5 Groups (p < 0.005, |FC| > 1.2)

| Marker ID | Gene Symbol | Entrez GeneID | Ensembl | UniProtKB |
|---|---|---|---|---|
| 58423554>ZNF417andZNF814 | | | ENSG00000204514 | |
| chr19.58423428-58423557>ZNF417andZNF814 | ZNF417 and ZNF814 | 147687 and 730051 | ENSG00000173480 and ENSG00000204514 | Q8TAU3 and B7Z6K7 |
| chrX.149924161-149924396>MTMR1 | MTM R1 | 8776 | ENSG00000063601 | Q13613 |
| chr19.5208248-5208402>PTPRS | PTPRS | 5802 | ENSG00000105426 | Q13332 |
| chr14.20872770-20872931>TEP1 | TEP1 | 7011 | ENSG00000129566 | Q99973 |
| chr20.416929-419485>TBC1D20 | TBC1D20 | 128637 | ENSG00000125875 | Q966Z9 |
| chr15.59943710-59944525>GTF2A2 | GTF2A2 | 2958 | ENSG00000140307 | P52657 |
| chrX.15862547-15863639>AP1S2 | AP1S2 | 8905 | ENSG00000182287 | P56377 |
| chr15.64017491-64017712>HERC1 | HERC1 | 8925 | ENSG00000103657 | Q15751 |
| chr5.77656415-77656552>SCAMP1 | SCAMP1 | 9522 | ENSG00000085365 | O15126 |
| chr19.47646729-47646862>SAE1 | SAE1 | 10055 | ENSG00000142230 | Q9UBE0 |
| chr19.47646751-47646862>SAE1 | SAE1 | 10055 | ENSG00000142230 | Q9UBE0 |
| chr3.81552424-81552865>chordybo | chordybo | "NoInfo" | "NoInfo" | "NoInfo" |
| chr1.201780731-201780885>NAV1 | NAV1 | 89796 | ENSG00000134369 | Q8NEY1 |
| chr11.61129205-61129720>CYBASC3 | CYBASC3 (CYB561A3) | 220002 | ENSG00000162144 | Q8NBI2 |
| chr11.6523983-6524156>FXC1 andDNHID1 | FXC1 (TIMM10B) and DNHD1 | 26515 and 144132 | ENSG00000132286 and ENSG00000179532 | Q9Y5J6 and Q96M86 |
| chr19.8441789-8441951>lyta | lyta | "NoInfo" | "NoInfo" | "NoInfo" |
| chr6.153291674-153292549>FBX05 | FBX05 | 26271 | ENSG00000112029 | Q9UKT4 |
| chr6.153291660-153292549>FBX05 | FBX05 | 26271 | ENSG00000112029 | Q9UKT4 |
| chr6.153291654-153292549>FBX05 | FBX05 | 26271 | ENSG00000112029 | Q9UKT4 |
| chr7.29549802-29552165>klerky | klerky | "NoInfo" | "NoInfo" | "NoInfo" |
| chr22.41175013-41175129>SLC25A17 | SLC25A17 | 10478 | ENSG00000100372 | O43808 |
| chr4.76874494-76874938>sporsmorby | sporsmorby | "NoInfo" | "NoInfo" | "NoInfo" |
| chr5.39274505-39274630>FYB | FYB | 2533 | ENSG00000082074 | O15117 |
| chr10.32324818-32324922>KIF5B | KIF5B | 3799 | ENSG00000170759 | P33176 |
| chr14.52957557-52957723>TXNDC16 | TXNDC16 | 57544 | ENSG00000087301 | Q9P2K2 |
| chr14.88452833-88452946>GALC | GALC | 2581 | ENSG00000054983 | P54803 |
| chr20.30720816-30720929>TM9SF4 | TM9SF4 | 9777 | ENSG00000101337 | Q92544 |
| chr19.54610118-54610266>NDUFA3 | NDUFA3 | 4696 | ENSG00000170906 | O95167 |
| chr10.92500578-92502285>HTR7 | HTR7 | 3363 | ENSG00000148680 | P34969 |
| chr3.25639711-25639423>RARB | RABB | 5915 | ENSG00000077092 | P10826 |
| chr5.14381239-14381361>TRIO | TRIO | 7204 | ENSG00000038382 | O75962 |
| chr2.243168539-243168819>samemo | samemo | "NoInfo" | "NoInfo" | "NoInfo" |
| chr3.137963865-137964523>vusmyby | vusmyby | "NoInfo" | "NoInfo" | "NoInfo" |
| chr3.137963930-137964523>ARMC8 | ARMC8 | 25852 | ENSG00000114098 | Q8IUR7 |
| chr3.137963930-137964524>ARMC8 | ARMC8 | 25852 | ENSG00000114098 | Q8IUR7 |
| chr14.100743755-100744113>YY1 | YY1 | 7528 | ENSG00000100811 | P25490 |
| Table 1E—Exon Usage Upregulated in Subjects Who Have Not Experienced ischemic Stroke/ICH | | | | |
| chr20.32880178-32880359>AHCY | AHCY | 191 | ENSG00000101444 | P23526 |
| chr2.242611606-242612016>ATG4B | ATG4B | 23192 | ENSG00000168397 | Q9Y4P1 |
| chr9.96866557-96866667>PTPDC1 | PTPDC1 | 138639 | ENSG00000158079 | A2A3K4 |
| chr17.42982993-42984756>GFAP | GFAP | 2670 | ENSG00000131095 | P14136 |
| chr22.41252435-41253036>ST13 | ST13 | 6767 | ENSG00000100380 | P50502 |
| chr1.53416427-53416558>SCP2 | SCP2 | 6342 | ENSG00000116171 | P22307 |
| chr6.32806430-32806547>TAP2andHLA-DOB | TAP2 and HLA-DOB | 6891 and 3112 | ENSG00000204267 and ENSG00000241106 | Q03519 and P13765 |
| chr14.19683027-19683434>DUXAP10 | DUXAP10 | 503639 | ENSG00000257227 | "NoInfo" |
| chr9.95018962-95019082>IARS | IARS | 3376 | ENSG00000196305 | P41252 |
| chr19.39138368-39138547>ACTN4 | ACTN4 | 81 | ENSG00000130402 | O43707 |
| chr9.140473077-140473340>WDR85 | WDR85 (DPH7) | 92715 | ENSG00000148399 | Q9BTV6 |
| chrX.48367956-48368344>PORCN | PORCN | 64840 | ENSG00000102312 | Q9H237 |
| chr2.101606718-101606908>NPAS2 | NPAS2 | 4862 | ENSG00000170485 | Q99743 |
| chr7.101475858-101476865>snorkar | snorkar | "NoInfo" | "NoInfo" | "NoInfo" |
| chr19.45543176-45543569>SFRS16 | SFRS16 (CLASRP) | 11129 | ENSG00000104859 | Q8N2M8 |
| chr18.28642978-28643439>DSC2 | DSC2 | 1824 | ENSG00000134755 | Q02487 |
| chr22.36892014-36892255>FOXRED2andTXN2 | FOXRED2 and TXN2 | 80020 and 25828 | ENSG00000100350 and ENSG00000100348 | Q8IWF2 and Q99757 |
| chr18.43417478-43417850>SIGLEC15 | SIGLEC15 | 284266 | ENSG00000197046 | Q6ZMC9 |

TABLE 7

Differential Exon Usage in the 5 Groups (p < 0.005, FC > |1.21|). FC—Fold Change

| | | CE Stroke vs. Controls | | CE Stroke vs. ICH | | CE Stroke vs. LV | | CE Stroke vs. Lacunar | |
|---|---|---|---|---|---|---|---|---|---|
| Upregulated in CE IS | | | | | | | | | |
| Marker ID | Gene Symbol | p-value | FC | p-value | FC | p-value | FC | p-value | FC |
| chr1.86861716-86861978 > ODF2L | ODF2L | 4.89E-04 | 32.54 | 8.33E-02 | 1.68 | 4.39E-04 | 52.79 | 4.15E-04 | 77.95 |
| chr10.38299602-38299711 > ZNF33A | ZNF33A | 1.34E-03 | 8.75 | 4.81E-04 | >500 | 3.54E-03 | 4.52 | 4.80E-04 | Not Estimable |
| chr10.38299604-38299711 > ZNF33A | ZNF33A | 1.34E-03 | 8.75 | 4.81E-04 | >500 | 3.54E-03 | 4.52 | 4.80E-04 | Not Estimable |
| chr10.49253461-49254183 > BMS1P7 | BMS1P7 | 3.00E-04 | 11.83 | 1.29E-04 | >500 | 2.16E-03 | 3.62 | 5.90E-04 | 6.62 |
| chr14.70242552-70243105 > SLC10A1 | SLC10A1 | 3.87E-04 | Not Estimable | 1.52E-02 | 2.52 | 4.05E-03 | 3.93 | 7.65E-03 | 3.10 |
| chr17.34856670-34856799 > MYO19 | MYO19 | 6.48E-04 | 7.89 | 2.45E-03 | 3.85 | 1.19E-03 | 5.32 | 4.55E-04 | 11.01 |
| chr17.73000302-73002233 > CDR2L | CDR2L | 1.76E-05 | 10.40 | 1.03E-05 | 19.45 | 1.19E-05 | 15.70 | 2.54E-05 | 7.93 |
| chr19.18959976-18960255 > UPF1 | UPF1 | 6.28E-04 | 4.27 | 8.00E-05 | 21.25 | 4.87E-05 | Not Estimable | 9.17E-05 | 16.73 |
| chr19.58427747-58427959 > ZNF417andZNF814 | ZNF417 and ZNF814 | 4.40E-04 | 4.45 | 3.91E-02 | 1.64 | 5.11E-05 | 31.22 | 4.31E-05 | 62.20 |
| chr19.58427747-58427960 > ZNF417andZNF814 | ZNF417 and ZNF814 | 4.40E-04 | 4.45 | 3.91E-02 | 1.64 | 5.11E-05 | 31.22 | 4.31E-05 | 62.20 |
| chr2.119988299-119988610 > STEAP3 | STEAP3 | 4.66E-04 | 199.47 | 1.78E-03 | 6.53 | 4.46E-04 | >500 | 5.08E-04 | 68.51 |
| chr2.179463448-179463831 > CCDC141andTTN | CCDC141 and TTN | 4.17E-06 | 56.83 | 5.56E-05 | 4.49 | 3.38E-06 | >500 | 3.38E-06 | >500 |
| chr2.25258142-25260098 > LOC729723 | LOC729723 | 1.67E-03 | 4.92 | 4.83E-04 | 13.26 | 6.86E-04 | 8.95 | 5.62E-04 | 10.97 |
| chr20.43995515-43996064 > SYS1-DBNDD2 | SYS1-DBNDD2 | 1.17E-02 | 9.29 | 9.88E-02 | 2.21 | 2.68E-02 | -1.76 | 3.16E-02 | 3.81 |
| chr22.19115606-19115962 > skatee | skatee | 1.69E-02 | 1.83 | 6.02E-04 | 3.72 | 5.45E-05 | 16.63 | 2.53E-04 | 5.12 |
| chr3.188326949-188327339 > LPP | LPP | 1.18E-03 | 9.73 | 6.73E-04 | 24.42 | 5.40E-04 | 61.39 | 4.89E-04 | 196.57 |
| chr3.48456585-48456756 > PLXNB1 | PLXNB1 | 1.81E-05 | Not Estimable | 3.29E-04 | 4.01 | 1.81E-05 | >500 | 7.19E-04 | 3.20 |
| chr3.49448633-49449166 > myforbo | myforbo | 3.99E-04 | 5.56 | 2.06E-04 | 8.39 | 8.58E-02 | 1.50 | 1.01E-04 | 19.14 |
| chr4.15570247-15570813 > klawgu | klawgu | 3.67E-04 | 7.05 | 8.78E-03 | 2.30 | 6.85E-02 | 1.58 | 5.41E-04 | 5.61 |
| chr6.37225553-37225749 > TBC1D22B | TBC1D22B | 2.24E-01 | 1.22 | 2.12E-02 | 1.59 | 1.12E-01 | -1.24 | 7.61E-04 | 2.56 |
| chr7.142630429-142630905 > TRPV5 | TRPV5 | 1.01E-03 | 4.98 | 4.08E-03 | 2.99 | 1.34E-04 | >500 | 1.68E-04 | 42.44 |
| chr7.158334118-158334468 > PTPRN2 | PTPRN2 | 1.50E-04 | Not Estimable | 2.64E-04 | 17.40 | 3.29E-03 | 3.27 | 2.01E-04 | 33.34 |
| chr8.104406853-104407319 > shuskeebu | shuskeebu | 9.62E-05 | 18.92 | 4.82E-03 | 2.47 | 2.53E-04 | 7.00 | 1.48E-03 | 3.32 |

| | | CE Stroke vs. LV | | Controls vs. LV | | ICH vs. LV | | LV vs. Lacunar | |
|---|---|---|---|---|---|---|---|---|---|
| Upregulated in LV IS | | | | | | | | | |
| Marker ID | Gene Symbol | p-value | FC | p-value | FC | p-value | FC | p-value | FC |
| chr1.214836934-214837426 > CENPF | CENPF | 5.00E-04 | -3.69 | 5.93E-02 | -1.51 | 1.21E-03 | -2.91 | 1.98E-04 | 5.17 |
| chr10.46918169-46918362 > FAM35BandRHEBP1 | FAM35B and RHEBP1 | 1.26E-02 | -2.69 | 2.31E-03 | -5.33 | 4.16E-04 | <-500 | 7.30E-04 | 16.07 |
| chr11.62389338-62389648 > B3GAT3 | B3GAT3 | 2.98E-04 | -184.49 | 1.74E-03 | -5.23 | 1.16E-02 | -2.57 | 3.51E-03 | 3.78 |
| chr12.54645834-54646011 > CBX5 | CBX5 | 4.19E-04 | -9.67 | 1.51E-04 | <-500 | 1.53E-04 | <-500 | 7.79E-04 | 6.06 |
| chr12.56334947-56335109 > DGKA | DGKA | 3.08E-02 | -2.03 | 3.68E-03 | -3.73 | 4.70E-04 | -19.19 | 9.49E-04 | 7.91 |
| chr13.103506107-103506222 > BIVMandERCC5 | BIVM and ERCC5 | 3.55E-07 | -8.46 | 1.47E-07 | -18.25 | 7.87E-08 | -119.86 | 1.72E-07 | 15.06 |
| chr14.53248502-53248629 > GNPNAT1 | GNPNAT1 | 3.32E-03 | -3.53 | 2.07E-04 | <-500 | 4.12E-04 | -13.92 | 4.11E-02 | 1.85 |
| chr15.101847418-101849508 > PCSK6 | PCSK6 | 2.64E-05 | -9.47 | 1.70E-04 | -3.93 | 1.94E-03 | -2.29 | 1.42E-05 | 18.68 |
| chr15.81584265-81585378 > IL16 | IL16 | 4.03E-04 | -7.21 | 1.56E-02 | -2.08 | 1.94E-03 | -3.49 | 1.93E-03 | 14.76 |
| chr16.4475881-4476093 > DNAJA3 | DNAJA3 | 4.39E-04 | -9.19 | 2.89E-01 | -1.28 | 2.48E-02 | -1.98 | 3.13E-03 | 3.32 |
| chr16.72146312-72146549 > DHX38 | DHX38 | 3.43E-04 | <-500 | 3.58E-04 | -207.50 | 6.13E-04 | -15.82 | 3.43E-04 | >500 |
| chr17.43002077-43003867 > KIF18B | KIF18B | 7.66E-04 | -4.84 | 4.20E-04 | -6.67 | 3.80E-02 | -1.75 | 2.95E-03 | 3.02 |
| chr2.173420100-173420447 > PDK1 | PDK1 | 5.32E-04 | -8.27 | 6.79E-03 | -2.69 | 2.85E-03 | -3.49 | 3.74E-04 | 11.68 |
| chr2.20756227-20757428 > dawgorbu | dawgorbu | 5.41E-04 | -3.87 | 2.90E-05 | Not Estimable | 2.42E-04 | -5.27 | 1.12E-04 | 8.19 |

TABLE 7-continued

Differential Exon Usage in the 5 Groups (p < 0.005, FC > |1.21|). FC—Fold Change

| Marker ID | Gene Symbol | p-value | FC | p-value | FC | p-value | FC | p-value | FC | FC |
|---|---|---|---|---|---|---|---|---|---|---|
| chr20.33056659-33057236 > vytaw | vytaw | 3.05E−04 | −11.22 | 2.33E−03 | −3.50 | 7.30E−04 | −5.73 | 1.25E−04 | | Not Estimable |
| chr20.43995515-43996064 > SYS1-DBNDD2 | SYS1-DBNDD2 | 2.68E−02 | −1.76 | 8.54E−05 | −16.38 | 7.51E−04 | −3.90 | 2.23E−04 | | 6.72 |
| chr20.52560545-52561535 > BCAS1 | BCAS1 | 1.65E−04 | −247.51 | 3.31E−03 | −3.31 | 6.66E−04 | −6.90 | 3.85E−04 | | 11.11 |
| chr22.18613610-18614498 > PEX26andTUBA8 | PEX26 and TUBA8 | 1.36E−02 | −2.14 | 3.42E−04 | −8.12 | 9.20E−04 | −4.61 | 7.57E−02 | | 1.57 |
| chr22.29141852-29141989 > HSCB | HSCB | 4.31E−03 | −3.84 | 9.81E−03 | −2.87 | 4.12E−04 | −167.51 | 2.88E−03 | | 4.61 |
| chr3.49448633-49449166 > myforbo | myforbo | 8.58E−02 | 1.50 | 1.68E−02 | −3.71 | 8.50E−03 | −5.60 | 3.98E−03 | | 12.77 |
| chr3.8606070-8609805 > LMCD1 | LMCD1 | 6.35E−03 | −3.28 | 2.63E−03 | −4.75 | 1.48E−03 | −6.74 | 3.77E−04 | | Not Estimable |
| chr4.15570247-15570813 > klawgu | klawgu | 6.85E−02 | 1.58 | 1.98E−02 | −4.45 | 3.12E−01 | −1.45 | 2.90E−02 | | 3.54 |
| chr5.162902464-162902678 > HMMR | HMMR | 2.07E−04 | <−500 | 1.05E−03 | −5.96 | 1.57E−03 | −4.80 | 4.74E−03 | | 3.13 |
| chr5.176715528-176715926 > NSD1 | NSD1 | 3.78E−04 | −8.90 | 1.22E−04 | Not Estimable | 1.01E−03 | −4.81 | 3.10E−04 | | 10.77 |
| chr5.61688639-61688817 > DIMT1L | DIMT1L | 1.15E−03 | −4.55 | 2.66E−04 | −12.85 | 5.61E−03 | −2.70 | 1.79E−04 | | 26.01 |
| chr6.100023529-100023947 > RPS3P5 | RPS3P5 | 6.84E−05 | −7.70 | 2.96E−05 | −17.42 | 1.92E−04 | −4.63 | 4.47E−05 | | 10.72 |
| chr6.111619174-111619773 > slyjey | slyjey | 6.80E−05 | −6.99 | 4.07E−04 | −3.47 | 1.65E−02 | −1.74 | 2.30E−05 | | 19.83 |
| chr6.37225553-37225749 > TBC1D22B | TBC1D22B | 1.12E−01 | −1.24 | 9.78E−03 | −1.52 | 6.80E−04 | −1.98 | 2.94E−05 | | 3.18 |
| chr7.2282560-2282683 > NUDT1 | NUDT1 | 5.87E−04 | −3.95 | 3.45E−05 | Not Estimable | 3.70E−05 | −150.96 | 1.65E−04 | | 7.00 |
| chr8.90798887-90799401 > RIPK2 | RIPK2 | 1.00E−04 | −18.86 | 1.65E−04 | −10.01 | 3.30E−02 | −1.74 | 4.32E−04 | | 5.31 |
| chr9.131486273-131486409 > ZDHHC12 | ZDHHC12 | 1.41E−05 | −6.54 | 2.13E−05 | −5.43 | 5.90E−06 | −11.68 | 8.83E−06 | | 8.53 |
| chrX.152226503-152227128 > PNMA3 | PNMA3 | 3.13E−03 | −4.43 | 4.20E−04 | −126.98 | 5.52E−04 | −26.32 | 1.74E−03 | | 6.14 |

| Upregulated in Lacunar IS | | CE Stroke vs. Lacunar | | Controls vs. Lacunar | | ICH vs. Lacunar | | LV vs. Lacunar | |
|---|---|---|---|---|---|---|---|---|---|
| Marker ID | Gene Symbol | p-value | FC | p-value | FC | p-value | FC | p-value | FC |
| chr1.155691308-155691471 > DAP3 | DAP3 | 1.44E−03 | −5.83 | 1.51E−02 | −2.40 | 4.78E−04 | −18.04 | 9.64E−04 | −7.72 |
| chr1.160580214-160580588 > SLAMF1 | SLAMF1 | 9.00E−05 | −50.28 | 6.08E−04 | −4.99 | 8.40E−05 | −75.82 | 1.30E−04 | −17.92 |
| chr1.246729640-246730091 > CNST | CNST | 1.49E−04 | <−500 | 1.49E−04 | <−500 | 5.30E−04 | −7.83 | 1.12E−02 | −2.35 |
| chr11.119039480-119040011 > NLRX1 | NLRX1 | 2.47E−03 | −4.13 | 8.08E−04 | −7.84 | 5.40E−04 | −11.67 | 3.97E−04 | −18.66 |
| chr11.62475067-62475387 > GNG3 | GNG3 | 2.61E−02 | −2.07 | 2.51E−04 | <−500 | 8.27E−03 | −2.76 | 6.18E−04 | −10.50 |
| chr12.111065735-111066029 > TCTN1 | TCTN1 | 2.36E−04 | <−500 | 5.53E−04 | −11.15 | 2.41E−04 | −407.21 | 2.36E−04 | <−500 |
| chr12.123262038-123262230 > CCDC62 | CCDC62 | 7.34E−03 | −3.02 | 6.85E−04 | −12.40 | 1.61E−03 | −5.83 | 4.55E−04 | −27.30 |
| chr12.2966630-2968829 > FOXM1 | FOXM1 | 4.11E−04 | −4.71 | 9.88E−04 | −3.47 | 2.51E−03 | −2.72 | 1.60E−04 | −7.77 |
| chr12.94914730-94915694 > LOC400061 | LOC400061 | 8.26E−04 | −2.46 | 2.57E−01 | −1.20 | 1.49E−05 | −9.38 | 4.11E−06 | Not Estimable |
| chr14.96795821-96795971 > ATG2B | ATG2B | 1.42E−04 | −4.39 | 5.92E−04 | −2.96 | 1.69E−02 | −1.70 | 6.23E−05 | −6.19 |
| chr15.52970203-52970319 > KIAA1370 | KIAA1370 | 7.48E−02 | −1.68 | 2.15E−02 | −2.19 | 2.45E−03 | −4.32 | 2.70E−04 | <−500 |
| chr16.15013757-15013940 > zoner | zoner | 8.81E−03 | −2.19 | 3.72E−02 | −1.70 | 2.46E−03 | −2.90 | 5.61E−05 | Not Estimable |
| chr18.33077683-33077895 > INO80C | INO80C | 1.26E−03 | −4.39 | 3.20E−04 | −10.51 | 6.38E−02 | −1.64 | 2.82E−03 | −3.28 |
| chr19.35173682-35173954 > ZNF302 | ZNF302 | 5.42E−04 | −24.66 | 7.08E−04 | −14.32 | 4.23E−04 | −74.20 | 4.45E−04 | −52.73 |
| chr2.101627502-101628002 > TBC1D8 | TBC1D8 | 2.60E−04 | −13.65 | 1.09E−03 | −4.69 | 1.25E−04 | <−500 | 3.07E−04 | −11.16 |
| chr2.160143094-160143317 > WDSUB1 | WDSUB1 | 1.02E−03 | −8.14 | 3.24E−04 | Not Estimable | 6.23E−03 | −3.18 | 2.45E−03 | −4.63 |
| chr2.29258330-29258510 > FAM179A | FAM179A | 2.28E−05 | <−500 | 7.40E−05 | −9.36 | 5.57E−05 | −12.23 | 4.93E−03 | −2.20 |
| chr20.32079185-32079982 > spawvor | spawvor | 1.44E−05 | Not Estimable | 1.47E−04 | −5.01 | 3.41E−04 | −3.73 | 6.92E−05 | −7.31 |
| chr21.47706315-47706712 > C21orf57 | C21orf57 | 3.23E−05 | −21.91 | 9.74E−05 | −7.03 | 1.42E−04 | −5.74 | 1.96E−05 | −2028.81 |
| chr22.24316496-24316679 > GSTTP1andDDT | GSTTP1 and DDT | 4.42E−03 | −3.29 | 7.91E−04 | −7.77 | 9.06E−02 | −1.60 | 4.00E−04 | −17.20 |

TABLE 7-continued

Differential Exon Usage in the 5 Groups (p < 0.005, FC > |1.21|). FC—Fold Change

| | | | | | | | | |
|---|---|---|---|---|---|---|---|---|
| chr22.44514918-44515020 > PARVB | PARVB | 3.20E-03 | -3.27 | 6.91E-04 | -6.35 | 4.81E-02 | -1.74 2.99E-04 | -13.44 |
| chr5.156821041-156822687 > ADAM19 | ADAM19 | 3.01E-04 | -16.01 | 2.15E-02 | -2.06 | 1.13E-03 | -5.14 2.42E-03 | -3.71 |
| chr6.146285293-146285525 > SHPRH | SHPRH | 8.44E-04 | -4.84 | 3.55E-04 | -8.05 | 4.01E-02 | -1.75 2.61E-04 | -10.55 |
| chr6.146285293-146285559 > SHPRH | SHPRH | 8.44E-04 | -4.84 | 3.55E-04 | -8.05 | 4.01E-02 | -1.75 2.61E-04 | -10.55 |
| chr6.163984476-163984751 > QKI | QKI | 3.99E-07 | -5.23 | 6.22E-08 | -15.32 | 7.43E-07 | -4.34 2.09E-07 | -6.72 |
| chr6.168370462-168372588 > MLLT4 | MLLT4 | 7.37E-03 | -2.24 | 9.05E-04 | -3.79 | 2.40E-03 | -2.86 4.22E-04 | -5.10 |
| chr6.30610545-30612432 > C6orf134 | C6orf134 | 3.16E-04 | -5.69 | 1.56E-04 | -8.92 | 5.98E-04 | -4.30 1.39E-02 | -1.97 |
| chr7.99674926-99675056 > ZNF3 | ZNF3 | 6.70E-04 | -6.08 | 4.74E-04 | -7.65 | 9.91E-03 | -2.37 2.97E-04 | -11.79 |
| chr8.10340434-10340741 > LOC346702 | LOC346702 | 5.43E-05 | -6.06 | 1.95E-05 | -12.38 | 7.60E-06 | <-500 1.33E-05 | -20.57 |
| chr9.46687439-46688197 > KGFLP1 | KGFLP1 | 1.22E-05 | <-500 | 1.22E-05 | <-500 | 1.22E-05 | <-500 3.46E-05 | -10.97 |
| chrX.40495835-40495964 > CXorf38 | CXorf38 | 1.50E-03 | -7.97 | 4.89E-04 | Not Estimable | 5.85E-04 | -49.12 5.41E-04 | -86.98 |

| | | CE Stroke vs. ICH | | Controls vs. ICH | | ICH vs. LV | | ICH vs. Lacunar | |
|---|---|---|---|---|---|---|---|---|---|
| Upregulated in ICH | | p-value | FC | p-value | FC | p-value | FC | p-value | FC |
| Marker ID | Gene Symbol | | | | | | | | |
| chr1.10509776-10510379 > APITD1andCORT | APITD1 and CORT | 7.04E-04 | -4.22 | 4.26E-04 | -5.20 | 1.17E-04 | 13.61 | 8.89E-05 | 20.93 |
| chr1.112991564-112991794 > CTTNBP2NL | CTTNBP2NL | 2.49E-02 | -1.96 | 7.67E-03 | -2.53 | 4.28E-04 | 8.64 | 3.22E-03 | 3.21 |
| chr1.114499947-114500540 > wawleybo | wawleybo | 1.41E-01 | -1.44 | 1.46E-03 | -4.21 | 3.22E-04 | 11.02 | 8.68E-04 | 5.33 |
| chr1.145509166-145509612 > RBM8A.1 | RBM8A.1 | 1.52E-03 | -4.05 | 2.57E-03 | -3.37 | 4.91E-04 | 7.24 | 3.48E-04 | 9.57 |
| chr1.145790974-145791170 > GPR89A | GPR89A | 2.08E-04 | -9.88 | 1.17E-02 | -2.13 | 3.99E-02 | 1.71 | 1.49E-03 | 3.53 |
| chr1.150778337-150778492 > CTSK | CTSK | 6.96E-06 | -2.75 | 1.17E-06 | -3.85 | 5.52E-03 | 1.44 | 1.17E-04 | 1.96 |
| chr1.150939858-150940190 > LASS2 | LASS2 | 3.59E-05 | -8.01 | 6.54E-05 | -5.76 | 9.12E-04 | 2.65 | 1.47E-04 | 4.20 |
| chr1.154928545-154928780 > SHC1andPYGO2andPBXIP1 | SHC1 and PYGO2 and PBXIP1 | 3.65E-04 | Not Estimable | 1.55E-03 | -6.39 | 4.42E-03 | 3.72 | 1.44E-02 | 2.53 |
| chr1.161196029-161196394 > TOMM40L | TOMM40L | 1.18E-02 | -2.53 | 9.42E-04 | -7.43 | 2.63E-04 | >500 | 6.66E-04 | 10.15 |
| chr1.168262382-168262516 > SFT2D2andTBX19 | SFT2D2 and TBX19 | 1.10E-03 | -3.16 | 5.90E-03 | -2.19 | 4.08E-04 | 4.29 | 1.13E-04 | 8.20 |
| chr1.17056-17742 > WASH7P | WASH7P | 7.18E-04 | -10.55 | 1.11E-03 | -7.10 | 4.84E-04 | 18.86 | 2.00E-03 | 4.94 |
| chr1.180049625-180049796 > CEP350 | CEP350 | 1.98E-02 | -1.72 | 9.32E-04 | -2.93 | 2.29E-04 | 4.37 | 2.51E-03 | 2.39 |
| chr1.180049652-180049796 > CEP350 | CEP350 | 1.98E-02 | -1.72 | 9.32E-04 | -2.93 | 2.29E-04 | 4.37 | 2.51E-03 | 2.39 |
| chr1.19470474-19470585 > UBR4 | UBR4 | 4.12E-04 | -2.86 | 8.91E-03 | -1.76 | 2.07E-05 | 8.19 | 1.23E-04 | 3.84 |
| chr1.201780731-201780885 > NAV1 | NAV1 | 6.28E-05 | -6.82 | 1.22E-04 | -4.98 | 4.14E-05 | 8.94 | 1.12E-01 | 1.36 |
| chr1.235956803-235956912 > LYST | LYST | 4.09E-04 | -7.06 | 9.57E-05 | Not Estimable | 1.31E-01 | 1.44 | 1.86E-03 | 3.52 |
| chr1.243419358-243419542 > SDCCAG8 | SDCCAG8 | 3.06E-04 | -87.36 | 2.16E-03 | -4.61 | 1.69E-02 | 2.32 | 7.16E-03 | 2.94 |
| chr1.243652316-243652442 > SDCCAG8 | SDCCAG8 | 1.83E-03 | -2.98 | 1.58E-03 | -8.34 | 6.05E-03 | 2.28 | 6.33E-04 | 4.10 |
| chr1.26799700-26800018 > HMGN2 | HMGN2 | 1.04E-03 | -2.73 | 3.52E-05 | -10.65 | 7.29E-05 | 6.45 | 1.74E-04 | 4.42 |
| chr1.27431807-27432578 > SLC9A1 | SLC9A1 | 4.90E-02 | -1.58 | 3.25E-04 | -4.86 | 1.19E-02 | 1.96 | 3.45E-03 | 2.47 |
| chr1.45987501-45987609 > PRDX1 | PRDX1 | 3.62E-05 | <-500 | 1.49E-05 | -8.59 | 9.31E-05 | 3.89 | 4.92E-05 | 4.78 |
| chr1.46467098-46468407 > MAST2 | MAST2 | 3.48E-04 | -3.59 | 1.16E-04 | -5.26 | 5.31E-05 | 8.00 | 1.14E-02 | 1.83 |
| chr1.46805848-46806591 > NSUN4andFAAH | NSUN4 and FAAH | 6.05E-05 | <-500 | 1.71E-04 | -10.12 | 1.51E-02 | 1.99 | 6.05E-05 | >500 |
| chr1.63269390-63269533 > ATG4C | ATG4C | 3.01E-05 | -7.06 | 1.05E-05 | -18.05 | 6.94E-05 | 4.82 | 1.23E-05 | 14.55 |
| chr1.78207302-78207433 > USP33 | USP33 | 1.91E-03 | -3.35 | 4.75E-03 | -2.62 | 1.69E-02 | 2.01 | 4.67E-04 | 5.92 |
| chr1.85039599-85040103 > CTBSandGNG5 | CTBS and GNG5 | 1.53E-03 | -6.62 | 2.47E-03 | -4.94 | 4.75E-04 | 42.06 | 5.65E-04 | 23.30 |
| chr1.85127881-85128058 > SSX2IP | SSX2IP | 1.86E-01 | -1.31 | 6.50E-04 | -3.62 | 1.03E-02 | 1.98 | 1.57E-04 | 6.44 |
| chr1.89271574-89271700 > PKN2 | PKN2 | 6.12E-04 | -6.28 | 1.13E-02 | -2.29 | 1.87E-04 | 23.55 | 1.20E-03 | 4.46 |
| chr10.11272033-11272456 > CELF2 | CELF2 | 6.92E-04 | -2.68 | 1.36E-04 | -3.96 | 1.47E-05 | 13.37 | 6.22E-05 | 5.22 |
| chr10.32324818-32324922 > KIF5B | KIF5B | 2.07E-03 | -2.30 | 1.93E-01 | -1.26 | 2.91E-04 | 3.49 | 8.95E-03 | 1.84 |
| chr10.51592090-51592619 > LOC100287554 | LOC100287554 | 9.51E-03 | -2.27 | 4.56E-04 | -6.21 | 1.87E-03 | 3.42 | 9.11E-04 | 4.43 |
| chr10.69828759-69829524 > HERC4 | HERC4 | 9.83E-04 | -5.89 | 1.21E-02 | -2.38 | 5.78E-04 | 8.60 | 1.86E-04 | >500 |
| chr10.75230828-75230967 > PPP3CB | PPP3CB | 8.45E-04 | -4.23 | 4.34E-03 | -2.61 | 2.62E-04 | 7.78 | 4.88E-02 | 1.65 |
| chr10.92500578-92502285 > HTR7 | HTR7 | 8.97E-05 | -3.59 | 5.98E-02 | -1.38 | 3.65E-05 | 2.65 | 4.87E-03 | 1.82 |
| chr10.99195666-99196308 > EXOSC1 | EXOSC1 | 2.77E-04 | -36.28 | 1.45E-02 | -2.32 | 5.19E-04 | 10.77 | 2.56E-03 | 3.92 |

TABLE 7-continued

Differential Exon Usage in the 5 Groups (p < 0.005, FC > |1.21|). FC—Fold Change

| Location | Gene | | | | | | | | |
|---|---|---|---|---|---|---|---|---|---|
| chr10.99433338-99433902 > DHDPSLandPI4K2A | DHDPSL and PI4K2A | 9.07E-05 | -29.65 | 7.99E-05 | -46.47 | 2.70E-04 | 7.33 | 1.53E-04 | 11.94 |
| chr11.111889680-111893310 > DIXDC1 | DIXDC1 | 1.93E-04 | -8.50 | 6.36E-03 | -2.33 | 1.87E-02 | 1.90 | 3.94E-04 | 5.46 |
| chr11.111889680-111893374 > DIXDC1 | DIXDC1 | 1.93E-04 | -8.50 | 6.36E-03 | -2.33 | 1.87E-02 | 1.90 | 3.94E-04 | 5.46 |
| chr11.125490667-125490901 > STT3AandCHEK1 | STT3A and CHEK1 | 6.31E-08 | <-500 | 7.17E-08 | -95.82 | 6.83E-08 | 148.17 | 1.54E-07 | 14.95 |
| chr11.47738539-47739064 > FNBP4 | FNBP4 | 3.24E-04 | -10.00 | 2.29E-03 | -3.47 | 2.00E-04 | 19.17 | 1.66E-04 | 29.34 |
| chr11.61129205-61129720 > CYBASC3 | CYBASC3 | 2.94E-04 | -16.63 | 2.29E-04 | -28.81 | 7.91E-04 | 6.27 | 1.34E-02 | 2.28 |
| chr11.62105383-62105784 > saroro | saroro | 2.68E-04 | <-500 | 2.68E-04 | <-500 | 2.68E-04 | >500 | 2.68E-04 | >500 |
| chr11.6523983-6524156 > FXC1andDNHD1 | FXC1 and DNHD1 | 2.16E-04 | -20.50 | 2.28E-03 | -3.58 | 7.96E-04 | 5.63 | 1.59E-02 | 2.15 |
| chr11.7479027-7479174 > veemee | veemee | 5.89E-05 | <-500 | 1.17E-03 | -3.62 | 3.17E-03 | 2.75 | 3.03E-04 | 6.49 |
| chr11.836251-836525 > CD151 | CD151 | 4.18E-05 | -7.43 | 6.65E-05 | -5.80 | 1.16E-05 | 38.09 | 1.80E-05 | 15.64 |
| chr11.89933252-89935719 > CHORDC1 | CHORDC1 | 8.39E-05 | -12.95 | 3.53E-04 | -4.87 | 4.83E-03 | 2.33 | 1.37E-04 | 8.21 |
| chr12.10561988-10562183 > KLRC4andKLRK1 | KLRC4 and KLRK1 | 2.87E-03 | -3.91 | 8.17E-03 | -2.76 | 1.16E-03 | 6.12 | 3.22E-04 | 33.90 |
| chr12.40441853-40442012 > SLC2A13 | SLC2A13 | 6.39E-05 | -5.50 | 3.03E-05 | -8.23 | 7.21E-06 | >500 | 1.36E-05 | 18.27 |
| chr12.48094974-48095387 > RPAP3 | RPAP3 | 6.56E-03 | -2.64 | 7.99E-02 | -1.59 | 2.33E-03 | 3.59 | 4.90E-04 | 7.84 |
| chr12.54789679-54790160 > ITGA5 | ITGA5 | 9.53E-03 | -2.85 | 1.58E-03 | -6.27 | 5.00E-04 | 28.60 | 5.65E-04 | 20.66 |
| chr12.58345541-58345678 > XRCC6BP1 | XRCC6BP1 | 4.42E-05 | -135.95 | 1.80E-04 | -7.31 | 1.49E-03 | 3.11 | 8.16E-05 | 15.47 |
| chr12.6761437-6761584 > ING4 | ING4 | 1.90E-05 | -4.46 | 2.22E-04 | -2.56 | 1.61E-03 | 1.94 | 4.32E-05 | 3.55 |
| chr12.96258857-96259166 > SNRPF | SNRPF | 6.80E-06 | -15.03 | 3.06E-06 | <-500 | 1.16E-05 | 9.15 | 3.05E-06 | Not Estimable |
| chr13.100543572-100543866 > CLYBL | CLYBL | 1.02E-02 | -2.73 | 8.81E-04 | -9.28 | 3.93E-04 | 47.46 | 7.38E-04 | 11.24 |
| chr13.113864293-113864812 > PCID2 | PCID2 | 4.40E-04 | -10.60 | 6.02E-04 | -7.93 | 1.27E-03 | 4.99 | 1.01E-02 | 2.47 |
| chr13.41593364-41593568 > ELF1 | ELF1 | 4.35E-04 | <-500 | 9.67E-04 | -11.29 | 4.35E-04 | >500 | 2.23E-03 | 5.56 |
| chr14.100743755-100744113 > YY1 | YY1 | 4.40E-03 | -3.15 | 1.05E-02 | -2.47 | 2.73E-04 | 26.26 | 3.87E-04 | 13.52 |
| chr14.105236090-105236707 > AKT1 | AKT1 | 4.84E-05 | -8.22 | 2.03E-04 | -4.18 | 2.23E-05 | 18.04 | 8.26E-05 | 6.02 |
| chr14.20872770-20872931 > TEP1 | TEP1 | 1.47E-03 | -2.28 | 8.24E-05 | -4.38 | 3.09E-04 | 3.06 | 1.40E-02 | 1.67 |
| chr14.50246313-50246524 > KLHDC2 | KLHDC2 | 3.77E-02 | -1.71 | 4.58E-04 | -5.34 | 6.75E-03 | 2.34 | 1.83E-03 | 3.20 |
| chr14.52957557-52957723 > TXNDC16 | TXNDC16 | 1.34E-04 | -4.79 | 3.06E-03 | -2.21 | 3.24E-04 | 3.59 | 7.61E-04 | 2.90 |
| chr14.76107075-76107403 > FLVCR2andTTLL5andC14orf179 | FLVCR2 and TTLL5 and C14orf179 | 1.92E-03 | -2.58 | 6.71E-05 | -9.03 | 1.22E-01 | 1.36 | 6.13E-04 | 3.38 |
| chr14.88431849-88431973 > GALC | GALC | 5.67E-04 | -3.67 | 2.77E-03 | -2.48 | 1.18E-03 | 3.01 | 1.19E-04 | 7.15 |
| chr14.88452833-88452946 > GALC | GALC | 3.97E-04 | -3.47 | 2.38E-02 | -1.65 | 8.56E-05 | 6.09 | 1.30E-03 | 2.63 |
| chr14.96997812-96999040 > PAPOLA | PAPOLA | 1.96E-03 | -2.78 | 6.03E-04 | -3.85 | 3.36E-04 | 4.77 | 8.69E-02 | 1.46 |
| chr15.30711214-30711348 > rukaru | rukaru | 3.01E-04 | -11.05 | 9.53E-04 | -4.94 | 2.39E-03 | 3.45 | 5.73E-04 | 2.68 |
| chr15.38619054-38620016 > koyzawbu | koyzawbu | 2.03E-03 | -2.87 | 5.39E-02 | -1.58 | 2.95E-04 | 5.53 | 9.82E-04 | 3.50 |
| chr15.57545460-57545666 > stoyguby | stoyguby | 3.39E-05 | -5.43 | 8.44E-04 | -2.40 | 9.44E-05 | 3.83 | 3.07E-03 | 1.98 |
| chr15.59102429-59102587 > FAM63B | FAM63B | 3.05E-03 | -3.01 | 8.90E-04 | -4.60 | 2.53E-04 | 10.19 | 5.47E-04 | 5.82 |
| chr15.59943710-59944525 > GTF2A2 | GTF2A2 | 2.05E-02 | -2.18 | 4.44E-04 | -15.25 | 9.30E-04 | 7.02 | 8.26E-03 | 2.74 |
| chr15.64017491-64017712 > HERC1 | HERC1 | 3.68E-04 | -3.52 | 1.84E-04 | -4.37 | 1.36E-03 | 2.59 | 6.20E-03 | 1.99 |
| chr15.66811217-66811416 > ZWILCH | ZWILCH | 1.42E-06 | -15.75 | 4.47E-06 | -6.69 | 1.61E-05 | 4.16 | 8.06E-05 | 2.88 |
| chr15.66811217-66811467 > ZWILCH | ZWILCH | 1.42E-06 | -15.75 | 4.47E-06 | -6.69 | 1.61E-05 | 4.16 | 8.06E-05 | 2.88 |
| chr15.75165540-75165688 > SCAMP2 | SCAMP2 | 4.19E-04 | -4.48 | 6.10E-03 | -2.22 | 1.95E-03 | 2.82 | 5.15E-02 | 1.57 |
| chr15.80191177-80191467 > ST20andMTHFS | ST20 and MTHFS | 7.04E-04 | -5.57 | 2.00E-03 | -3.59 | 2.33E-04 | 13.85 | 3.18E-04 | 9.74 |
| chr15.94774950-94775234 > MCTP2 | MCTP2 | 4.31E-04 | Not Estimable | 9.26E-04 | -11.80 | 1.11E-03 | 9.54 | 4.31E-04 | Not Estimable |
| chr16.18799866-18800440 > ARL6IP1andRPS15A | ARL6IP1 and RPS15A | 2.45E-04 | -6.56 | 2.34E-03 | -2.85 | 1.10E-02 | 2.06 | 8.95E-04 | 3.74 |
| chr16.22277711-22277845 > EEF2K | EEF2K | 3.16E-05 | -114.30 | 1.08E-04 | -8.32 | 2.29E-02 | 1.75 | 3.03E-05 | 207.60 |
| chr16.30593851-30595166 > syrar | syrar | 4.87E-05 | <-500 | 6.03E-04 | -4.33 | 4.87E-05 | >500 | 4.87E-05 | >500 |
| chr16.3493611-3493837 > ZNF174andNAT15andCLUAP1 | ZNF174 and NAT15 and CLUAP1 | 3.54E-04 | <-500 | 5.17E-04 | -24.09 | 3.54E-04 | >500 | 3.54E-04 | >500 |
| chr17.18087711-18088067 > jeeroy | jeeroy | 1.76E-04 | -13.21 | 6.59E-04 | -4.99 | 1.02E-04 | 43.74 | 1.19E-04 | 26.41 |
| chr17.18486655-18486837 > CCDC144B | CCDC144B | 1.37E-02 | -2.53 | 3.39E-04 | <-500 | 3.82E-04 | 76.21 | 1.16E-03 | 7.53 |
| chr17.27581220-27581513 > CRYBA1 | CRYBA1 | 1.03E-04 | -21.86 | 1.74E-03 | -3.27 | 1.66E-03 | 11.01 | 2.63E-04 | 7.47 |
| chr17.36351796-36351996 > TBC1D3 | TBC1D3 | 3.07E-04 | -28.30 | 5.13E-03 | -3.10 | 4.66E-04 | 12.72 | 6.73E-04 | 8.57 |
| chr17.40280569-40280818 > RAB5C | RAB5C | 2.04E-01 | -1.25 | 8.87E-05 | -4.79 | 2.28E-02 | 1.61 | 4.01E-03 | 2.03 |
| chr17.57728564-57728677 > CLTC | CLTC | 3.52E-03 | -2.77 | 3.21E-04 | -7.06 | 8.42E-04 | 4.33 | 1.79E-03 | 3.34 |
| chr17.61473104-61473289 > TANC2 | TANC2 | 3.52E-03 | -2.04 | 7.45E-04 | -2.65 | 4.20E-05 | 6.30 | 1.10E-05 | 20.53 |
| chr17.62745780-62746126 > LOC146880 | LOC146880 | 3.51E-03 | -2.39 | 1.24E-03 | -3.00 | 4.23E-04 | 4.10 | 2.41E-04 | 5.09 |
| chr17.77079383-77079672 > ENGASE | ENGASE | 3.74E-04 | Not Estimable | 2.87E-03 | -4.54 | 2.80E-02 | 2.14 | 5.58E-03 | 3.43 |
| chr18.48443613-48443878 > ME2 | ME2 | 1.24E-01 | -1.52 | 1.43E-03 | -5.39 | 4.98E-03 | 3.20 | 4.15E-04 | 17.42 |

TABLE 7-continued

Differential Exon Usage in the 5 Groups ($p < 0.005$, FC > |1.21|). FC—Fold Change

| Location | Gene | | | | | | | | |
|---|---|---|---|---|---|---|---|---|---|
| chr18.54318248-54318824 > TXNL1 | TXNL1 | 3.27E-04 | -6.40 | 1.59E-04 | -11.19 | 1.61E-03 | 3.33 | 1.10E-04 | 18.33 |
| chr18.67508480-67516323 > DOK6 | DOK6 | 2.50E-06 | -3.44 | 3.70E-07 | -5.86 | 1.18E-06 | 2.00 | 1.02E-06 | 4.24 |
| chr19.11411543-11411912 > tojaw | tojaw | 1.12E-03 | -5.75 | 3.37E-03 | -19.59 | 4.08E-04 | 14.07 | 2.24E-03 | 4.10 |
| chr19.13009896-13010199 > SYCE2 | SYCE2 | 5.66E-02 | -1.66 | 1.16E-04 | -220.29 | 3.22E-04 | 9.45 | 1.70E-04 | 23.14 |
| chr19.1877203-1877424 > FAM108A1 | FAM108A1 | 9.46E-06 | -12.34 | 3.12E-05 | -5.70 | 4.87E-06 | 38.02 | 5.84E-06 | 24.14 |
| chr19.1953385-1953505 > C19orf34 | C19orf34 | 4.17E-03 | -3.77 | 1.47E-03 | -6.50 | 3.53E-04 | Not Estimable | 9.95E-04 | 8.89 |
| chr19.36515246-36515534 > CLIP3 | CLIP3 | 5.36E-02 | -1.78 | 2.47E-04 | <-500 | 2.47E-04 | >500 | 2.48E-04 | >500 |
| chr19.44128266-44128394 > CADM4 | CADM4 | 1.35E-01 | -1.38 | 7.22E-04 | -3.71 | 2.08E-02 | 1.80 | 2.51E-04 | 5.61 |
| chr19.44619641-44619995 > ZNF225 | ZNF225 | 1.90E-04 | -12.35 | 3.11E-04 | -7.83 | 1.23E-02 | 2.14 | 4.26E-04 | 6.35 |
| chr19.47646729-47646862 > SAE1 | SAE1 | 3.77E-03 | -2.25 | 4.22E-04 | -3.71 | 1.10E-03 | 2.88 | 8.17E-02 | 1.43 |
| chr19.47646751-47646862 > SAE1 | SAE1 | 3.77E-03 | -2.25 | 4.22E-04 | -3.71 | 1.10E-03 | 2.88 | 8.17E-02 | 1.43 |
| chr19.49314066-49314178 > BCAT2 | BCAT2 | 4.79E-03 | -3.77 | 3.15E-03 | -4.55 | 1.48E-03 | 7.25 | 4.22E-04 | Not Estimable |
| chr19.5208248-5208402 > PTPRS | PTPRS | 2.10E-03 | -4.21 | 4.27E-04 | -13.18 | 8.85E-04 | 6.65 | 5.17E-03 | 3.05 |
| chr19.52207575-52207733 > NCRNA00085 | NCRNA00085 | 6.15E-05 | -5.27 | 1.16E-05 | -18.46 | 8.15E-06 | 41.81 | 1.56E-05 | 12.72 |
| chr19.54610118-54610266 > NDUFA3 | NDUFA3 | 1.16E-04 | -6.91 | 9.25E-03 | -1.98 | 3.81E-05 | 21.56 | 4.72E-04 | 3.80 |
| chr19.58423428-58423554 > ZNF417andZNF814 | ZNF417 and ZNF814 | 2.95E-03 | -3.70 | 3.90E-04 | -15.56 | 2.11E-04 | >500 | 1.83E-02 | 2.20 |
| chr19.58423428-58423557 > ZNF417andZNF814 | ZNF417 and ZNF814 | 2.95E-03 | -3.70 | 3.90E-04 | -15.56 | 2.11E-04 | Not Estimable | 1.83E-02 | 2.20 |
| chr19.8441789-8441951 > lyta | lyta | 5.40E-04 | -8.82 | 3.08E-04 | -17.86 | 1.76E-03 | 4.33 | 3.90E-03 | 3.23 |
| chr19.9720432-9722012 > ZNF562andZNF561 | ZNF562 and ZNF561 | 6.18E-04 | -29.45 | 4.65E-03 | -469.78 | 4.39E-03 | 4.01 | 5.13E-04 | 75.31 |
| chr2.110584278-110584424 > RGPD5 | RGPD5 | 5.04E-05 | -11.19 | 9.25E-04 | -3.01 | 3.59E-04 | 3.92 | 1.20E-02 | 1.87 |
| chr2.111302237-111302383 > RGPD6 | RGPD6 | 5.04E-05 | -11.19 | 9.25E-04 | -3.01 | 3.59E-04 | 3.92 | 1.20E-02 | 1.87 |
| chr2.113175261-113175491 > RGPD8 | RGPD8 | 7.54E-05 | -5.13 | 3.91E-05 | -7.04 | 7.22E-06 | >500 | 1.04E-05 | 31.99 |
| chr2.118864235-118864479 > INSIG2 | INSIG2 | 5.60E-02 | -1.54 | 1.23E-02 | -7.34 | 2.27E-03 | 2.62 | 9.07E-04 | 3.27 |
| chr2.172848099-172848599 > HAT1 | HAT1 | 1.42E-04 | -4.52 | 4.48E-05 | -7.86 | 8.43E-05 | 5.58 | 1.49E-05 | 29.53 |
| chr2.17953901-17954051 > GEN1 | GEN1 | 9.89E-05 | -25.31 | 6.70E-05 | <-500 | 6.92E-05 | 199.20 | 1.58E-03 | 3.38 |
| chr2.182339687-182340015 > ITGA4 | ITGA4 | 1.90E-05 | -7.51 | 4.08E-03 | -1.92 | 1.03E-04 | 3.82 | 1.08E-05 | 11.34 |
| chr2.198175302-198175503 > ANKRD44 | ANKRD44 | 7.11E-04 | -5.58 | 3.26E-04 | -9.66 | 1.03E-02 | 2.31 | 2.81E-02 | 1.89 |
| chr2.208446079-208446884 > FAM119A | FAM119A | 3.71E-05 | -9.30 | 3.05E-04 | -3.59 | 4.39E-03 | 2.08 | 5.29E-05 | 7.28 |
| chr2.231663444-231663879 > CAB39 | CAB39 | 6.76E-03 | -2.27 | 1.48E-03 | -3.25 | 3.64E-02 | 1.69 | 3.63E-04 | 5.44 |
| chr2.234112772-234113219 > INPP5D | INPP5D | 1.03E-03 | -3.44 | 4.25E-04 | -4.68 | 1.22E-04 | 9.78 | 2.17E-03 | 2.82 |
| chr2.242282407-242282508 > SEPT2 | SEPT2 | 4.07E-02 | -2.55 | 1.80E-03 | -3.12 | 1.84E-04 | 8.63 | 9.02E-04 | 3.85 |
| chr2.243168539-243168819 > samemo | samemo | 4.94E-03 | -2.98 | 1.72E-02 | -2.18 | 2.23E-03 | 37.87 | 5.29E-04 | 8.73 |
| chr2.73957016-73957156 > TPRKB | TPRKB | 2.11E-05 | -8.51 | 8.41E-06 | -23.94 | 1.24E-05 | 13.51 | 6.75E-06 | 43.24 |
| chr2.88336462-88336570 > KRCC1 | KRCC1 | 1.75E-03 | -3.55 | 5.15E-03 | -2.62 | 2.74E-02 | 1.86 | 1.75E-04 | 15.65 |
| chr20.18449588-18449705 > POLR3F | POLR3F | 4.95E-05 | -10.82 | 1.16E-03 | -2.83 | 2.93E-04 | 4.13 | 1.75E-05 | Not Estimable |
| chr20.23401942-23402097 > NAPB | NAPB | 6.00E-05 | <-500 | 4.50E-04 | -5.29 | 5.97E-05 | >500 | 1.09E-04 | 17.28 |
| chr20.30720816-30720929 > TM9SF4 | TM9SF4 | 4.31E-04 | -2.58 | 7.10E-02 | -1.36 | 1.55E-03 | 2.11 | 8.38E-03 | 1.71 |
| chr20.34487292-34487561 > PHF20 | PHF20 | 1.17E-03 | -5.87 | 7.20E-04 | -8.27 | 4.74E-04 | 12.86 | 2.59E-03 | 3.97 |
| chr20.416929-419485 > TBC1D20 | TBC1D20 | 1.36E-03 | -3.68 | 3.76E-04 | -6.52 | 7.71E-04 | 4.55 | 7.72E-03 | 2.33 |
| chr20.43808628-43808775 > rotora | rotora | 2.81E-06 | -11.96 | 1.75E-03 | -3.84 | 4.47E-04 | 7.75 | 3.40E-03 | 3.09 |
| chr21.40619627-40619758 > BRWD1 | BRWD1 | 7.54E-05 | -4.31 | 7.25E-06 | -21.38 | 1.26E-05 | 10.81 | 3.76E-05 | 5.59 |
| chr21.47608408-47608855 > klorley | klorley | 1.80E-02 | -2.14 | 1.56E-03 | -4.41 | 4.26E-04 | 10.24 | 6.69E-03 | 2.71 |
| chr22.20093700-20093800 > DGCR8 | DGCR8 | 6.95E-03 | -2.58 | 8.09E-04 | -5.52 | 2.17E-04 | 19.30 | 2.11E-03 | 3.65 |
| chr22.31733654-31734031 > sneypoy | sneypoy | 5.37E-02 | -1.82 | 3.99E-04 | -39.22 | 1.49E-03 | 6.03 | 1.08E-02 | 2.67 |
| chr22.41175013-41175129 > SLC25A17 | SLC25A17 | 7.16E-04 | -7.40 | 3.66E-04 | -14.98 | 6.05E-03 | 2.87 | 9.34E-02 | 1.58 |
| chr22.45254869-45255776 > PRR5-ARHGAP8 | PRR5-ARHGAP8 | 1.71E-02 | -2.04 | 9.61E-05 | <-500 | 3.03E-04 | 8.85 | 1.52E-03 | 3.77 |
| chr22.50320903-50321181 > CRELD2 | CRELD2 | 1.98E-03 | -4.87 | 3.50E-02 | -1.97 | 5.27E-04 | 14.94 | 4.59E-04 | 19.20 |
| chr22.51221467-51221714 > RABL2B | RABL2B | 4.84E-06 | <-500 | 9.09E-06 | -18.75 | 5.55E-05 | 85.86 | 2.67E-05 | 7.08 |
| chr3.122283274-122283460 > DTX3L | DTX3L | 3.86E-03 | -2.45 | 8.96E-04 | -3.51 | 1.54E-01 | 1.35 | 4.78E-04 | 4.34 |
| chr3.137963865-137964523 > vusmyby | vusmyby | 4.47E-04 | -6.75 | 1.85E-02 | -2.01 | 7.96E-04 | 4.93 | 2.47E-04 | 10.96 |
| chr3.137963930-137964523 > ARMC8 | ARMC8 | 4.47E-04 | -6.75 | 1.85E-02 | -2.01 | 7.96E-04 | 4.93 | 2.47E-04 | 10.96 |
| chr3.137963930-137964524 > ARMC8 | ARMC8 | 4.47E-04 | -6.75 | 1.85E-02 | -2.01 | 7.96E-04 | 4.93 | 2.47E-04 | 10.96 |
| chr3.150280329-150280447 > EIF2A | EIF2A | 1.05E-02 | -1.55 | 4.23E-05 | -3.25 | 1.90E-04 | 2.48 | 1.23E-03 | 1.93 |
| chr3.15778540-15778740 > ANKRD28 | ANKRD28 | 1.71E-04 | -3.90 | 1.21E-05 | -23.79 | 1.60E-03 | 2.36 | 2.11E-05 | 11.26 |
| chr3.167452594-167452717 > PDCD10 | PDCD10 | 4.97E-03 | -3.83 | 4.68E-04 | Not Estimable | 2.62E-03 | 5.24 | 1.60E-03 | 7.32 |
| chr3.20019802-20020396 > RAB5A | RAB5A | 4.94E-02 | -1.54 | 3.15E-04 | -4.25 | 8.07E-04 | 3.20 | 1.83E-03 | 2.64 |
| chr3.23929058-23929280 > UBE2E1 | UBE2E1 | 1.32E-03 | -3.40 | 3.40E-04 | -5.78 | 6.07E-02 | 1.57 | 2.24E-04 | 7.41 |
| chr3.25637911-25639423 > RARB | RARB | 6.84E-03 | -2.86 | 4.19E-02 | -1.86 | 4.93E-04 | 12.19 | 2.09E-03 | 4.35 |

TABLE 7-continued

Differential Exon Usage in the 5 Groups (p < 0.005, FC > |1.21|). FC—Fold Change

| | | | | | | | | | |
|---|---|---|---|---|---|---|---|---|---|
| chr3.39162488-39162680 > TTC21A | TTC21A | 2.31E-02 | -1.64 | 3.37E-04 | -3.48 | 5.93E-05 | 6.73 | 3.03E-05 | 10.81 |
| chr3.52385978-52386119 > DNAH1 | DNAH1 | 2.86E-05 | -25.66 | 1.71E-04 | -5.17 | 1.52E-02 | 1.80 | 3.60E-04 | 3.92 |
| chr3.52561845-52561947 > NT5DC2 | NT5DC2 | 5.07E-02 | Not Estimable | 5.07E-05 | <-500 | 6.23E-05 | 50.64 | 5.07E-05 | Not Estimable |
| chr3.69028819-69028938 > C3orf64 | C3orf64 | 4.34E-04 | -276.88 | 1.44E-03 | -7.40 | 6.00E-03 | 25.32 | 9.40E-04 | 11.26 |
| chr3.81552424-81552865 > chordybo | chordybo | 2.18E-04 | -6.44 | 4.03E-05 | Not Estimable | 4.30E-03 | 4.65 | 7.72E-03 | 2.16 |
| chr4.122723829-122723948 > EXOSC9 | EXOSC9 | 1.45E-03 | -2.35 | 3.00E-04 | -3.21 | 1.36E-02 | 1.70 | 9.05E-05 | 4.55 |
| chr4.122723829-122723983 > EXOSC9 | EXOSC9 | 1.45E-03 | -2.35 | 3.00E-04 | -3.21 | 1.36E-02 | 1.70 | 9.05E-05 | 4.55 |
| chr4.157731989-157732169 > PDGFC | PDGFC | 7.75E-04 | -2.40 | 6.25E-03 | -1.79 | 4.00E-05 | 4.91 | 9.27E-05 | 3.76 |
| chr4.175223190-175223337 > KIAA1712 | KIAA1712 | 3.59E-04 | -10.22 | 9.07E-02 | -1.55 | 6.69E-03 | 2.62 | 1.66E-03 | 4.04 |
| chr4.40800804-40800921 > NSUN7 | NSUN7 | 6.85E-02 | -1.65 | 4.03E-03 | -10.82 | 2.93E-04 | 16.64 | 1.48E-03 | 4.51 |
| chr4.76874494-76874938 > sporsmorby | sporsmorby | 8.09E-03 | -2.96 | 4.72E-03 | -28.20 | 2.56E-02 | 2.16 | 2.57E-01 | 1.34 |
| chr5.134343647-134343829 > PCBD2andCATSPER3 | PCBD2 and CATSPER3 | 1.80E-02 | -2.37 | 6.68E-03 | -3.17 | 3.53E-03 | Not Estimable | 5.92E-04 | 17.76 |
| chr5.139929370-139930496 > APBB3andSRA1 | APBB3 and SRA1 | 2.46E-01 | -1.21 | 2.97E-04 | -3.06 | 1.24E-02 | 1.69 | 1.95E-03 | 2.17 |
| chr5.140895496-140896575 > DIAPH1 | DIAPH1 | 2.42E-03 | -3.84 | 3.56E-04 | -14.80 | 2.77E-04 | 23.85 | 9.58E-04 | 5.96 |
| chr5.140895875-140896575 > DIAPH1 | DIAPH1 | 5.18E-05 | -5.97 | 9.76E-06 | -34.42 | 1.45E-05 | 16.01 | 1.20E-05 | 21.48 |
| chr5.14381239-14381361 > TRIO | TRIO | 7.18E-02 | -3.91 | 1.44E-02 | -1.95 | 2.22E-04 | 6.59 | 1.32E-03 | 3.25 |
| chr5.145493406-145493874 > LARS | LARS | 4.03E-04 | -11.34 | 3.32E-03 | -3.36 | 8.40E-04 | 6.17 | 5.02E-04 | 9.06 |
| chr5.35053745-35054334 > fugey | fugey | 4.00E-04 | -9.01 | 8.14E-04 | -5.54 | 3.29E-04 | 10.88 | 1.32E-04 | Not Estimable |
| chr5.39274505-39274630 > FYB | FYB | 1.63E-02 | -2.33 | 3.89E-04 | -24.35 | 1.29E-03 | 6.00 | 4.56E-02 | 1.85 |
| chr5.70531277-70532281 > goychyby | goychyby | 1.10E-02 | -2.03 | 2.29E-04 | -6.29 | 6.59E-04 | 3.97 | 2.19E-03 | 2.81 |
| chr5.77656415-77656552 > SCAMP1 | SCAMP1 | 1.07E-03 | -4.46 | 2.97E-04 | -9.88 | 4.46E-04 | 7.11 | 3.67E-02 | 1.79 |
| chr6.109248281-109249436 > ARMC2 | ARMC2 | 2.72E-03 | -2.24 | 1.30E-02 | -1.77 | 2.08E-04 | 4.04 | 8.43E-02 | 1.40 |
| chr6.122792844-122793050 > SERINC1 | SERINC1 | 1.45E-02 | -2.14 | 5.74E-03 | -2.63 | 2.50E-03 | 3.31 | 3.03E-04 | 9.93 |
| chr6.144289727-144290115 > PLAGL1andHYMAI | PLAGL1 and HYMAI | 1.74E-01 | -1.44 | 4.00E-04 | -32.52 | 4.43E-04 | 23.92 | 4.81E-03 | 3.42 |
| chr6.153291654-153292549 > FBXO5 | FBXO5 | 3.31E-04 | -3.25 | 1.32E-03 | -2.43 | 4.35E-03 | 2.01 | 2.30E-02 | 1.61 |
| chr6.153291660-153292549 > FBXO5 | FBXO5 | 3.31E-04 | -3.25 | 1.32E-03 | -2.43 | 4.35E-03 | 2.01 | 2.30E-02 | 1.61 |
| chr6.153291674-153292549 > FBXO5 | FBXO5 | 3.31E-04 | -3.25 | 1.32E-03 | -2.43 | 4.35E-03 | 2.01 | 2.30E-02 | 1.61 |
| chr6.158088239-158089557 > fyjaw | fyjaw | 8.63E-04 | -4.25 | 2.52E-02 | -1.85 | 1.77E-03 | 3.33 | 2.99E-04 | 7.26 |
| chr6.3021094-3022352 > teyvybo | teyvybo | 3.80E-05 | -140.84 | 4.06E-05 | -74.72 | 9.11E-04 | 3.45 | 1.27E-04 | 8.48 |
| chr6.34360041-34360260 > RPS10andNUDT3 | RPS10 and NUDT3 | 5.81E-04 | -4.24 | 8.57E-05 | -15.64 | 7.24E-05 | 20.73 | 1.60E-04 | 8.25 |
| chr6.41036580-41036692 > C6orf130andUNC5CL | C6orf130 and UNC5CL | 3.57E-04 | -5.13 | 1.22E-04 | -10.16 | 7.37E-04 | 3.87 | 1.49E-03 | 3.13 |
| chr6.41751200-41751976 > PRICKLE4andTOMM6 | PRICKLE4 and TOMM6 | 4.62E-03 | -2.80 | 2.51E-04 | -12.58 | 4.03E-04 | 7.96 | 9.63E-04 | 4.78 |
| chr6.79664949-79665569 > PHIPandTRNAF13P | PHIP and TRNAF13P | 1.35E-03 | -2.92 | 2.55E-05 | Not Estimable | 1.30E-04 | 6.84 | 5.14E-05 | 15.62 |
| chr7.149598-152547 > kehera | kehera | 1.33E-02 | -1.71 | 1.29E-04 | -2.42 | 9.72E-02 | 1.36 | 4.40E-04 | 2.99 |
| chr7.22980878-22987334 > FAM126A | FAM126A | 5.13E-04 | -2.56 | 4.24E-05 | -4.72 | 8.77E-03 | 1.71 | 1.84E-03 | 2.09 |
| chr7.2635311-2636062 > dochuby | dochuby | 3.67E-04 | -4.19 | 1.69E-04 | -5.80 | 4.01E-03 | 2.30 | 2.63E-02 | 1.70 |
| chr7.29549802-29552165 > klerky | klerky | 1.88E-04 | -6.48 | 3.73E-03 | -2.44 | 2.29E-02 | 1.77 | 8.77E-02 | 1.46 |
| chr7.45083306-45083697 > CCM2 | CCM2 | 2.52E-02 | -1.90 | 8.39E-04 | -4.83 | 1.36E-03 | 3.96 | 3.71E-04 | 7.72 |
| chr7.5938415-5938550 > CCZ1 | CCZ1 | 5.04E-07 | -252.68 | 2.41E-06 | -8.08 | 7.48E-06 | 4.89 | 1.37E-06 | 12.27 |
| chr7.74166365-74166897 > GTF2I | GTF2I | 2.27E-03 | -3.76 | 5.26E-04 | -8.20 | 7.50E-04 | 6.36 | 2.45E-04 | 22.31 |
| chr7.76870183-76870364 > CCDC146 | CCDC146 | 1.69E-05 | -12.37 | 4.46E-04 | -6.24 | 4.43E-04 | 2.97 | 6.52E-06 | Not Estimable |
| chr8.104455023-104455428 > DCAF13 | DCAF13 | 4.47E-02 | -1.81 | 1.12E-02 | -2.44 | 5.04E-03 | 3.04 | 4.85E-04 | 10.67 |
| chr8.133984843-133984986 > TG | TG | 3.27E-02 | -1.99 | 2.69E-04 | <-500 | 2.69E-04 | Not Estimable | 2.69E-04 | >500 |
| chr8.24256387-24256553 > ADAMDEC1 | ADAMDEC1 | 1.89E-02 | -2.37 | 1.55E-03 | -6.56 | 3.81E-04 | Not Estimable | 5.79E-02 | 1.82 |
| chr8.30948350-30948458 > WRN | WRN | 9.84E-05 | -8.13 | 4.33E-05 | -19.99 | 6.54E-04 | 3.52 | 1.58E-04 | 6.10 |
| chr8.62438536-62438671 > ASPH | ASPH | 1.08E-03 | -5.20 | 5.24E-03 | -2.88 | 2.06E-02 | 2.07 | 3.63E-04 | 11.88 |
| chr8.74858684-74859055 > TCEB1 | TCEB1 | 2.36E-04 | -11.51 | 1.83E-04 | -16.10 | 3.38E-04 | 8.24 | 1.05E-03 | 4.38 |
| chr9.17135038-17135423 > CNTLN | CNTLN | 3.03E-02 | -1.91 | 1.90E-04 | -3.97 | 8.64E-04 | 5.73 | 4.80E-04 | 8.60 |
| chr9.33264164-33264493 > CHMP5 | CHMP5 | 1.44E-04 | -11.82 | 8.33E-04 | -4.08 | 1.94E-04 | 8.91 | 4.09E-04 | 5.53 |
| chr9.35737655-35737936 > GBA2 | GBA2 | 6.33E-03 | -3.43 | 4.89E-04 | -96.76 | 1.37E-03 | 8.06 | 5.25E-04 | 55.35 |
| chrX.118985730-118985836 > UPF3B | UPF3B | 1.13E-04 | <-500 | 1.55E-03 | -3.93 | 3.89E-03 | 2.93 | 8.72E-04 | 4.99 |
| chrX.138864706-138864887 > ATP11C | ATP11C | 3.68E-02 | -3.31 | 1.76E-03 | -23.71 | 1.59E-02 | 2.23 | 9.95E-04 | 5.80 |
| chrX.149924161-149924396 > MTMR1 | MTMR1 | 1.84E-03 | -6.49 | 4.58E-03 | <-500 | 2.92E-03 | 4.89 | 6.99E-03 | 3.33 |
| chrX.153744234-153744566 > FAM3A | FAM3A | 1.07E-04 | -54.24 | 3.85E-04 | -7.03 | 2.63E-04 | 9.43 | 8.88E-04 | 4.53 |
| chrX.15862547-15863639 > AP1S2 | AP1S2 | 9.09E-05 | -5.62 | 1.65E-04 | -4.42 | 4.01E-03 | 2.12 | 6.08E-02 | 1.46 |
| chrX.16870674-16871149 > RBBP7 | RBBP7 | 6.02E-03 | -2.99 | 2.65E-03 | -3.99 | 8.60E-04 | 7.37 | 3.25E-04 | 29.04 |
| chrX.2839944-2840065 > ARSD | ARSD | 1.44E-03 | -3.53 | 4.55E-02 | -1.67 | 3.00E-03 | 2.86 | 3.95E-04 | 6.06 |

TABLE 7-continued

Differential Exon Usage in the 5 Groups (p < 0.005, FC > |1.21|). FC—Fold Change

| Marker ID | Gene Symbol | p-value | FC | p-value | FC | p-value | FC | p-value | FC |
|---|---|---|---|---|---|---|---|---|---|
| chrX.74282163-74282417 > ABCB7 | ABCB7 | 1.09E-03 | -5.81 | 8.03E-04 | -7.10 | 1.32E-02 | 2.36 | 3.38E-04 | 19.17 |
| chrX.76776266-76776394 > ATRX | ATRX | 3.40E-06 | -5.28 | 1.40E-04 | -2.35 | 1.89E-03 | 1.75 | 6.84E-06 | 4.23 |
| chrX.77303661-77305892 > ATP7A | ATP7A | 1.55E-04 | -10.33 | 2.03E-03 | -3.04 | 3.29E-01 | 1.22 | 1.05E-03 | 3.70 |

| | | CE Stroke vs. Controls | | Controls vs. ICH | | Controls vs. LV | | Controls vs. Lacunar | |
|---|---|---|---|---|---|---|---|---|---|
| Upregulated in Controls | | | | | | | | | |
| Marker ID | Gene Symbol | p-value | FC | p-value | FC | p-value | FC | p-value | FC |
| chr1.53416427-53416558 > SCP2 | SCP2 | 4.14E-04 | -3.65 | 3.66E-02 | 1.59 | 1.42E-03 | 2.69 | 6.07E-03 | 2.06 |
| chr14.19683027-19683434 > DUXAP10 | DUXAP10 | 3.62E-05 | -29.94 | 1.14E-04 | 7.36 | 2.52E-05 | >500 | 4.66E-05 | 17.76 |
| chr17.42982993-42984756 > GFAP | GFAP | 6.98E-04 | -5.06 | 1.25E-02 | 2.15 | 4.86E-03 | 2.65 | 2.89E-04 | 8.76 |
| chr18.28642978-28643439 > DSC2 | DSC2 | 2.44E-02 | -1.84 | 5.93E-03 | 2.41 | 1.09E-03 | 3.79 | 1.88E-04 | 9.74 |
| chr18.43417478-43417850 > SIGLEC15 | SIGLEC15 | 3.26E-04 | <-500 | 2.04E-03 | 5.10 | 1.43E-02 | 2.49 | 4.84E-02 | 1.87 |
| chr19.39138368-39138547 > ACTN4 | ACTN4 | 1.33E-05 | -8.92 | 1.30E-04 | 3.51 | 5.83E-06 | 22.30 | 3.57E-05 | 5.30 |
| chr19.45543176-45543569 > SFRS16 | SFRS16 | 1.43E-04 | <-500 | 4.87E-03 | 2.87 | 3.81E-04 | 9.97 | 2.38E-04 | 18.83 |
| chr2.101606718-101606908 > NPAS2 | NPAS2 | 2.57E-04 | -6.61 | 5.03E-04 | 4.72 | 7.16E-05 | 30.24 | 3.23E-03 | 2.67 |
| chr2.242611606-242612016 > ATG4B | ATG4B | 8.42E-05 | -8.04 | 3.53E-05 | 20.98 | 1.89E-04 | 5.17 | 1.07E-03 | 2.97 |
| chr20.32880178-32880359 > AHCY | AHCY | 2.22E-03 | -4.21 | 5.50E-03 | 3.04 | 3.66E-04 | 18.76 | 1.14E-02 | 2.48 |
| chr22.36892014-36892255 > FOXRED2andTXN2 | FOXRED2 and TXN2 | 2.48E-04 | -5.82 | 1.19E-02 | 1.99 | 4.04E-03 | 2.43 | 7.88E-02 | 1.49 |
| chr22.41252435-41253036 > ST13 | ST13 | 1.56E-03 | -7.62 | 3.49E-03 | 4.55 | 4.81E-04 | >500 | 4.81E-04 | >500 |
| chr6.32806430-32806547 > TAP2andHLA-DOB | TAP2 and HLA-DOB | 9.55E-05 | <-500 | 2.92E-03 | 3.07 | 2.70E-04 | 9.81 | 7.48E-04 | 5.03 |
| chr7.101475858-101476865 > snorkar | snorkar | 2.78E-04 | -23.06 | 2.33E-02 | 2.05 | 2.70E-03 | 3.68 | 6.83E-03 | 2.75 |
| chr9.140473077-140473340 > WDR85 | WDR85 | 3.68E-05 | -31.77 | 4.74E-04 | 3.93 | 1.31E-04 | 6.90 | 6.73E-05 | 11.64 |
| chr9.95018962-95019082 > IARS | IARS | 1.52E-05 | -7.76 | 2.30E-04 | 3.02 | 7.17E-05 | 4.05 | 2.90E-05 | 5.60 |
| chr9.96866557-96866667 > PTPDC1 | PTPDC1 | 3.10E-07 | Not Estimable | 7.27E-04 | 1.95 | 8.40E-07 | 13.03 | 3.13E-07 | >500 |
| chrX.48367956-48368344 > PORCN | PORCN | 4.63E-05 | -86.44 | 4.10E-05 | >500 | 4.91E-05 | 58.47 | 7.98E-05 | 16.02 |

TABLE 8

Over-represented Pathways and Gene Ontology for the Upregulated Exons

Cardioembolic Stroke

SIGNIFICANTLY ENRICHED CANONICAL PATHWAYS OF CARDIOEMBOLIC STROKE

| Ingenuity Canonical Pathways | -log(p-value) | B-H p-value | Ratio | Molecules |
|---|---|---|---|---|
| Semaphorin Signaling in Neurons | 1.41E00 | 6.9E-03-7.47E-02 | 1.89E-02 | PLXNB1 |

GENE ONTOLOGY OF CARDIOEMBOLIC STROKE

| Category | Term | Count | % | PValue | Genes | List Total | Pop Hits | Pop Total | Fold Enrichment | Benjamini | FDR |
|---|---|---|---|---|---|---|---|---|---|---|---|
| | | | | | Annotation Cluster 1 Enrichment Score: 1.5478345985149118 | | | | | | |
| GOTERM_MF_FAT | GO: 0046872~metal ion binding | 9 | 47.37 | 0.03 | STEAP3, ZNF33A, UPF1, LPP, ZNF417, ZNF814, TRPV5, TTN, SLC10A1 | 14 | 4140 | 12983 | 2.02 | 0.89 | 24.97 |
| GOTERM_MF_FAT | GO: 0043169~cation binding | 9 | 47.37 | 0.03 | STEAP3, ZNF33A, UPF1, LPP, ZNF417, ZNF814, TRPV5, TTN, SLC10A1 | 14 | 4179 | 12983 | 2.00 | 0.69 | 26.24 |
| GOTERM_MF_FAT | GO: 0043167~ion binding | 9 | 47.37 | 0.03 | STEAP3, ZNF33A, UPF1, LPP, ZNF417, ZNF814, TRPV5, TTN, SLC10A1 | 14 | 4241 | 12983 | 1.97 | 0.58 | 28.33 |
| | | | | | Annotation Cluster 2 Enrichment Score: 1.4272404656779223 | | | | | | |
| GOTERM_CC_FAT | GO: 0005887~integral to plasma membrane | 4 | 21.05 | 0.03 | PLXNB1, PTPRN2, TRPV5, SLC10A1 | 9 | 1188 | 12782 | 4.78 | 0.75 | 25.81 |
| GOTERM_CC_FAT | GO: 0031226~intrinsic to plasma membrane | 4 | 21.05 | 0.03 | PLXNB1, PTPRN2, TRPV5, SLC10A1 | 9 | 1215 | 12782 | 4.68 | 0.53 | 27.17 |
| GOTERM_CC_FAT | GO: 0044459~plasma membrane part | 5 | 26.32 | 0.03 | PLXNB1, LPP, PTPRN2, TRPV5, SLC10A1 | 9 | 2203 | 12782 | 3.22 | 0.40 | 27.86 |
| GOTERM_CC_FAT | GO: 0005886~plasma membrane | 6 | 31.58 | 0.05 | STEAP3, PLXNB1, LPP, PTPRN2, TRPV5, SLC10A1 | 9 | 3777 | 12782 | 2.26 | 0.46 | 40.79 |
| | | | | | Annotation Cluster 3 Enrichment Score: 1.2281900079975664 | | | | | | |
| GOTERM_BP_FAT | GO: 0030001~metal ion transport | 3 | 15.79 | 0.05 | STEAP3, TRPV5, SLC10A1 | 12 | 465 | 13528 | 7.27 | 1.00 | 48.17 |
| GOTERM_CC_FAT | GO: 0005886~plasma membrane | 6 | 31.58 | 0.05 | STEAP3, PLXNB1, LPP, PTPRN2, TRPV5, SLC10A1 | 9 | 3777 | 12782 | 2.26 | 0.46 | 40.79 |
| GOTERM_BP_FAT | GO: 0006812~cation transport | 3 | 15.79 | 0.07 | STEAP3, TRPV5, SLC10A1 | 12 | 553 | 13528 | 6.12 | 1.00 | 59.48 |

TABLE 8-continued

Over-represented Pathways and Gene Ontology for the Upregulated Exons

Large Vessel IS

SIGNIFICANTLY ENRICHED CANONICAL PATHWAYS OF LARGE VESSEL ISCHEMIC STROKE

| Ingenuity Canonical Pathways | -log(p-value) | -log(B-H p-value) | Ratio | Molecules |
|---|---|---|---|---|
| Oxidized GTP and dGTP Detoxification | 2.44E00 | 1E00 | 3.33E-01 | NUDT1 |
| UDP-N-acetyl-D-glucosamine Biosynthesis II | 2.14E00 | 1E00 | 1.67E-01 | GNPNAT1 |
| Glycoaminoglycan-protein Linkage Region Biosynthesis | 2.08E00 | 1E00 | 1.43E-01 | B3GAT3 |
| UDP-N-acetyl-D-galactosamine Biosynthesis II | 1.97E00 | 1E00 | 1.11E-01 | GNPNAT1 |
| Thyroid Hormone Metabolism II (via Conjugation and/or Degradation) | 1.44E00 | 7.92E-01 | 3.23E-02 | B3GAT3 |
| Nucleotide Excision Repair Pathway | 1.38E00 | 7.92E-01 | 2.86E-02 | ERCC5 |

GENE ONTOLOGY OF LARGE VESSEL ISCHEMIC STROKE

| Category | Term | Count | % | PValue | Genes | List Total | Pop Hits | Pop Total | Fold Enrichment | Benjamini | FDR |
|---|---|---|---|---|---|---|---|---|---|---|---|
| | | | | | Annotation Cluster 1 Enrichment Score: 1.9116473785151364 | | | | | | |
| GOTERM_CC_FAT | GO: 0070013~intracellular organelle lumen | 8 | 26.67 | 0.01 | PDK1, ERCC5, PNMA3, CENPF, PCSK6, DIMT1L, DNAJA3, CBX5 | 20 | 1779 | 12782 | 2.87 | 0.64 | 11.29 |
| GOTERM_CC_FAT | GO: 0043233~organelle lumen | 8 | 26.67 | 0.01 | PDK1, ERCC5, PNMA3, CENPF, PCSK6, DIMT1L, DNAJA3, CBX5 | 20 | 1820 | 12782 | 2.81 | 0.43 | 12.68 |
| GOTERM_CC_FAT | GO: 0031974~membrane-enclosed lumen | 8 | 26.67 | 0.01 | PDK1, ERCC5, PNMA3, CENPF, PCSK6, DIMT1L, DNAJA3, CBX5 | 20 | 1856 | 12782 | 2.75 | 0.34 | 13.98 |
| | | | | | Annotation Cluster 2 Enrichment Score: 1.6656724740025078 | | | | | | |
| GOTERM_BP_FAT | GO: 0043066~negative regulation of apoptosis | 4 | 13.33 | 0.01 | ERCC5, RIPK2, PCSK6, DNAJA3 | 20 | 354 | 13528 | 7.64 | 1.00 | 16.49 |
| GOTERM_BP_FAT | GO: 0043069~negative regulation of programmed cell death | 4 | 13.33 | 0.01 | ERCC5, RIPK2, PCSK6, DNAJA3 | 20 | 359 | 13528 | 7.54 | 0.95 | 17.07 |
| GOTERM_BP_FAT | GO: 0060548~negative regulation of cell death | 4 | 13.33 | 0.01 | ERCC5, RIPK2, PCSK6, DNAJA3 | 20 | 360 | 13528 | 7.52 | 0.87 | 17.19 |
| GOTERM_BP_FAT | GO: 0042981~regulation of | 4 | 13.33 | 0.10 | ERCC5, RIPK2, PCSK6, DNAJA3 | 20 | 804 | 13528 | 3.37 | 0.96 | 77.51 |

TABLE 8-continued

Over-represented Pathways and Gene Ontology for the Upregulated Exons apoptosis

Annotation Cluster 3
Enrichment Score: 1.3439751095199926

| Category | Term | Count | % | PValue | Genes | List Total | Pop Hits | Pop Total | Fold Enrichment | Bonferroni | FDR |
|---|---|---|---|---|---|---|---|---|---|---|---|
| GOTERM_BP_FAT | GO: 0016481~negative regulation of transcription | 4 | 13.33 | 0.03 | LMCD1, CENPF, NSD1, CBX5 | 20 | 459 | 13528 | 5.89 | 0.94 | 30.30 |
| GOTERM_MF_FAT | GO: 0003682~chromatin binding | 3 | 10.00 | 0.03 | CENPF, NSD1, CBX5 | 24 | 150 | 12983 | 10.82 | 0.98 | 28.76 |
| GOTERM_BP_FAT | GO: 0010629~negative regulation of gene expression | 4 | 13.33 | 0.03 | LMCD1, CENPF, NSD1, CBX5 | 20 | 504 | 13528 | 5.37 | 0.95 | 36.94 |
| GOTERM_BP_FAT | GO: 0045934~negative regulation of nucleobase, nucleoside, nucleotide and nucleic acid metabolic process | 4 | 13.33 | 0.03 | LMCD1, CENPF, NSD1, CBX5 | 20 | 512 | 13528 | 5.28 | 0.89 | 38.15 |
| GOTERM_BP_FAT | GO: 0051172~negative regulation of nitrogen compound metabolic process | 4 | 13.33 | 0.03 | LMCD1, CENPF, NSD1, CBX5 | 20 | 519 | 13528 | 5.21 | 0.86 | 39.20 |
| GOTERM_BP_FAT | GO: 0010558~negative regulation of macromolecule biosynthetic process | 4 | 13.33 | 0.04 | LMCD1, CENPF, NSD1, CBX5 | 20 | 547 | 13528 | 4.95 | 0.87 | 43.44 |
| GOTERM_BP_FAT | GO: 0031327~negative regulation of cellular biosynthetic process | 4 | 13.33 | 0.04 | LMCD1, CENPF, NSD1, CBX5 | 20 | 561 | 13528 | 4.82 | 0.86 | 45.56 |
| GOTERM_BP_FAT | GO: 0009890~negative regulation of biosynthetic process | 4 | 13.33 | 0.04 | LMCD1, CENPF, NSD1, CBX5 | 20 | 573 | 13528 | 4.72 | 0.84 | 47.38 |
| GOTERM_MF_FAT | GO: 0008134~transcription factor binding | 4 | 13.33 | 0.06 | LMCD1, CENPF, NSD1, DNAJA3 | 24 | 513 | 12983 | 4.22 | 0.98 | 51.71 |
| GOTERM_BP_FAT | GO: 0010605~negative regulation of macromolecule metabolic process | 4 | 13.33 | 0.08 | LMCD1, CENPF, NSD1, CBX5 | 20 | 734 | 13528 | 3.69 | 0.96 | 69.72 |
| GOTERM_BP_FAT | GO: 0045892~negative regulation of transcription, DNA-dependent | 3 | 10.00 | 0.09 | LMCD1, NSD1, CBX5 | 20 | 356 | 13528 | 5.70 | 0.96 | 72.98 |
| GOTERM_BP_FAT | GO: 0051253~negative regulation of RNA metabolic process | 3 | 10.00 | 0.09 | LMCD1, NSD1, CBX5 | 20 | 362 | 13528 | 5.61 | 0.95 | 74.03 |

Lacunar IS

| Ingenuity Canonical Pathways | −log(p-value) | −log(B-H p-value) | Ratio | Molecules |
|---|---|---|---|---|

TABLE 8-continued

Over-represented Pathways and Gene Ontology for the Upregulated Exons

| | | |
|---|---|---|
| SIGNIFICANTLY ENRICHED CANONICAL PATHWAYS OF LACUNAR ISCHEMIC STROKE | | |
| Eumelanin Biosynthesis | 2.34E00 | 7.03E-01 | DDT |
| G Protein Signaling Mediated by Tubby | 1.43E00 | 6.15E-01 | GNG3 |

GENE ONTOLOGY OF LACUNAR ISCHEMIC STROKE
Not Available with 0.1 Ease
Intracerebral hemorrhage (ICH)

SIGNIFICANTLY ENRICHED CANONICAL PATHWAYS OF HEM

| | | | |
|---|---|---|---|
| Regulation of eIF4 and p70S6K Signaling | 3.54E00 | 1.14E00 | SHC1, AKT1, RPS10, ITGA5, RPS15A, EIF2A, ITGA4 |
| PTEN Signaling | 3.24E00 | 1.14E00 | MAST2, SHC1, AKT1, ITGA5, INPP5D, ITGA4 |
| Actin Cytoskeleton Signaling | 2.53E00 | 8.12E-01 | SHC1, DIAPH1, ITGA5, TRIO, SLC9A1, PDGFC, ITGA4 |
| IL-3 Signaling | 2.47E00 | 8.12E-01 | SHC1, AKT1, PPP3CB, INPP5D |
| Caveolar-mediated Endocytosis Signaling | 2.45E00 | 8.12E-01 | RAB5A, RAB5C, ITGA5, ITGA4 |
| Ephrin Receptor Signaling | 2.38E00 | 8.12E-01 | SHC1, AKT1, ITGA5, GNG5, PDGFC, ITGA4 |
| PI3K/AKT Signaling | 2.36E00 | 8.12E-01 | SHC1, AKT1, ITGA5, INPP5D, ITGA4 |
| FcγRIIB Signaling in B Lymphocytes | 2.27E00 | 8.12E-01 | SHC1, AKT1, INPP5D |
| Clathrin-mediated Endocytosis Signaling | 2.25E00 | 8.12E-01 | RAB5A, RAB5C, PPP3CB, CLTC, ITGA5, PDGFC |
| DNA Double-Strand Break Repair by Homologous Recombination | 2.2E00 | 8.08E-01 | GEN1, ATRX |
| Neuregulin Signaling | 2.14E00 | 8.08E-01 | SHC1, AKT1, ITGA5, ITGA4 |
| PAK Signaling | 2.12E00 | 8.08E-01 | SHC1, ITGA5, PDGFC, ITGA4 |
| Telomerase Signaling | 1.96E00 | 6.84E-01 | SHC1, AKT1, TEP1, ELF1 |
| HGF Signaling | 1.88E00 | 6.48E-01 | AKT1, ITGA5, ELF1, ITGA4 |
| iCOS-iCOSL Signaling in T Helper Cells | 1.83E00 | 6.48E-01 | SHC1, AKT1, PPP3CB, INPP5D |
| Natural Killer Cell Signaling | 1.81E00 | 3.64E-01 | SHC1, AKT1, KLRC4-KLRK1/KLRK1, INPP5D |
| GM-CSF Signaling | 1.78E00 | 6.48E-01 | SHC1, AKT1, PPP3CB |
| 4-hydroxyproline Degradation I | 1.76E00 | 6.48E-01 | HOGA1 |
| Anandamide Degradation | 1.76E00 | 5E-01 | FAAH |
| Macropinocytosis Signaling | 1.67E00 | 4.41E-02 | RAB5A, ITGA5, PDGFC |

TABLE 8-continued

Over-represented Pathways and Gene Ontology for the Upregulated Exons

| Term | Count | % | PValue | Genes |
|---|---|---|---|---|
| EIF2 Signaling | | | 1.64E00 | 5.8E-01 | SHC1, AKT1, RPS10, RPS15A, EIF2A |
| mTOR Signaling | | | 1.61E00 | 5.8E-01 | AKT1, RPS10, RPS15A, PDGFC, ARHGAP8/PRR5-ARHGAP8 |
| NF-κB Activation by Viruses | | | 1.59E00 | 5.8E-01 | AKT1, ITGA5, ITGA4 |
| Tyrosine Biosynthesis IV | | | 1.59E00 | 5.8E-01 | PCBD2 |
| FLT3 Signaling in Hematopoietic Progenitor Cells | | | 1.57E00 | 5.8E-01 | SHC1, AKT1, INPP5D |
| IL-4 Signaling | | | 1.55E00 | 5.69E-01 | SHC1, AKT1, INPP5D |
| PDGF Signaling | | | 1.53E00 | 5.69E-01 | SHC1, PDGFC, INPP5D |
| Reelin Signaling in Neurons | | | 1.5E00 | 5.57E-01 | AKT1, ITGA5, ITGA4 |
| Phenylalanine Degradation I (Aerobic) | | | 1.46E00 | 5.35E-01 | PCBD2 |
| FAK Signaling | | | 1.4E00 | 5E-01 | AKT1, ITGA5, ITGA4 |
| CTLA4 Signaling in Cytotoxic T Lymphocytes | | | 1.38E00 | 5E-01 | AKT1, AP1S2, CLTC |
| G Beta Gamma Signaling | | | 1.38E00 | 5E-01 | SHC1, AKT1, GNG5 |
| Virus Entry via Endocytic Pathways | | | 1.37E00 | 5E-01 | CLTC, ITGA5, ITGA4 |
| VEGF Signaling | | | 1.35E00 | 5E-01 | SHC1, AKT1, PDGFC |
| Fcγ Receptor-mediated Phagocytosis in Macrophages and Monocytes | | | 1.32E00 | 5E-01 | AKT1, FYB, INPP5D |
| PPAR Signaling | | | 1.31E00 | 5E-01 | SHC1, SRA1, PDGFC |
| Tec Kinase Signaling | | | 1.31E00 | 5E-01 | GTF2I, ITGA5, GNG5, ITGA4 |
| Glioma Signaling | | | 1.3E00 | 5E-01 | SHC1, AKT1, PDGFC |
| Huntington's Disease Signaling | | | 1.3E00 | 2.17E-02 | SHC1, AKT1, CLTC, GNG5, NAPB |

GENE ONTOLOGY OF HEM

Annotation Cluster 1
Enrichment Score: 2.0008035747785273

| Category | Term | Count | % | PValue | Genes | List Total | Pop Hits | Pop Total | Fold Enrichment | Benjamini | FDR |
|---|---|---|---|---|---|---|---|---|---|---|---|
| GOTERM_BP_FAT | GO: 0015031~protein transport | 19 | 10.05291005 | 6.74E-04 | RGPD6, SCAMP1, ARL6IP1, FYB, RGPD5, RGPD8, SCAMP2, RAB3C, CHMP5, NAPB, CLTC, AKT1, SFT2D2, AP1S2, TOMM6, ATG4C, LYST, FXC1, TOMM40L, RAB5A, PPP3CB | 138 | 762 | 13528 | 2.44 | 0.57 | 1.09 |

TABLE 8-continued

Over-represented Pathways and Gene Ontology for the Upregulated Exons

| | | | | | | | | | |
|---|---|---|---|---|---|---|---|---|---|
| GOTERM_BP_FAT | GO: 0045184~establishment of protein localization | 19 | 10.05291005 | 7.50E-04 | RGPD6, SCAMP1, ARL6IP1, FYB, RGPD5, RGPD8, SCAMP2, RAB5C, CHMP5, NAPB, CLTC, AKT1, SFT2D2, AP1S2, TOMM6, ATG4C, LYST, FXC1 TOMM40L, RAB5A, PPP3CB | 138 | 769 | 13528 | 2.42 | 0.37 | 1.21 |
| GOTERM_BP_FAT | GO: 0008104~protein localization | 19 | 10.05291005 | 3.43E-03 | RGPD6, SCAMP1, ARL6IP1, FYB, RGPD5, RGPD8, SCAMP2, RAB5C, CHMP5, NAPB, CLTC, AKT1, SFT2D2, AP1S2, TOMM6, ATG4C, LYST, FXC1, TOMM40L, RAB5A, PPP3CB | 138 | 882 | 13528 | 2.11 | 0.76 | 5.43 |
| GOTERM_BP_FAT | GO: 0046907~intracellular transport | 15 | 7.936507937 | 6.75E-03 | RGPD6, ARL6IP1, FYB, SCAMP1, RGPD5, RGPD8, SCAMP2, KIF5B, CHMP5, NAPB, CLTC, AKT1, AP1S2, ATG4C, LYST, FXC1, PPP3CB | 138 | 657 | 13528 | 2.24 | 0.88 | 10.42 |
| GOTERM_BP_FAT | GO: 0006886~intracellular protein transport | 9 | 4.76190476 | 3.64E-02 | FYB, ARL6IP1, AKT1, AP1S2, ATG4C, FXC1, PPP3CB, NAPB, CLTC | 138 | 374 | 13528 | 2.36 | 1.00 | 45.30 |
| GOTERM_BP_FAT | GO: 0034613~cellular protein localization | 9 | 4.76190476 | 5.75E-02 | FYB, ARL6IP1, AKT1, AP1S2, ATG4C, FXC1, PPP3CB, NAPB, CLTC | 138 | 411 | 13528 | 2.15 | 1.00 | 61.82 |
| GOTERM_BP_FAT | GO: 0070727~cellular macromolecule localization | 9 | 4.76190476 | 5.95E-02 | FYB, ARL6IP1, AKT1, AP1S2, ATG4C, FXC1, PPP3CB, NAPB, CLTC | 138 | 414 | 13528 | 2.13 | 1.00 | 63.10 |
| GOTERM_BP_FAT | GO: 0006605~protein targeting | 6 | 3.174603175 | 6.75E-02 | FYB, ARL6IP1, AKT1, ATG4C, FXC1, PPP3CB | 138 | 215 | 13528 | 2.74 | 0.99 | 67.90 |

Annotation Cluster 2
Enrichment Score: 1.946654262059368

| | | | | | | | | | |
|---|---|---|---|---|---|---|---|---|---|
| GOTERM_CC_FAT | GO: 0015630~microtubule cytoskeleton | 16 | 8.465608466 | 3.54E-04 | SDCCAG8, SEPT2, KIF5B, TTLL5, DNHD1, CHEK1, DNAH1, WRN, AKT1, PBXIP1, CEP350, ATG4C, NAV1, LYST, FBXO5, CNTLN | 128 | 549 | 12782 | 2.91 | 0.09 | 0.46 |
| GOTERM_CC_FAT | GO: 0005856~cytoskeleton | 23 | 12.16931217 | 1.70E-02 | FYB, CTTNBP2NL, SDCCAG8, SEPT2, KIF5B, DIAPH1, UBR4, DNHD1, TTLL5, DNAH1, CHEK1, WRN, ZNF174, AKT1, MAST2, PBXIP1, NAV1, CEP350, ATG4C, LYST, FAAH, FBXO5, CNTLN | 128 | 1381 | 12782 | 1.66 | 0.58 | 20.05 |
| GOTERM_CC_FAT | GO: 0043232~intracellular non-membrane-bounded organelle | 37 | 19.57671958 | 1.85E-02 | CTTNBP2NL, SDCCAG8, SEPT2, HMGN2, DIAPH1, RPS15A, TTLL5, DNAH1, CHEK1, ZNF174, AKT1, DCAF13, PBXIP1, DGCR8, FBXO5, CNTLN, ZWILCH, FYB, EXOSC9, KIF5B, UBR4, SYCE2, DNHD1, WRN, EXOSC1, ATRX, PAPOLA, MAST2, NAV1, APITD1, CEP350, ATG4C, LYST, FAAH, TEP1, RPS10, CORT, TBX19 | 128 | 2596 | 12782 | 1.42 | 0.54 | 21.53 |
| GOTERM_CC_FAT | GO: 0043228~non-membrane-bounded organelle | 37 | 19.57671958 | 1.85E-02 | CTTNBP2NL, SDCCAG8, SEPT2, HMGN2, DIAPH1, RPS15A, TTLL5, DNAH1, CHEK1, ZNF174, AKT1, DCAF13, PBXIP1, DGCR8, FBXO5, CNTLN, ZWILCH, FYB, EXOSC9, KIF5B, UBR4, SYCE2, DNHD1, WRN, EXOSC1, ATRX, PAPOLA, MAST2, NAV1, APITD1, CEP350, ATG4C, LYST, FAAH, TEP1, RPS10, CORT, TBX19 | 128 | 2596 | 12782 | 1.42 | 0.54 | 21.53 |
| GOTERM_CC_FAT | GO: 0044430~cytoskeletal part | 15 | 7.936507937 | 9.00E-02 | SDCCAG8, SEPT2, KIF5B, TTLL5, DNHD1, CHEK1, DNAH1, WRN, AKT1, PBXIP1, CEP350, ATG4C, NAV1, FBXO5, CNTLN | 128 | 952 | 12782 | 1.57 | 0.68 | 70.68 |

TABLE 8-continued

Over-represented Pathways and Gene Ontology for the Upregulated Exons

| Category | Term | Count | % | PValue | Genes | List Total | Pop Hits | Pop Total | Fold Enrichment | Bonferroni | FDR |
|---|---|---|---|---|---|---|---|---|---|---|---|
| | Annotation Cluster 3 | | | | | | | | | | |
| | Enrichment Score: 1.456758529493377 | | | | | | | | | | |
| GOTERM_CC_FAT | GO:0030136~clathrin-coated vesicle | 6 | 3.174603175 | 0.01 | SCAMP1, ATP7A, AP1S2, PI4K2A, RAB5A, CLTC | 128 | 132 | 12782 | 4.54 | 0.58 | 12.44 |
| GOTERM_CC_FAT | GO:0030665~clathrin coated vesicle membrane | 4 | 2.116402116 | 0.02 | SCAMP1, AP1S2, PI4K2A, CLTC | 128 | 53 | 12782 | 7.54 | 0.63 | 18.55 |
| GOTERM_BP_FAT | GO:0006892~post-Golgi vesicle-mediated transport | 4 | 2.116402116 | 0.02 | SCAMP1, AP1S2, SCAMP2, CLTC | 138 | 58 | 13528 | 6.76 | 0.99 | 29.07 |
| GOTERM_CC_FAT | GO:0030135~coated vesicle | 6 | 3.174603175 | 0.02 | SCAMP1, ATP7A, AP1S2, PI4K2A, RAB5A, CLTC | 128 | 159 | 12782 | 3.77 | 0.54 | 24.29 |
| GOTERM_CC_FAT | GO:0030140~trans-Golgi network transport vesicle | 3 | 1.587301587 | 0.02 | ATP7A, AP1S2, CLTC | 128 | 24 | 12782 | 12.48 | 0.49 | 26.56 |
| GOTERM_CC_FAT | GO:0030133~transport vesicle | 4 | 2.116402116 | 0.03 | ATP7A, AP1S2, PI4K2A, CLTC | 128 | 66 | 12782 | 6.05 | 0.51 | 30.76 |
| GOTERM_CC_FAT | GO:0030662~coated vesicle membrane | 4 | 2.116402116 | 0.04 | SCAMP1, AP1S2, PI4K2A, CLTC | 128 | 73 | 12782 | 5.47 | 0.54 | 37.96 |
| GOTERM_CC_FAT | GO:0005768~endosome | 8 | 4.232804233 | 0.04 | SCAMP1, ATP7A, SCAMP2, RAB5C, CHMP5, PI4K2A, RAB5A, CYBASC3 | 128 | 315 | 12782 | 2.54 | 0.53 | 39.32 |
| GOTERM_CC_FAT | GO:0030659~cytoplasmic vesicle membrane | 5 | 2.645502646 | 0.05 | SCAMP1, AP1S2, PI4K2A, RAB5A, CLTC | 128 | 139 | 12782 | 3.59 | 0.60 | 48.53 |
| GOTERM_CC_FAT | GO:0012506~vesicle membrane | 5 | 2.645502646 | 0.06 | SCAMP1, AP1S2, PI4K2A, RAB5A, CLTC | 128 | 151 | 12782 | 3.31 | 0.65 | 57.50 |
| GOTERM_CC_FAT | GO:0044431~Golgi apparatus part | 7 | 3.703703704 | 0.07 | SCAMP1, ATP7A, AP1S2, SCAMP2, PDGFC, CLIP3, CLTC | 128 | 294 | 12782 | 2.38 | 0.68 | 62.65 |
| GOTERM_CC_FAT | GO:0012505~endomembrane system | 13 | 6.878306878 | 0.09 | ARL6IP1, SCAMP1, RGPD6, RGPD5, RGPD8, SCAMP2, CLTC, AP1S2, STT3A, INSIG2, SERINC1, PI4K2A, RAB5A, PDGFC, ASPH | 128 | 782 | 12782 | 1.66 | 0.69 | 69.95 |
| GOTERM_CC_FAT | GO:0005798~Golgi-associated vesicle | 3 | 1.587301587 | 0.09 | ATP7A, AP1S2, CLTC | 128 | 51 | 12782 | 5.87 | 0.67 | 71.19 |
| | Annotation Cluster 4 | | | | | | | | | | |
| | Enrichment Score: 1.2483614903873126 | | | | | | | | | | |
| GOTERM_BP_FAT | GO:0006665~sphingolipid metabolic process | 4 | 2.116402116 | 0.04 | GBA2, SERINC1, LASS2, GALC | 138 | 75 | 13528 | 5.23 | 1.00 | 48.90 |
| GOTERM_BP_FAT | GO:0006643~membrane lipid metabolic process | 4 | 2.116402116 | 0.05 | GBA2, SERINC1, LASS2, GALC | 138 | 81 | 13528 | 4.84 | 1.00 | 55.78 |
| GOTERM_BP_FAT | GO:0006672~ceramide metabolic process | 3 | 1.587301587 | 0.07 | GBA2, LASS2, GALC | 138 | 42 | 13528 | 7.00 | 1.00 | 67.83 |
| GOTERM_BP_FAT | GO:0046519~sphingoid metabolic process | 3 | 1.587301587 | 0.08 | GBA2, LASS2, GALC | 138 | 45 | 13528 | 6.54 | 1.00 | 72.33 |
| | Annotation Cluster 5 | | | | | | | | | | |
| | Enrichment Score: 1.1612816039563372 | | | | | | | | | | |
| GOTERM_CC_FAT | GO:0042470~melanosome | 4 | 2.116402116 | 0.06 | RAB5C, RAB5A, CLTC, PRDX1 | 128 | 89 | 12782 | 4.49 | 0.64 | 54.53 |
| GOTERM_CC_FAT | GO:0048770~pigment granule | 4 | 2.116402116 | 0.06 | RAB5C, RAB5A, CLTC, PRDX1 | 128 | 89 | 12782 | 4.49 | 0.64 | 54.53 |
| GOTERM_CC_FAT | GO:0009898~internal side of plasma membrane | 7 | 3.703703704 | 0.10 | AP1S2, MTMR1, MAST2, RAB5C, RAB5A, CLTC, GNG5 | 128 | 316 | 12782 | 2.21 | 0.67 | 72.75 |

TABLE 8-continued

Over-represented Pathways and Gene Ontology for the Upregulated Exons

Controls

SIGNIFICANTLY ENRICHED CANONICAL PATHWAYS OF CONTROLS

| Ingenuity Canonical Pathways | −log(p-value) | −log(B-H p-value) | Ratio | Molecules |
|---|---|---|---|---|
| Antigen Presentation Pathway | 3.35E00 | 1.71E00 | 5.41E-02 | HLA-DOB, TAP2 |
| Bile Acid Biosynthesis, Neutral Pathway | 1.96E00 | 8.31E-01 | 7.69E-02 | SCP2 |
| Methionine Degradation I (to Homocysteine) | 1.87E00 | 8.31E-01 | 6.25E-02 | AHCY |
| Cysteine Biosynthesis III (mammalia) | 1.82E00 | 8.31E-01 | 5.56E-02 | AHCY |
| Superpathway of Methionine Degradation | 1.58E00 | 8.31E-01 | 3.23E-02 | AHCY |
| B Cell Development | 1.54E00 | 8.31E-01 | 2.94E-02 | HLA-DOB |
| tRNA Charging | 1.48E00 | 8.31E-01 | 2.56E-02 | IARS |
| Graft-versus-Host Disease Signaling | 1.4E00 | 8.31E-01 | 2.08E-02 | HLA-DOB |
| Autoimmune Thyroid Disease Signaling | 1.39E00 | 8.31E-01 | 2.04E-02 | HLA-DOB |
| Primary Immunodeficiency Signaling | 1.36E00 | 8.31E-01 | 1.92E-02 | TAP2 |
| Nur77 Signaling in T Lymphocytes | 1.32E00 | 8.31E-01 | 1.75E-02 | HLA-DOB |
| Regulation of Cellular Mechanics by Calpain Protease | 1.32E00 | 8.31E-01 | 1.75E-02 | ACTN4 |

SIGNIFICANTLY ENRICHED CANONICAL PATHWAYS OF CONTROLS
Annotation Cluster 1
Enrichment Score: 1.5564318042098894

| Category | Term | Count | % | PValue | Genes | List Total | Pop Hits | Pop Total | Fold Enrichment | Benjamini | FDR |
|---|---|---|---|---|---|---|---|---|---|---|---|
| GOTERM_CC_FAT | GO: 0044432~endoplasmic reticulum part | 4 | 21.05263158 | 0.00 | TAP2, FOXRED2, HLA-DOB, PORCN | 14 | 347 | 12782 | 10.52 | 0.30 | 4.79 |

TABLE 8-continued

Over-represented Pathways and Gene Ontology for the Upregulated Exons

| | | | | | | | | |
|---|---|---|---|---|---|---|---|---|
| GOTERM_MF_FAT | GO: 0001882~nucleoside binding | 5 | 26.31578947 | 0.07 | IARS, ACTN4, TAP2, FOXRED2, HLA-DOB | 14 | 1612 | 12983 | 2.88 | 1.00 | 52.67 |
| GOTERM_CC_FAT | GO: 0005783~endoplasmic reticulum | 4 | 21.05263158 | 0.07 | TAP2, FOXRED2, HLA-DOB, PORCN | 14 | 960 | 12782 | 3.80 | 0.94 | 52.80 |

Discussion

Although DAS is implicated in many human diseases, this is the first study to report DAS for ICH, IS and controls, and is the first to show that DAS is different for different causes of IS. Identification of specific DAS for different stroke etiologies suggests the immune response varies for each condition. This will likely be important for understanding pathogenesis of each stroke cause and biomarker development.

This study identified several pathways, molecular functions and genes previously reported in human IS using 3'-biased microarrays [6, 11]. These include: actin cytoskeleton signaling, CCR5 signaling in macrophages, NF-κB activation, α-adrenergic signaling, cellular growth and proliferation, cell death and survival, cell morphology, hematopoiesis, hematological system development and function and inflammatory response/disease [4, 5, 12, 13]. This study's small sample sizes preclude detailed interpretations of biological pathways. However, these pilot data suggest DAS involvement in IS and ICH pathophysiology which varies in ICH and in different IS etiologies.

Results suggest DAS differs in blood leukocytes following different cerebrovascular events. Due to the pilot nature of the study, and the lack of human transcriptome data following ICH, we will discuss only a few of the genes with differential exon usage in ICH. Among the genes that differentiated ICH were INPP5D (inositol polyphosphate-5-phosphatase) and ITA4 (integrin alpha 4). INPP5D is a regulator of myeloid cell proliferation and programming and was previously identified as correlating with increased tendency to hemorrhagic transformation of ischemic stroke [14]. ITA4 is involved in leukocyte recruitment [15] and leukocytes are intimately associated with IS and ICH [11]. For example, leukocytes are involved in clotting, and interact with injured vessels and brain following ICH and IS [11]. In addition, vascular endothelial growth factor (VEGF) signaling, which predisposes to hemorrhage because of new vessel formation [16], was implicated in ICH by several DAS genes, including NAV1 (neuron navigator 1), PDGFC (platelet derived growth factor C) and CCM2 (cerebral cavernous malformation 2). CCM2 mutations cause cerebral cavernous malformations leading to a predisposition for abnormal vessels and cerebral hemorrhage [17]. Interestingly, exosomes may be involved in ICH as evidenced by the differential expression of EXOSC1 (exosome component 1) and EXOSC9 (exosome component 9), coding for core components of the exosome complex [18]. Although exosomes have been implicated in neuroinflammation, neurodegeneration and cancer, they have not previously been associated with ICH [19, 20]. Finally, DGCR8 (microprocessor complex subunit) is involved in the biogenesis of microRNAs [21], thus suggesting an interplay between alternative splicing and miRNA in ICH.

REFERENCES

[1] Moore D F, Li H, Jeffries N, Wright V, Cooper R A, Jr., Elkahloun A, et al. Using peripheral blood mononuclear cells to determine a gene expression profile of acute ischemic stroke: a pilot investigation. Circulation. 2005; 111:212-21.

[2] Tang Y, Xu H, Du X, Lit L, Walker W, Lu A, et al. Gene expression in blood changes rapidly in neutrophils and monocytes after ischemic stroke in humans: a microarray study. Journal of cerebral blood flow and metabolism: official journal of the International Society of Cerebral Blood Flow and Metabolism. 2006; 26:1089-102.

[3] Stamova B, Xu H, Jickling G, Bushnell C, Tian Y, Ander B P, et al. Gene expression profiling of blood for the prediction of ischemic stroke. Stroke; a journal of cerebral circulation. 2010; 41:2171-7.

[4] Jickling G C, Xu H, Stamova B, Ander B P, Zhan X, Tian Y, et al. Signatures of cardioembolic and large-vessel ischemic stroke. Annals of Neurology. 2010; 68:681-92.

[5] Jickling G C, Stamova B, Ander B P, Zhan X, Tian Y, Liu D, et al. Profiles of lacunar and nonlacunar stroke. Annals of Neurology. 2011; 70:477-85.

[6] Sharp F R, Jickling G C, Stamova B, Tian Y, Zhan X, Liu D, et al. Molecular markers and mechanisms of stroke: RNA studies of blood in animals and humans. Journal of Cerebral Blood Flow and Metabolism: official journal of the International Society of Cerebral Blood Flow and Metabolism. 2011; 31:1513-31.

[7] Gamazon E R, Stranger B E. Genomics of alternative splicing: evolution, development and pathophysiology. Human Genetics. 2014; 133:679-87.

[8] Poulos M G, Batra R, Charizanis K, Swanson M S. Developments in RNA splicing and disease. Cold Spring Harbor Perspectives In Biology. 2011; 3:a000778.

[9] Jickling G C, Stamova B, Ander B P, Zhan X, Liu D, Sison S M, et al. Prediction of cardioembolic, arterial, and lacunar causes of cryptogenic stroke by gene expression and infarct location. Stroke; a journal of cerebral circulation. 2012; 43:2036-41.

[10] Trapnell C, Pachter L, Salzberg S L. TopHat: discovering splice junctions with RNA-Seq. Bioinformatics. 2009; 25:1105-11.

[11] Sharp F R, Jickling G C. Whole genome expression of cellular response to stroke. Stroke; a journal of cerebral circulation. 2013; 44:S23-5.

[12] Tian Y, Stamova B, Jickling G C, Liu D, Ander B P, Bushnell C, et al. Effects of gender on gene expression in the blood of ischemic stroke patients. Journal of Cerebral Blood Flow and Metabolism: official journal of the International Society of Cerebral Blood Flow and Metabolism. 2012; 32:780-91.

[13] Xu H, Tang Y, Liu D Z, Ran R, Ander B P, Apperson M, et al. Gene expression in peripheral blood differs after cardioembolic compared with large-vessel atherosclerotic stroke: biomarkers for the etiology of ischemic stroke. Journal of cerebral blood flow and metabolism: official journal of the International Society of Cerebral Blood Flow and Metabolism. 2008; 28:1320-8.

[14] Jickling G C, Ander B P, Stamova B, Zhan X, Liu D, Rothstein L, et al. RNA in blood is altered prior to hemorrhagic transformation in ischemic stroke. Annals of Neurology. 2013; 74:232-40.

[15] Hammond M D, Ambler W G, Ai Y, Sansing L H. alpha4 integrin is a regulator of leukocyte recruitment after experimental intracerebral hemorrhage. Stroke; a journal of cerebral circulation. 2014; 45:2485-7.

[16] Jeney V, Balla G, Balla J. Red blood cell, hemoglobin and heme in the progression of atherosclerosis. Frontiers in Physiology. 2014; 5:379.

[17] Kar S, Samii A, Bertalanffy H. PTEN/PI3K/Akt/VEGF signaling and the cross talk to KRIT1, CCM2, and PDCD10 proteins in cerebral cavernous malformations. Neurosurgical Review. 2014.

[18] Shen V, Kiledjian M. A view to a kill: structure of the RNA exosome. Cell. 2006; 127:1093-5.

[19] Gupta A, Pulliam L. Exosomes as mediators of neuroinflammation. Journal of Neuroinflammation. 2014; 11:68.

[20] Candelario K M, Steindler D A. The role of extracellular vesicles in the progression of neurodegenerative disease and cancer. Trends in Molecular Medicine. 2014; 20:368-74.

[21] Gregory R I, Yan K P, Amuthan G, Chendrimada T, Doratotaj B, Cooch N, et al. The Microprocessor complex mediates the genesis of microRNAs. Nature. 2004; 432: 235-40.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A solid support comprising a set of oligonucleotide probes, wherein the oligonucleotide probes in the set hybridize under stringent hybridization conditions to different genes and wherein the different genes comprise ZNF33A; FAM35B and RHEBP1; SLAMF1 and UBR4;
    wherein the probes are immobilized to the solid support, labeled and greater than 50 nucleotides in length and wherein the solid support comprises probes to no more than 292 genes.

2. A reaction mixture comprising a set of oligonucleotide probes, wherein the oligonucleotide probes in the set hybridize under stringent hybridization conditions to different genes and wherein the different genes comprise ZNF33A; FAM35B and RHEBP1; SLAMF1 and UBR4;
    wherein the oligonucleotide probes are greater than 50 nucleotides in length and one or more of the oligonucleotide probes comprise a label comprising a fluorophore, chemiluminescent agent, enzyme or antibody and the mixture comprises probes to no more than 292 genes.

3. The reaction mixture of claim 2, further comprising one or more oligonucleotide probes that hybridize to one or more exons of one or more genes selected from the group consisting of DUXAP10 and SCP2.

4. A kit comprising a set of oligonucleotide probes, wherein the oligonucleotide probes in the set hybridize under stringent hybridization conditions to different genes and wherein the different genes comprise ZNF33A; FAM35B and RHEBP1; SLAMF1 and UBR4; wherein the oligonucleotide probes are greater than 50 nucleotides in length and one or more of the oligonucleotide probes comprise a label comprising a fluorophore, chemiluminescent agent, enzyme or antibody and the kit comprises probes to no more than 292 genes.

5. The solid support of claim 1, wherein the solid support is a microarray.

6. The solid support of claim 5, wherein the microarray is suitable or configured for use in a microfluidic device.

7. The solid support of claim 1, further comprising one or more oligonucleotide probes that hybridize to one or more exons of one or more genes selected from the group consisting of DUXAP10 and SCP2.

8. A kit comprising the solid support of claim 1.

9. A kit comprising the reaction mixture of claim 2.

10. The kit of claim 4, further comprising one or more oligonucleotide probes that hybridize to one or more exons of one or more genes selected from the group consisting of DUXAP10 and SCP2.

11. The solid support of claim 1, further comprising one or more oligonucleotide probes that hybridize to one or more genes selected from the group consisting of ODF2L, CENPF, and DAP3.

12. The reaction mixture of claim 2, further comprising one or more oligonucleotide probes that hybridize to one or more genes selected from the group consisting of ODF2L, CENPF, and DAP3.

13. The kit of claim 4, further comprising one or more oligonucleotide probes that hybridize to one or more genes selected from the group consisting of ODF2L, CENPF, and DAP3.

* * * * *